United States Patent
Eshhar et al.

(10) Patent No.: US 11,326,147 B2
(45) Date of Patent: May 10, 2022

(54) REDIRECTED, GENETICALLY-ENGINEERED T REGULATORY CELLS AND THEIR USE IN SUPPRESSION OF AUTOIMMUNE AND INFLAMMATORY DISEASE

(71) Applicant: YEDA RESEARCH AND DEVELOPMENT CO., LTD., Rehovot (IL)

(72) Inventors: Zelig Eshhar, Rehovot (IL); Eran Elinav, Jerusalem (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 16/361,852

(22) Filed: Mar. 22, 2019

(65) Prior Publication Data
US 2020/0056152 A1   Feb. 20, 2020

Related U.S. Application Data

(63) Continuation of application No. 12/525,270, filed as application No. PCT/US2008/052724 on Jan. 31, 2008, now abandoned.

(60) Provisional application No. 60/951,052, filed on Jul. 20, 2007, provisional application No. 60/898,408, filed on Jan. 31, 2007.

(51) Int. Cl.
C12N 5/0783   (2010.01)
A61K 39/00   (2006.01)

(52) U.S. Cl.
CPC ........ *C12N 5/0636* (2013.01); *A61K 39/0008* (2013.01); *A61K 39/0011* (2013.01)

(58) Field of Classification Search
None
See application file for complete search history.

(56) References Cited

U.S. PATENT DOCUMENTS

| | | |
|---|---|---|
| 2002/0137697 A1 | 9/2002 | Eshhar et al. |
| 2003/0147865 A1 | 8/2003 | Salomon et al. |
| 2003/0157057 A1 | 8/2003 | Horwitz |
| 2004/0115217 A1 | 6/2004 | Weiner et al. |
| 2005/0059624 A1 | 5/2005 | Hoerr |
| 2009/0226404 A1 | 9/2009 | Schuler |

FOREIGN PATENT DOCUMENTS

| | | | |
|---|---|---|---|
| EP | 1795599 A1 | 9/2005 | |
| WO | 02/072796 A2 | 9/2002 | |
| WO | 03/066072 A2 | 8/2003 | |
| WO | WO-2005070090 A2 * | 8/2005 | ........... A61P 3/10 |
| WO | 2007/065957 A2 | 6/2007 | |
| WO | 2008/121420 A1 | 10/2008 | |

OTHER PUBLICATIONS

Hennecke et al. "Composition and arrangement of genes define the strength of IRES-driven translation in bicistronic mRNAs" Nucleic Acids Research, 29(16): 3327-3334 (2001).
Willemsen et al., "T Cell Retargeting with MHC Class I-Restricted Antibodies: The CD28 Costimulatory Domain Enhances Antigen-Specific Cytotoxicity and Cytokine Production" J. Immunol 174:7853-7858 (2005).
Zhang et al., "Generation of Antitumor Responses by Genetic Modification of Primary Human T Cells with a Chimeric NKG2D Receptor" Cancer Res 66(11):5927-5933 (2006).
Zou., "Regulatory T cells, tumour immunity and immunotherapy" Nature Reviews Immunology 6:295-307 (2006).
Dieckmann et al., "Ex Vivo Isolation and Characterization of CD4+CD25+ T Cells with Regulatory Properties from Human Blood", J. Exp. Med., pp. 1303-1310 vol. 193: (2001).
Kowolik et al., "CD28 Costimulation Provided through a CD19-Specific Chimeric Antigen Receptor Enhances In vivo Persistence and Antitumor Efficacy of Adoptively Transferred T Cells," Canc. Res., pp. 10995-11004, vol. 66: (2006).
Tang et al., "Cutting Edge:CD28 Controls Peripheral Homeostasis of CD4+CD25 Regulatory T Cells", J. Immunol. vol. 171: 3348-3352 , (2003).
Gross et al., "Expression of immunoglobulin-T-cell receptor chimeric molecules as functional receptors with antibody-type specificity" PNAS, 86: 10024-10028 (1989).
Rosenberg et al., "Vitiligo in patients with melanoma: normal tissue antigens can be targets for cancer immunotherapy" Journal of immunotherapy, 1996, 19: 81-84 (1996).
Fitzer-Attas et al., "Harnessing syk family tyrosine kinases as signaling domains for chimeric single chain of the variable domain receptors: optimal design for T cell activation" Journal of Immunology, 160 : 145-154 (1998).
Geiger et al, "The TCR ζ-chain immunoreceptor tyrosine-based activation motifs are sufficient for the activation and differentiation of primary T lymphocytes" Journal of Immunology, 162: 5931-5939 (1999).

(Continued)

*Primary Examiner* — Amy E Juedes
(74) *Attorney, Agent, or Firm* — Browdy and Neimark, PLLC

(57) ABSTRACT

A redirected Treg cell is endowed with specificity toward a selected target antigen or ligand. The cell contains a chimeric receptor polypeptide that is expressed in a single, continuous chain, with an extracellular recognition region displayed on the surface of the cell, a transmembrane region and an intracellular signaling region. The extracellular recognition region is specific for the selected target antigen or ligand. The intracellular signaling region includes a combination of T-cell signaling polypeptide moieties, which combination, upon binding of the extracellular recognition region to the selected target antigen or ligand, triggers activation of the redirected Treg cells to cause suppression of T-cell mediated immunity. Such redirected Treg cells may be used to suppress undesired activity of T effector cells thereby mediating an immune or inflammatory response. They are particularly useful in treating T effector cell-mediated diseases, such as inflammatory bowel disease, transplant rejection and GVH disease.

17 Claims, 43 Drawing Sheets

Specification includes a Sequence Listing.

(56) References Cited

OTHER PUBLICATIONS

Jyothi et al., "Targeting autoantigen-specific T cells and suppression of autoimmune encephalomyelitis with receptor-modified T lymphocytes" Nature Biotechnology, 20: 1215-1220 (2002).
Haynes et al., "Rejection of syngeneic colon carcinoma by CTLs expressing single-chain antibody receptors codelivering CD28 costimulation" Journal of Immunology, 169: 5780-5786 (2002).
Hori et al, "Control of regulatory T cell development by the transcription factor Foxp3" Science, 299 : 1057-1061 (2003).
Fontenot et al, "Foxp3 programs the development and function of CD4+CD25+ regulatory T cells" Nature Immunoloy, 4: 330-336 (2003).
Hofbauer et al., "Clonal tracking of autoaggressive T cells in polymyositis by combining laser microdissection, single-cell PCR, and CDR3-spectratype analysis" PNAS, 100: 4090-4095 (2003).
Walker et al., "Induction of Foxp3 and acquisition of T regulatory activity by stimulated human CD4+CD25- T cells" Journal of clinical investigation, 112: 1437-1443 (2003).
Mekala and Geiger, "Immunotherapy of autoimmune encephalomyelitis with redirected CD4+CD25+ T lymphocytes" Blood, 2005, 105: 2090-2092 (2005).
Walker et al, "De novo generation of antigen-specific CD4+CD25+ regulatory T cells from human CD4+CD25- cells" PNAS, 102: 4103-4108 (2005).
Dejaco et al, "Imbalance of regulatory T cells in human autoimmune diseases" Immunology, 117: 289-300 (2005).
Abrams et al., "Muscarinic receptors: their distribution and function in body systems, and the implications for treating overactive bladder" British Journal of Pharmacology, 148: 565-578 (2006).
Smith et al., "Splice variants of human FOXP3 are functional inhibitors of human CD4+ T-cell activation" Immunology, 119: 203-211 (2006).
Strauss et al., "Functional and phenotypic characteristics of CD4+ CD25highFoxp3+ Treg clones obtained from peripheral blood of patients with cancer" International Journal Cancer, 121 : 2473-2483 (2007).
Allan et al., "Generation of potent and stable human CD4+ T regulatory cells by activation-independent expression of FOXP3" Mol. Ther., 16: 194-202 (2007).
Velasquez-Lopera et al., "Human spleen contains different subsets of dendritic cells and regulatory T lymphocytes" Clinical and Experimental Immunology, 154: 107-114 (2008).
Hombach et al., "Redirecting human CD4+CD25+ regulatory T cells from the peripheral blood with pre-defined target specificity" Gene Ther., 16: 1088-1096 (2009).
Bluestone et al., "T cells in the control of organ-specific autoimmunity" J. Clin Invest., 125: 2250-2260 (2015).
Kühl et al., "Diversity of intestinal macrophages in inflammatory bowel diseases" Front Immunol. 6:1-7 (2015).
Van Eldik et al., "The roles of inflammation and immune mechanisms in Alzheimer's disease" Alzheimer's & Dementia, TRCI 2 : 99-109 (2016).
Diller et al., "Balancing inflammation: the link between Th17 and regulatory T cells" Mediators Inflamm., 2016: 1-8 (2017).
Vuddamalay & van Meerwijk, "CD28- and CD28lowCD8+ regulatory T cells: Of mice and men" Front. Immunol, 8: 1-7 (2017).
Mekala et al.,"IL-10-dependent infectious tolerance after the treatment of experimental allergic encephalomyelitis with redirected CD4(+) CD25(+) T lymphocytes," PNAS 102(33):11817-11822 (2005).
Friedmann-Morvinski, et al.,"Redirected primary T cells harboring a chimeric receptor require costimulation for their antigen-specific activation," BLOOD, pp. 3087-3093, vol. 105, No. 8 (2005).
Friedmann-Morvinski, et al., "Adoptive immunotherapy of cancer using effector lymphocytes redirected with antibody specificity," Update on Cancer Therapeutics, pp. 25-32, vol. 1, No. 1, Elsevier, Amsterdam, NL (2006).

Abken, et al.,"Immune response manipulation: Recombinant immunoreceptors endow T-cells with predefined specificity," Current Pharmaceutical Design, pp. 1992-2001, vol. 9, No. 24 (2003).
Eshhar, et al.,"Functional expression of chimeric receptor genes in human T cells," Journal of Immunological Methods, pp. 67-76, vol. 248, No. 1-2 (2001).
Eshhar, et al.,"The T-body approach: redirecting T cells with antibody specificity," Handbook of Experimental Pharmacology, pp. 329-342, No. 181 (2008).
"ESGCT 2007 Invited presentations," Human gene therapy, pp. 941-954, vol. 18, No. 10 (2007).
Elinav, et al.,"Redirection of regulatory T cells with predetermined specificity for the treatment of experimental colitis in mice," Gastroenterology, pp. 2014-2024, vol. 134, No. 7 (2008).
Eshhar et al., "TheT-body approach: potential for cancer immunotherapy", Springer Semin Immunopathol., pp. 199-209, vol. 18: (1996).
Vagi et al., "Crucial role of FOXP3 in the development and function of human CD2S+CD4+ regulatory T cells" Int. Immunol. pp. 1643-1656, vol. 16: (2004).
Gyobu et al.,, "Generation and Targeting of Human Tumor-Specific Tcl and Thl Cells Transduced with a Lentivirus Containing a Chimeric Immunoglobulin T-Cell Receptor" Canc. Res. pp. 1490-1495, vol. 64: , (2004).
Chandran et al., "Inflammatoty bowel disease: dysfunction of GALT and gut bacterial flora (I)", Surg J. R Coil. Surg. Edinb Irel. pp. 63-75 (2003).
Kerlero de Rosbo et al., "Reactivity to Myelin Antigens in MultipleS clerosis", J. Clin. INvest., pp. 2602-2608 vol. 92:, (1993).
Allan et al "The role of 2 FOXP3 isoforms in the generation of human CD4+ Tregs" J. Clin. Invest. 115:3276-3284 (2005).
Finney et al. "Activation of Resting Human Primary T Cells with Chimeric Receptors: Costimulation from CD28, Inducible Costimulator, CD134, and CD137 in Series with Signals from the TCR(zeta)Chain" J Immunol 172:104-113 (2004).
Valencia et al. "TNF downmodulates the function of human CD4+ CD25hi T-regulatory cells" Blood 108(1)No. 1 253-261 (2006).
Yang et al., "Molecular antagonism and plasticity of regulatory and inflammatory T cell programs" Immunity 29(1): 44-56 (2008).
Zao et al., "Changes of CD4+CD25+Foxp3+ regulatory T cells in aged Balb/c mice" J. Leukoc. Biol. 81:1386-1394 (2007).
Crellin et al., "Altered activation of AKT is required for the suppressive function of human CD4+CD25+ T regulatory cells" Blood, 109(5):2014-2022 (2007).
Elinav et al., "Amelioration of Colitis by Genetically Engineered Murine Regulatory T Cells Redirected by Antigen-Specific Chimeric Receptor" Gastroenterology 136:1721-1731 (2009).
Allan et al., "Activation-induced FOXP3 in human T effector cells does not suppress proliferation or cytokine production" International Immunology, vol. 19, No. 4, pp. 345-354 (2007).
Levings et al., "Human CD25+CD4+T Regulatory Cells Suppress Naive and Memory T Cell Proliferation and Can Be Expanded In Vitro without Loss of Function" J. Exp. Med. 193(11) 1295-1301 (2001).
MacDonald et al., "Supplemental Material for Alloantigen-specific T regulatory cells generated with a chimeric antigen receptor" https://dm5migu4zj3pb.cloudfront.net/manuscripts/82000/82771/JCI82771.sd.pdf pp. 1-4 (2016).
MacDonald et al., "Alloantigen-specific T regulatory cells generated with a chimeric antigen receptor" J Clin Invest. 126(4):1413-1424 (2016).
Moeller et al., "A functional role for CD28 costimulation in tumor recognition by single-chain receptor-modified T cells" Cancer Gene Therapy 11:371-379 (2004).
Jena et al., "Redirecting T-cell specificity by introducing a tumor-specific chimeric antigen receptor," Blood, 116:1035-1044 (2010).
Berry et al., "Adoptive immunotherapy for cancer: the next generation of gene-engineered immune cells," Tissue Antigens 74:277-289 (2009).

* cited by examiner

FIG. 28 A

```
                                  XbaI       NcoI
                                   |          |
                                  TCTAGACTGCCATGGATTTTCAGGTG
1381  ---------+---------+---------+---------+---------+---------+ 1440
                                  AGATCTGACGGTACCTAAAAGTCCAC
                                            M  D  F  Q  V  - 5
                                            ←----------

XbaI
                                         |
       CAGATTTTCAGCTTCCTGCTAATCAGTGCCTCAGTCATAATGTCTAGAGGAGATATTGTG
1441  ---------+---------+---------+---------+---------+---------+ 1500
       GTCTAAAAGTCGAAGGACGATTAGTCACGGAGTCAGTATTACAGATCTCCTCTATAACAC
        Q  I  F  S  F  L  L  I  S  A  S  V  I  M  S  R  G  D  I  V   -25
       ---------------- LEADER ---------------------→←-******

ATGACCCAGTCTCCAAAATTCATGTCCACATCAGTAGGAGGCAGGGTCAGCATCACCTGC
1501  ---------+---------+---------+---------+---------+---------+ 1560
       TACTGGGTCAGAGGTTTTAAGTACAGGTGTAGTCATCCTCCGTCCCAGTCGTAGTGGACG
        M  T  Q  S  P  K  F  M  S  T  S  V  G  G  R  V  S  I  T  C   -45
       ********************  SP6  **********************************

AAGGCCAGTCAGAATGTGGGTACTGCTGTAGCCTGGTATCAACAGAAACCAGGACAATCT
1561  ---------+---------+---------+---------+---------+---------+ 1620
       TTCCGGTCAGTCTTACACCCATGACGACATCGGACCATAGTTGTCTTTGGTCCTGTTAGA
        K  A  S  Q  N  V  G  T  A  V  A  W  Y  Q  Q  K  P  G  Q  S   -65
       ********************  SP6  **********************************

CCTAAACTACTGATTTACTCGGCATCCAATCGGTACACTGGAGTCCCTGATCGCTTCACA
1621  ---------+---------+---------+---------+---------+---------+ 1680
       GGATTTGATGACTAAATGAGCCGTAGGTTAGCCATGTGACCTCAGGGACTAGCGAAGTGT
        P  K  L  L  I  Y  S  A  S  N  R  Y  T  G  V  P  D  R  F  T   -85
       ********************  SP6  **********************************

GGCAGTGGATCTGGGACAGATTTCACTCTCACCATCAGCAATATGCAGTCTGAAGACCTG
1681  ---------+---------+---------+---------+---------+---------+ 1740
       CCGTCACCTAGACCCTGTCTAAAGTGAGAGTGGTAGTCGTTATACGTCAGACTTCTGGAC
        G  S  G  S  G  T  D  F  T  L  T  I  S  N  M  Q  S  E  D  L   -105
       ********************  SP6  **********************************

GCAGATTATTTCTGCCAGCAATATAGCAGCTATCCTCTCACGTTCGGTGCTGGCACCAAG
1741  ---------+---------+---------+---------+---------+---------+ 1800
       CGTCTAATAAAGACGGTCGTTATATCGTCGATAGGAGAGTGCAAGCCACGACCGTGGTTC
        A  D  Y  F  C  Q  Q  Y  S  S  Y  P  L  T  F  G  A  G  T  K   -125
       ********************  SP6  **********************************

SalI
              |
       CTGGAAATWAAAGGGTCGACTTCCGGTAGCGGCAAATCCTCTGAAGGCAAAGGTCAGGTC
1801  ---------+---------+---------+---------+---------+---------+ 1860
       GACCTTTAWTTTCCCAGCTGAAGGCCATCGCCGTTTAGGAGACTTCCGTTTCCAGTCCAG
        L  E  I  K  G  S  T  S  G  S  G  K  S  S  E  G  K  G  Q  V   -145
       ********************  SP6  **********************************
```

Fig. 28 B

```
                                                                EcoRV
                                                                  |
       CAGCTGCAGCAGTCTGGACCTGAGCTGGTGAAGCCTGGGGCTTCAGTGAGGATATCCTGC
1861   ---------+---------+---------+---------+---------+---------+ 1920
       GTCGACGTCGTCAGACCTGGACTCGACCACTTCGGACCCCGAAGTCACTCCTATAGGACG
        Q  L  Q  Q  S  G  P  E  L  V  K  P  G  A  S  V  R  I  S  C  -165
       *******************  SP6  *********************************

AAGGCTTCTGGCTACACCTTCACAAGCTACTATATACACTGGGTGAAGCAGAGGCCTGGA
1921   ---------+---------+---------+---------+---------+---------+ 1980
       TTCCGAAGACCGATGTGGAAGTGTTCGATGATATATGTGACCCACTTCGTCTCCGGACCT
        K  A  S  G  Y  T  F  T  S  Y  Y  I  H  W  V  K  Q  R  P  G  -185
       *******************  SP6  *********************************

CAGGGACTTGAGTGGATTGGATGGATTTATCCTGGAAATGTTAATACTAAGTACAATGAG
1981   ---------+---------+---------+---------+---------+---------+ 2040
       GTCCCTGAACTCACCTAACCTACCTAAATAGGACCTTTACAATTATGATTCATGTTACTC
        Q  G  L  E  W  I  G  W  I  Y  P  G  N  V  N  T  K  Y  N  E  -205
       *******************  SP6  *********************************

AAGTTCAAGGGCAAGGCCACACTGACTGCAGACAAATCCTCCAGCACAGCCTACATGCAG
2041   ---------+---------+---------+---------+---------+---------+ 2100
       TTCAAGTTCCCGTTCCGGTGTGACTGACGTCTGTTTAGGAGGTCGTGTCGGATGTACGTC
        K  F  K  G  K  A  T  L  T  A  D  K  S  S  S  T  A  Y  M  Q  -225
       *******************  SP6  *********************************

CTCAGCAGCCTGACCTCTGAGGACTCTGCGGTCTATTTCTGTGCAAGAAACTACGGTAGT
2101   ---------+---------+---------+---------+---------+---------+ 2160
       GAGTCGTCGGACTGGAGACTCCTGAGACGCCAGATAAAGACACGTTCTTTGATGCCATCA
        L  S  S  L  T  S  E  D  S  A  V  Y  F  C  A  R  N  Y  G  S  -245
       *******************  SP6  *********************************

BstEII
                                                     |
       AGCTACGGGCTTGCTTACTGGGGCCAAGGAACTACGGTCACCGTGAAAGGGAAACACCTT
2161   ---------+---------+---------+---------+---------+---------+ 2220
       TCGATGCCCGAACGAATGACCCCGGTTCCTTGATGCCAGTGGCACTTTCCCTTTGTGGAA
        S  Y  G  L  A  Y  W  G  Q  G  T  T  V  T  V  K  G  K  H  L  -265
       ************  SP6  *************><@@@@@@@ CD28  @@@@@@@@@

TGTCCAAGTCCCCTATTTCCCGGACCTTCTAAGCCCTTTTGGGTGCTGGTGGTGGTTGGT
2221   ---------+---------+---------+---------+---------+---------+ 2280
       ACAGGTTCAGGGGATAAAGGGCCTGGAAGATTCGGGAAAACCCACGACCACCACCAACCA
        C  P  S  P  L  F  P  G  P  S  K  P  F  W  V  L  V  V  V  G  -285
       @@@@@@@@@@@@@@@@@@@@@@@@  CD28  @@@@@@@@@@@@@@@@@@@@@@@@@@@@

GGAGTCCTGGCTTGCTATAGCTTGCTAGTAACAGTGGCCTTTATTATTTTCTGGGTGAGG
2281   ---------+---------+---------+---------+---------+---------+ 2340
       CCTCAGGACCGAACGATATCGAACGATCATTGTCACCGGAAATAATAAAAGACCCACTCC
        G  V  L  A  C  Y  S  L  L  V  T  V  A  F  I  I  F  W  V  R  -305
       @@@@@@@@@@@@@@@@@@@@@@@@  CD28  @@@@@@@@@@@@@@@@@@@@@@@@@@@@
```

Fig. 28 C

```
            AGTAAGAGGAGCAGGCTCCTGCACAGTGACTACATGAACATGACTCCCCGCCGCCCCGGG
     2341   ---------+---------+---------+---------+---------+---------+ 2400
            TCATTCTCCTCGTCCGAGGACGTGTCACTGATGTACTTGTACTGAGGGGCGGCGGGGCCC
             S  K  R  S  R  L  L  H  S  D  Y  M  N  M  T  P  R  R  P  G   -325
            @@@@@@@@@@@@@@@@@@@@@@@@@@  CD28  @@@@@@@@@@@@@@@@@@@@@@@@@@

BglII
                                                               |
            CCCACCCGCAAGCATTACCAGCCCTATGCCCCACCACGCGACTTCGCAGCCTATAGATCT
     2401   ---------+---------+---------+---------+---------+---------+ 2460
            GGGTGGGCGTTCGTAATGGTCGGGATACGGGGTGGTGCGCTGAAGCGTCGGATATCTAGA
             P  T  R  K  H  Y  Q  P  Y  A  P  P  R  D  F  A  A  Y  R  S   -345
            @@@@@@@@@@@@@@@@@@@@@@@@@@  CD28  @@@@@@@@@@@@@@@@@@@@><%%%%%

CAAGTGCGAAAGGCAGCTATAACCAGCTATGAGAAATCAGATGGTGTTTACACGGGCCTG
     2461   ---------+---------+---------+---------+---------+---------+ 2520
            GTTCACGCTTTCCGTCGATATTGGTCGATACTCTTTAGTCTACCACAAATGTGCCCGGAC
             Q  V  R  K  A  A  I  T  S  Y  E  K  S  D  G  V  Y  T  G  L   -365
            %%%%%%%%%%%%%%%%%%%%%%%%%%  GAMMA  %%%%%%%%%%%%%%%%%%%%%%%%%%

AGCACCAGGAACCAGGAGACTTACGAGACTCTGAAGCATGAGAAACCACCACAGTAGCTT
     2521   ---------+---------+---------+---------+---------+---------+ 2580
            TCGTGGTCCTTGGTCCTCTGAATGCTCTGAGACTTCGTACTCTTTGGTGGTGTCATCGAA
             S  T  R  N  Q  E  T  Y  E  T  L  K  H  E  K  P  P  Q  *  L   -385
            %%%><

XhoI
              |
            TAGACTCGAG
     2581   ----------+ 2591
            ATCTGAGCTC
            *  T  R  G   389
```

Nucleotide Sequence is SEQ ID NO:1
Amino Acid Sequence is SEQ ID NO:2

FIG. 29 A pBullet plasmid with CR construct: scFv of mAb HB9081 fused to C28/FcRγ (SEQ ID NO:3).

*Plasmid sequence →*
```
gattgactga gtcgcccggg tacccgtgta tccaataaac cctcttgcag ttgcatccga
cttgtggtct cgctgttcct tgggagggtc tcctctgagt gattgactac ccgtcagcgg
gggtctttca tttgggggct cgtccgggat cgggagaccc ctgcccaggg accaccgacc
caccaccggg aggtaagctg gccagcaact tatctgtgtc tgtccgattg tctagtgtct
atgactgatt ttatgcgcct gcgtcggtac tagttagcta actagctctg tatctggcgg
acccgtggtg gaactgacga gttcggaaca cccggccgca acctgggag acgtccagg
gacttcgggg gccgttttg tggcccgacc tgagtcctaa aatcccgatc gtttaggact
ctttggtgca ccccccttag aggagggata tgtggttctg gtaggagacg agaacctaaa
acagttcccg cctccgtctg aattttgct ttcggtttgg gaccgaagcc gcgccgcgcg
tcttgtctgc tgcagcatcg ttctgtgttg tctctgtctg actgtgtttc tgtatttgtc
tgaaaatatg ggcccgggct agcctgttac cactcccta agtttgacct taggtcactg
gaaagatgtc gagcggatcg ctcacaacca gtcggtagat gtcaagaaga gacgttggt
taccttctgc tctgcagaat ggccaacctt taacgtcgga tggccgcgag acggcacctt
taaccgagac ctcatcaccc aggttaagat caaggtcttt tcacctggcc cgcatggaca
cccagaccag gtccctaca tcgtgacctg ggaagcttg gcttttgacc ccctcctg
ggtcaagccc tttgtacacc ctaagcctcc gcctcctctt cctccatccg cccgtctct
ccccttgaa cctcctcgtt cgaccccgcc tcgatcctcc ctttatccag ccctcactcc
ttctctaggc gcccccatat ggccatatga gatcttatat ggggcacccc cgccccttgt
aaacttccct gaccctgaca tgacaagagt tactaacagc ccctctctcc aagctcactt
acaggctctc tacttagtcc agcacgaagt ctggagacct ctggcggcag cctaccaaga
acaactggac cgaccggtgg tacctcaccc ttaccgagtc ggcgacacag tgtgggtccg
ccgacaccag actaagaacc tagaacctcg ctggaaagga ccttacacag tcctgctgac
caccccacc gccctcaaag tagacggcat cgcagcttgg atacacgccg cccacgtgaa
ggctgccgac cccgggggtg gaccatcctc taga*ctgcc*
```
*Leader →*
ATG GAT TTT CAG GTG CAG ATT TTC AGC TTC CTG CTA ATC AGT GCC TCA
      Start of scFv- (L chain)
<u>GTC ATA ATG TCT AGA GGA GAT ATT GTG CTC ACA CAG TCT CCA TCC TCC</u>
<u>CTG GCT GTG TCA GCA GGA GAG AAG GTC ACT ATG AGC TGC AAA TCC AGT</u>
<u>CAG AGT CTG CTC AAC AGT AGA ACC CGA AAG AAC TAC TTG GCT TGG TAC</u>
<u>CAG CAG AAA CCA GGG CAG TCT CCT AAA CTG CTG ATC TAC TGG GCA TCC</u>
<u>ACT AGG GAA TCT GGG GTC CCT GAT CGC TTC ACA GGC AGT GGA TCT GGG</u>
<u>ACA GAT TTC ACT CTC ACC ATC AGC AGT GTG CAG GCT GAA GAC CTG GCA</u>
<u>GTT TAT TAC TGC AAG CAA TCT TAT AAT CTG TAC ACG TTC GGA GGG GGG</u>
         End of L chain
<u>ACC AAG CTG GAA ATA AAA GGG TCG ACT</u> tcc ggt agc ggc aaa tcc tct
       Start of H chain
gaa ggc aaa ggt gag gtc *CAG CTG CAG CAG TCT GGA GGT GGC CTG GTG*
*CAG CCT GGA GGA TCC CTG AAA CTC TCC TGT GCA GCC TCA GGA TTC GAT*
*TTT AGT AGA TAC TGG ATG AGT TGG GTC CGG CAG GCT CCA GGG AAA GGG*
*CTA GAA TGG ATT GGA GAA ATT AAT CCA GAT AGC AGT ACG ATA AAC TAT*
*ACG CCA TCT CTA AAG GAT AAA TTC ATC ATC TCC AGA GAC AAC GCC AAA*
*AAT ACG CTG TAC CTG CAA ATG AGC AAA GTG AGA TCT GAG GAC ACA GCC*
*CTT TAT TAC TGT GCA AGA CGT TAT GGT AAC TAC TGG TAC TTC GAT GTC*
    End of H chain  Bst Ell site  Start of CD28/FcRγ →
*TGG GGC GCA GGG ACC* ACG GTC ACC GTG AAA GGG AAA CAC CTT TGT CCA
AGT CCC CTA TTT CCC GGA CCT TCT AAG CCC TTT TGG GTG CTG GTG GTG
GTT GGT GGA GTC CTG GCT TGC TAT AGC TTG CTA GTA ACA GTG GCC TTT
ATT ATT TTC TGG GTG AGG AGT AAG AGG AGC AGG CTC CTG CAC AGT GAC
TAC ATG AAC ATG ACT CCC CGC CGC CCC GGG CCC ACC CGC AAG CAT TAC
CAG CCC TAT GCC CCA CCA CGC GAC TTC GCA GCC TAT AGA TCT CAA GTG
CGA AAG GCA GCT ATA ACC AGC TAT GAG AAA TCA GAT GGT GTT TAC ACG
GGC CTG AGC ACC AGG AAC CAG GAG ACT TAC GAG ACT CTG AAG CAT GAG

Fig. 29 B

*end of FcRγ/ IRES + Plasmid sequence*
AAA CCA CCA CAG TAG ctttagactc gagcgggatc aattccgccc ccccctaac

```
gttactggcc gaagccgctt ggaataaggc cggtgtgcgt ttgtctatat gttattttcc
accatattgc cgtcttttgg caatgtgagg gcccggaaac ctggccctgt cttcttgacg
agcattccta ggggtctttc ccctctcgcc aaaggaatgc aaggtctgtt gaatgtcgtg
aaggaagcag ttcctctgga agcttcttga agacaaacaa cgtctgtagc gacccttttgc
aggcagcgga accccccacc tggcgacagg tgcctctgcg gccaaaagcc acgtgtataa
gatacacctg caaaggcggc acaaccccag tgccacgttg tgagttggat agttgtggaa
agagtcaaat ggctctcctc aagcgtattc aacaaggggc tgaaggatgc ccagaaggta
ccccattgta tgggatctga tctgggcct cggtgcacat gctttacatg tgtttagtcg
aggttaaaaa aacgtctagg ccccccgaac cacggggacg tggttttcct ttgaaaaaca
cgataatagc atgctgagca agggcgagga gctgttcacc ggggtggtgc ccatcctggt
cgagctggac ggcgacgtaa acggccacaa gttcagcgtg tccggcgagg gcgagggcga
tgccacctac ggcaagctga ccctgaagtt catctgcacc accggcaagc tgcccgtgcc
ctggcccacc ctcgtgacca ccttcgccta cggcctgcag tgcttcgccc gctaccccga
ccacatgaag cagcacgact tcttcaagtc cgccatgccc gaaggctacg tccaggagcg
caccatcttc ttcaaggacg acggcaacta caagacccgc gccgaggtga agttcgaggg
cgacaccctg gtgaaccgca tcgagctgaa gggcatcgac ttcaaggagg acggcaacat
cctggggcac aagctggagt acaactacaa cagccacaac gtctatatca tggccgacaa
gcagaagaac ggcatcaagg tgaacttcaa gatccgccac aacatcgagg acggcagcgt
gcagctcgcc gaccactacc agcagaacac ccccatcggc gacggccccg tgctgctgcc
cgacaaccac tacctgagca cccagtccgc cctgagcaaa gaccccaacg agaagcgcga
tcacatggtc ctgctggagt tcgtgaccgc cgccgggatc actctcggca tggacgagct
gtacaagtga gtgtaaactc gaggatccgc gccgctcgcg actcgagaga tccggattag
tccaatttgt taaagacagg atatcagtgg tccaggctct agttttgact caacaatatc
accagctgaa gcctatagag tacgagccat agataaaata aagattttta tttagtctcc
agaaaagggg gggaatgaaa gaccccacct gtaggtttgg caagctagct taagtaacgc
cattttgcag gcatggaaaa atacataact gagaatagag aagttcagat caaggtcagg
aacagatgga acagctgaat atgggccaaa caggatatct gtggtaagca gttcctgccc
cggctcaggg ccaagaacag atggaacagc tgaatatggg ccaaacagga tatctgtggt
aagcagttcc tgccccggct cagggccaag aacagatggt cccagatgc ggtccagccc
tcagcagttt ctagagaacc atcagatgtt tccagggtgc cccaaggacc tgaaatgacc
ctgtgcctta tttgaactaa ccaatcagtt cgcttctcgc ttctgttcgc gcgcttctgc
tccccgagct caataaaaga gcccacaacc cctcactcgg ggcgccagtc ctccgattga
ctgagtcgcc cgggtacccg tgtatccaat aaaccctctt gcagttgcat ccgacttgtg
gtctcgctgt tccttgggag ggtctcctct gagtgattga ctacccgtca gcggggtgct
ttcacatgca gcatgtatca aaattaattt ggttttttt cttaagtatt tacattaaat
ggccatagtc tgctcgatcg aggagctttt tgcaaaagcc taggcctcca aaaagcctc
ttcactactt ctggaatagc tcagaggccg aggcggcctc ggcctctgca taaataaaaa
aaattagtca gccatgcatg gtaatagcga tgactaatac gtagatgtac tgccaagtag
gaaagtccca taaggtcatg tactgggcat aatgccaggc gggccattta ccgtcattga
cgtcaatagg gggcgtactt ggcatatgat acacttgatg tactgccaag tgggcagttt
accgtaaata ctccacccat tgacgtcaat ggaaagtccc tattggcgtt actatgggaa
catacgtcat tattgacgtc aatgggcggg ggtcgttggg cggtcagcca ggcgggccat
ttaccgtaag ttatgtaacg gactctagcc catcgatggg aattccggtc tccctatagt
gagtcgtatt aatttcgata gccagacca ttccttgcgg cggcggtgct caacggcctc
aacctactac tgggctgctt cctaatgcag gagtcgcata agggagagcg tcgaatggtg
cactctcagt acaatctgct ctgatgccgc atagttaagc cagcccgac acccgccaac
acccgctgac gcgccctgac gggcttgtct gctcccggca tccgcttaca gacaagctgt
gaccgtctcc gggagctgca tgtgtcagag gttttaccg tcatcaccga acgcgcgag
acgaaagggc ctcgtgatac gcctatttt ataggttaat gtcatgataa taatggtttc
ttagacgtca ggtggcactt ttcgggaaa tgtgcgcgga acccctattt gtttatttt
ctaaatacat tcaaatatgt atccgctcat gagacaataa ccctgataaa tgcttcaata
atattgaaaa aggaagagta tgagtattca actttccgt gtcgccctta ttcccttttt
tgcggcattt tgccttcctg ttttttgctca cccagaaacg ctggtgaaag taaaagatgc
tgaagatcag ttgggtgcac gagtgggtta catcgaactg gatctcaaca gcggtaagat
ccttgagagt tttcgccccg aagaacgttt tccaatgatg agcactttta aagttctgct
atgtggcgcg gtattatccc gtattgacgc cgggcaagag caactcggtc gccgcataca
ctattctcag aatgacttgg ttgagtactc accagtcaca gaaaagcatc ttacggatgg
catgacagta agagaattat gcagtgctgc cataaccatg agtgataaca ctgcggccaa
cttacttctg acaacgatcg gaggaccgaa ggagctaacc gcttttttgc acaacatggg
ggatcatgta actcgccttg atcgttggga accggagctg aatgaagcca taccaaacga
```

Fig. 29 C

```
cgagcgtgac accacgatgc ctgtagcaat ggcaacaacg ttgcgcaaac tattaactgg
cgaactactt actctagctt cccggcaaca attaatagac tggatggagg cggataaagt
tgcaggacca cttctgcgct cggcccttcc ggctggctgg tttattgctg ataaatctgg
agccggtgag cgtgggtctc gcggtatcat tgcagcactg gggccagatg gtaagccctc
ccgtatcgta gttatctaca cgacggggag tcaggcaact atggatgaac gaaatagaca
gatcgctgag ataggtgcct cactgattaa gcattggtaa ctgtcagacc aagtttactc
atatatactt tagattgatt taaaacttca tttttaattt aaaaggatct aggtgaagat
ccttttgat aatctcatga ccaaaatccc ttaacgtgag ttttcgttcc actgagcgtc
agaccccgga gaaaagatca aaggatcttc ttgagatcct ttttttctgc gcgtaatctg
ctgcttgcaa acaaaaaaac caccgctacc agcggtggtt tgtttgccgg atcaagagct
accaactctt tttccgaagg taactggctt cagcagagcg cagataccaa atactgttct
tctagtgtag ccgtagttag gccaccactt caagaactct gtagcaccgc ctacatacct
cgctctgcta atcctgttac cagtggctgc tgccagtggc gataagtcgt gtcttaccgg
gttggactca agacgatagt taccggataa ggcgcagcgg tcggctgaa cggggggttc
gtgcacacag cccagcttgg agcgaacgac ctacaccgaa ctgagatacc tacagcgtga
gctatgagaa agcgccacgc ttcccgaagg gagaaaggcg gacaggtatc cggtaagcgg
cagggtcgga acaggagagc gcacgaggga gcttccaggg ggaaacgcct ggtatcttta
tagtcctgtc gggtttcgcc acctctgact tgagcgtcga ttttgtgat gctcgtcagg
gggcggagc ctatggaaaa acgccagcaa cgcggccttt ttacggttcc tggccttttg
ctggccttt gctcacatgt tctttcctgc gttatcccct gattctgtgg ataaccgtat
taccgccttt gagtgagctg ataccgctcg ccgcagccga acgaccgagc gcagcgagtc
agtgagcgag gaagcggaag agcgcccaat acgcaaaccg cctctccccg cgcgttggcc
gattcattaa tgcagcaatt agtcagcaac catagtcccg ccctaactc cgcccatccc
gccctaact ccgccagtt ccgcccattc tccgcccat gcatggtgat gcggttttgg
cagtacatca atgggcgtgg atagcggttt gactcacggg gatttccaag tctccacccc
attgacgtca atgggagttt gttttggcac caaaatcaac gggactttcc aaaatgtcgt
aacaactccg ccccattgac gcaaatgggc ggtaggcgtg tacggtggga ggtctatata
agcagagctc gtttagtgaa ccgcgccagt cctcc
```

Fig. 30A.    Amino Acid Sequence of Human CD14 (SEQ ID NO:4)

```
         (signal)
1    MERASCLLLL LLPLVHVSAT TPEPCELDDE DFRCVCNFSE PQPDWSEAFQ CVSAVEVEIH
                                                    LPS-binding motif
61   AGGLNLEPFL KRVDADADPR QYADTVKALR VRRLTVGAAQ VPAQLLVGAL RVLAYSRLKE
121  LTLEDLKITG TMPPLPLEAT GLALSSLRLR NVSWATGRSW LAELQQWLKP GLKVLSIAQA
181  HSPAFSCEQV RAFPALTSLD LSDNPGLGER GLMAALCPHK FPAIQNLALR NTGMETPTGV
241  CAALAAAGVQ PHSLDLSHNS LRATVNPSAP RCMWSSALNS LNLSFAGLEQ VPKGLPAKLR
301  VLDLSCNRLN RAPQPDELPE VDNLTLDGNP FLVPGTALPH EGSMNSGVVP ACARSTLSVG
361  VSGTLVLLQG ARGFA      375
```

Fig. 30B.    Amino Acid Sequence of Human MD-2 (SEQ ID NO:5)

```
         (signal)
1    MLPFLFFSTL FSSIFTEAQK QYWVCNSSDA SISYTYCDKM QYPISINVNP CIELKGSKGL
61   LHIFYIPRRD LKQLYFNLYI TVNTMNLPKR KEVICRGSDD DYSFCRALKG ETVNTTISFS
     <-LPS-binding motif
121  FKGIKFSKGK YKVVEAISG  SPEEMLFCLE FVILHQPNSN             160
```

Fig. 31A    Chimeric Receptor: CD14 motif -CD28-FcRγ (SEQ ID NO:6)

Leader→
ATG GAT TTT CAG GTG CAG ATT TTC AGC TTC CTG CTA ATC AGT GCC TCA
ATG
       Xbal site  CD14 coding region→
GTC ATA ATG TCT AGA CAG GTT CCT GCT CAG CTA CTG GTA GGC GCC CTG
         Q  V  P  A  Q  L  L  V  G  A  L
                  Bst EII site  CD28/FcRγ coding region→
CGT GTG CTA GCG TAC TCC CGC CTC AAG GTC ACC GTG AAA GGG AAA CAC
 R  V  L  A  Y  S  R  L  K        V  K
CTT TGT CCA AGT CCC CTA TTT CCC GGA CCT TCT AAG CCC TTT TGG GTG
CTG GTG GTG GTT GGT GGA GTC CTG GCT TGC TAT AGC TTG CTA GTA ACA
GTG GCC TTT ATT ATT TTC TGG GTG AGG AGT AAG AGG AGC AGG CTC CTG
CAC AGT GAC TAC ATG AAC ATG ACT CCC CGC CGC CCC GGG CCC ACC CGC
                               BglII site→
AAG CAT TAC CAG CCC TAT GCC CCA CCA CGC GAC TTC GCA GCC TAT AGA
TCT CAA GTG CGA AAG GCA GCT ATA ACC AGC TAT GAG AAA TCA GAT GGT
GTT TAC ACG GGC CTG AGC ACC AGG AAC CAG GAG ACT TAC GAG ACT CTG
          end of FcRγ
AAG CAT GAG AAA CCA CCA CAG TAG
         Q Fig. 31B A  Chimeric, Bicistronic Receptor:
     CD14 motif-CD28-FcRγ-IRES-GFP-Foxp3  (SEQ ID NO:7)

Leader→
ATG GAT TTT CAG GTG CAG ATT TTC AGC TTC CTG CTA ATC AGT GCC TCA
       Xbal site  CD14 coding region→
GTC ATA ATG TCT AGA CAG GTT CCT GCT CAG CTA CTG GTA GGC GCC CTG
         Q  V  P  A  Q  L  L  V  G  A  L
                  Bst EII site  CD28/FcRγ coding region→
CGT GTG CTA GCG TAC TCC CGC CTC AAG GTC ACC GTG AAA GGG AAA CAC
 R  V  L  A  Y  S  R  L  K        V  K
CTT TGT CCA AGT CCC CTA TTT CCC GGA CCT TCT AAG CCC TTT TGG GTG
CTG GTG GTG GTT GGT GGA GTC CTG GCT TGC TAT AGC TTG CTA GTA ACA
GTG GCC TTT ATT ATT TTC TGG GTG AGG AGT AAG AGG AGC AGG CTC CTG
CAC AGT GAC TAC ATG AAC ATG ACT CCC CGC CGC CCC GGG CCC ACC CGC
                               BglII site→
AAG CAT TAC CAG CCC TAT GCC CCA CCA CGC GAC TTC GCA GCC TAT AGA TCT CAA GTG CGA AAG GCA GCT ATA ACC AGC TAT GAG AAA TCA GAT GGT
GTT TAC ACG GGC CTG AGC ACC AGG AAC CAG GAG ACT TAC GAG ACT CTG
         end of FcRγ/ IRES→
AAG CAT GAG AAA CCA CCA CAG TAG CTT TAG ACT CGA GCG GGA TCA ATT
CCG CCC CCC CCC TAA CGT TAC TGG CCG AAG CCG CTT GGA ATA AGG CCG
GTG TGC GTT TGT CTA TAT GTT ATT TTC CAC CAT ATT GCC GTC TTT TGG
CAA TGT GAG GGC CCG GAA ACC TGG CCC TGT CTT CTT GAC GAG CAT TCC
TAG GGG TCT TTC CCC TCT CGC CAA AGG AAT GCA AGG TCT GTT GAA TGT
CGT GAA GGA AGC AGT TCC TCT GGA AGC TTC TTG AAG ACA AAC AAC GTC
TGT AGC GAC CCT TTG CAG GCA GCG GAA CCC CCC ACC TGG CGA CAG GTG
CCT CTG CGG CCA AAA GCC ACG TGT ATA AGA TAC ACC TGC AAA GGC GGC
ACA ACC CCA GTG CCA CGT TGT GAG TTG GAT AGT TGT GGA AAG AGT CAA
ATG GCT CTC CTC AAG CGT ATT CAA CAA GGG GCT GAA GGA TGC CCA GAA

Fig. 31B B

```
GGT ACC CCA TTG TAT GGG ATC TGA TCT GGG GCC TCG GTG CAC ATG CTT
TAC ATG TGT TTA GTC GAG GTT AAA AAA ACG TCT AGG CCC CCC GAA CCA
                                                    Pae I site
CGG GGA CGT GGT TTT CCT TTG AAA AAC ACG ATA ATA GCA TGC AGC GCT
ACC GGT CGC CAC C
```
Starts GFP/Foxp3 region →
```
ATG GTG AGC AAG GGC GAG GAG CTG TTC ACC GGG GTG GTG CCC ATC CTG
GTC GAG CTG GAC GGC GAC GTA AAC GGC CAC AAG TTC AGC GTG TCC GGC
GAG GGC GAG GGC GAT GCC ACC TAC GGC AAG CTG ACC CTG AAG TTC ATC
TGC ACC ACC GGC AAG CTG CCC GTG CCC TGG CCC ACC CTC GTG ACC ACC
CTG ACC TAC GGC GTG CAG TGC TTC AGC CGC TAC CCC GAC CAC ATG AAG
CAG CAC GAC TTC TTC AAG TCC GCC ATG CCC GAA GGC TAC GTC CAG GAG
CGC ACC ATC TTC TTC AAG GAC GAC GGC AAC TAC AAG ACC CGC GCC GAG
GTG AAG TTC GAG GGC GAC ACC CTG GTG AAC CGC ATC GAG CTG AAG GGC
ATC GAC TTC AAG GAG GAC GGC AAC ATC CTG GGG CAC AAG CTG GAG TAC
AAC TAC AAC AGC CAC AAC GTC TAT ATC ATG GCC GAC AAG CAG AAG AAC
GGC ATC AAG GTG AAC TTC AAG ATC CGC CAC AAC ATC GAG GAC GGC AGC
GTG CAG CTC GCC GAC CAC TAC CAG CAG AAC ACC CCC ATC GGC GAC GGC
CCC GTG CTG CTG CCC GAC AAC CAC TAC CTG AGC ACC CAG TCC GCC CTG
AGC AAA GAC CCC AAC GAG AAG CGC GAT CAC ATG GTC CTG CTG GAG TTC
GTG ACC GCC GCC GGG ATC ACT CTC GGC ATG GAC GAG CTG TAC AAG TCC
GGC CGG ACT CAG ATC TCG AGC TCA AGC TTC GAA TTC ATG CCC AAC CCC
AGG CCT GGC AAG CCC TCG GCC CCT TCC TTG GCC CTT GGC CCA TCC CCA
GGA GCC TCG CCC AGC TGG AGG GCT GCA CCC AAA GCC TCA GAC CTG CTG
GGG GCC CGG GGC CCA GGG GGA ACC TTC CAG GGC CGA GAT CTT CGA GGC
GGG GCC CAT GCC TCC TCT TCT TCC TTG AAC CCC ATG CCA CCA TCG CAG
CTG CAG CTG CCC ACA CTG CCC CTA GTC ATG GTG GCA CCC TCC GGG GCA
CGG CTG GGC CCC TTG CCC CAC TTA CAG GCA CTC CTC CAG GAC AGG CCA
CAT TTC ATG CAC CAG CTC TCA ACG GTG GAT GCC CAC GCC CGG ACC CCT
GTG CTG CAG GTG CAC CCC CTG GAG AGC CCA GCC ATG ATC AGC CTC ACA
CCA CCC ACC ACC GCC ACT GGG GTC TTC TCC CTC AAG GCC CGG CCT GGC
CTC CCA CCT GGG ATC AAC GTG GCC AGC CTG GAA TGG GTG TCC AGG GAG
CCG GCA CTG CTC TGC ACC TTC CCA AAT CCC AGT GCA CCC AGG AAG GAC
AGC ACC CTT TCG GCT GTG CCC CAG AGC TCC TAC CCA CTG CTG GCA AAT
GGT GTC TGC AAG TGG CCC GGA TGT GAG AAG GTC TTC GAA GAG CCA GAG
GAC TTC CTC AAG CAC TGC CAG GCG GAC CAT CTT CTG GAT GAG AAG GGC
AGG GCA CAA TGT CTC CTC CAG AGA GAG ATG GTA CAG TCT CTG GAG CAG
CAG CTG GTG CTG GAG AAG GAG AAG CTG AGT GCC ATG CAG GCC CAC CTG
GCT GGG AAA ATG GCA CTG ACC AAG GCT TCA TCT GTG GCA TCA TCC GAC
AAG GGC TCC TGC TGC ATC GTA GCT GCT GGC AGC CAA GGC CCT GTC GTC
CCA GCC TGG TCT GGC CCC CGG GAG GCC CCT GAC AGC CTG TTT GCT GTC
CGG AGG CAC CTG TGG GGT AGC ATG GAA AGC AGC ACA TTC CCA GAG TTC
CTC CAC AAC ATG GAC TAC TTC AAG TTC CAC AAC ATG CGA CCC CTT TTC
ACC TAC GCC ACG CTC ATC CGC TGG GCC ATC CTG GAG GCT CCA GAG AAG
CAG CGG ACA CTC AAT GAG ATC TAC CAC TGG TTC ACA CGC ATG TTT GCC
TTC TTC AGA AAC CAT CCT GCC ACC TGG AAG AAC GCC ATC CGC CAC AAC
CTG AGT CTG CAC AAG TGC TTT GTG CGG GTG GAG AGC GAG AAG GGG GCT
GTG TGG ACC GTG GAT GAG CTG GAG TTC CGC AAG AAA CGG AGC CAG AGG
```
← end Foxp3  BamHI site
```
CCC AGC AGG TGT TCC AAC CCT ACA CCT GGC CCC TGA GGATCCgcgc
```

Fig. 31B C

*Additional vector sequence →*
```
cgctcgcgct cgagagatcc ggattagtcc aatttgttaa agacaggata tcagtggtcc
aggctctagt tttgactcaa caatatcacc agctgaagcc tatagagtac gagccataga
taaaataaaa gattttattt agtctccaga aaaagggggg aatgaaagac cccacctgta
ggtttggcaa gctagcttaa gtaacgccat tttgcaggca tggaaaaata cataactgag
aatagagaag ttcagatcaa ggtcaggaac agatggaaca gctgaatatg ggccaaacag
gatatctgtg gtaagcagtt cctgcccgg ctcagggcca agaacagatg gaacagctga
atatgggcca aacaggatat ctgtggtaag cagttcctgc cccggctcag ggccaagaac
agatggtccc cagatgcggt ccagccctca gcagtttcta gagaaccatc agatgtttcc
agggtgcccc aaggacctga aatgaccctg tgccttattt gaactaacca atcagttcgc
ttctcgcttc tgttcgcgcg cttctgctcc ccgagctcaa taaaagagcc cacaacccct
cactcggggc gccagtcctc cgattgactg agtcgcccgg gtaccgtgt atccaataaa
ccctcttgca gttgcatccg acttgtggtc tcgctgttcc ttgggagggt ctcctctgag
tgattgacta cccgtcagcg ggggtctttc acatgcagca tgtatcaaaa ttaatttggt
ttttttctt aagtatttac attaa
```

Fig. 32A    Chimeric Receptor:  <u>MD2 motif - CD28-FcRγ</u> (SEQ ID NO:8)

Leader→
ATG GAT TTT CAG GTG CAG ATT TTC AGC TTC CTG CTA ATC AGT GCC TCA
                <u>Xbal site</u>   MD2 coding region→
GTC ATA ATG <u>TCT AGA</u> TTC TCC TTC AAG GGA ATA AAA TTT TCT AAG GGA
                       F   S   F   K   G   I   K   F   S   K   G end of MD2  <u>Bst Ell site</u>   CD28/FcRγ coding region→
AAA TAC AAA <u>GGT CAC CTC</u> GTG AAA GGG AAA CAC CTT TGT CCA AGT CCC
 K   Y   K
CTA TTT CCC GGA CCT TCT AAG CCC TTT TGG GTG CTG GTG GTG GTT GGT
GGA GTC CTG GCT TGC TAT AGC TTG CTA GTA ACA GTG GCC TTT ATT ATT
TTC TGG GTG AGG AGT AAG AGG AGC AGG CTC CTG CAC AGT GAC TAC ATG
AAC ATG ACT CCC CGC CGC CCC GGG CCC ACC CGC AAG CAT TAC CAG CCC
                                                <u>Bgl II site</u>
TAT GCC CCA CCA CGC GAC TTC GCA GCC TAT <u>AGA TCT</u> CAA GTG CGA AAG
GCA GCT ATA ACC AGC TAT GAG AAA TCA GAT GGT GTT TAC ACG GGC CTG
AGC ACC AGG AAC CAG GAG ACT TAC GAG ACT CTG AAG CAT GAG AAA CCA
CCA CAG TAG
    end of FcRγ

Fig. 32B A     Chimeric, Bicistronic Receptor:
        <u>MD2 motif-CD28-FcRγ-IRES-GFP-FOXP3</u>     (SEQ ID NO:9)

Leader→
ATG GAT TTT CAG GTG CAG ATT TTC AGC TTC CTG CTA ATC AGT GCC TCA
                <u>Xbal site</u>   MD2 coding region→
GTC ATA ATG <u>TCT AGA</u> TTC TCC TTC AAG GGA ATA AAA TTT TCT AAG GGA
                       F   S   F   K   G   I   K   F   S   K   G end of MD2  <u>Bst Ell site</u>   CD28/FcRγ coding region→
AAA TAC AAA <u>GGT CAC CTC</u> GTG AAA GGG AAA CAC CTT TGT CCA AGT CCC
 K   Y   K
CTA TTT CCC GGA CCT TCT AAG CCC TTT TGG GTG CTG GTG GTG GTT GGT
GGA GTC CTG GCT TGC TAT AGC TTG CTA GTA ACA GTG GCC TTT ATT ATT
TTC TGG GTG AGG AGT AAG AGG AGC AGG CTC CTG CAC AGT GAC TAC ATG
AAC ATG ACT CCC CGC CGC CCC GGG CCC ACC CGC AAG CAT TAC CAG CCC
                                                <u>Bgl II site</u>
TAT GCC CCA CCA CGC GAC TTC GCA GCC TAT <u>AGA TCT</u> CAA GTG CGA AAG
GCA GCT ATA ACC AGC TAT GAG AAA TCA GAT GGT GTT TAC ACG GGC CTG
AGC ACC AGG AAC CAG GAG ACT TAC GAG ACT CTG AAG CAT GAG AAA CCA
    end of FcRγ/ IRES→
CCA CAG <u>TAG</u> CTT TAG ACT CGA GCG GGA TCA ATT CCG CCC CCC CCC TAA
CGT TAC TGG CCG AAG CCG CTT GGA ATA AGG CCG GTG TGC GTT TGT CTA
TAT GTT ATT TTC CAC CAT ATT GCC GTC TTT TGG CAA TGT GAG GGC CCG
GAA ACC TGG CCC TGT CTT CTT GAC GAG CAT TCC TAG GGG TCT TTC CCC
TCT CGC CAA AGG AAT GCA AGG TCT GTT GAA TGT CGT GAA GGA AGC AGT
TCC TCT GGA AGC TTC TTG AAG ACA AAC AAC GTC TGT AGC GAC CCT TTG
CAG GCA GCG GAA CCC CCC ACC TGG CGA CAG GTG CCT CTG CGG CCA AAA
GCC ACG TGT ATA AGA TAC ACC TGC AAA GGC GGC ACA ACC CCA GTG CCA
CGT TGT GAG TTG GAT AGT TGT GGA AAG AGT CAA ATG GCT CTC CTC AAG
CGT ATT CAA CAA GGG GCT GAA GGA TGC CCA GAA GGT ACC CCA TTG TAT
GGG ATC TGA TCT GGG GCC TCG GTG CAC ATG CTT TAC ATG TGT TTA GTC
GAG GTT AAA AAA ACG TCT AGG CCC CCC GAA CCA CGG GGA CGT GGT TTT

Fig. 32B B

*Pae I site*

CCT TTG AAA AAC ACG ATA ATA GCA TGC AGC GCT ACC GGT CGC CAC C
*Starts GFP/Foxp3 region*
ATG GTG AGC AAG GGC GAG GAG CTG TTC ACC GGG GTG GTG CCC ATC CTG
GTC GAG CTG GAC GGC GAC GTA AAC GGC CAC AAG TTC AGC GTG TCC GGC
GAG GGC GAG GGC GAT GCC ACC TAC GGC AAG CTG ACC CTG AAG TTC ATC
TGC ACC ACC GGC AAG CTG CCC GTG CCC TGG CCC ACC CTC GTG ACC ACC
CTG ACC TAC GGC GTG CAG TGC TTC AGC CGC TAC CCC GAC CAC ATG AAG
CAG CAC GAC TTC TTC AAG TCC GCC ATG CCC GAA GGC TAC GTC CAG GAG
CGC ACC ATC TTC TTC AAG GAC GAC GGC AAC TAC AAG ACC CGC GCC GAG
GTG AAG TTC GAG GGC GAC ACC CTG GTG AAC CGC ATC GAG CTG AAG GGC
ATC GAC TTC AAG GAG GAC GGC AAC ATC CTG GGG CAC AAG CTG GAG TAC
AAC TAC AAC AGC CAC AAC GTC TAT ATC ATG GCC GAC AAG CAG AAG AAC
GGC ATC AAG GTG AAC TTC AAG ATC CGC CAC AAC ATC GAG GAC GGC AGC
GTG CAG CTC GCC GAC CAC TAC CAG CAG AAC ACC CCC ATC GGC GAC GGC
CCC GTG CTG CTG CCC GAC AAC CAC TAC CTG AGC ACC CAG TCC GCC CTG
AGC AAA GAC CCC AAC GAG AAG CGC GAT CAC ATG GTC CTG CTG GAG TTC
GTG ACC GCC GCC GGG ATC ACT CTC GGC ATG GAC GAG CTG TAC AAG TCC
GGC CGG ACT CAG ATC TCG AGC TCA AGC TTC GAA TTC ATG CCC AAC CCC
AGG CCT GGC AAG CCC TCG GCC CCT TCC TTG GCC CTT GGC CCA TCC CCA
GGA GCC TCG CCC AGC TGG AGG GCT GCA CCC AAA GCC TCA GAC CTG CTG
GGG GCC CGG GGC CCA GGG GGA ACC TTC CAG GGC CGA GAT CTT CGA GGC
GGG GCC CAT GCC TCC TCT TCT TCC TTG AAC CCC ATG CCA CCA TCG CAG
CTG CAG CTG CCC ACA CTG CCC CTA GTC ATG GTG GCA CCC TCC GGG GCA
CGG CTG GGC CCC TTG CCC CAC TTA CAG GCA CTC CTC CAG GAC AGG CCA
CAT TTC ATG CAC CAG CTC TCA ACG GTG GAT GCC CAC GCC CGG ACC CCT
GTG CTG CAG GTG CAC CCC CTG GAG AGC CCA GCC ATG ATC AGC CTC ACA
CCA CCC ACC ACC GCC ACT GGG GTC TTC TCC CTC AAG GCC CGG CCT GGC
CTC CCA CCT GGG ATC AAC GTG GCC AGC CTG GAA TGG GTG TCC AGG GAG
CCG GCA CTG CTC TGC ACC TTC CCA AAT CCC AGT GCA CCC AGG AAG GAC
AGC ACC TTT CGG GCT GTG CCC AGC TCC TAC CCA CTG CTG GCA AAT
GGT GTC TGC AAG TGG CCC GGA TGT GAG AAG GTC TTC GAA GAG CCA GAG
GAC TTC TCC AAG CAC TGC CAG GCG GAC CAT CTT CTG GAT GAG AAG GGC
AGG GCA CAA TGT CTC CTC CAG AGA GAG ATG GTA CAG TCT CTG GAG CAG
CAG CTG GTG CTG GAG AAG GAG AAG CTG AGT GCC ATG CAG GCC CAC CTG
GCT GGG AAA ATG GCA CTG ACC AAG GCT TCA TCT GTG GCA TCA TCC GAC
AAG GGC TCC TGC TGC ATC GTA GCT GCT GGC AGC CAA GGC CCT GTC GTC
CCA GCC TGG TCT GGC CCC CGG GAG GCC CCT GAC AGC CTG TTT GCT GTC
CGG AGG CAC CTG TGG GGT AGC CAT GGA AAC AGC ACA TTC CCA GAG TTC
CTC CAC AAC ATG GAC TAC TTC AAG TTC CAC AAC ATG CGA CCC CCT TTC
ACC TAC GCC ACG CTC ATC CGC TGG GCC ATC CTG GAG GCT CCA GAG AAG
CAG CGG ACA CTC AAT GAG ATC TAC CAC TGG TTC ACA CGC ATG TTT GCC
TTC TTC AGA AAC CAT CCT GCC ACC TGG AAG AAC GCC ATC CGC CAC AAC
CTG AGT CTG CAC AAG TGC TTT GTG CGG GTG GAG AGC GAG AAG GGG CT
GTG TGG ACC GTG GAT GAG CTG GAG TTC CGC AAG AAA CGG AGC CAG AGG
← *end Foxp3 BamHI site*
CCC AGC AGG TGT TCC AAC CCT ACA CCT GGC CCC TGA GGATCC

Fig. 33A Chimeric Receptor: MD2 motif-CD14 motif-CD28-FcRγ (SEQ ID NO:10)

```
Leader→
ATG GAT TTT CAG GTG CAG ATT TTC AGC TTC CTG CTA ATC AGT GCC TCA
        Xbal site   MD2 coding region→
GTC ATA ATG TCT AGA TTC TCC TTC AAG GGA ATA AAA TTT TCT AAG GGA
                     F   S   F   K   G   I   K   F   S   K   G
    end of MD2    ???-->
AAA TAC AAA GGG TCG ACT TCC GGT AGC GGC AAA TCC TCT GAA GGC AAA
 K   Y   K   G   S   T   S   G   S   G   K   S   S   E   G   K
        CD14 coding region→
GGT CAG GTT CCT GCT CAG CTA CTG GTA GGC GCC CTG CGT GTG CTA GCG
 G   Q   V   P   A   Q   L   L   V   G   A   L   R   V   L   A
              end of CD14  Bst EII site   CD28/FcRγ coding region→
TAC TCC CGC CTC AAG GTC ACC GTG AAA GGG AAA CAC CTT TGT CCA AGT
 Y   S   R   L   K
CCC CTA TTT CCC GGA CCT TCT AAG CCC TTT TGG GTG CTG GTG GTG GTT
GGT GGA GTC CTG GCT TGC TAT AGC TTG CTA GTA ACA GTG GCC TTT ATT
ATT TTC TGG GTG AGG AGT AAG AGG AGC AGG CTC CTG CAC AGT GAC TAC
ATG AAC ATG ACT CCC CGC CGC CCC GGG CCC ACC CGC AAG CAT TAC CAG
                                                    Bgl II site
CCC TAT GCC CCA CCA CGC GAC TTC GCA GCC TAT AGA TCT CAA GTC GA
AAG GCA GCT ATA ACC AGC TAT GAG AAA TCA GAT GGT GTT TAC ACG GGC
CTG AGC ACC AGG AAC CAG GAG ACT TAC GAG ACT CTG AAG CAT GAG AAA
        end of FcRγ
        TAG                                         CCA CCA CAG TAG
```

Fig. 33B A Chimeric, Bicistronic Receptor:
MD2 motif-CD14 motif -CD28-FcRγ-IRES-GFP-Foxp3 (SEQ ID NO:11)

```
Leader→
ATG GAT TTT CAG GTG CAG ATT TTC AGC TTC CTG CTA ATC AGT GCC TCA
        Xbal site   MD2 coding region→
GTC ATA ATG TCT AGA TTC TCC TTC AAG GGA ATA AAA TTT TCT AAG GGA
                     F   S   F   K   G   I   K   F   S   K   G
    end of MD2    Flexible Linker→
AAA TAC AAA GGG TCG ACT TCC GGT AGC GGC AAA TCC TCT GAA GGC AAA
 K   Y   K   G   S   T   S   G   S   G   K   S   S   E   G   K
        CD14 coding region→
GGT CAG GTT CCT GCT CAG CTA CTG GTA GGC GCC CTG CGT GTG CTA GCG
 G   Q   V   P   A   Q   L   L   V   G   A   L   R   V   L   A end of CD14  Bst EII site  CD28/FcRγ coding region→
TAC TCC CGC CTC AAG GTC ACC GTG AAA GGG AAA CAC CTT TGT CCA AGT
 Y   S   R   L   K
CCC CTA TTT CCC GGA CCT TCT AAG CCC TTT TGG GTG CTG GTG GTG GTT
GGT GGA GTC CTG GCT TGC TAT AGC TTG CTA GTA ACA GTG GCC TTT ATT
ATT TTC TGG GTG AGG AGT AAG AGG AGC AGG CTC CTG CAC AGT GAC TAC
ATG AAC ATG ACT CCC CGC CGC CCC GGG CCC ACC CGC AAG CAT TAC CAG
                                                    Bgl II site
CCC TAT GCC CCA CCA CGC GAC TTC GCA GCC TAT AGA TCT CAA GTC GA
AAG GCA GCT ATA ACC AGC TAT GAG AAA TCA GAT GGT GTT TAC ACG GGC
CTG AGC ACC AGG AAC CAG GAG ACT TAC GAG ACT CTG AAG CAT GAG AAA
```

Fig. 33B B

*end of FcRγ/ IRES→*

```
CCA CCA CAG TAG CTT TAG ACT CGA GCG GGA TCA ATT CCG CCC CCC CCC
TAA CGT TAC TGG CCG AAG CCG CTT GGA ATA AGG CCG GTG TGC GTT TGT
CTA TAT GTT ATT TTC CAC CAT ATT GCC GTC TTT TGG CAA TGT GAG GGC
CCG GAA ACC TGG CCC TGT CTT CTT GAC GAG CAT TCC TAG GGT CTT TTC
CCC TCT CGC CAA AGG AAT GCA AGG TCT GTT GAA TGT CGT GAA GGA AGC
AGT TCC TCT GGA AGC TTC TTG AAG ACA AAC AAC GTC TGT AGC GAC CCT
TTG CAG GCA GCG GAA CCC CCC ACC TGG CGA CAG GTG CCT CTG CGG CCA
AAA GCC ACG TGT ATA AGA TAC ACC TGC AAA GGC GGC ACA ACC CCA GTG
CCA CGT TGT GAG TTG GAT AGT TGT GGA AAG AGT CAA ATG GCT CTC CTC
AAG CGT ATT CAA CAA GGG GCT GAA GGA TGC CCA GAA GGT ACC CCA TTG
TAT GGG ATC TGA TCT GGG GCC TCG GTG CAC ATG CTT TAC ATG TGT TTA
GTC GAG GTT AAA AAA ACG TCT AGG CCC CCC GAA CCA CGG GGA CGT GGT
```
                                                                               *Pae I site*

```
TTT CCT TTG AAA AAC ACG ATA ATA GCA TGC AGC GCT ACC GGT CGC CAC C
```
*Starts GFP/Foxp3 region*
```
ATG GTG AGC AAG GGC GAG GAG CTG TTC ACC GGG GTG GTG CCC ATC CTG
GTC GAG CTG GAC GGC GAC GTA AAC GGC CAC AAG TTC AGC GTG TCC GGC
GAG GGC GAG GGC GAT GCC ACC TAC GGC AAG CTG ACC CTG AAG TTC ATC
TGC ACC ACC GGC AAG CTG CCC GTG CCC TGG CCC ACC CTC GTG ACC ACC
CTG ACC TAC GGC GTG CAG TGC TTC AGC CGC TAC CCC GAC CAC ATG AAG
CAG CAC GAC TTC TTC AAG TCC GCC ATG CCC GAA GGC TAC GTC CAG GAG
CGC ACC ATC TTC TTC AAG GAC GAC GGC AAC TAC AAG ACC CGC GCC GAG
GTG AAG TTC GAG GGC GAC ACC CTG GTG AAC CGC ATC GAG CTG AAG GGC
ATC GAC TTC AAG GAG GAC GGC AAC ATC CTG GGG CAC AAG CTG GAG TAC
AAC TAC AAC AGC CAC AAC GTC TAT ATC ATG GCC GAC AAG CAG AAG AAC
GGC ATC AAG GTG AAC TTC AAG ATC CGC CAC AAC ATC GAG GAC GGC AGC
GTG CAG CTC GCC GAC CAC TAC CAG CAG AAC ACC CCC ATC GGC GAC GGC
CCC GTG CTG CTG CCC GAC AAC CAC TAC CTG AGC ACC CAG TCC GCC CTG
AGC AAA GAC CCC AAC GAG AAG CGC GAT CAC ATG GTC CTG CTG GAG TTC
GTG ACC GCC GCC GGG ATC ACT CTC GGC ATG GAC GAG CTG TAC AAG TCC
GGC CGG ACT CAG ATC TCG AGC TCA AGC TTC GAA TTC ATG CCC AAC CCC
AGG CCT GGC AAG CCC TCG GCC CCT TCC TTG GCC CTT GGC CCA TCC CCA
GGA GCC TCG CCC AGC TGG AGG GCT GCA CCC AAA GCC TCA GAC CTG CTG
GGG GCC CGG GGC CCA GGG GGA ACC TTC CAG GGC CGA GAT CTT CGA GGC
GGG GCC CAT GCC TCC TCT TCT TCC TTG AAC CCC ATG CCA CCA TCG CAG
CTG CAG CTG CCC ACA CTG CCC CTA GTC ATG GTG GCA CCC TCC GGG GCA
CGG CTG GGC CCC TTG CCC CAC TTA CAG GCA CTC CTC CAG GAC AGG CCA
CAT TTC ATG CAC CAG CTC TCA ACG GTG GAT GCC CAC GCC CGG ACC CCT
GTG CTG CAG GTG CAC CCC CTG GAG AGC CCA GCC ATG ATC AGC CTC ACA
CCA CCC ACC ACC GCC ACT GGG GTC TTC TCC CTC AAG GCC CGG CCT GGC
CTC CCA CCT GGG ATC AAC GTG GCC AGC CTG GAA TGG GTG TCC AGG GAG
CCG GCA CTG CTC TGC ACC TTC CCA AAT CCC AGT GCA CCC AGG AAG GAC
AGC ACC TTG TCG GCT GTG CCC CAG AGC TCC TAC CCA CTG CTG GCA AAT
GGT GTC TGC AAG TGG CCC GGA TGT GAG AAG GTC TTC GAA GAG CCA GAG
GAC TTC CTC AAG CAC TGC CAG GCG GAC CAT CTT CTG GAT GAG AAG GGC
AGG GCA CAA TGT CTC CTC CAG AGA GAG ATG GTA CAG TCT CTG GAG CAG
CAG CTG GTG CTG GAG AAG GAG AAG CTG AGT GCC ATG CAG GCC CAC CTG
GCT GGG AAA ATG GCA CTG ACC AAG GCT TCA TCT GTG GCA TCA TCC GAC
AAG GGC TCC TGC TGC ATC GTA GCT GCT GGC AGC CAA GGC CCT GTC GTC
CCA GCC TGG TCT GGC CCC CGG GAG GCC CCT GAC AGC CTG TTT GCT GTC
CGG AGG CAC CTG TGG GGT AGC ATG GAA AGC ACA TTC CCA GAG TTC
CTC CAC AAC ATG GAC TAC TTC AAG TTC CAC AAC ATG CGA CCC CCT TTC
ACC TAC GCC ACG CTC ATC CGC TGG GCC ATC CTG GAG GCT CCA GAG AAG
CAG CGG ACA CTC AAT GAG ATC TAC CAC TGG TTC ACA CGC ATG TTT GCC
TTC TTC AGA AAC CAT CCT GCC ACC TGG AAG AAC GCC ATC CGC CAC AAC
CTG AGT CTG CAC AAG TGC TTT GTG CGG GTG GAG AGC GAG AAG GGG GCT
GTG TGG ACC GTG GAT GAG CTG GAG TTC CGC AAG AAA CGG AGC CAG AGG
```
                                                              *← end Foxp3*   *BamHI site*
```
CCC AGC AGG TGT TCC AAC CCT ACA CCT GGC CCC TGA GGATCC
```

FIG. 34

Chimeric Receptor: <u>MD2-CD28-FcRγ</u>  (SEQ ID NO:13)

*Leader→*

```
ATG GAT TTT CAG GTG CAG ATT TTC AGC TTC CTG CTA ATC AGT GCC TCA
                Xbal site    MD2 coding region→
GTC ATA ATG TCT AGA ATG TTA CCA TTT CTG TTT TTT TCC ACC CTG TTT
                         M   L   P   F   L   F   F   S   T   L   F
TCT TCC ATA TTT ACT GAA GCT CAG AAG CAG TAT TGG GTC TGC AAC TCA
 S   S   I   F   T   E   A   Q   K   Q   Y   W   V   C   N   S
TCC GAT GCA AGT ATT TCA TAC ACC TAC TGT GAT AAA ATG CAA TAC CCA
 S   D   A   S   I   S   Y   T   Y   C   D   K   M   Q   Y   P
ATT TCA ATT AAT GTT AAC CCC TGT ATA GAA TTG AAA GGA TCC AAA GGA
 I   S   I   N   V   N   P   C   I   E   L   K   G   S   K   G
TTA TTG CAC ATT TTC TAC ATT CCA AGG AGA GAT TTA AAG CAA TTA TAT
 L   L   H   I   F   Y   I   P   R   R   D   L   K   Q   L   Y
TTC AAT CTC TAT ATA ACT GTC AAC ACC ATG AAT CTT CCA AAG CGC AAA
 F   N   L   Y   I   T   V   N   T   M   N   L   P   K   R   K
GAA GTT ATT TGC CGA GGA TCT GAT GAC GAT TAC TCT TTT TGC AGA GCT
 E   V   I   C   R   G   S   D   D   D   Y   S   F   C   R   A
CTG AAG GGA GAG ACT GTG AAT ACA ACA ATA TCA TTC TCC TTC AAG GGA
 L   K   G   E   T   V   N   T   T   I   S   F   S   F   K   G
ATA AAA TTT TCT AAG GGA AAA TAC AAA TGT GTT GTT GAA GCT ATT TCT
 I   K   F   S   K   G   K   Y   K   V   V   E   A   I   S   G
GGG AGC CCA GAA GAA ATG CTC TTT TGC TTG GAG TTT GTC ATC CTA CAC
 S   P   E   E   M   L   F   C   L   E   F   V   I   L   H   Q
                        Bst Ell site    CD28/FcRγ coding region→
CAA CCT AAT TCA AAT GGT CAC CTC GTG AAA GGG AAA CAC CTT TGT CCA
 P   N   S   N AGT CCC CTA TTT CCC GGA CCT TCT AAG CCC TTT TGG GTG CTG GTG GTG
GTT GGT GGA GTC CTG GCT TGC TAT AGC TTG CTA GTA ACA GTG GCC TTT
ATT ATT TTC TGG GTG AGG AGT AAG AGG AGC AGG CTC CTG CAC AGT GAC
TAC ATG AAC ATG ACT CCC CGC CGC CCC GGG CCC ACC CGC AAG CAT TAC
                                                      Bgl II site
CAG CCC TAT GCC CCA CCA CGC GAC TTC GCA GCC TAT AGA TCT CAA GTG
CGA AAG GCA GCT ATA ACC AGC TAT GAG AAA TCA GAT GGT GTT TAC ACG
GGC CTG AGC ACC AGG AAC CAG GAG ACT TAC GAG ACT CTG AAG CAT GAG
              ← end FcRγ
AAA CCA CCA CAG TAG
```

Fig. 35 A

Chimeric Bicistronic Receptor: MD2-CD28-FcRγ-IRES-GFP-Foxp3 (SEQ ID NO:14)

*Leader→*
ATG GAT TTT CAG GTG CAG ATT TTC AGC TTC CTG CTA ATC AGT GCC TCA
            *Xbal site   MD2 coding region→*
GTC ATA ATG TCT AGA ATG TTA CCA TTT CTG TTT TTT TCC ACC CTG TTT
                  M   L   P   F   L   F   F   S   T   L   F
TCT TCC ATA TTT ACT GAA GCT CAG AAG CAG TAT GGT GTC TGC AAC TCA
 S   S   I   F   T   E   A   Q   K   Q   Y   W   V   C   N   S
TCC GAT GCA AGT ATT TCA TAC ACC TAC TGT GAT AAA ATG CAA TAC CCA
 S   D   A   S   I   S   Y   T   Y   C   D   K   M   Q   Y   P
ATT TCA ATT AAT GTT AAC CCC TGT ATA GAA TTG AAA GGA TCC AAA GGA
 I   S   I   N   V   N   P   C   I   E   L   K   G   S   K   G
TTA TTG CAC ATT TTC TAC ATT CCA AGG AGA GAT TTA AAG CAA TTA TAT
 L   L   H   I   F   Y   I   P   R   R   D   L   K   Q   L   Y
TTC AAT CTC TAT ATA ACT GTC AAC ACC ATG AAT CTT CCA AAG CGC AAA
 F   N   L   Y   I   T   V   N   T   M   N   L   P   K   R   K
GAA GTT ATT TGC CGA GGA TCT GAT GAC GAT TAC TCT TTT TGC AGA GCT
 E   V   I   C   R   G   S   D   D   D   Y   S   F   C   R   A
CTG AAG GGA GAG ACT GTG AAT ACA ACA ATA TCA TTC TCC TTC AAG GGA
 L   K   G   E   T   V   N   T   T   I   S   F   S   F   K   G
ATA AAA TTT TCT AAG GGA AAA TAC AAA TGT GTT GTT GAA GCT ATT TCT
 I   K   F   S   K   G   K   Y   K   V   V   E   A   I   S   G
GGG AGC CCA GAA GAA ATG CTC TTT TGC TTG GAG TTT GTC ATC CTA CAC
 S   P   E   E   M   L   F   C   L   E   F   V   I   L   H   Q
                     *BstII site   CD28/FcRγ coding region→*
CAA CCT AAT TCA AAT GGT CAC CTC GTG AAA GGG AAA CAC CTT TGT CCA
 P   N   S   N
AGT CCC CTA TTT CCC GGA CCT TCT AAG CCC TTT TGG GTG CTG GTG GTG
GTT GGT GGA GTC CTG GCT TGC TAT AGC TTG CTA GTA ACA GTG GCC TTT
ATT ATT TTC TGG GTG AGG AGT AAG AGG AGC AGG CTC CTG CAC AGT GAC
TAC ATG AAC ATG ACT CCC CGC CGC CCC GGG CCC ACC CGC AAG CAT TAC
                                                                              *BgI II site*
CAG CCC TAT GCC CCA CCA CGC GAC TTC GCA GCC TAT AGA TCT CAA GTG
CGA AAG GCA GCT ATA ACC AGC TAT GAG AAA TCA GAT GGT GTT TAC ACG
GGC CTG AGC ACC AGG AAC CAG GAG ACT TAC GAG ACT CTG AAG CAT GAG
          *← end FcRγ / IRES→*
AAA CCA CCA CAG TAG CTT TAG ACT CGA GCG GGA TCA ATT CCG CCC CCC
CCC TAA CGT TAC TGG CCG AAG CCG CTT GGA ATA AGG CCG GTG TGC GTT
TGT CTA TAT GTT ATT TTC CAC CAT ATT GCC GTC TTT TGG CAA TGT GAG
GGC CCG GAA ACC TGG CCC TGT CTT CTT GAC GAG CAT TCC TAG GGG TCT
TTC CCC TCT CGC CAA AGG AAT GCA AGG TCT GTT GAA TGT CGT GAA GGA
AGC AGT TCC TCT GGA AGC TTC TTG AAG ACA AAC AAC GTC TGT AGC GAC
CCT TTG CAG GCA GCG GAA CCC CCC ACC TGG CGA CAG GTG CCT CTG CGG
CCA AAA GCC ACG TGT ATA AGA TAC ACC TGC AAA GGC GGC ACA ACC CCA
GTG CCA CGT TGT GAG TTG GAT AGT TGT GGA AAG AGT CAA ATG GCT CTC
CTC AAG CGT ATT CAA CAA GGG GCT GAA GGA TGC CCA GAA GGT ACC CCA
TTG TAT GGG ATC TGA TCT GGG GCC TCG GTG CAC ATG CTT TAC ATG TGT
TTA GTC GAG GTT AAA AAA ACG TCT AGG CCC CCC GAA CCA CGG GGA CGT
                                                        *Pae I site*
GGT TTT CCT TTG AAA AAC ACG ATA ATA GCA TGC AGC GCT ACC GGT CGC
    *Starts GFP/Foxp3 region*
CAC C  ATG GTG AGC AAG GGC GAG GAG CTG TTC ACC GGG GTG GTG CCC
ATC CTG GTC GAG CTG GAC GGC GAC GTA AAC GGC CAC AAG TTC AGC GTG
TCC GGC GAG GGC GAG GGC GAT GCC ACC TAC GGC AAG CTG ACC CTG AAG
TTC ATC TGC ACC ACC GGC AAG CTG CCC GTG CCC TGG CCC ACC CTC GTG

Fig. 35 B

```
ACC ACC CTG ACC TAC GGC GTG CAG TGC TTC AGC CGC TAC CCC GAC CAC
ATG AAG CAG CAC GAC TTC TTC AAG TCC GCC ATG CCC GAA GGC TAC GTC
CAG GAG CGC ACC ATC TTC TTC AAG GAC GAC GGC AAC TAC AAG ACC CGC
GCC GAG GTG AAG TTC GAG GGC GAC ACC CTG GTG AAC CGC ATC GAG CTG
AAG GGC ATC GAC TTC AAG GAG GAC GGC AAC ATC CTG GGG CAC AAG CTG
GAG TAC AAC TAC AAC AGC CAC AAC GTC TAT ATC ATG GCC GAC AAG CAG
AAG AAC GGC ATC AAG GTG AAC TTC AAG ATC CGC CAC AAC ATC GAG GAC
GGC AGC GTG CAG CTC GCC GAC CAC TAC CAG CAG AAC ACC CCC ATC GGC
GAC GGC CCC GTG CTG CTG CCC GAC AAC CAC TAC CTG AGC ACC CAG TCC
GCC CTG AGC AAA GAC CCC AAC GAG AAG CGC GAT CAC ATG GTC CTG CTG
GAG TTC GTG ACC GCC GCC GGG ATC ACT CTC GGC ATG GAC GAG CTG TAC
AAG TCC GGC CGG ACT CAG ATC TCG AGC TCA AGC TTC GAA TTC ATG CCC
AAC CCC AGG CCT GGC AAG CCC TCG GCC CCT TCC TTG GCC CTT GGC CCA
TCC CCA GGA GCC TCG CCC AGC TGG AGG GCT GCA CCC AAA GCC TCA GAC
CTG CTG GGG GCC CGG GGC CCA GGG GGA ACC TTC CAG GGC CGA GAT CTT
CGA GGC GGG GCC CAT GCC TCC TCT TCT TCC TTG AAC CCC ATG CCA CCA
TCG CAG CTG CAG CTG CCC ACA CTG CCC CTA GTC ATG GTG GCA CCC TCC
GGG GCA CGG CTG GGC CCC TTG CCC CAC TTA CAG GCA CTC CTC CAG GAC
AGG CCA CAT TTC ATG CAC CAG CTC TCA ACG GTG GAT GCC CAC GCC CGG
ACC CCT GTG CTG CAG GTG CAC CCC CTG GAG AGC CCA GCC ATG ATC AGC
CTC ACA CCA CCC ACC ACC GCC ACT GGG GTC TTC TCC CTC AAG GCC CGG
CCT GGC CTC CCA CCT GGG ATC AAC GTG GCC AGC CTG GAA TGG GTG TCC
AGG GAG CCG GCA CTG CTC TGC ACC TTC CCA AAT CCC AGT GCA CCC AGG
AAG GAC AGC ACC CTT TCG GCT GTG CCC CAG AGC TCC TAC CCA CTG CTG
GCA AAT GGT GTC TGC AAG TGG CCC GGA TGT GAG AAG GTC TTC GAA GAG
CCA GAG GAC TTC CTC AAG CAC TGC CAG GCG GAC CAT CTT CTG GAT GAG
AAG GGC AGG GCA CAA TGT CTC CTC CAG AGA GAG ATG GTA CAG TCT CTG
GAG CAG CAG CTG GTG CTG GAG AAG GAG AAG CTG AGT GCC ATG CAG GCC
CAC CTG GCT GGG AAA ATG GCA CTG ACC AAG GCT TCA TCT GTG GCA TCA
TCC GAC AAG GGC TCC TGC TGC ATC GTA GCT GCT GGC AGC CAA GGC CCT
GTC GTC CCA GCC TGG TCT GGC CCC CGG GAG GCC CCT GAC AGC CTG TTT
GCT GTC CGG AGG CAC CTG TGG GGT AGC CAT GGA AAC AGC ACA TTC CCA
GAG TTC CTC CAC AAC ATG GAC TAC TTC AAG TTC CAC AAC ATG CGA CCC
CCT TTC ACC TAC GCC ACG CTC ATC CGC TGG GCC ATC CTG GAG GCT CCA
GAG AAG CAG CGG ACA CTC AAT GAG ATC TAC CAC TGG TTC ACA CGC ATG
TTT GCC TTC TTC AGA AAC CAT CCT GCC ACC TGG AAG AAC GCC ATC CGC
CAC AAC CTG AGT CTG CAC AAG TGC TTT GTG CGG GTG GAG AGC GAG AAG
GGG GCT GTG TGG ACC GTG GAT GAG CTG GAG TTC CGC AAG AAA CGG AGC
                                                    ← end Foxp3  BamHI site
CAG AGG CCC AGC AGG TGT TCC AAC CCT ACA CCT GGC CCC TGA GGATCCgcgc
```

*Vector sequence →*
```
cgctcgcgac tcgagagatc cggattagtc caatttgtta aagacaggat atcagtggtc
caggctctag ttttgactca acaatatcac cagctgaagc ctatagagta cgagccatag
ataaaataaa agattttatt tagtctccag aaaaaggggg gaatgaaaga ccccacctgt
aggtttggca agctagctta agtaacgcca ttttgcaggc atggaaaaat acataactga
gaatagagaa gttcagatca aggtcaggaa cagatggaac agctgaatat gggccaaaca
ggatatctgt ggtaagcagt tcctgccccg gctcagggcc aagaacagat ggaacagctg
aatatgggcc aaacaggata tctgtggtaa gcagttcctg ccccggctca gggccaagaa
cagatggtcc ccagatgcgg tccagccctc agcagtttct agagaaccat cagatgtttc
cagggtgccc caaggacctg aaatgaccct gtgccttatt tgaactaacc aatcagttcg
cttctcgctt ctgttcgcgc gcttctgctc cccgagctca ataaaagagc ccacaacccc
tcactcgggg cgccagtcct ccgattgact gagtcgcccg ggtacccgtg tatccaataa
accctcttgc agttgcatcc gacttgtggt ctcgctgttc cttgggaggg tcctctctga
gtgattgact acccgtcagc gggggtcttt cacatgcagc atgtatcaaa attaatttgg
ttttttttct taagtattta cattaa
```

REDIRECTED, GENETICALLY-ENGINEERED T REGULATORY CELLS AND THEIR USE IN SUPPRESSION OF AUTOIMMUNE AND INFLAMMATORY DISEASE

The Sequence Listing in ASCII text file format of 90,390 bytes in size, created on Mar. 20, 2019, with the file name "2019-03-22SequenceListing_ESHHAR7B_ST25," filed in the U.S. Patent and Trademark Office on even date herewith, is hereby incorporated herein by reference.

BACKGROUND OF THE INVENTION

Field of the Invention

The invention in the field of immunology and medicine relates to genetic modification of T regulatory cells with chimeric receptors with antibody-type specificity, and the use of such cells to suppress the action of T effector cells and treat any of a number of diseases and conditions in which such suppression is beneficial, primarily autoimmune and inflammatory diseases such as inflammatory bowel diseases (IBD), organ-specific autoimmune diseases, allograft rejection and Graft-vs. Host disease.

Description of the Background Art

Regulatory T-Cells (Tregs)

One line of research that led to discovery of Treg cells was the observation that thymectomy of mice of certain susceptible strains on postnatal day 3 results in a spectrum of organ-specific autoimmune effects, which were preventable by "reconstitution" of these animals early in life with normal adult lymphocytes (Asano M et al., *J Exp Med* 1996; 184:387-96). The effectors and suppressors of autoimmunity in this model of multi-organ autoimmunity were CD4+ T-cells. It was subsequently shown that the regulatory CD4+ Tregs that prevent disease coexpressed CD25. CD4+CD25+ Tregs represent 5-10% of total peripheral CD4+ cells in mice and 3-6% of total peripheral blood CD4+ T-cells in humans (Jonuleit H et al., *J Exp Med* 2001; 193:1285-94).

Over the past decade, CD4+CD25+ Tregs have been studied for their function in autoimmune disease. CD4+ CD25+ Tregs suppressed disease induced by cloned autoantigen-specific T effector cells (Suri-Payer, E et al., *J. Immunol.*, 1998; 160:1212-18). The CD4+CD25+ Treg cells appeared to be members of a unique lineage of regulatory T-cells. These authors noted that, although the target antigen(s) and mechanism of action of the CD4+CD25+ T-cells remained to be determined, they likely played an important role in modulating other autoimmune diseases that are mediated by activation of self-reactive T-cells. Tregs prevent organ-specific autoimmune diseases including autoimmune thyroiditis, autoimmune gastritis, insulitis and arthritis.

More recently, it was discovered that Tregs express a transcription factor known as Foxp3 intracellularly. The absence of the transcription factor called Scurfin (also forkhead box P3) and encoded by the gene Foxp3 was known to cause a rapidly fatal lymphoproliferative disease, similar to that seen in mice lacking cytolytic T lymphocyte-associated antigen 4 (CTLA-4). Khattri R et al. (*Nat Immunol.* 2003; 4:337-42) showed that Foxp3 was highly expressed by Treg cells and was associated with their activity and phenotype. Foxp3-deficient mice lacked Treg cells whereas mice that overexpressed Foxp3 possess more Treg cells. Tregs constitutively express the transcription factor Foxp3 and the inhibitory costimulatory molecule CTLA-4 (Chen W et al., *J Exp Med* 1998; 188:1849-57.

Foxp3 is believed to act through negative transcriptional regulation of cytokine genes, including IL2, IL4 and IFN-γ (Kasprowicz D J et al., *J Immunol.* 2003; 171:1216-23, 2003), though many aspects of Foxp3 activity and regulation of its expression remain obscure.

Loser K et al., *Gene Ther* 2005; 12:1294-304, generated Tregs in vitro by infecting naïve CD4+CD25− T-cells with a retrovirus encoding Foxp3. Foxp3-infected T-cells were similar to naturally occurring Treg cells as evidenced by surface marker expression and function. These authors investigated the effects of Foxp3-infected T-cells on contact hypersensitivity responses mediated by T effector cells by injecting into sensitized mice Foxp3- or control virus-infected T-cells. Only injection of Foxp3-infected T-cells significantly inhibited CHS compared to controls, indicating that Foxp3-infected T-cells are suppressive in vivo. The authors then used Foxp3-infected T-cells to treat autoimmune-prone CD40L transgenic (Tg) mice, which develop a severe systemic autoimmune disease including autoreactive T-cells and autoantibodies. Injection of Foxp3-infected T-cells into these mice inhibited the ongoing development of autoimmune dermatitis and activation of cytotoxic CD8+ T-cells. This treatment also reduced serum concentrations of antinuclear antibodies, which was paralleled with reduced renal immunoglobulin depositions and increased kidney function. The authors concluded that newly in vitro-generated regulatory T-cells can be used to treat inflammatory and ongoing autoimmune disorders successfully.

Suri-Payer E and Fritzsching B (*Springer Semin Immunopathol.* 2006; 28:3-16) recently summarized evidence for a role for Treg in suppression of innate and adaptive immune responses in experimental models of autoimmunity including arthritis, colitis, diabetes, autoimmune encephalomyelitis, lupus, gastritis, oophoritis, prostatitis, and thyroiditis. A common observation from such studies is that Tregs are activated in an antigen-specific manner, but exert their suppressive function in an antigen-independent manner, mainly by producing and secreting suppressive cytokines such as IL-10 and TGF-β. Tregs can suppress "conventional" T-cells in vitro by direct cell contact. It is appreciated, however, that down-regulation of antigen-presenting cell (APC) function, such as that of dendritic cells, and attenuation of secretion of inhibitory cytokines such as IL-10 and TGF-β might be important for Treg function in vivo. The final outcome of autoimmunity vs. tolerance depends on the balance between stimulatory signals to T effector cells and inhibitory signals from Treg. Whereas earlier studies analyzed the capacity of Tregs to prevent onset of autoimmune disease, more recent reports indicate successful treatment of ongoing disease.

In vivo, adoptive transfer of Tregs achieved the following effects:

(1) suppressed development of autoimmunity;

(2) suppressed acute rejection of transplanted solid organs; and (3) suppressed anti-tumor immunity, A review of Sakaguchi S et al., *Immunol Rev.* 2006; 212:8-27, noted that naturally arising CD25+CD4+ Treg cells play key roles in the maintenance of immunologic self-tolerance and negative control of a variety of physiological and pathological immune responses. Most of these cells are produced by the normal thymus as a functionally mature T cell subpopulation. Natural Tregs specifically express Foxp3, a transcription factor that plays a critical role in their development and function. Complete depletion of Foxp3-expressing natural Tregs (whether they are CD25+ or CD25-) activated even weak or rare self-reactive T effector cell clones, inducing severe and widespread autoimmune/inflammatory diseases. Natural Tregs are highly dependent on exogenously provided interleukin (IL)-2 for their survival in the periphery. In addition to Foxp3 and IL-2/IL-2 receptor, a deficiency or functional alteration of other molecules (expressed by T-cells or non-T-cells), may affect the development or function of Tregs, self-reactive T effector cells, or both, and consequently tip the balance between the two populations in the periphery toward autoimmunity. Thus, Tregs suppress the activity of T effector cells that are a major cause of antigen-specific autoimmune inflammatory disorders. Tregs induce anergy and promote suppression by a process that involves both cell-cell contact, and probably more importantly, by their secretion of TGF-β and IL-10.

Sakaguchi et al., supra, stated that elucidation of the molecular and cellular basis of Treg-mediated active maintenance of self-tolerance will facilitate (1) our understanding of the pathogenesis of autoimmune disease and (2) development of novel methods of autoimmune disease prevention and treatment.

The present invention is directed to one such novel approach to prevent or treat autoimmune disease and related immune/inflammatory conditions by imposing Treg-mediated control over T effector cells.

Engineering of Chimeric Receptors with Antibody Specificity into T-Cells

Efforts to confer antibody-like specificity to T lymphocytes arose as a response to certain basic discoveries and the failure to convert them to therapeutic success. Human tumor-associated antigens have been shown to exist as peptides associated with major histocompatibility complex (MHC) proteins. The lack of success in vaccinating tumor patients with a large variety of tumor-associated antigen vaccines were thus frustrating (Rosenberg S A et al., Nat Med 2004; 10:909-15). Passive vaccination with anti-tumor antibodies (Abs), tumor infiltrating lymphocytes (TILs), or lymphokine activated killer (LAK) cells showed very limited effectiveness (primarily for vascular tumors). More recent successes with the adoptive transfer of TILs into stage IV melanoma patients ((Dudley M E, et al., J Immunother 2001; 24:363-73; Dudley M E, et al., Science 2002; 298: 850-4) were still burdened by the fact that the results were limited to a few cancers and to individuals from whom it is possible to derive specific TILs.

To overcome such limitations in adoptive cellular immunotherapy of cancer, and in order to develop an approach that was not restricted to individual patients or limited to a specific form of cancer, one of the present inventors and his colleagues developed the "T-body" approach (Gross G et al., Proc Natl Acad Sci USA, 1989; 86:10024-8; Gross G and Eshhar, Z, FASEB J 1992; 6:3370-8), See also the following patent publications by Eshhar and colleagues, all of which are incorporated by reference in their entirety: US Pat Pub 2002-0137697, U.S. Pat. Nos. 5,912,172, 5,906,936, International Patent publications WO00/31239, WO97/15669, WO95/14710 and WO93/19163. In these approaches, a chimeric receptor (CR), was made, for example, by fusing the variable portion of an antibody, such as an anti-tumor monoclonal antibody (mAb), to a lymphocyte intracellular triggering domain, so as to be expressed by the T-cell into which the gene has been transfected as the extracellular domain of that T-cell triggering molecule. Following the expression of such CR genes in immune effector cells (T-cells and natural killer (NK) cells), the resulting engineered cells (nicknamed "T-bodies") recognized their tumor targets and efficiently killed them. Thus, the chimeric immune receptor confers redirected antigenic specificity coupled to direct, MHC-independent triggering of cellular activation in response to binding of pre-defined target antigen.

Originally, the heterodimeric CR configuration comprised the two T cell receptor (TCR) α and β chains in which each pair of TCR variable domains ($V_\alpha$ and $V_\beta$) was replaced with a pair of $V_H$ and $V_L$ domain derived from a selected antibody. These two Ab-derived coding sequences were co-transfected into T cell lines and were found to confer antibody specificity (Gross et al., 1989, supra). Thus, T-cells could be activated to effector function such as cell killing or cytotoxic activity against an immunologically specific target in a manner that was MHC independent (and thereby non-restricted) (Gross et al., 1992, supra).

In "second generation" CR's, the single chain configuration of the CR was further manipulated to obtain a configuration that would be useful particularly for cancer or antiviral therapy. Here, a single chain Fv (scFv) of an antibody was linked to transmembrane and cytoplasmic domains of lymphocyte triggering moieties such as the TCR/CD3 complex-associated ζ chain, or the Fc receptor γ chain (Eshhar Z et al., Proc Natl Acad Sci USA 1993; 90:720-4). This single chain configuration, which combined antibody recognition and T cell signaling in a single continuous protein, was a modular structure with functional domains that are simple to manipulate, and could be readily expressed in human lymphocytes using retrovirus-based vectors (Eshhar Z et al., J Imm Meth 2001; 248:67-76). Other such receptors designed by some of the present inventors and colleagues, and discussed in more detail below, are referred to as tripartite chimeric receptors (TpCR) that also include a costimulatory domain(s) (e.g. CD28, 4-1BB).

With time, it has emerged that redirection of the specificity of T effector cells using single chain CRs has become a valid therapeutic option for cancer. Many investigators have adapted this "T-body" approach to endow T-cells with various specificities and functions (Gross & Eshhar, supra; Willemsen R A et al., Hum Immunol 2003; 64:56-68; Baxevanis C N et al., Cancer Immunol Immunother 2004; 53:893-903). For a recent review, see: Eshhar, Z. "The T-Body Approach: Redirecting T Cells with Antibody Specificity," in Therapeutic Antibodies. Handbook of Experimental Pharmacology 181, Chernajovsky & Nissim (eds.), Springer-Verlag, 2008, pp. 329-342.

In the present invention, the inventors have conceived expanded uses of such CR's for the treatment of undesired immune/inflammatory conditions such as autoimmune diseases (with a particular initial emphasis on inflammatory bowel disease, IBD) and graft rejection.

Chronic Inflammatory Disease and Animal Models

Inflammatory conditions, particularly chronic inflammatory diseases, are of particular importance in clinical medicine. These diseases, caused by actions of the immune system, involve inappropriate or excessive activation of certain T-cells, expression of regulatory cytokines and chemokines, loss of immune tolerance, and the like. Examples of autoimmune and/or chronic inflammatory diseases are multiple sclerosis, inflammatory bowel diseases (IBD), joint diseases such as rheumatoid arthritis, and systemic lupus erythematosus. Some of these diseases are rather organ/tissue-specific as follows: intestine (Crohn's Disease), skin (psoriasis), myelinated nerves (multiple sclerosis or MS), pancreatic islet or β cells (insulin dependent diabetes mellitus (IDDM) or Type I Diabetes), salivary glands (Sjogren's disease), skeletal muscle (myasthenia gravis), the thyroid (Hashimoto's thyroiditis; Graves' Disease), the anterior chamber of the eye (uveitis), joint tissue (rheumatoid arthritis), and various cardiovascular diseases.

Inflammatory bowel disease (IBD) is a collective term used to describe two intestinal disorders whose etiology is not completely understood: Crohn's disease and ulcerative colitis. IBD occurs worldwide and afflicts several million people (0.3% of people in Western countries), and its incidence is on the rise (Tsironi E, et al., *Am J Gastroenterol.* 2004; 99:1749-55). The course and prognosis of IBD varies widely. Onset of IBD is predominant in young adulthood and presents typically with diarrhea, abdominal pain, and fever; anemia and weight loss are also common signs. Between 10% and 15% of people with IBD require surgery over a ten year period. Patients with IBD are also at increased risk for the development of intestinal cancer. These diseases are accompanied by a high frequency of psychological symptoms, including anxiety and depression.

Although the pathogenesis of this common T cell-mediated disorder remains uncertain, it is believed to result from loss of tolerance in the intestinal immune system due to the presence of constant antigenic stimulation provided by the very large numbers of resident bacteria (Podolsky D K, *N Engl J Med* 2002; 347:417-29). Unfortunately, new therapies for IBD are few, and both diagnosis and treatment have been hampered by a lack of detailed knowledge of the etiology. A combination of genetic factors, exogenous triggers and endogenous microflora can contribute to the immune-mediated damage of intestinal mucosa. Bacteria have been implicated in initiation and progression of Crohn's Disease since intestinal inflammation frequently responds to antibiotics. Common intestinal colonists and novel pathogens have been implicated, either because of direct detection or disease-associated anti-microbial immune responses. In many genetically susceptible animal models of chronic colitis, luminal microorganisms appear to be a necessary cofactor for disease.

The initiating step in autoimmune disease pathology is often obscure in humans where the diseases are largely sporadic, and symptoms may appear years after the first pathogenic T cell is activated. It has therefore been difficult to design effective therapies to block induction of disease. In contrast, there are common features in many of the later stages of these diseases. Inflammation at the disease site/target organ is typically present, caused by the release of inflammatory, also termed "proinflammatory," cytokines (e.g. TNF-α and interferons) by T-cells and by other cells that contribute to the activation steps and effector pathways of immune/inflammatory processes. These cells include (among others) macrophages, dendritic cells and their precursors, B lymphocytes and plasma cells and NK cells (including NKT-cells). These reactions often involve destruction of "target" cells and tissue damage.

Studies using murine models of experimental chronic inflammation are helping to define nature of the immunological dysregulation that initiates inflammation and leads to destruction of specific end organs as well as for testing therapies. See, for example, Mombaerts et al. *Cell*, 1993; 75:274-82; Tarrant et al., 2998; *J Immunol*, 161:122-7; Powrie et al., *Immunity,* 1994; 1:553-62; Hong et al., *J Immunol,* 1999; 162:7480-91; Horak, *Clin Immunol Immunopathol,* 1995, 76(3 Pt 2):S172-173; Ehrhardt et al. *J Immunol,* 1997; 158:566-73; Davidson et al., *J Immunol,* 1998; 161:3143-9; Kuhn et al. *Cell*, 1993. 75:263-74; Neurath et al., *J Exp Med,* 1995. 182:1281-90. W. Strober, 2002; *Annu. Rev. Immunol.* 20:495-54 reviews mucosal models of inflammation, and is incorporated by reference in its entirety. One hallmark of the better of these models is that the histopathology and pathophysiology resembles that of the parallel human conditions, further enhancing the models' utility in testing novel treatment strategies. In the case of IBD this development has not been uniform. Most emphasis has been placed on modulation of immune mechanisms (Blumberg R S et al., *Curr Opin Immunol.* 1999; 11:648-56; Strober et al., supra) and recently of the enteric flora (Sartor R B, *Curr Opin Gastroenterol.* 2001; 4:324-330).

Bhan A K et al., 1999 *Immunol Rev* 169:195-207 reviewed studies of colitis in transgenic (Tg) and knockout (KO) animal models for mucosal inflammation in IBD. Genetics and the environment, particularly the normal enteric flora, were factors in the development of mucosal inflammation, as stated above. Normal mucosal homeostasis was disrupted by cytokine imbalance, abrogation of oral tolerance, breach of epithelial barriers, and loss of immunoregulatory cells. Some but not all immunodeficiencies, in the appropriate setting, led to colitis. CD4+T effector cells have been identified as the pathogenic lymphocytes in colitis, and can mediate inflammation by either the Th1 or the Th2 pathway. The Th1 pathway dominates in most colitis models (and human Crohn's Disease). In contrast, in the colitis observed in mice, the T cell receptor (TCR) α chain knockout mice (TCRα KO mice) shared many features of ulcerative colitis including the dominance of Th2 pathway in colon inflammation. Such models are important for the development of therapeutic strategies to treat IBD. In a later review, the same group (Mizoguchi A et al., 2003, *Inflamm Bowel Dis.* 9:246-259) noted that exaggerated immune responses to normal enteric microflora are involved in the initiation and perpetuation of chronic intestinal inflammation. A major pathway involves development of "acquired" immune responses by the interactions of CD4+TCRαβ+ T-cells with antigen-presenting cells (APC), particularly dendritic cells. CD4+CD25+ Treg cells attenuated activated T cell responses.

The progression from the acute to the chronic phase of IBD has not been well characterized in animal models and cannot be easily evaluated in patients. Spencer D M et al. *Gastroenterol.* 2002; 122:94-105 reported changes in the mucosal immune response over time in experimental colitis. Severity of colitis, body mass, stool consistency and blood content, serum amyloid A, and tissue histology were examined in mice deficient in interleukin-10 (IL-10) over 35 weeks. The corresponding production of IL-12, IL-18, IFNγ, TNFα, IL-4, and IL-13 by lamina propria mononuclear cells in the inflamed intestine was measured. Administration of a neutralizing anti-IL-12 monoclonal antibody (mAb) at distinct times during disease progression permitted evaluation of the therapeutic potential of this agent. Lamina propria mononuclear cells from mice with early disease synthesized progressively more IL-12 and IFNγ, whereas production of both cytokines declined dramatically and returned to pre-disease levels in the late phase. Consistent with this pattern, the neutralizing anti-IL-12 reversed early, but not late, disease. In contrast, IL-4 and IL-13 production increased progressively from pre- to early to late disease. It was concluded that colitis developing in IL-10-deficient mice evolves into two distinct phases. IL-12 plays a pivotal role in early colitis, whereas other immune mechanisms, presumably mediated by IL-4 and IL-13, predominate in late disease to sustain chronic inflammation.

IL-10 and Chronic Inflammatory Disease

It has been known for some years that IL-10 affects the growth and differentiation of many hemopoietic cell types in vitro and is a particularly potent suppressor of macrophage and T cell functions. These observation were based in part from use of IL-10-deficient (knockout, KO) mutant mice by gene targeting (Kuhn R et al., *Cell* 1993; 75:263-74). In these mice, lymphocyte development and antibody responses are normal, but most animals are growth retarded, anemic and suffer from chronic enterocolitis. Alterations in the intestine include extensive mucosal hyperplasia, inflammation, and aberrant epithelial expression of major histocompatibility complex (MHC) class II molecules. In contrast, IL-10 KO mutants kept under specific pathogen-free conditions, develop only localized inflammation (limited to the proximal colon). It was concluded that (1) bowel inflammation in these mutants originated from uncontrolled immune responses stimulated by enteric antigens and (2) IL-10 is an essential (negative) regulator in the intestinal tract.

In a study validating this IL-10 KO mouse model of colitis, T. Scheinin, T et al. (*Clin Exp Immunol* 2003; 133:38-43) emphasized that a valuable animal model must respond to existing therapy in a way that resembles the response of human disease. Since refractory Crohn's Disease responded well to anti-TNFα antibody therapy, the investigators examined responses of IL-10 KO mice to anti-TNFα therapy, using a new scoring system similar to the Crohn's Disease "Activity Index" in humans. Stool samples were tested for cytokines and the findings compared with histology. Results showed that anti-TNF antibody therapy starting at 4 weeks markedly ameliorated the disease (as judged by the clinical score or by gut histology). A marked diminution of inflammatory cytokines in stool samples was noted, adding a further accurate measure of clinical improvement. The authors concluded that this model is useful for evaluating other therapeutic modalities of relevance to Crohn's Disease.

Treg Cells and Inflammatory Bowel Disease

One of the commonly used animal models of IBD involves adoptive transfer of CD45RB$^{hi}$CD4+ T-cells into SCID mice, leading to the development of massive colon mononuclear cell infiltrates, epithelial cell hyperplasia and ulceration (Thornton A M, et al., *J Immunol* 2000; 164(1): 183-90). Cotransfer of large numbers of CD4+CD25+ Tregs prevented the development of colitis or cured established colitis, an affect that required signaling through CTLA-4 (Read S, et al., *J Exp Med* 2000; 192:295-302; 2000; Morrissey P J, et al., *J Exp Med* 1993; 178:237-44). Even after the development of immune-mediated colitis, adoptive transfer of $10^6$ CD4+CD25+ cells caused significant improvement of intestinal inflammation (Fantini M C et al., *Gut* 2006; 55:671-80; Mottet C, et al., *J Immunol* 2003; 170(8):3939-43; Uraushihara K, et al., *J Immunol* 2003; 171:708-16).

In humans suffering from IBD, peripheral regulatory CD4+CD25+ cells retain suppressive activity. However, in contrast to other intestinal inflammatory disorders, the number of these regulatory cells decreases in peripheral blood during active inflammation and only slightly increases in intestinal lesions (Maul J, et al., *Gastroenterology* 2005; 128(7):1868-78). This aberration suggests that Treg homing defects, as well as dysregulated in situ activation contribute to the pathogenesis of IBD There is therefore a recognized need in the art to find modalities to suppress autoimmune/inflammatory reactions and diseases, including but not limited to IBD, as well as to suppress rejection of organ and tissue grafts and prevent Graft vs. Host (GVH) disease. The present invention provides a novel approach, that of redirecting Treg cells, as a means to recruit Tregs to sites of inflammation, and activate them to suppress such immune/inflammatory reactions and protect against, alleviate and even cure such disease as IBD.

SUMMARY OF THE INVENTION

The present invention is based on the inventors' conception that CR-mediated redirection and activation of Treg cells at sites of inflammation results in suppression of inflammatory conditions, commonly part of organ-specific autoimmune disease and exemplified herein as inflammation in the colon in experimental IBD. The inventors have further conceived of using these cells to overcome rejection of mismatched cells and tissues by T effector cells that arise in transplant recipients or to inhibit the pathogenic action of transplanted immunocompetent cells in the case of GVH disease.

The invention relies on the inventors' innovative T-body approach that has thus far proven useful for immunotherapy of cancer (and is currently in phase I/II clinical trials). The invention provides a new approach to the exploitation of Treg cells for amelioration of pathologic and undesired immune responses, particularly immunotherapy of autoimmune and inflammatory conditions, including various organ-predominant autoimmune diseases, and other pathologic or undesirable immune responses such as graft rejection and graft vs. host disease.

According to this invention, Treg cells are endowed with CRs that are specific for a selected target antigen or ligand. Such modification causes activation of redirected Tregs at sites of inflammation to suppress the proinflammatory effector-type immune responses. Based on the present inventors' (and their colleagues') results with redirecting antitumor effector lymphocytes, it is expected that Tregs, endowed with predefined specificity, will migrate/home to and accumulate in, a targeted site, such as the inflamed colon, where they will suppress disease-mediating T effector cells. To avoid the necessity of migration or homing to the targeted site, the Tregs may, where possible, be administered directly at or to such site, where they will become activated and suppress disease-mediating T effector cells.

Such redirected Treg cells, also referred to as "T-bodies," are Treg cells that have been genetically engineered to express a CR, preferably a tripartite chimeric receptor (TpCR) that is made of a single chain extracellular recognition unit, a transmembrane region, and an intracellular signaling region.

The extracellular recognition region is specific for a selected target antigen or ligand and may preferably be a single chain antibody variable (scFv) region or another ligand that is capable of binding to the target antigen or ligand. The extracellular recognition region preferably does not comprise an MHC protein extracellular domain. The redirected Tregs of the present invention are sometimes referred to herein as "T-bodies" despite the fact that the extracellular recognition region is not necessarily an antibody domain. Thus, this term is not intended to be limited to Tregs with antibody-like specificity, but also includes Tregs with ligand-receptor-like specificity or otherwise.

A flexible spacer region may be present between the extracellular recognition region and the transmembrane region. Such flexible spacer is preferably an immunoglobulin (Ig)-like hinge, such as any hinge region derived from the Ig superfamily.

The intracellular region includes a combination of T-cell signaling polypeptide moieties, fused in tandem, which combination of moieties, upon binding of the extracellular recognition region to the selected target antigen or ligand, triggers activation of the Treg cells to cause suppression of T-cell mediated immunity. The T-cell signaling moieties preferably include one or more cytoplasmic domains of a costimulatory molecule (e.g., CD28) and a cytoplasmic T-cell stimulatory domain, e.g., of FcRγ or a CD3-ζ chain. The redirected Treg cells become specifically activated, upon binding of the extracellular recognition region of the CR to its target antigen or ligand, in a manner that is preferably (1) not restricted by, or dependent upon, the binding of the target antigen or ligand to an MHC, nor is it otherwise dependent in any way on the MHC (HL-A) haplotype of the recipient and (2) independent of engagement of costimulatory ligand(s) on a target cell.

A preferred target disease of this invention is an IBD such as ulcerative colitis, in which the present methods, as used successfully in an animal model, will permit Treg cells to reach bowel lesions in IBD patients and become efficiently activated at the inflammation site. The present invention results in site-specific Treg accumulation, ultimately resulting in CR-mediated, antigen-specific activation that results in the production of suppressive cytokines which in turn suppress effector autoimmune T-cells in an antigen-nonspecific manner, leading to alleviation of symptoms and thereby treating the disease.

The present therapeutic approach has several unique advantages. In contrast to other immunotherapeutic models, it involves T-bodies redirected with a CR, and preferably a TpCR, that combines antibody/antigen or ligand/receptor recognition with stimulatory and costimulatory motifs. Thus, T-bodies can be fully activated in a way that is not restricted by the MHC and is independent of a requirement for costimulation. The second advantage of the present invention stems from the fact that, although Treg activation is antigen-dependent, the suppressive action of these cells is antigen-, TCR-, and MHC-independent. By exploiting this property, one can construct a chimeric receptor that is specific for one or more tissue-associated antigens rather than requiring specificity for an unknown number of yet undefined autoimmune disease-specific antigens. Expression of such chimeric receptors in Tregs redirects these cells and their activation to the appropriate target tissue (in a preferred embodiment, the colon) so that they are activated in an antigen-specific manner, where their potent suppressive effects take place without a need for further recognition of disease-associated-antigens (the "bystander effect"). By using specifically-activated Tregs, many fewer cells are required to treat autoimmune inflammatory conditions; such as IBD, or allograft-associated reactions in patients than would have been possible prior to this invention when much higher numbers of non-specific Tregs would have been needed.

The present inventors have constructed strains of transgenic (Tg) mice whose T-cells and natural killer (NK) cells express an antigen-specific TpCR. For exemplification of the invention, the inventors selected the trinitrophenyl (TNP) hapten as the specific target of the TpCRs. TNP-specific Tregs isolated from these Tg mice suppressed TNP-specific effector T-cells in vitro and in vivo and were able to suppress trinitrobenzenesulfonic acid (TNBS)-induced colitis in mice. In this embodiment, the target antigen for Treg and the pathogenic antigen—the hapten TNP—are the same. In another example, TNP-specific Tregs suppressed oxazolone-induced colitis in mice in which a low dose of TNP was introduced into the colon together with the oxazolone challenge. However, the TNP-specific Tregs had no effect on the oxazolone-induced colitis in the absence of TNP introduction. This establishes the "bystander" effect of the present invention, i.e., that the target antigen need not be the pathogenic antigen, as long as the redirected Tregs are activated in the vicinity of the pathogenic or undesired immune response.

One distinct advantage of the present invention is that it provides cells and methods that permit antigen-specific activation and antigen-nonspecific action of Treg cells used to suppress effector T cell responses (and treat consequent pathologies) in a way that does not require identity between the ligand (e.g., the antigen) recognized by the TpCR (e.g., by its target recognition portion) and the ligand/antigen that plays a pathogenic role in the disease process. Thus, the antigen that is pathogenic does not have to be recognized by the T effector cells being suppressed, and, indeed, may be unrelated to the disease or condition being treated. Thus, the invention exploits the "bystander" effect. As long as the Treg is in the correct vicinity where T effector cells are located and mediating their undesired effects, the redirected Tregs of the present invention can be triggered or activated at that location to release of suppressive cytokines (e.g., IL-10 and TGF-β), that will result in suppression of any "bystander" effector T-cells, and by this mechanism, quell an ongoing inflammatory/autoimmune response.

The unique characteristics of the Tg system used in the present examples enables evaluation of the suppressive effect of antigen-specific Tregs in IBD both in vitro and in vivo. Different means are used to induce Tregs, allowing those of skill in the art to select the optimal method for generating efficient numbers of antigen-specific redirected Tregs for a desired antigen or disease/condition. According to this invention, redirected human Tregs constitute an effective cell-based therapeutic modality for IBD or ulcerative colitis and, more broadly, for any T effector cell-mediated disease or condition.

To overcome the scarcity of antigen-specific Tregs, the present invention includes methods to induce these cells using cytokines (e.g. TGF-β) or by expression of transgenes (e.g. encoding the Foxp3 transcription factor) that will, together with the TpCR, allow antigen-specific Treg expansion.

According to the present invention, human Treg cells, derived from either the subject with the autoimmune/inflammatory disease or condition to be treated, or from an HLA-matched healthy donor (or a universal cell that is not recognized by the recipient's immune system), are endowed with antigen/ligand-specificity, by transduction with the antigen/ligand-specific TpCR as disclosed herein. Alternatively, the cells being endowed with antigen-specificity are the entire T-cell population and the nucleic acid construct including the sequence encoding the TpCR further includes a Foxp3 transgene that is present as an independently transcribed cistron. In another such alternative, a Foxp3 transgene is separately transfected into the T-cell population, to turn the T-cells into Treg cells. Examples provided below include studies using murine colonoscopy, in vivo imaging and immunofluorescence, and provide the basis for a novel cell-based therapeutic modality for IBD, and, by extension, for other pathologic and undesired immune responses mediated by antigen specific T effector cells.

Various embodiments of the invention are described more specifically below.

The present invention is directed to a redirected regulatory T lymphocyte (Treg cell) endowed with specificity toward a selected target antigen or ligand, which cell comprises a chimeric nucleic acid that encodes a chimeric receptor (CR) polypeptide that comprises, expressed in a single, continuous chain, an extracellular recognition region, a transmembrane region and an intracellular signaling region, and is expressed in the Treg cell so as to display the extracellular region on the cell surface, wherein
  (a) the extracellular recognition region of the chimeric receptor is specific for the selected target antigen or ligand, and does not comprise an MHC protein extracellular domain; and
  (b) the intracellular region comprises a combination of T-cell signaling polypeptide moieties which combination of moieties, upon binding of the extracellular recognition region to the selected target antigen or ligand, triggers activation of the Treg cells to cause suppression of T-cell mediated immunity.

In preferred embodiments of the present invention, the extracellular recognition region is an antibody-derived scFv domain that is specific for a selected antigen. In another preferred embodiment, the extracellular recognition region is a member of a ligand-receptor pair, which is specific for the other member of that pair.

Preferably, the extracellular recognition region is linked to the transmembrane region through a flexible spacer, which, more preferably, is a hinge from a molecule of the immunoglobulin family.

The intracellular signaling region preferably includes a signaling moiety from a chain of an antigen-specific T-cell receptor, which more preferably is one having a polypeptide region comprising an immunoreceptor tyrosine-based activation motif (ITAM). Non-limiting examples of antigen-specific T-cell receptors are chains of the TCR/CD3 complex, a TCR α, β, γ or δ chain, and the γ chain of an Ig Fc receptor (FcRγ). The chain of an antigen-specific T-cell receptor is preferably the CD3/ζ chain or an FcRγ subunit.

The intracellular signaling region further preferably includes a signaling moiety of a costimulatory-receptor protein of a T-cell. The costimulatory-receptor protein is preferably selected from CD28, OX40, CD40L (gp39), 4-1BB and PD-1 (or preferably the human form or homolog of these costimulatory molecules). Most preferred among these is CD28 or 4-1BB. In another preferred embodiment, the intracellular signaling region includes more than one of the costimulatory-receptor protein signaling moieties. For example, the combination of T-cell signaling polypeptide moieties in the intracellular signaling region may include both CD28 and 4-1BB. In a particularly preferred embodiment, the extracellular hinge and transmembrane regions of CD28 are used as the extracellular hinge and transmembrane regions of the chimeric receptor.

The intracellular signaling region may also include a signaling moiety from a cytokine receptor of a T-cell, such as the IL-2 receptor or the TGF-β receptor. The latter may help to induce the T-cell containing the chimeric receptor to adopt the characteristics of a Treg cell.

The intracellular region may also include a signal-transducing enzyme that (a) is an enzyme in the signal transduction pathway of an antigen-specific T-cell receptor or (b) is an enzyme with corresponding specificity and activity as the enzyme of (a), derived from a non-T-cell lymphocyte. Such enzyme is preferably a kinase, such as the Syk kinase.

The chimeric nucleic acid encoding the CR may also include a nucleotide sequence that encodes Foxp3 arranged such that Foxp3 is expressed by the Treg cell independently of the chimeric receptor. In other words, the chimeric nucleic acid may be bicistronic such that the Foxp3 transgene is present as an independently transcribed cistron.

The target antigen or ligand is preferably one that is present or expressed at a site or target tissue of an immune or inflammatory response mediated by effector T-cells. The autoimmune or inflammatory response may comprise an autoimmune response or disease, an allograft or xenograft response or rejection, or graft vs. host (GVH) disease. In an alternative preferred embodiment, the target antigen or ligand may be an autoantigen or an antigen that is cross-reactive with an autoantigen, i.e., is also bound by an antibody that is specific to the autoantigen. The autoantigen may be a pathogenic antigen in the pathophysiology of the autoimmune disease.

The antigen is not necessarily an autoantigen, but can be, for example, an antigen that is part of the bacterial flora, such as LPS derived from the bacteria native to the colon.

The autoimmune disease or graft response and the antigen/ligand or antigens/ligands against which the Treg is specific is preferably selected from the following group:
  (a) inflammatory bowel disease (IBD), wherein the antigen or ligand is one that is expressed in diseased colon or ileum;
  (b) rheumatoid arthritis, wherein the antigen or ligand is an epitope of collagen or an antigen present in joints;
  (c) Type I diabetes mellitus or autoimmune insulitis, wherein the antigen or ligand is a pancreatic 1 cell antigen;
  (d) multiple sclerosis, wherein the antigen or ligand is, for example, a myelin basic protein (MBP) antigen or MOG-1 or MOG2-2, or a neuronal antigen.
  (e) autoimmune thyroiditis, wherein the antigen or ligand is a thyroid antigen;
  (f) autoimmune gastritis, wherein the antigen or ligand is a gastric antigen;
  (g) autoimmune uveitis or uveoretinitis, wherein the antigen or ligand is S-antigen or another uveal or retinal antigen
  (h) autoimmune orchitis, wherein the antigen or ligand is a testicular antigen;
  (i)) autoimmune oophoritis, wherein the antigen or ligand is an ovarian antigen;
  (j) psoriasis, wherein the antigen or ligand is a keratinocyte antigen or another antigen present in dermis or epidermis;
  (k) vitiligo, where the antigen or ligand is a melanocyte antigen such as melanin or tyrosinase;
  (l) autoimmune prostatitis, wherein the antigen or ligand is a prostate antigen;
  (m) any undesired immune response, wherein the antigen or ligand is an activation antigen or other antigen expressed on T effector cells present at the site of the undesired response;
  (n) tissue rejection, wherein the antigen or ligand is the MHC specific to the transplanted tissue; and
  (o) an inflammatory condition, wherein the antigen or ligand is one that is expressed on nonlymphoid cells of the hemopoietic lineage that participate in inflammation.

Most preferred is a Treg cell that is able to act and suppress IBD or ulcerative colitis, and may be specific for an antigen associated with IBD such as carcinoembryonic antigen (CEA) or an antigen of intestinal bacterial flora such as bacterial lipopolysaccharide (LPS) or a component thereof, preferably a Lipid A component.

The Treg may be specific for an activation antigen expressed on T effector cells such as CD69 or CD107a. The Treg may be specific for an antigen expressed on a dendritic cell, macrophage/monocyte, granulocyte or eosinophil present at the inflammation site.

In a preferred embodiment, the above Treg cell is specific for an antigen that is introduced exogenously to a subject to the site or target tissue of the immune or inflammatory response, either before, concomitantly with, or after administration of the Treg cell.

The above Treg cell preferably is one that expresses CD4 or CD8, along with CD25 on its surface and expresses the Foxp3 transcription factor intracellularly. The Foxp3 transcription factor may be expressed in the cell endogenously (i.e., from the cells' own Foxp3 gene); this expression is enhanced by exposure of cells to TGF-β or another cytokine that induces Foxp3 expression and induces a Treg phenotype in T-cells. In another embodiment of the above Treg cell, Foxp3 is expressed from a nucleic acid that has been introduced into the cell exogenously (i.e., transduced) as a recombinant nucleic acid expression construct encoding Foxp3 and regulating its expression. The above Treg may be obtained from a mammalian subject prior to introduction of the chimeric nucleic acid and prior to stimulation that induces Foxp3 expression or prior to transducing the exogenous Foxp3-encoding construct. The chimeric nucleic acid encoding the chimeric receptor and the nucleic acid construct encoding Foxp3 may be co-transduced into the cell. In one embodiment, co-transduction is achieved using a bicistronic vector that includes, in a single vector, a sequence of (i) the chimeric nucleic acid encoding the chimeric receptor and (ii) the nucleic acid construct encoding Foxp3, under the control of a common (or separate) promoter and regulatory sequences.

The above Treg cells may be enriched or purified from a mixed population of lymphocytes or T-cells on the basis of the Treg cells' expression of CD4 (or CD8) and CD25 and/or Foxp3. The cell may be subjected to the following treatment:
(a) exposure ex vivo of:
  (i) peripheral blood mononuclear cells,
  (ii) peripheral blood lymphocytes,
  (iii) T-cells enriched or purified from (i) or (ii), or
  (iv) a subset of T-cells enriched or purified from (iii);
  to an amount of TGF-β or other Treg-inducing cytokine or agent that is effective to convert T-cells to a Treg phenotype and to induce expression of Foxp3; and
(b) optionally, culturing and expanding the exposed cells of step (a).

Preferred Treg cells comprise the above cell that has been transduced with an expression vector encoding Foxp3.

Also provided herein is an immunoregulatory pharmaceutical composition for suppressing a T effector cell-mediated immune/inflammatory response or treating a T effector cell-mediated immune/inflammatory disease or condition, comprising a redirected Treg as described above and a pharmaceutically and immunologically acceptable carrier, excipient or diluent.

This invention is also directed to a method for producing the above redirected Treg that expresses a chimeric receptor as described. This method preferably comprises:
(a) obtaining from a subject and, optionally, enriching or isolating and propagating, a population of lymphocytes or T-cells;
(b) inducing the Treg phenotype in these lymphocytes by suitably stimulating or activating the cells by exposure to TGF-β or another cytokine or agent that induces Foxp3 expression and a Treg phenotype;
(c) before or after step (b), transducing the cells ex vivo with an expression vector encoding the chimeric receptor to be expressed in the Treg; and
(d) optionally, growing or expanding in vitro the cells obtained as above.

In another embodiment, this method comprises:
(a) obtaining from a subject and, optionally, enriching or isolating and propagating, a population of lymphocytes or T-cells;
(b) transducing the cells ex vivo with a vector encoding the chimeric receptor;
(c) before, after, or concomitantly with step (b), transducing the cells ex vivo with a recombinant nucleic acid expression construct encoding Foxp3; and
(d) optionally, growing or expanding in vitro the cells obtained as above.

This invention further is directed to a method of suppressing undesired activity of T effector cells in mediating an immune or inflammatory response, comprising delivering to a population of T effector cells to be suppressed (or to a site where such T effector cells are present) an amount/number of redirected Tregs as above, effective to suppress activity of the T effector cells.

Also intended is a method of suppressing undesired activity of T effector cells as indicated above, which method comprises delivering to a population of T effector cells to be suppressed (or to a site where such T effector cells are present) an amount/number of redirected Tregs produced according to the above methods that are effective for suppressing the T effector cell activity.

This delivering is preferably in vivo. The redirected Treg cells are delivered by injection or infusion to a subject in whom the T effector cell activity is to be suppressed, preferably by a route selected from intravenous, intramuscular, subcutaneous, intraperitoneal, intra-articular, intrathecal, intraluminal, intracerebroventricularly, rectal, and topical. In one embodiment, the Treg cells are delivered regionally or locally to a site of inflammation.

The above method is intended for use in situations wherein the T effector cells mediate an autoimmune inflammatory response or disorder, rejection of a transplant or GVH disease.

In one embodiment, the method for treating or ameliorating symptoms of a disease or condition in a subject that is mediated by undesired activity of T effector cells comprises administering to the subject in need thereof an effective amount/number of Treg cells as described above, or a pharmaceutical composition described above, wherein the target recognition domain of the redirected Treg cells is specific for an antigen/ligand present in the subject in the vicinity of the T effector cells so that, upon recognizing and binding the antigen, these redirected Treg cells are activated to secrete suppressive cytokines that suppress the T effector cells in an antigen-nonspecific manner. As noted above, the Treg cell activation occurs in a manner that is not restricted by the MHC and does not require costimulation by a ligand for the costimulatory signaling protein.

Also included is a method for treating or ameliorating symptoms of a disease or condition in a subject that is mediated by undesired activity of T effector cells, the method comprising: (a) producing redirected Treg cells using the production methods described above; (b) administering to the subject in need thereof an effective amount/number of these Treg cells, thereby treating or ameliorating symptoms of the disease or condition.

Stated more generally, the invention is directed to a method for suppressing a T effector cell-mediated immune/inflammatory process in a subject in need thereof, comprising administering to the subject an effective amount/number of redirected Treg cells that express on their surface an antigen-specific chimeric receptor that includes portions that activate Treg cells upon contact with the antigen for which the receptor is specific, the antigen being one that is present in the vicinity of the immune/inflammatory activity. The disease or condition to be treated or ameliorated is preferably: (a) IBD; (b) rheumatoid arthritis; (c) Type I diabetes mellitus or autoimmune insulitis; (d) multiple sclerosis; (e) thyroiditis; (f) gastritis; (g) uveitis or uveoretinitis; (h) orchitis; (i)) oophoritis; (j) psoriasis; (k) prostatitis; (l) encephalomyelitis; (m) vitiligo; (n) rejection of a mismatched cell, tissue or organ graft; or (o) GVH disease.

The present method is used to inhibit the rejection of transplanted cells, tissue, or an organ (allo- or xeno-) that is, for example, mismatched for a major and/or one or more minor histocompatibility antigens. In the case of GVH disease, the recipient generally has received a transplant of allogeneic, semi-allogeneic or non-MHC-mismatched bone marrow cells or enriched or isolated hematopoietic stem cells that are responsible for mediating pathogenic effects.

The present invention is further directed to the novel chimeric DNA that can be used to produce the redirected T-cells described above, as well as to the chimeric receptor protein encoded thereby. Such chimeric DNA comprises:

a first DNA segment encoding an extracellular recognition region specific for a selected target antigen or ligand, which does not comprise an MHC protein extracellular domain, the selected target antigen or ligand being one that is present or expressed at a site or target tissue of a pathogenic or undesired immune response mediated by effector T-cells;

a second DNA segment encoding a transmembrane region; and a third DNA segment encoding an intracellular signaling region comprising a combination of T-cell signaling polypeptide moieties, which combination of moieties, upon transfection of the chimeric DNA into a regulatory T lymphocyte (Treg cell) and binding of the extracellular recognition region to the selected target antigen or ligand thereof, triggers activation of the Treg cells to cause suppression of T-cell mediated immunity, which chimeric DNA, upon transfection into a Treg cell, expresses the extracellular recognition region, the transmembrane region and the intracellular signaling region in one single, continuous chain on the surface of the transfected cell such that the transfected Treg is triggered to activate and cause suppression of T-cell mediated immunity when the expressed extracellular recognition region binds to its selected target antigen or ligand.

Figure 1:
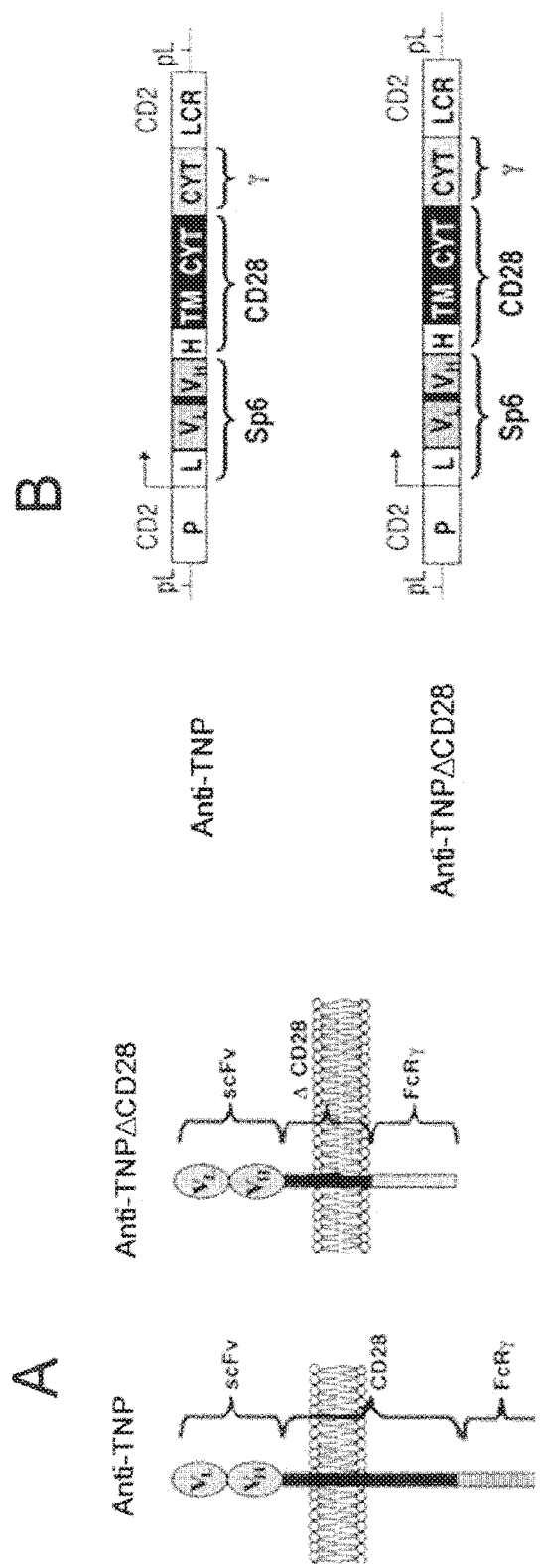
FIG. 1: Schematic diagram of TNP-specific TPCR structure. (A) Schematic presentation of the TNP-specific chimeric receptors. The TNP-specific CR encompasses a scFv derived from the anti-TNP mAb, Sp6. In the tripartite configuration, the scFv is joined in tandem to a short portion of CD28 (lacking the ligand-binding site) of the extracellular and including the transmembrane, and cytoplasmic domains fused to the FcRγ ITAM domain. (B) Chimeric receptor transgene constructs. Constructs used to generate the transgenic mice were placed under the control of the human CD2 promoter/enhancer that directs expression only in T and NK cells. CYT indicates cytoplasmic domain; H, hinge domain; L, immunoglobulin leader; LCR, locus control region; P, promoter; pL, plasmid sequence; TM, transmembrane domain; VH and VL, immunoglobulin heavy and light-chain variable domains, respectively; ΔCD28, truncated CD28 containing part of the extracellular and the transmembrane domain, and lacking the cytoplasmic signaling moiety.

a. TNP-TPCR: extracellular recognition region comprised an scFv ofa TNP-specific mAb.

b. MD2-TPCR: extracellular recognition region comprised an LPS binding fragment or motif of the human MD2 protein, an LPS co-receptor (that interacts with TLR4 receptors). The fragment of MD2 corresponds to residues 120-132 of SEQ ID NO:5. The sequences of such chimeric nucleic acids used here are SEQ ID NO:8 and 9.

c. CD14-TPCR: extracellular recognition region comprised an LPS binding fragment of the human CD14 protein, a known LPS receptor. The fragment of CD14 corresponds to residues 100-119 of SEQ ID NO:4. The sequences of such chimeric nucleic acids used here are SEQ ID NO:6 and 7.

d. MD2-CD14-TPCR: the extracellular recognition region comprised both the MD2 fragment and the CD14 fragments described above. The sequences of such chimeric nucleic acids used here are SEQ ID NO:10 and 11.

Each of the constructs encoded as stimulatory and costimulatory moieties, tandemly linked sequences encoding CD28 and FcRγ. Results are shown as side-by-side light and fluorescence micrographs.

FIG. 28. An annotated nucleotide sequence (SEQ ID NO: 1) and amino acid sequence (SEQ ID NO:2) of a TNP-specific tripartite CR as used herein. The annotations include the origin of the regions (scFv, here the "Sp6" mAb), the "CD28" region, and the FcRγ regions (indicated as "GAMMA"), as well as restriction sites, leader sequence, etc. The mature protein begins at amino acid residue 23.

FIG. 29. An annotated nucleotide sequence (SEQ ID NO:3) of a pBullet plasmid that includes a CR-encoding construct that comprises a nucleotide sequence encoding the scFv of mAb HB 9081 (i.e., produced by a hybridoma given ATCC Accession No. HB9081) fused to C28/FcRγ. This mAb and, hence, the scFv, is specific for LPS. Annotations show various restriction enzyme recognition sites, the leader sequence, and plasmid sequences.

FIG. 30A-30B. FIG. 30A is an annotated amino acids sequence of Human CD14 (SEQ ID NO:4). See GenBank Accession No. P08571. A signal sequence and an LPS-binding motif (residues 100-119) are noted. This protein serves as an LPS receptor on cells. FIG. 30B is an annotated amino acids sequence of Human MD-2 protein (SEQ ID NO:5). See GenBank Accession No. NP_056179. A signal sequence and an LPS-binding motif (residues 120-132) are noted. This LPS-binding protein interacts with TLR-4 as a co-receptor.

FIG. 31A-31B. FIG. 31A is an annotated nucleotide sequence (SEQ ID NO:6) showing the nucleotide sequence of a Chimeric Receptor comprising CD14 motif-CD28-FcRγ. FIG. 31B is an annotated nucleotide sequence (SEQ ID NO:7) showing the nucleotide sequence of a chimeric, bicistronic receptor: CD14 motif-CD28-FcRγ-IRES-GFP-Foxp3. Also shown is the amino acid sequence (single letter code) of the CD14 motif (residues 110-119 of SEQ ID NO:4). Annotations show various restriction sites, beginnings and ends of protein regions, IRES region, etc.

FIG. 32A-32B. FIG. 32A is an annotated nucleotide sequence (SEQ ID NO:8) showing the nucleotide sequence of a Chimeric Receptor comprising MD2 motif-CD28-FcRγ. FIG. 32B is an annotated nucleotide sequence (SEQ ID NO:9) showing the nucleotide sequence of a chimeric, bicistronic receptor: MD2 motif-CD28-FcRγ-IRES-GFP-Foxp3. Also shown is the amino acid sequence of the MD2 motif (residues 120-132 of SEQ ID NO:4. Annotations show various restriction sites, beginnings and ends of protein regions, IRES region, etc.

FIGS. 33A and 33B. FIG. 33A is an annotated nucleotide sequence (SEQ ID NO: 10) showing the nucleotide sequence of a Chimeric Receptor comprising MD2 motif-CD14 motif-CD28-FcRγ. FIG. 33B is an annotated nucleotide sequence (SEQ ID NO:11) showing the nucleotide sequence of a chimeric, bicistronic receptor: MD2 motif-CD14 motif-CD28-FcRγ-IRES-GFP-Foxp3. Also shown is the amino acid sequence of the MD2 motif (residues 120-132 of SEQ ID NO:4) and the amino acid sequence of the CD14 motif (residues 100-119 of SEQ ID NO:3). Nucleotides 106-148 of SEQ ID NO:11 (double underlined) encode a flexible linker (14 amino acids, SEQ ID NO:12, also double underlined). Annotations show various restriction sites, beginnings and ends of protein regions, IRES region, etc.

FIG. 34 is an annotated nucleotide sequence (SEQ ID NO: 13) showing the nucleotide sequence of a Chimeric Receptor comprising MD2-CD28-FcRγ (SEQ ID NO:13). Also shown is the amino acid sequence of the full length MD2 protein (SEQ ID NO:4). The LPS-binding region of this amino acid sequence is underscored. Annotations show various restriction sites, beginnings and ends of protein regions, etc.

FIG. 35 is an annotated nucleotide sequence (SEQ ID NO: 14) showing the nucleotide sequence of a chimeric, bicistronic receptor: MD2-CD28-FcRγ-IRES-GFP-Foxp3. Also shown is the amino acid sequence of the full length MD2 protein (SEQ ID NO:4). The LPS-binding region of this amino acid sequence is underscored. Annotations show various restriction sites, beginnings and ends of protein coding regions, IRES, vector sequence, etc.

DESCRIPTION OF THE PREFERRED EMBODIMENTS

Definitions

"Regulatory T lymphocyte" or "Treg cell" or "Treg," as used in the present specification and claims are synonymous and are intended to have its standard definition as used in the art. Treg cells are a specialized subpopulation of T cells that act in a "regulatory" way to suppress activation of the immune system and thereby maintain immune system homeostasis and tolerance to self-antigens. Tregs have sometimes been referred to suppressor T-cells. Treg cells are characterized by expression of the forkhead family transcription factor Foxp3 (forkhead box p3). They may also express CD4 or CD8 surface proteins. They usually also express CD25. As used in the present specification and claims, and unless otherwise specified, Tregs include natural Tregs and induced or adaptive Tregs and Tregs that have been created using recombinant DNA technology. Naturally-occurring Treg cells (CD4+CD25+Foxp3+) arise like all other T cells in the thymus. In contrast, adaptive Treg cells (also known as Tr1 cells or Th3 cells) may originate during a normal immune response. Antigen-specific activation of human effector T-cells leads to inducible expression of Foxp3 in a subgroup of the activated effector cells, and this subgroup can develop a regulatory (Treg) phenotype. One way to induce Tregs is by prolonged exposure of T effector cells to TGF-β. T-cells may also be converted to Treg cells by transfection or transduction of the Foxp3 gene into a mixed population of T-cells. A T-cell that is caused to express Foxp3 adopts the Treg phenotype and such recombinant Tregs are also defined herein as "Tregs".

"Redirected Treg" is intended to be a comprehensive term for Tregs carrying a chimeric receptor (CR) as described and claimed herein which confers on the cells the ability to bind to and be activated by a target antigen or ligand that is different from that to which a Treg population may have been previously specific (as controlled by its endogenous antigen-specific TCR). Redirected Tregs are "MHC-independent" and "non-MHC restricted" in the process of their activation and in their actions as they do not require association of a peptide derived from their target antigen or ligand with MHC in order to recognize it. However, for special purposes, it may be possible to design a redirected Treg that recognizes a specific epitope of an MHC molecule per se, e.g., functioning as a transplantation antigen. In such a case these redirected Tregs are still non-MHC restricted.

The term "selected target antigen or ligand" means a molecule to which the extracellular recognition region of the redirected Treg is intended to bind so as to activate that Treg. If the selected target is an antigen, then an antibody can be raised against it and the binding regions of such an antibody used to construct the extracellular recognition region of the redirected Treg. If the target molecule is a member of a receptor/ligand pair (defined below), then the other member of that pair can be used as part of the extracellular recognition region of the redirected Treg. Generally, in designing a redirected Treg for use according to this invention, the intended target tissue or site where the Treg is to be employed is first identified, and then, an antigen or ligand that is present on or near this intended target tissue or site is identified. An antibody or ligand/receptor that binds thereto is then identified, or, if necessary, created or constructed for use on the redirected Treg.

The term "ligand" as used herein, and particularly as part of the term "target antigen or ligand" or the term "receptor/ ligand pair" refers to a molecule that is able to bind to and form a complex with another biomolecule to serve a biological purpose. Often the binding partner of a ligand is called a receptor so that the two binding partners are termed a "receptor/ligand pair." For the purpose of the present specification and claims, the term "receptor," when used in the sense of a "receptor/ligand pair," has a broader meaning than, for example, a typical definition of a "receptor" as a protein in or on a cell that binds to a specific ligand. It is rather intended to mean any binding partner for a ligand. Either member of a binding pair can be considered the "ligand" while the other member is considered the "receptor." Thus, a classical receptor may qualify as a "ligand" when used herein in the term "target antigen or ligand" as it is one member of a receptor/ligand binding pair. For example, IL-2 can be a ligand because it binds to and forms a complex with another biomolecule, i.e., an IL-2 receptor (IL-2R), to serve a biological purpose. However, IL-2R is also a "ligand" because it is a molecule that binds to and forms a complex with another biomolecule, i.e., IL-2, to serve a biological purpose. Thus, under the present usage, if IL-2R is considered a ligand in the IL2R/IL-2 binding pair, IL-2 may be considered the receptor, and vice versa.

A "chimeric receptor," as used in the present specification and claims, is a recombinant polypeptide that includes an extracellular recognition region that is derived from one molecule and at least one intracellular signaling moiety that is derived from a different molecule. In that sense it is chimeric.

A "chimeric nucleic acid" is a recombinant polynucleotide that includes a sequence that encodes a chimeric receptor.

The terms "recombinant" or "recombinantly" when applied to a polynucleotide, polypeptide or cell means that the molecule or cell is made using genetic engineering techniques and would not exist but for the hand of man.

The term "T-cell signaling polypeptide moiety" means that portion of a molecule endogenous to a T-cell that mediates signaling. It may be a portion of a T-cell receptor molecule that mediates signaling, or a downstream signal-transducing enzyme or a portion thereof that mediates signaling, i.e., that has enzymatic activity.

The term "antibody-derived scFv domain" means a single-chain antibody in which the $V_L$ of a specific antibody is linked to the $V_H$ thereof by a flexible linker or spacer.

The term "an MHC protein extracellular domain" refers to the disclosure of Meal D J et al. (*Proc Natl Acad Sci USA* 2005; 102:11817-22), discussed below, and Jodi M D et al., *Nat. Biotechnol.*, 2002, 20:1215-1220. These publications describe Treg cells redirected against T-cells in a murine system. They used the class II MHC Is a and Is 13 chains as extracellular regions of two separate chimeric receptors for use in a redirected Treg. The term MHC protein extracellular domain is defined so as to encompass what was used in the Meal et al. and Jodi et al. publications and any analogs or fractions thereof that would have been obvious to a person of ordinary skill in the art to substitute for such domains for the purpose disclosed by Meal et al. and by Jodi et al., i.e., to cause binding of the redirected Treg to a T lymphocyte specifically directed to a particular autoantigen.

The term "flexible spacer" means any flexible peptide moiety that will facilitate the functionality of the extracellular recognition region. When this region is not rigidly attached to the transmembrane region, but is allowed some degree of flexibility with respect to the cell membrane, the ability of the recognition region to recognize and bind to its target antigen or ligand is facilitated. Small neutral amino acids, such as glycine and serine, confer such flexibility. Examples are Gly$_4$Ser and Gly$_4$Ser$_3$.

The "immunoglobulin superfamily" (Igs) means the large group of cell surface and soluble proteins that are involved in the recognition, binding, or adhesion processes of cells. Molecules are categorized as members of this superfamily based on shared structural features with immunoglobulins (also known as antibodies); they all possess a domain known as an immunoglobulin domain or fold. Members of the Igs include various cell surface antigen receptors, co-receptors and co-stimulatory molecules of the immune system, molecules involved in antigen presentation to lymphocytes, cell adhesion molecules and certain cytokine receptors. They are commonly, though not exclusively, associated with roles in the immune system.

The term "hinge" when referring to a region of a molecule of the Igs means the region between the $C_H1$ and $C_H2$ domains consisting of a small number of amino acids. The hinge is flexible and allows the binding region to move freely relative to the rest of the molecule. At the hinge region are the disulfide bridges which link the two dimers, creating the tetramer structural unit. Examples of such immunoglobulin hinge sequences may be found in U.S. Pat. No. 6,165,476, which is incorporated herein by reference.

The term "antigen-specific receptor of a T-cell" refers to a receptor that is found on a T-cell that is antigen-specific, i.e., naturally has an extracellular region that binds specifically to a particular antigen in preference to another. Examples of such antigen-specific receptors of a T-cell are the TCR α, β, γ or δ chains, the TCRαβ dimer and TCR dimer.

The term "TCR/CD3 complex" is sometimes called the "TCR complex." CD3 is a protein complex composed of four chains in mammals (CD3γ, CD3δ and two CD3ε chains), that associate with molecules known as the T cell receptor (TCR; see above) and with the ζ-chain and η-chain (as homo- or heterodimers) to generate an activation signal in T lymphocytes. The intracellular tails of these CD3 molecules contain a single conserved motif known as an "immunoreceptor tyrosine-based activation motif" or ITAM for short, which is essential for the signaling capacity of the TCR. The CD3-γ,-δ, and -εchains and the ζ- and η-chains, also known as CD3-ζ and CD3-η chains, together with the TCR, form what is known as the T cell receptor complex.

The term "T-cell costimulatory-receptor protein" means a receptor of the T-cell that provides a costimulatory signal. During the activation of T cells, costimulation is often crucial to the generation of an effective immune response. T cells require two signals to become fully activated. A first, antigen-specific, signal is provided through the T cell receptor/CD3 complex. A second signal, the costimulatory signal, is antigen-nonspecific and is provided by costimulatory molecules expressed on the T cell membrane. Examples of T-cell costimulatory-receptor proteins are CD28, OX40, CD40L, 4-1BB and PD-1.

The present invention is based on the conception that regulatory T-cells (Treg) that have been modified to possess antibody-type antigen specificity, can be harnessed to suppress T effector cells function in vivo. The action of these Treg cells is mediated in an antigen-nonspecific manner, primarily by release of suppressive cytokines in the vicinity where the Tregs are activated or stimulated by an antigen recognized by their TpCR. Once activated, Tregs can suppress bystander T cell responses. Thus, transfer of these cells that have been engineered to express the CRs (as described herein) to a subject in whom it is desired to suppress a T effector cell response and its attendant or consequent inflammation, and their delivery to, and activation at, the site of such inflammatory activity, results in therapeutic effects.

Thus, preferred target diseases or conditions for this invention are autoimmune diseases, more preferably, organ-specific, T cell-mediated autoimmune diseases. Other examples of undesired immune responsiveness to be targeted herein are graft rejection of solid tissue and organ grafts as well as grafts of suspended cells (e.g. bone marrow (BM) transplants or hemopoietic stem cell (HSV) transplant). Another target disease is graft-vs-host disease (GVH) that is a common consequence of a mismatched BM or HSV transplant. An additional condition targeted by this invention is transplant rejection (e.g., of a mismatched kidney) where the recipient's immune effector cells reject the graft.

Because the Foxp3 transcription factor (a member of the forkhead family) appears to be essential for Treg development and function, and is a distinctive marker for these cells (along with CD4 and CD25), the present invention provides methods for producing Tregs, as well as providing the Tregs produced by those methods, that are based on induction of Foxp3 in T-cells in a process of driving cells along the pathway to Treg status.

In another embodiment, DNA encoding Foxp3 is transduced or transfected into T-cells using any suitable expression vector as a delivery vehicle in a process to drive these cells to become Tregs. Further support for this conception is found in reports that prevention of Foxp3 expression in vivo results in animals with a propensity for development of autoimmune and lymphoproliferative disorders (Sakaguchi S, et al., *J Immunol* 1995; 155:1151-64; Hori S et al., *Science* 2003; 299:1057-61; Khattri R, et al., supra; Fontenot J D et al., *Nat Immunol*. 2003; 4:330-6.).

The starting population can be total PBL, T-cells that have been enriched or isolated from PBL, or CD4+ T-cells that have been enriched or isolated from such T-cells (either expressing CD25 or not). These cells can be redirected by transducing the TpCR prior to, concomitantly with, or after transducing DNA encoding Foxp3 DNA, preferably in the form of a Foxp3 expression vector. Walker M R. et al., 2005, *Proc Natl Acad Sci USA*. 102:4103-8, have shown that antigen-specific human CD4+CD25+ Treg cells can be generated de novo from CD4+CD25− cells. The advantage of the present invention over the approach described by Walker et al. is that the antigen-specificity and Treg activation requirements are independent of the MHC. This important improvement makes isolation and activation of antigen-specific Tregs simpler and allows for therapeutic methods (described below) in which the antigen can be conveniently administered together with the transferred Treg cells to a desired site, such as an inflammatory site, exemplified by the colon in IBD.

Naturally-Occurring Vs. Inducible Tregs

"Classical" naturally-occurring Tregs are thymus-derived, express high levels of Foxp3 and suppress activation of effector lymphocytes. Antigen-specific activation of human effector T-cells leads to inducible expression of Foxp3 in a subgroup of the activated effector cells, which subgroup can develop a regulatory (Treg) phenotype. These induced regulatory T-cells can suppress (independently of cell contact) freshly isolated effector cells (Walker M R., et al., 2005, supra; Walker M R., et al., 2003, *J Clin Invest*. 112:1437-43). In mice, both in vitro and in vivo induction of Tregs is achieved by prolonged exposure of effector cells to TGF-β (Wan Y R, et al., 2005, *Proc Natl Acad Sci USA*. 102:5126-31; Mantini M C, et al., 2004, *J Immunol*. 72:5149-53; Mantini et al., 2006, supra). This small, peripherally generated population of inducible Tregs are believed to play a central role in regulating and containing ongoing immune responses just as the lack of Treg induction is associated with a propensity for autoimmunity.

Genetic Manipulation of CD4+CD25+T Regulatory Cells

According to the present invention, approaches that specifically redirect regulatory T-cells to suppress the activity of pathological T-cells are beneficial in inflammatory conditions by facilitating localization of Tregs to inflammatory sites and their specific activation by inflammation-associated antigens. When specifically activated in inflammatory lesions, such Tregs are expected to attenuate inflammatory disease by suppressing pathogenic effector T lymphocytes in an antigen-nonspecific, MHC-unrestricted, manner.

The MHC-independent activation and action of Treg cells according to the present invention is an important advantage. Such action is contrasted with the report of Meal D J et al. (*Proc Natl Acad Sci USA* 2005; 102:11817-22) of a study of experimental allergic encephalomyelitis (EAE) which described CD4+25+ Treg cells redirected against myelin basic protein (MBP) epitope 89-101-reactive T cells by a CR that included the MBP epitope linked to MHC class II protein. By enforcing the interaction between a Treg cell and the autoreactive T cells directed against MBP epitope 89-101, the Treg activity is antigen-specifically focused against the autoreactive T-cells. Such a model requires some degree of MHC-dependency as a single CR can only have domains of a single MHC and thus can only be used for patients with that HLA characteristic.

In contrast, the Treg cells of the present invention act to suppress pathogenic T effector cells in an MHC-independent manner, making them more advantageous for treating autoimmune/inflammatory conditions because they can target common target antigens shared among many individuals. In the model of Meal et al., supra, Tregs acted by MHC- and antigen-restricted engagement. As such these Tregs, which express the ligand that is recognized by the TCR of the autoreactive T-cells, are stimulated by such interaction and suppress the effector cells. However, as a clinical approach this suffers from the disadvantage that it would require full donor-recipient MHC compatibility in the human population in which MHC (HLA) diversity is substantial. Moreover, such an approach would be limited to suppression of clones that are autoreactive against a single, recognizable peptide epitope in the context of defined MHC-II (HLA-DR). An additional significant advantage of the present invention is that it overcomes the requirement that the pathogenic antigen be known. Indeed, disease-associated antigens in a large number of human autoimmune disorders, including human IBD, are not yet known and may be multiple in number.

The "T-Body" Approach of the Present Invention

The "T-body" approach was designed by one of the present inventors and his colleagues as a novel modality for specific redirection and activation of effector T lymphocytes towards pre-defined targets, mostly those associated with neoplastic processes (e.g., Pin thus JHU et al., *J Clin Invest* 2004; 114:1774-81) and infectious diseases (Bitton N, et al., *Curr Top Microbiol Immunol* 2001; 260:271-300). The T-body approach was intended to overcome the relative inaccessibility of antibodies to certain sites (such as solid tumors) and the general ineffectiveness of tumor-infiltrating lymphocytes to combat solid tumors by combining into one effector cell population the properties of the humoral and cellular arms of the immune system (Gross G et al., 1989; supra Eshhar Z, et al., *Br J Cancer Suppl*, 1990; 10:27-9).

The preferred T-body chimeric receptors comprise a ligand binding portion, preferably (1) a single chain antibody variable region (scFv) directed against a disease-associated antigen, linked to (2) an optional extracellular spacer and a transmembrane region and (3) one or more intracytoplasmic moieties of T cell costimulatory and stimulator/signaling molecules. Such CRs as initially developed enable non-MHC restricted, specific antibody-type recognition, homing and penetration of neoplastic tissues. Within the target tissues, antigen-specific activation of chimeric-receptor bearing T effector cells enabled T cell-mediated destruction of tumor cells either by direct cytotoxicity or by induction of a local inflammatory response.

While the scFv domain is the preferred recognition unit of the present invention, in other embodiments, it may be substituted by another structure that serves as a targeting ligand (or ligand binding partner) that will facilitate bringing the Treg cells expressing the CR to a selected site or a selected antigen. Capon and colleagues have disclosed a number of CRs of this sort, such as one where a ligand binding partner polypeptide is fused at its C-terminus to the N-terminus of an immunoglobulin constant region. See, for example, Roberts M R. et al., *Blood* 1994; 84:2878-89; Ashkenazi A et al., *Int Rev Immunol.* 1993; 10:219-27; Chamow S M et al., *Int J Cancer Suppl.* 1992; 7:69-72. See also U.S. Pat. Nos. 6,710,169; 6,407,221; 6,406,697; 6,319,494; 6,117,655; 6,103,521; 6,077,947; 5,741,899; 5,714,147; 5,514,582; 5,455,165; 5,428,130; 5,359,046; 5,336,603; 5,225,538; and 5,116,964. All of these documents are incorporated by reference in their entirety.

The CR polypeptide of the present invention is characterized broadly as comprising (1) an extracellular portion or domain capable of binding to a ligand (such as a target antigen) in a non-MHC restricted manner, (2) an optional extracellular spacer and a transmembrane domain and (3) a cytoplasmic region (one or more domains) capable of activating an intracellular signaling pathway.

Examples of preferred T cell CRs comprise a first binding domain, a preferred example of which is an extracellular scFv fragment derived from a monoclonal antibody (mAb) specific for a selected antigen. The foregoing domain is fused to a spacer domain (preferably a hinge domain of the Ig family that provides spacing and flexibility), a transmembrane domain, a costimulatory region, for example parts of a CD28 molecule, and a further intracellular signaling moiety for T-cells. Examples of the latter include a TCR/CD3 complex-associated chain ζ or η chain, or an ITAM-containing cytoplasmic region such as the γ chain of an Ig Fc receptor (FcRγ). An ITAM is an "immunoreceptor tyrosine-based activation motif; for reviews, see Humphrey M B et al., *Immunol Rev.* 2005 December; 208:50-65; Pitcher L A et al., *Trends Immunol.* 2003; 24:554-60; Isakov N, *Receptors Channels.* 1998; 5:243-53; Daeron M, *Annu Rev Immunol.* 1997; 15:203-34; Isakov N, *J Leukoc Biol.* 1997; 61:6-16; Cambier J C, *J Immunol.* 1995; 155:3281-5; Flaswinkel H et al., *Semin Immunol.* 1995; 7:21-7, all of which are incorporated by reference in their entirety. It is also possible to use the intracellular portions of TCR α, β, γ or δ receptor molecules in the CR for this purpose. The signaling moiety of a cytokine receptor may also be present in the chimeric receptor chain for use in the present invention. For example, adding the signaling portion of the IL-2 receptor will cause the Treg cell to further act as if it had been subjected to external IL-2 upon binding of the extracellular targeting domain to the selected target antigen or ligand. Furthermore, adding the signaling moiety of the TGFβ receptor will induce a T effector cell to become a Treg cell and thus this may also be a useful addition to the chimeric receptor chain of the present invention. Such CRs expressed on T-cells are known to be functional and, upon exposure to antigen, promote cytokine production (and, when expressed on appropriate effector cell type in the prior art, promoted lysis of antigen-bearing target cells (Stancovski I, et al., *J Immunol* 1993; 151:6577-82)).

An early configuration of a scFv-based CR comprised an extra-cellular recognition domain and an intracellular signaling moiety. Full activation of such T-bodies through the CR required either pre-stimulation of the T-body or activation of a costimulatory pathway by exposure to CD08/CD86 (B7)-bearing antigen presenting cells (APCs).

The creation of a tripartite chimeric receptor (TpCR) by one of the present inventors and by others (Pule M A, et al., *Mol Ther.* 2005; 12:933-41)), in which the signaling domain of the costimulatory CD28 molecule was added to the cytoplasmic domain of the CR, enabled antigen-mediated activation of both the stimulatory and costimulatory signaling pathways independent of B7-CD28 interactions (Eshhar et al., 2001, supra). This approach facilitates full activation of scFv-expressing lymphocytes, resulting in improved effects (in the case of T effector cells, improved anti-tumor; Pin thus JHU et al., supra).

Another useful intracellular signaling domain for the present invention is all or part of the cytoplasmic domain of a phosphotyrosine kinase (e.g., a molecule of the Syk family) which is fused to the CR. See, for example, Eshhar Z & Fitzer-Attas C J, *Adv Drug Deliv Rev.* 1998; 31:171-82; Fitzer-Attas C J et al., *J Immunol.* 1998; 160:145-54.; and Eshhar Z et al., *Springer Semin Immunopathol.* 1996; 18(2): 199-209. Use of such a signaling moiety bypasses membrane-proximal signaling events that are often defective in T-cells of subjects with acute or chronic inflammation or cancer.

Costimulatory Domains/Regions and Signals in the Tripartite Chimeric Receptor

Retroviral-mediated expression of CRs in T-cells in general requires T cell activation which activation is commonly achieved by combined use of anti-CD3 and anti-CD28 antibodies. Such pre-activation was sufficient to prime the T-cells to respond to a signal mediated through the CR upon interaction with the antigen for which the CR is specific—both in vitro and in vivo (e.g., Schwartz R H; *Annu Rev Immunol* 2003; 21:305-34). A costimulatory signal is advantageous for optimal and sustained T cell function and antigen-driven re-activation, even by targets that often lack ligands for costimulatory molecules.

Antigen stimulation alone of CRs that lack a structure or mechanism for costimulatory signaling is generally inadequate to activate resting or naïve lymphocytes (Brocker T et al., *J Exp Med* 1995; 181:1653-9). Thus, in the absence of costimulatory signaling by CD28, resting T lymphocytes typically undergo anergy or apoptosis (Boussiotis V A et al., *Immunol Rev* 1996; 153:5-26). For further discussion of CD28 and its interactions with B7, see also, L. Chen (ed.) *The B7-CD28 Family Molecules*, Landes Bioscience, 2003, which is incorporated by reference in its entirety.

To overcome these limitations in the CR's used in the present invention, the first (recognition) domain, preferably an scFv domain, is linked through an Ig hinge spacer and transmembrane segments to the intracellular segment of a costimulatory signaling molecule, preferably CD28, and then to an intracellular activation region, such as from the CD3 ζ chain or the FcR γ chain. Co-expression of two CRs, each with the same scFv, the first linked to CD3 ζ and the second to CD28, was found to provide the requisite stimulatory and costimulatory signals for T cell activation (Beecham E J et al., *J Immunother* 2000; 23:631-42).

Thus, in one preferred embodiment herein, an extracellular recognition site, preferably an antibody-based recognition site such as an scFv, is linked to a CD28 intracellular domain "in series" and further linked to the intracellular signaling region of the TCR complex ζ chain. Such a construct was 20-fold more potent in stimulating IL-2 production upon exposure to solid phase antigen (compared with transfectants expressing CR's lacking the CD28 domain (Finney H M et al., *J Immunol* 1998; 161:2791-7)). Intracellularly, this domain in the CR binds the p85 subunit of phosphatidylinositol 3'-kinase.

One of the present inventors designed a novel tripartite CR composed of a scFv recognition moiety fused to the non-ligand binding part of the extracellular domain (ECD) of CD28, the entire transmembrane and intracellular domains of CD28, and the intracellular stimulatory domain of FcRγ ("scFv-CD28-γ") (Eshhar et al., 2001, supra). Human PBL transduced with a nucleic acid construct encoding this CR were specifically stimulated to produce IL-2. Activation was dependent on CD28 costimulatory activity.

The present inventors' laboratory has generated several lines of Tg mice expressing CRs under control of T cell-specific regulatory sequences. T lymphocytes from unprimed, naïve mice that are Tg for the scFv-CD28-γ TpCR manifested potent responses (proliferation, IL-2 secretion, and rescue from apoptosis) upon stimulation solely by the cognate antigen in immobilized form (Friedmann-Morvinski D et al., supra).

According to the present invention, molecules other than, or in addition to, CD28 are exploited to provide costimulatory signals when included in the present CR configuration. Preferred examples of these are the members of the "inducible co-stimulator" (ICOS) family, including OX40 (CD134), CD40 ligand (CD40L, CD154), PD-1 ("programmed death receptor-1), and 4-1BB (CD137). Each of these ligand/receptor pairs possess distinct functions that differ according to the nature of the stimulus and the "antigenic history" of the T-cells on which they are expressed. For example, CD28 signaling is accompanied by induction of ICOS, which, in turn, co-stimulates CD4+ T cell activation. The engagement of OX40 (studied in the context of tumor-specific adoptive immunotherapy) improved survival and anti-metastatic actions of T effector cells by CD4+T helper cell-dependent mechanism (Weinberg A D, *Trends Immunol* 2002; 23:102-9). Activation of OX40 promotes expression of anti-apoptotic proteins Bcl-XL and Bcl-2 and, accordingly, enhances the survival and hence the number of antigen-specific CD4+T-cells, resulting in strong antigen-specific CD4+ T cell memory. Engagement of 4-1BB (CD137) costimulatory receptor with its ligand, 4-1BBL, increased TCR-induced proliferation, survival, and cytokine production in both CD4+ and CD8+ T-cells (Cheuk A T et al., *Cancer Gene Ther* 2004; 11:215-26). Cell survival was associated with increased expression of the anti-apoptotic genes bcl-XL and bfl-l. In general, the interacting ligand/receptor pair 4-1BB/4-1BBL acts to amplify existing costimulatory signals, particularly those emanating from CD28 (Guinn B A et al., *J Immunol* 1999; 162:5003-10). Human CD4+ T-cells express PD-1 and its ligands, PD-L1 and PD-L2, upon activation. Antibodies to the receptor can be agonists or antagonists of the apoptotic pathway. PD-1 engagement can promote ICOS- or CD28-mediated costimulation. (e.g., Bennett F et al., *J Immunol.* 2003; 170:711-8.

The activity of costimulatory domains of CD28, ICOS, OX40 (CD134), and 4-1BB (CD137) in CRs is also known in human CD4+ and CD8+ T-cells (Finney H M et al., *J Immunol* 2004; 172:104-13). In that study, the tripartite genes were electroporated into cells to avoid pre-activation of the cells. When CR-bearing T-cells were stimulated by their specific antigen (CD33), cytokine release and cytotoxic activity were dramatically enhanced compared to cells in which the CRs lacked costimulatory signaling structures. Inclusion of the 4-1BB signaling domain as the costimulatory moiety in a TpCR on human T-cells with specificity against the CD19 antigen (anti-CD19-1BB-ζ) led to potent cytotoxicity against CD19-bearing acute lymphoblastic leukemia target cells in vitro (Imai C, et al., 2004; 18:676-84).

While the present invention includes the use of an intracellular domain or part of any of these costimulatory sequences in the CR, it is not certain that signaling evoked by these molecules has practical advantages over use of the CD28 costimulatory sequences alone. So, even though the performance of CD28 appears thus far to be quite satisfactory both in vitro and in vivo, the present invention includes within its scope the use of additional or alternative costimulatory systems to CD28 for generating Treg cells that perform optimally in suppressing T effector cells and treating autoimmune/inflammatory and other conditions as described herein. 4-1BB has been used successfully as an alternative to CD28 in T-bodies. See Zhang et al., *J. Immunol.*, 2007; 179:4910-4918.

Transfer of Redirected Tregs to Recipient Subjects

Use of transferred T-cells in vivo in adoptive therapy requires that transferred cells survive, overcome the host's homeostatic control mechanisms that may serve to hinder the acceptance of these cells, and migrate to (home to, or traffic to) and accumulate or localize at, the desired target site(s).

The immune system utilizes internal stimuli to regulate the total size of lymphocyte pools. The total number of peripheral T lymphocytes remains fairly constant, despite production of new cells, turnover of existing cells, and clonal expansion of antigen-specific cells during an immune response (Jameson S C. *Nat Rev Immunol* 2002; 2:547-56.). These "internal stimuli," include cytokines and self-peptide-MHC ligands for the TCR. At least two general mechanisms are believed to be responsible for homeostatic effects of bystander T-cells in limiting proliferation: (1) inhibition by physical T cell-T cell interactions; and/or (2) competition for limited "resources" (e.g., IL-7 and access to APCs with suitable self-MHC ligands). The most prominent cytokines in this process are those that signal through receptors containing a common γ chain, termed collectively "γC cytokines. "These include IL-2, IL-4, IL-7, IL-9, IL-15, and IL-21. Homeostatic control of naïve T cell expansion (examined in vitro) is supported by IL-4, IL-7, IL15 and IL21 through the CD28 transmembrane region, whereas only IL-7 appears to be required in vivo (Jameson, supra).

Lymphodepletion or "lymphoablation" is preferably performed to condition a recipient of the transduced Tregs of the present invention. Any method known in the art may be used, for example, irradiation, treatment with certain antimetabolites such as fludarabine, etc. Such treatments have been used in conjunction with adoptive T cell therapy in other contexts. Lymphodepletion in vivo performed as a precursor to adoptive cell transfer is known to boost antitumor immunotherapeutic activity in mice and in humans (as studied particularly with autologous, tumor-reactive T effector cells; Klebanoff C A et al., *Trends Immunol* 2005; 26:111-7). In clinical trials, objective response rates of 50% were seen in patients with solid metastatic tumors who had first been subjected to lymphodepletion. The mechanisms that are believed to underlie such effects include: the elimination of cellular cytokine 'sinks' for homeostatic γC-cytokines (such as IL-7, IL-15 and possibly IL-21 (which serve to activate and expand effector T-cells)), induction of tumor cell apoptosis and necrosis in conjunction with APC activation, and, most important for the present invention, the impairment of CD4+CD25+ Treg cells that suppress T effector cells.

As noted, treatment with homeostatic cytokines may be used to maintain the Treg populations in the recipient.

The present inventors' group found that activation of T-cells in general and T-bodies in particular (such as that required during the ex vivo manipulations to express the CR with certain vectors) down regulated expression of the chemokine receptor CXCR4, thereby impairing T cell homing in response to the chemokine SDF-1, for example. SDF-1 is a chemoattractant for T-cells that express the CXCR4 (Bleul C C et al., *J Exp Med* 1996; 184:1101-9; Beider K et al., *Blood* 2003; 102:1951-8). Using ErbB2-specific human T-bodies; these investigators showed that this homing is an essential step for the T effector cells to act in vivo, measured as inhibition of advanced prostate cancer progression and even cure (Pin thus et al., supra). Based on the foregoing knowledge, according to the present invention, redirected Treg cells must either home/migrate to the desired target sites or be administered to such sites.

Persistence of Responses of TpCR-Bearing T-Cells

A key factor for success of adoptively transferred T cell therapy (which thus far has been examined most thoroughly with T effector cells in cancer) is maintenance of the transduced T-cells' (effector) function. In one embodiment of the present invention, it is desired to maintain the function of Tregs that have been administered to perform a suppressive function. In another embodiment, it may be preferred that the Tregs act in shorter "bursts" to curtail a more acute (rather than a chronic) T effector response.

Because lymphocytes found in tumor patients include CD4+CD25+ Treg cells that suppress T effector cells (Wang H Y et al., *Immunity* 2004; 20:107-18; Curiel T J, et al., *Nat Med* 2004; 10:942-9), such "endogenous" suppressive activity must be overcome to optimize the action of redirected T effector cells. In the present invention, the objective is the converse: redirected Treg cells are administered to a subject in need thereof to quell or otherwise inhibit immune/inflammatory responses that characterize autoimmune conditions, transplant rejection, etc.

Examples of Clinical Trials Using Redirected T-Cells

While clinical trials using Tregs in accordance with the present invention have not yet been carried out, a number trials using redirected, CR-bearing T effector cells are described below. Advantage may be taken of various lessons learned in those trials in practicing the present invention.

In a Phase I trial in HIV infected subjects, autologous lymphocytes bearing a CD4-ζ CR were administered (Mitsuyasu R T, et al., 2000, *Blood* 96:785-93). Out of 24 patients, 11 also received concurrent IL-2 infusions for 5 days. The treatment was well tolerated. In some patients, a transient decrease of the viral load was observed in plasma and rectal mucosa (the tissue reservoir for HIV). All subjects tested negative for replication-competent retrovirus (the delivery vector) for up to 1 year after infusion.

Cell Genesys, Inc. conducted phase I clinical trials in colorectal cancer patients using an anti-TAG72-ζ CR made from the humanized CC49 mAb (Warren R et al., In: *7th International Conference on Gene Therapy of Cancer;* 1998).

The group of Junghans tested 24 doses of CR-bearing lymphocytes the antigen-specificity of which was directed to CEA in colorectal patients. Up to $10^{11}$ cells/patient were given. The treatment was adequately tolerated (Junghans R et al., *Proc Am Assoc Can Res,* 2000, 41:543).

Hwu and co-workers at the National Cancer Institute conducted a phase I clinical trial in ovarian cancer patients using T-bodies expressing a CR directed against the MoV18-murine anti-folate-binding protein. Large doses of the modified cells were infused into patients together with controlled administration of IL-2. No adverse side effects were reported. Neutralizing antibodies specific to murine MoV18 mAb determinants were found in the sera of several patients (Kershaw M H et al., *Clin Canc Res,* 2006; 12:6106-15.

A Phase I clinical trial in renal cell cancer (RCC) employed autologous G250-specific genetically modified T lymphocytes (Lamers C H J et al., *Daniel den Hoed Cancer News,* 2004, 2:8-10). Infusions of these cells were clinically well-tolerated. After 4-5 infusions, patients began to develop liver enzyme abnormalities, a finding explained by the reactivity of the infused T-cells with G250L expressed on bile duct epithelium, albeit at low levels. Treatment was thus limited to only low doses of CR-expressing T-bodies. The results showed in any case that the redirected T-cells did exert CR-dictated functions in vivo.

Two other Phase I clinical trials have been initiated though their results have not yet been reported to the best of the inventors' knowledge. One Phase I trial treated neuroblastoma patients with PBLs and Epstein Barr virus-specific CTLs, both expressing GD-2 specific chimeric T cell receptors (Brenner M K. World wide web URL clinicaltrials.gov/ct/show/NCT00085930, 2005). The other trial employs genetically modified CD20-specific CD8+CTLs for relapsed follicular lymphoma (Wang J, et al., *Mol Ther* 2004; 9:577-86

The present inventors recognize that certain events may interfere with the efficacy of the therapy using Treg cells expressing CR's in vivo in humans, for example:

(1) formation of neutralizing anti-idiotypic antibodies directed to an idiotope of the scFv part of the CR that could reduced the life-span or effectiveness of the Tregs;

(2) the low proportion of engineered cells that eventually reached the targeted sites and;

(3) the potential damage to healthy tissue that expresses the targeted antigen.

The use of Tregs according to the present invention has a much lower risk of (3). As described herein, direct administration of Tregs to sites of inflammation should overcome the limitation of (1)-(3). Adjustment of dose regimens (number of cells, frequency of administration) using routine clinical considerations are expected to limit the impact of the above limiting factors.

According to the present invention, an effective amount of redirected Treg cells are administered to a subject. Preferred carriers for the Treg cells are phosphate buffer, preferably 0.01-0.1M, more preferably 0.05M, or 0.8% saline. Acceptable diluents or carriers for various routes of administration are well-known.

While individual needs vary, determination of optimal ranges of effective amounts of a given cell type for a particular disease or condition is within the skill of the art.

The dosage administered will be dependent upon the age, health, and weight of the recipient, kind of concurrent treatment, if any, frequency of treatment, and the nature of the effect desired. Determination of the effective amounts can readily be made empirically by those of ordinary skill in the art without undue experimentation.

Typical dosages are between about $10^6$ and about $10^{11}$ Treg cells per injection or infusion, more preferably, about $10^7$ to about $10^{10}$ cells. If an antigen is to be administered with the cells (or separately, but to a site where it is intended to activate the cells), a dose of about 0.01 to 100 mg/kg/body preferably, 0.1 to 50 mg/kg/body wt is preferred.

An effective amount of Treg cells is that needed to induce a measurable change, generally a decrease, in the severity of any measurable symptom of the disease, preferably more than one symptom, and most preferably, would result in cessation of symptoms and cure of the disease or condition. For example, without limiting the invention, the above decrease may be at least about 10%, more preferably at least about 20%, more preferably at least about 30%, even more preferably, at least about 40%, and more preferably, at least about 50%, 60%, 70%, 80%, 90%, 95%, or 99%. It is within the skill of the clinical arts to determine when such therapeutic goals have been achieved, and to adjust the dose or frequency of administration accordingly, or to cease further treatment.

The Treg cells of the invention may be given once, or on multiple occasions, via a single or multiple routes. The cells may be administered daily, or preferably on alternate days, preferably weekly or biweekly. Administration can range over an interval of several days to weeks, or even months or years. The frequency and duration of administration can be determined empirically, or based on the clinical history and experience of the subject.

The cellular compositions of the present invention can be administered by any of a number of means and routes known in the art. Administration is preferably parenteral. Preferred routes include, intravenous, intramuscular, subcutaneous, intraperitoneal, intra-articular, intracerebroventricular, intraluminal (preferably into the lumen of the ileum or colon), rectal or the topical route. Also included is the "intrathecal" route, which is intended to encompass injection, infusion or instillation directly into a cavity or space (thecum) surrounding an organ or body region in which an undesired immune/inflammatory response is occurring. Such spaces include the pleural space, peritoneum, subarachnoid space or dural space, or pericardial space. The generic term for administration into a sheath encasing an organ is termed "intrathecal (see, for example, definition in Dorland's Medical Dictionary 29$^{th}$ Edition, WB Saunders (2000) and Stedman's Medical Dictionary, 27$^{th}$ Edition, Lippincott, Williams & Wilkins (2000)) as meaning "within a sheath." As used herein, this term is intended to be broader than a more commonly used definition which is limited to intracranial spaces.

The compositions, methods, and products of this invention are applicable to human and veterinary uses. The preferred subject is a human.

Transgenic Mice Expressing TNP-Specific Chimeric Receptors

Several Tg strains of mice that express the TNP-specific TpCR, that were recently produced by the present inventors and their colleagues (Friedmann-Morvinski D, 2005) are described herein. These mice are the source of TNP-specific T effector and T regulatory cells and are used as experimental animals in which the induction of colitis is evaluated using the 'classical' reactive hapten, TNBS. As a control for these CR-bearing cells, cells from erbB-2-specific TpCR Tg mice that were produced in the present inventors' laboratory are used as they express a CR specific for an irrelevant antigen.

All mature T-cells and NK cells in these Tg mice express the scFv-CD28-FcRγ construct. Naïve Tg T-cells can be fully activated by plastic-immobilized TNP without the need for pre-sensitization. (Friedmann-Morvinski D, et al., supra). Results in the Examples herein show that splenic CD4+CD25+ Tregs isolated from such mice specifically suppress proliferation and cytokine secretion by TNP-specific effector T-cells. Moreover, these Tregs are responsible for the delayed development and attenuation of TNBS-induced colitis in these animals. Of importance is the fact that the level of Tregs in the periphery of the TNP-specific TpCR-expressing strains is higher than in wild-type (WT) mice and that the Tregs do not require pre-activation to exhibit their suppressive activity in vivo. This is believed to result from the cross-reactivity of the SP6 mAb, from which the scFv of the TpCR was derived.

Delivery of DNA Encoding the CR into T-Cells

Genetic modification of human peripheral T-cells is achieved in one embodiment using retroviral vectors (Eshhar Z, et al., 2001, supra). As a non-limiting example, the pBullet vector is used, into which the CR-encoding cDNA (Weijtens M E, et al., 1998) is introduced. A bicistronic expression construct is used in which the TpCR and eGFP cDNA are expressed under control of the LTR. This serves to generate a packaging cell based on PG13 that is being used to pseudotype the retroviral vector with the gibbon ape leukemia virus (GALV). Flow cytometric sorting is done on the basis of eGFP expression, and packaging cells producing high-titer virions are selected to achieve high transduction efficacy.

To transduce human lymphocytes from healthy donors, lymphocytes are activated in culture with plate-bound anti-CD3 and anti-CD28 mAbs (or using commercial microbeads coated with these antibodies; e.g. from Invitrogen, Miltenyi Biotec, Inc.) and are transferred to plates coated with Retronectin™ (fibronectin fragment CH-296) plates together with fresh supernatants taken from the packaging cells. At the end of the process that takes 5-8 days, cells are propagated in the presence of IL-2 and then harvested and used. Following this ex vivo procedure, 45-70% of the cells are positive for CR (and GFP) expression.

Useful additional reagents are anti-idiotypic antibodies against idiotopes of the scFv of the TpCR. These enable direct labeling and visualization of TpCR on cell membranes. Such antibodies against the SP6 scFv (exemplified below) have been made and used by the present inventors.

Figure 27:
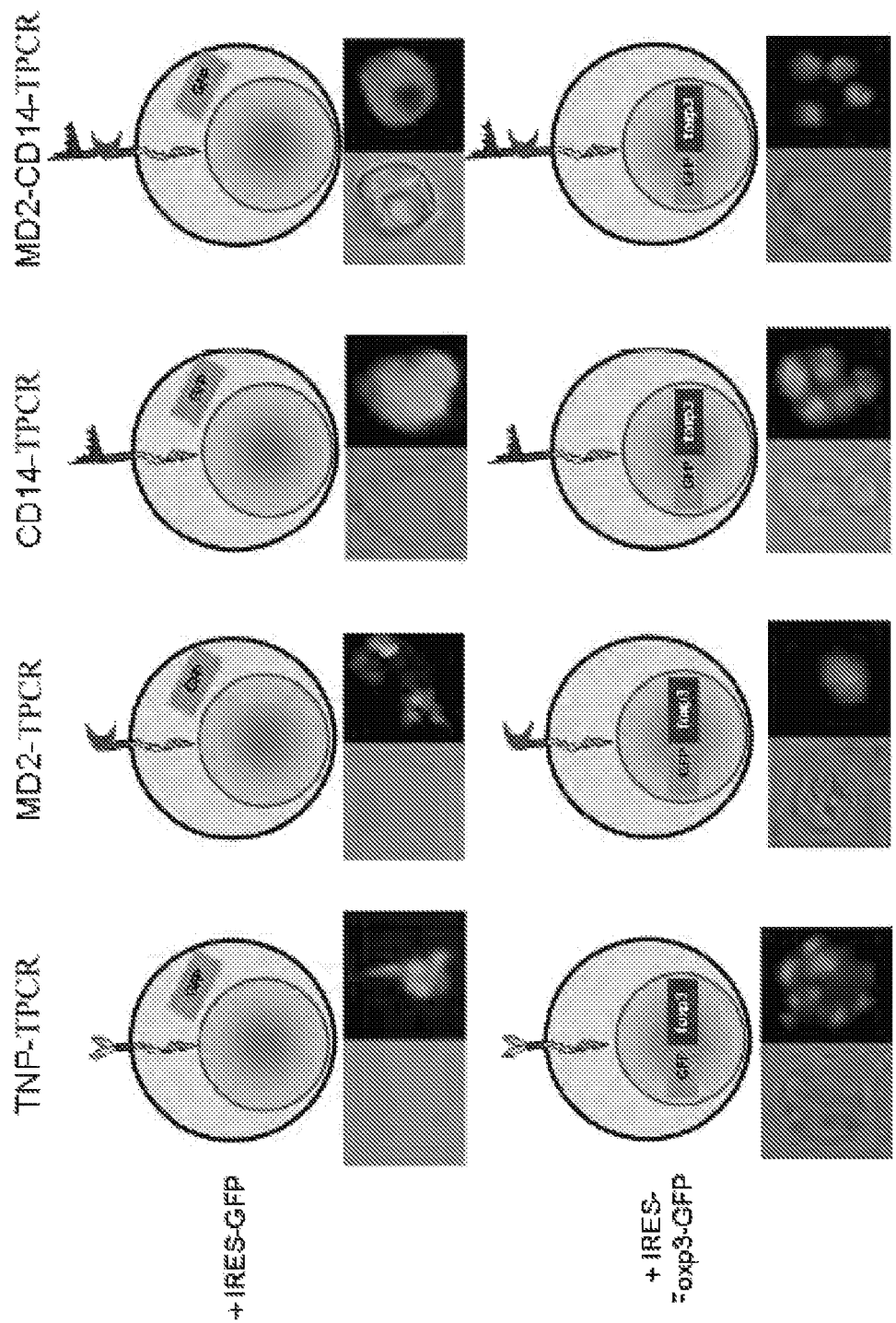
FIG. 27 shows 8 schematic drawings of T cells which are transduced with a retroviral vector that carried one of 8 CR constructs that include the detectable fluorescent protein, eGFP. Those depicted in the lower half of the Figure are bicistronic constructs that encode a fusion of GFP and the transcription factor Foxp3. Light and fluorescence microscopy were used to follow expression of the GFP in the cytoplasm of nucleus of the transduced cells. The constructs are labeled as follows (where "TPCR" refers to "tripartite chimeric receptor" even though, some of these CR's were "more" than tripartite).

An annotated nucleotide sequence (SEQ ID NO:1) and amino acid sequence (SEQ ID NO:2) of the TNP-specific TpCR used herein is shown in FIG. 27. The mature protein begins at amino acid residue 23 of SEQ ID NO:2.

A preferred sequence that excludes the scFv above, and that can be linked to any other appropriate ligand binding region, preferably a different scFv specific for another antigen, is that defined by the above sequences beginning at the CD28 region. Thus, a preferred nucleotide coding sequence is nucleotides 2203-2523 of SEQ ID NO:1 and amino acids 260-367 of SEQ ID NO:2. Additional nucleotides comprising a 5' restriction site, and amino acids "inadvertently" encoded thereby, may also be included in a preferred sequence. Additional coding sequence added at the 3'end of 2203-2523 of SEQ ID NO:1, or additional amino acids encoded thereby and added to at the C-terminus of 260-367 of SEQ ID NO:2, may be present, provided that they permit the encoded sequence, as expressed on the redirected Tregs, to function as a TpCR in ways described herein. Those skilled in the art of cloning and recombinant DNA technology will understand how to modify theses sequences to achieve the desired objective without undue experimentation.

Expression vectors comprising the foregoing sequences are also used in the present invention, in the production of redirected, TpCR-expressing Tregs.

Generation and Expression of TpCR and Foxp3-GFP Fusion Gene and its Expression

Redirected T-cells are "converted" to Tregs by causing them to express both Foxp3 transcription factor and the antigen-specific TpCR. Such manipulation permits production of large numbers of Tregs for evaluation and therapeutic use. Successful co-transduction or co-expression is tested by including a Foxp3-GFP fusion gene in the same construct as a TpCR to express both in the same cells. This approach is particularly useful when the starting cell populations are human PBL in which Tregs constitute only about 3-5% of CD4+ T-cells. This avoids the complications of another approach, also within the scope of the invention, in which large scale Treg propagation is required for effective transduction with retroviral vectors. Moreover it will simplify the isolation of the Tregs and assessment of their fate in vivo.

In one non-limiting example, messenger RNA (mRNA) for Foxp3 is cloned from purified Tregs using PCR. Foxp3 cDNA is cloned into an eGFP Clontech plasmid to create a Foxp3-GFP fusion protein. The fusion protein is cloned into the pBullet vector containing TpCR inserted after an IRES to create a bicistronic expression vector. Both a Foxp3-GFP single gene retroviral vector and a bicistronic TpCR-IRES-Foxp3-GFP double gene retroviral vector are transduced into isolated CD4+CD25− human peripheral blood T-cells following their activation with anti-CD3 and anti-CD28 antibodies. The resulting cells are tested for expression of the three genes by FACS using (1) antiidiotypic antibodies specific for the scFv idiotype, or anti-hinge region antibodies and (2) intracellular GFP and Foxp3 by staining fixed cells with primary antibodies specific for Foxp3 (Alexis Biochemicals, Lausanne, Switzerland).

In another embodiment, sequential expression protocols are used (first TpCR and then Foxp3-GFP genes) or co-expression protocols. Once the genes are expressed, relatively large number of Tregs can be obtained and separated using cell sorter (FACSaria fluorescence-activated cell sorting (Becton Dickinson, Mountain View, Calif.), sorting for GFP and TpCR co-expressing cells.

The Foxp3 construct may be in the form of a bicistronic vector that includes DNA encoding a reporter molecule such as a fluorescent protein. Suitable reporter molecules are well-known in the art and include fluorescent, chemiluminescent or chromogenic proteins, for example Green fluorescent protein (GFP) or enhanced yellow fluorescent protein (EYFP) or a fluorescent homologue thereof, firefly luciferase protein (encoded by the Luc gene) the enzymes chloramphenicol acetyl-transferase (CAT), or bacterial LacZ, (β-galactosidase) or the thymidine kinase gene (encoded by the HSV1 TK gene. GFP and EYFP are detected by fluorimetry or fluorescence histochemistry; enzymes are detected by use of a chromogenic substrate that is converted into a colored product which can be used in histochemical colorimetric detection of enzymatic activity. Luciferase is measured by activation of luciferin which emits light at a known wavelength. Reporter molecules may be detected in vivo by non-invasive detection techniques such as fluorescence optical imaging (FOI), bioluminescence optical imaging (BOI), cooled charged coupled device (CCD) camera optical imaging (CCOI) and positron emission tomography (PET).

Infection of human CD4+CD25− T lymphocytes with retroviral vectors carrying the Foxp3 gene was shown to convert these cells into ones with a Treg phenotype (Walker et al., 2005, supra; Wan et al., 2005, supra).

Any method for introducing DNA into a cell and expressing it may be used in the present invention, including, but not limited to vectors such as retroviral or lentiviral vectors, electroporation, lipofection, and the like.

The functionality of redirected Tregs can be determined using co-culture tests as described in the Examples. If APCs are to be used in such tests, a preferred source is irradiated monocytes. The antigen is loaded into irradiated human APCs which will present it to T effectors and Tregs. In the case of antigens such as CEA, human colon carcinoma cells stably transfected with the CEA epitope may be used. In such coculture tests, one may detect specific activation of TpCR-bearing Tregs through the TpCR. Treg activation is assessed by examining these cells' action on T effector cell (1) proliferation and (2) cytokine secretion profile, focusing on IL2, IL4, IL10, IFN-γ and TGF-β (using commercial ELISA kits, e.g., Ready-Set Go ELISA kit, Ebioscience CA). It is preferred to assay TGF-β and/or IL-10 as an indication of the cells' Treg phenotype.

In a preferred embodiment, the present invention redirects Tregs to sites of colonic inflammation, by introducing into such cells CRs with antibody-type specificity. In sites of inflammation the redirected Tregs are activated to suppress IBD-associated immune response.

Tregs endowed with predefined specificity migrate and home to inflamed sites in the colon where they undergo activation and, as a result, suppress T effector cells that mediate the disease processes.

The present redirected Tregs represent a novel form of the 'T-bodies' discussed above and are employed as a novel therapeutic modality in IBD. These T-bodies are T-cells that have been genetically engineered to express TpCR in which an antibody variable region is the recognition unit linked to T-cell costimulatory and stimulatory domains that enable specific activation of these T-cells but in a manner that is MHC independent and not MHC-restricted. Based on previous studies using tumor models described above, these redirected Tregs are tested in murine models of IBD models.

An important aspect of this invention is the inventors' conception that, in the context of treating IBD, the colon-associated antigen(s) to which the T-bodies are redirected and targeted are not necessarily the pathogenic autoantigens recognized by the autoaggressive T effector cells. Thus, this invention can exploit the phenomenon of "bystander" reactivity—where the presence of the relevant antigens at the sites of the inflammatory reactions serve to attract and "hold" or localize the redirected Tregs, permitting them to be activated and to exert their suppressive effects in a paracrine manner—acting on target effector cells in the vicinity irrespective of differences in the T effector cells' and Treg cells' antigen specificity.

CEA and LPS-Colonic Antigens as Targets for Redirected Human Tregs in IBD

Advantage was taken of a hapten-specific IBD model that is based on specificity to the hapten TNP to study the suppressive effects of Tregs. In human disease, other antigens that are expressed in intestinal or colonic tissue either normally or in the relevant disease state are preferred targets. The include carcinoembryonic antigen, CEA, and bacterial floral antigens such as lipopolysaccharide, LPS.

Human IBD is idiopathic to the extent that pathogenic antigen(s) remain unknown. Lack of knowledge of the antigen would appear to be an obstacle to implementing the T-bodies clinically. Nevertheless, according to the present invention, there is no requirement that a pathogenic antigen must also be the target antigen for Treg redirection and activation. Treg activation is indeed antigen-specific and thus depends on TCRs, or in the present Tregs, on antibody-based specificity, associated with costimulation together with the activation/mediated by the intracellular signaling moieties of the present constructs. However, once the Tregs are activated, their suppressive action is antigen-independent, and is carried out by secretion of suppressive cytokines (e.g., TGF-β and IL-10) even after the activating antigen has been eliminated. Thus, inducing colonic Treg activation by any local colon-associated antigen will promote potent Treg activation and proliferation, while the action of these cells in inhibiting local inflammatory processes proceeds independently of antigen. CEA is significantly overexpressed in diseased colon tissue in patients with active ulcerative colitis compared to normal individuals and to patients with quiescent IBD (Smithson J E et al., *J Pathol.* 1996; 180:146-51; Pavelic Z P et al., *Anticancer Res.* 1991; 11:1671-5). This enhanced tissue expression of CEA was independent of dysplastic changes and is a result of the mucosal reaction to the inflammatory process itself. Thus, CEA is a preferred candidate for Treg TpCR targeting in active ulcerative colitis.

A second candidate antigen (or "non-antigen" ligand) to which Tregs may be redirected is endotoxin or LPS, derived from the outer membrane of Gram-negative bacteria resident in the colon. In one embodiment, the antibody-like part (scFv) the CR's extracellular recognition region may be derived from an anti-LPS antibody, such as the mAb produced by the hybridoma with ATCC Accession No. HB9081. The nucleotide sequence of an scFv made from this mAb is shown as an annotation in FIG. 29 as part of the full sequence of a plasmid (pBullet) comprising this scFv—SEQ ID NO:3. Thus, a Treg expressing a TpCR that displays this scFv extracellularly will, at a site where LPS is present such as inflamed colon tissue (whether the gut lumen, the lamina propria or even regional lymph nodes and other gut-associate lymphatic tissue) bind the LPS and be activated to cause suppression of any T effectors cells in the vicinity in an antigen-nonspecific and MHC-independent manner.

Several types of non-antibody LPS receptors are known in the art. CD14 (SEQ ID NO:4) is a class of LPS receptor that is a GPI-anchored 356 aa glycoprotein. It contains a 19aa signal peptide, an extracellular domain which contain 11 leucine-rich repeat (LRR) domains, 4 N-glycosylation sites and an unknown number of O-glycosylation sites. At least 2 soluble forms of CD14 have been described, one retains GPI and is released from the cell surface which results in an approximately 48 kDa molecule and the other is released prior to the addition of the GPI anchor resulting in a higher molecular weight (>48 kDa).

While LPS interacts with CD14, CD14 is not capable of initiating a transmembrane activation signal because it is a glycosylphosphatidylinositol (GPI)-anchored protein. Thus, LPS must interact with a transmembrane receptor(s) that is responsible for signal transduction. LPS is recognized by the toll-like receptor TLR4 and MD-2 (SEQ ID NO:5; human), a molecule associated with the extracellular domain of TLR4. CD14 greatly enhances the formation of LPS-TLR4-MD-2 complexes, apparently by LPS loading onto TLR4-MD-2 but not in the interaction itself between LPS and TLR4-MD-2. (Akashi S, et al., J. Exp. Med. 198:1035-42 (2003)).

Interaction of LPS with MD-2 in a TLR4-MD-2 complex triggers an intracellular signal transduction cascade that leads to the production and release of proinflammatory cytokines, particularly TNF-α (Dauphinee S M et al., 2006, *Lab. Invest.* 86, 9-22). Patients with IBD show increased colon and serum levels of endotoxin, LBP, CD14, and MD-2 (Pastor Rojo O, et al., 2006, *Inflamm Bowel Dis.*, December 19 (epub); Amati L et al., *Curr Pharm Des.* 2003; 9:1937-45; Cario E et al., *J Immunol.* 2006; 176:4258-66). This change correlates with disease activity, and proinflammatory cytokine levels return to normal after treatment.

A motif of human MD-2, for example, from amino acids 119-132 (14 residues) of SEQ ID NO: can substitute for MD-2 in MD-2-TLR4 complex binding to the lipid A moiety of LPS, which (Mancek M et al., *Biochem Biophys Res Comm* 2002; 292: 880-5; Kobayashi M et al., *J Immunol.* 2006; 176:6211-8).

Thus, in one preferred TpCR of the present invention, the extracellular recognition region comprises, in place of an antibody-like structure (e.g., an scFv), a receptor that binds to a ligand that is not acting as an "antigen." A preferred ligand in the present invention is LPS. Thus, the extracellular recognition region may comprise any of the following receptor structures:

(a) CD14 (SEQ ID NO:4),
(b) an LPS-binding motif of CD14, such as residues 100-119 of SEQ ID NO:4,
(c) full length MD-2 (SEQ ID NO:5),
(d) an LPS-binding motif of MD-2 (residues 120-132 of SEQ ID NO:5),
(e) a combination of a CD14 and MD-2 or
(f) a combination of a CD14-motif and an MD-2 motif (as is encoded by the relevant segment of the chimeric nucleic acid of SEQ ID NO: 10.

Any of these constructs, when displayed on a Treg surface, will allow the redirected Treg to bind to, and be activated by LPS molecules, for example, at colon inflammatory sites, and thereby exert their suppressive activities in that vicinity. Again, this is an example of receptor-ligand binding/recognition that is not "antibody-like" but nevertheless permits the TpCR to act in accordance with this invention and activate Tregs in an antigen-nonspecific (and MHC-independent) manner.

The present invention includes an embodiment in which redirected Tregs bearing a TpCR are designed to be specific for an antigen, referred to herein as "AgX," that may have no inherent relationship with the tissue being targeted or the disease being treated. In this embodiment, the Tregs specific for AgX are activated specifically in a selected site by administering them together with AgX to that site. The site is one where T effector cells are situated and active, where the ongoing inflammation is to be suppressed. The AgX-specific antibody-like receptor of the Tregs will recognize AgX without a need for antigen presentation, MHC, etc., and the linked signaling moieties on the TpCR will serve to activate the Tregs to release inhibitory cytokines at that site. This process will lead to nonspecific suppression of the ongoing T effector cell and inflammatory activity.

The methods and compositions described herein are useful for any of a number of autoimmune diseases which involve undesired effector T-cells activity as an underlying cause or as a consequence of the pathophysiology. Such diseases include, but are not limited to, IBD, rheumatoid arthritis, Type I diabetes, multiple sclerosis, autoimmune thyroiditis, autoimmune uveoretinitis, autoimmune orchitis, autoimmune insulitis, autoimmune oophoritis, psoriasis, autoimmune polymyositis and the like. See, for example, Theofilopoulos, A., In: Stites, D P et al., eds., *Basic and Clinical Immunology*, Lange Medical Publications, Los Altos, Calif., 1988)).

Having now generally described the invention, the same will be more readily understood through reference to the following examples which are provided by way of illustration, and are not intended to be limiting of the present invention, unless specified.

Example I

Materials and Methods

The following materials and methods are used in various of the Examples that follow, as well as in carrying out certain embodiments of the invention.

Cell Fractionation and Isolation

CD4+CD25+ Tregs were purified from splenic lymphocytes or peripheral blood mononuclear cell populations using several methods. One method utilized magnetic bead separation (MACS). Spleens are mashed gently into HBSS/5% FCS to prepare single cell suspensions.

CD4+ T-cells were purified by negative selection by incubation with biotin-conjugated CD4 MACS beads (Miltenyi Biotec, Inc., Auburn, Calif.). Further purification of CD4+CD25+ cells was conducted by incubation with phycoerythrin (PE)-conjugated anti-CD25 antibodies or anti-CD45RB$^{high}$, followed by incubation with anti-PE microbeads (Miltenyi Biotec, Inc., Auburn, Calif.). Magnetic separation was conducted using magnetic columns according to manufacturer's instructions. For highly-purified (>99%) Treg and effector T lymphocyte subpopulation, high-speed cell sorting is be applied, using BD FACSaria (®) cell-sorting system (BD Bioscience)

Lamina propria lymphocytes from colon were isolated as previously described (Han X et al., *Gastroenterology*. 2005; 129:185-203). Briefly, colonic mucosa was dissected, followed by incubation with $Ca^{2+}$—$Mg^{2+}$-free Hanks' balanced salt (HBSS) solution containing 1 mM dithiothreitol (Sigma-Aldrich, St. Louis, Mo.) for 30 min to remove mucus, and then serially incubated twice times in medium containing 0.75 mM EDTA (Sigma-Aldrich) for 60 min at each incubation. The supernatants from these incubations containing epithelium and intraepithelial lymphocyte population are discarded, and the residual fragments pooled and treated with 2 mg/mL collagenase A (Worthington Biomedical, Freehold, N.J.) and 0.01% DNase (Worthington) in humidified air at 37° C. for 2 hours. The cells are then be pelleted twice through a 40% isotonic Percoll solution, after which they are purified further by Ficoll-Hypaque density gradient centrifugation (40%/75%).

In Vitro Induction of Tregs

Naturally-occurring Tregs are thymus derived, express high levels of Foxp3 forkhead transcription factor and suppress activation of effector lymphocytes. It has been discovered that antigen-specific activation of human effector T-cells may induce expression of Foxp3 in a subgroup of the activated effector cells, which in turn develop a regulatory phenotype. These induced regulatory T-cells were shown to be capable of cell-contact-dependent suppression of freshly isolated effector cells (Walker et al., 2003, supra). In mice, prolonged exposure of effector cells to TGF-β induces Tregs both in vitro and in vivo (Fantini et al., J Immunol. 2004 and 2006, supra). This small, peripherally generated population of inducible Tregs may be central in regulation and containment of ongoing immune response, while the inability to induce such Tregs may be responsible for a propensity to develop autoimmunity.

To test whether such induction occurred after stimulation of T effector cells through the TpCR, wildtype, TNP-Tg, Erbb2-Tg and TNP-CD28Δ-Tg T effector cells were isolated by FACS sorting and cultured for 7 days in the presence of either (1) anti CD3 Ab, (2) murine TGF-β, (3) mAb to TNP, (4) anti CD3 Ab+TGF-β, or (5) anti TNP Ab+TGF-β. Induction of Foxp3 in cells "developing" from these effector T-cells was assessed after seven days of culture using intracellular Foxp3 staining Antigen-specific activation of human effector T-cells leads to inducible expression of Foxp3 in a subgroup of activated effector cells, which in turn develop regulatory phenotype. These induced regulatory T-cells are capable of cell-contact-dependent suppression of freshly isolated effector cells. In mice, both in vitro and in vivo induction of Tregs can be achieved with prolonged exposure of effector cells to TGF-β (Fantini et al., 2004, 2006, supra). The present inventors adopted this technology to induce murine redirected Tregs from redirected effector T-cells (see FIG. 3).

Animals

Several mouse strains were used in the studies described below and are used in various other embodiments of the invention. These include transgenic mouse lines that specifically expresses anti-TNP or anti-Erb B2 TpCRs (bearing CD28-FcR □□ signaling control of a CD2 promoter, as well as a transgenic mouse line expressing human CEA (Saha A et al., *Immunology* 2006, 118:483-496)

All transgenic mice were back-crossed to Balb/c. Balb/c wild-type mice serve routinely as controls and recipients of adoptively transferred cells.

One cell-transfer colitis model is used in immune deficient $Rag^{-/-}$ and SCID mice.

All invasive procedures were and are conducted under Ketamine and Xylazine general aesthesia (127.5 and 4.5 mg/kg, respectively). Subcutaneous (S.C.) injections are conducted under local anesthesia with 10% Xylocaine spray.

Colitis Induction and Assessment:

To induce TNP hapten-mediated colitis mice were sensitized with 150 µl of the haptenating agent 2,4,6-trinitrobenzenesulfonic acid (TNBS, Sigma-Aldrich) at a concentration of 2.5% v/v in 50% ethanol by skin painting on day 1. On day 8, 150 µl of 1% TNBS in 50% ethanol was administered intrarectally via a 3.5 F catheter under general anesthesia.

OXA-induced colitis was induced by sensitizing mice with oxazolone (4-ethoxymethylene-2-phenyl-2-oxazolin-5-one; Sigma-Aldrich) at a concentration of 3% v/v in 100% ethanol by skin painting on day 1, followed by intrarectal administration of 150 µl at a concentration of 1% v/v in 50% ethanol on day 8.

In one preferred cell transfer colitis models, $CD_{45}RB^{high}$ (naïve) T-cells are transferred to immune deficient mice from syngeneic background (Powrie F et al., *J Exp Med*. 1994; 179:589-600. This model of mucosal inflammation allows separating T effector and Treg cell function within an inflammatory site.

In all models, colitis is assessed following induction using the following parameters: degree of colon ulcerations, intestinal and peritoneal adhesions, wall thickness, and degree of mucosal edema. Each parameter is graded on a scale from 0 (completely normal) to 4 (most severe) by two experienced, blinded observers. For histological evaluation of inflammation, distal colon tissue (last 10 cm) is removed and fixed in 10% formaldehyde. Five paraffin sections from each mouse are stained with hematoxylin-eosin using standard techniques. The degree of inflammation is graded semiquantitatively on microscopic cross sections of the colon from 0 to 4 as follows: Grade 0: Normal with no signs of inflammation; Grade 1: very low level of leukocyte infiltration; Grade 2: Low level of leukocyte infiltration; and Grade 3: High level of infiltration with high vascular density, and bowel wall thickening; Grade 4: Transmural infiltrates with loss of goblet cells, high vascular density, wall thickening, and disruption of normal bowel architecture.

Murine Colonoscopy

For continuous monitoring of colitis pathology, a newly-developed, high resolution mouse video endoscopic system has been used Becker C et al., Gut. 2005; 54:950-4. The experimental endoscopy system (from Karl Storz, Tuttlingen, Germany) consists of a miniature endoscope (1.9 mm outer diameter), a xenon light source, a triple chip camera, and an air pump. Parameters for grading of colitis include bowel wall thickening, granularity, fecal consistency, fibrin deposition and vascular pattern. Whole colon methylene blue chromoendoscopy staining is used, when appropriate, to visualize crypt pattern. A 3fr. Flexible biopsy forceps is used for biopsy-taking. Biopsies are either placed in formalin for paraffin embedding, sectioning and subsequent immunohistochemistry, frozen in liquid nitrogen for cryosections, or obtained and used for RNA isolation. A typical yield of a biopsy specimen is approximately 2 μg RNA In Vivo Imaging:

To follow migration (also referred to as homing or trafficking) of redirected Tregs in mice, a whole body CCD camera (IVIS® 100 Series Imaging System, Xenogen, Alameda Calif.). was used. Redirected Tregs were labeled with the near-infrared (NIR) lipophilic carbocyanine dye 1,1'-dioctadecyl-3, 3, 3', 3'-tetramethylindotricarbocyanine iodide (DiR, Invitrogen, USA). This dye has absorption and fluorescence maxima at 750 and 782 nm, respectively, enables the safe direct labeling of membranes of human lymphoid cells with very low light absorption and autofluorescence levels in living tissues (Miller M J et al., Proc Natl Acad Sci USA, 2003; 100:2604-9; Kalchenko V et al., submitted for publication, 2007). Additional in vivo visualization of Tregs labeled with carboxy fluorescein diacetate succinimide ester (CFSE) at colonic mucosa was performed by intrarectal insertion of a 300 and 650 μm diameter confocal microendoscope (Cell Vizio, MKT, Paris, France). This unique modality, previously untested in colitis models, allows repeated in vivo assessment of homing of CFSE-labeled redirected Tregs to the most inner layers of colon tissue following induction of inflammation.

Determination of Colon Cytokine Levels

Colon mRNA expression of selected cytokines is determined to allow assessment of redirected Treg effects on local intestinal immune response. in particular, levels of proinflammatory (TNFα and IFNγ) and anti-inflammatory cytokines (TGFβ and IL10), as well as levels of the $TH_1$ transcription factor Tbet and the $TH_2$ transcription factor GATA-3. Colon cytokine levels are assessed by measuring mRNA expression and protein levels.

Samples for mRNA isolation are removed from colons of mice using in vivo colonoscopy or during sacrifice. Total RNA is isolated and processed and cDNA produced by RT-PCR. In all experiments, mice are divided into the following groups: naïve mice, colitis-induced mice, and colitis-induced mice adoptively transferred with Tregs (naturally occurring, induced, or redirected, see detailed adoptive transfer experiments herein). The following sets of oligonucleotides and amplification conditions are used:

|  | SEQUENCE | SEQ ID NO: | Amplification conditions |
|---|---|---|---|
| TNF-α sense | 5'-AGTCCGGGCAGGTCTACTTT-3' | 15 | 60°/30 cycles |
| antisense | 5'-GAGGCAACCTGACCACTCTC-3' | 16 | |
| IFN-γ sense | 5'-TCTGGAGGAACTGGCAAAA-3' | 17 | 63°/35 cycles |
| antisense | 5'-TGAGCTCATTGAATGCTTGG-3' | 18 | |
| TGF-β sense | 5'-TACAGGGCTTTCGATTCAGC-3' | 19 | 63°/35 cycles |
| antisense | 5'-CGCACACAGCAGTTCTTCTC-3' | 20 | |
| IL-10 sense | 5'-TCCTTGGGAAGCAATTGAAG-3' | 21 | 63°/35 cycles |
| antisense | 5'-AACTGGCCACAGTTTTCAGG-3' | 22 | |
| T-bet sense | 5'-CTAAGCAAGGACGGCGAATGT-3' | 23 | 60°/35 cycles |
| antisense | 5'-GGCTGGGAACAGGATACTGG-3' | 24 | |
| GATA-3' sense | 5'-GCCTGCGGACTCTACCATAA-3' | 25 | 54.8°/30 cycles |
| antisense | 5'-CAGGGATGACATGTGTCTGG-3' | 26 | |
| GAPDH sense | 5'-GTGTTCCTACCCCCAATGTG-3' | 27 | 60°/25 cycles |
| Antisense | 5'-CTTGCTCAGTGTCCTTGCTG-3' | 28 | |

The relative mRNA expression compared to the housekeeping GAPDH is assessed using NIH image software and averaged from mice in each group.

IL-10 and IFN-γ protein expression levels in colon tissue are quantified by a cytofluorimetry-based ELISA system. In brief, whole proteins are isolated from colon specimens in the absence of detergent. Proteins (100 μg) are immediately used for cytokine determination according to manufacturer's instructions.

Foxp3 Immunohistochemistry of Colon Samples:

Foxp3 immunofluorescence is performed to estimate in situ the targeting of Treg to diseased colon, using TSA Cy3 and a fluorescence microscope (Olympus). In brief, cryosections are fixed in cold acetone for 10 minutes, followed by sequential incubation with methanol, avidin/biotin (Vector Laboratories, CA), and protein blocking reagent to eliminate nonspecific background staining. Slides are then incubated overnight with primary antibodies specific for Foxp3 (e.g., from Alexis Biochemicals, Lausanne, Switzerland). Subsequently, slides are incubated for 30 minutes at room temperature with biotinylated secondary antibodies, and treated with streptavidin-horseradish peroxidase and stained with Tyramide (Cy3 or FITC). Before examination, nuclei are counterstained with Hoechst 3342 (Molecular Probes, Ohio).

Example I

Phenotypic Characterization of TNP-Specific Tregs

The inventors have produced transgenic (Tg) mice expressing a TNP-specific tripartite chimeric receptor (TpCR) that serve as a source of redirected Treg cells specific for the trinitrophenyl (TNP) hapten. This hapten has served as a "classical" antigen for years in studying both antibodies and T cell-mediated immunity. A chemically reactive form of this hapten, TNBS, is a contact sensitizing agent that induces and evokes delayed-type hypersensitivity (DTH) responses as well as inducing colitis in animals, as described herein.

Generation of TNP-specific Tregs was achieved by the creation of Tg mice that express TNP-specific TpCR that comprises an scFv from the TNP-specific mAb Sp6 mAb linked to a truncated CD28 molecule which was inserted between the scFv and the cytoplasmic part of the FcR γ chain (abbreviated as γ herein (see FIG. 1). This construct includes the hinge region, transmembrane region, and cytoplasmic region of CD28 but lacks the B7 (ligand) binding site.

For the truncated form of CD28 (TpCR/CD28, FIG. 1) that does not include the CD28 intracellular signaling domain, the inventors cloned the vector at the same site. As a control, a Tg mouse expressing TpCR specific for another, irrelevant antigen (Erb-B2) was used.

For expression of TpCR in T-cells of Tg mice, a construct comprising an anti-TNP (Sp6-derived scFv-CD28-γ was cloned into a human CD2 promoter/enhancer minigene-based vector. Tg mice were generated at the Weizmann Institute's Department for Veterinary Resources by pronuclear microinjection of (BALB/c×C57BL/6)F$_1$ fertilized eggs derived from hyperovulated donor females. Founder mice were screened by PCR of DNA from tail samples. Several founder strains were obtained that express high level of the TpCR on their cell surfaces. These were backcrossed for more than nine generations to either BALB/c or C57BL/6 mice to obtain MHC-homogeneous mice.

The studies below describe the characterization of various Treg subpopulations in the different strains of TNP-CR transgenic mice, and the expression of TpCR on these Tregs.

Example II

Isolation of Tregs in which TNP-Specific TpCR are Highly Expressed

Tregs were isolated using double magnetic bead separation (Miltenyi Biotech) or by fluorescent cell sorting in which fluorescently labeled CD4+CD25+ cells were sorted using the FACSARIA cell sorting system.

Figure 2:
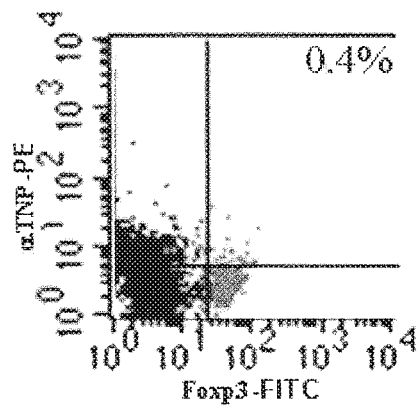
FIG. 2: Flow cytometry results of Foxp3 staining of TNP-specific Tregs. Splenocytes isolated from WT and TNP-Tg mice were stained for intracellular Foxp3 and for TNP-specific chimeric receptor using antiidiotypic antibody to the Sp6 scFv. Representative flow cytometry analyses are shown for an individual mouse out of five tested mice. Percentages indicate double-stained cells.
Figure 2:
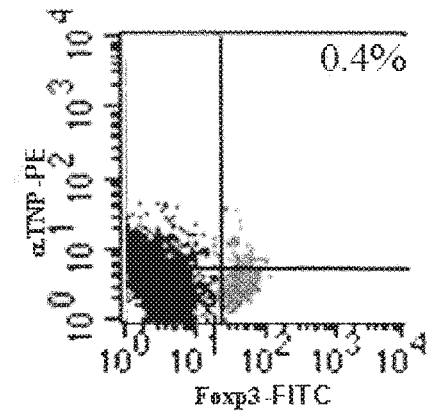
Figure 2:
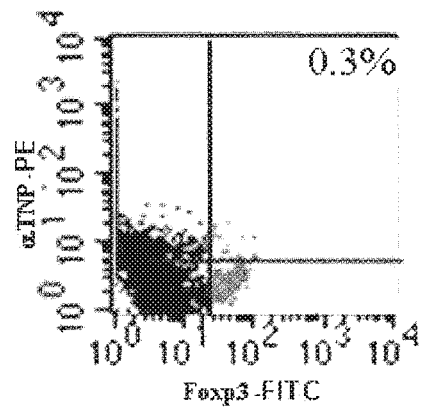
Figure 2:
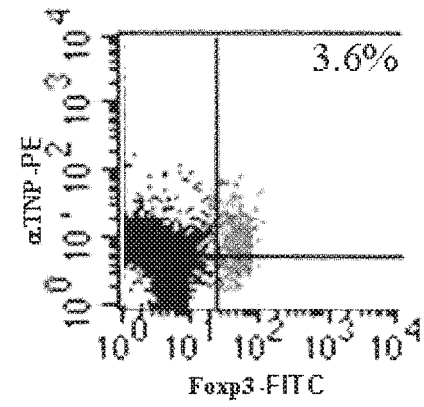

Treg expression of TNP-specific TpCR was assessed by containing cells for Foxp3 (considered the "gold standard" marker of Tregs) and PE-labeled mAb specific for TNP antibody (generated in the inventors' laboratory). Controls included groups stained with the appropriate isotype controls. As is shown in FIG. 2, Tregs from TNP-Tg mice, but not from wild-type mice, expressed high levels of TNP-specific TpCR.

Example III

TNP-Tg Mice Posses Increased Numbers of Foxp3+ Treg Population

Figure 3:
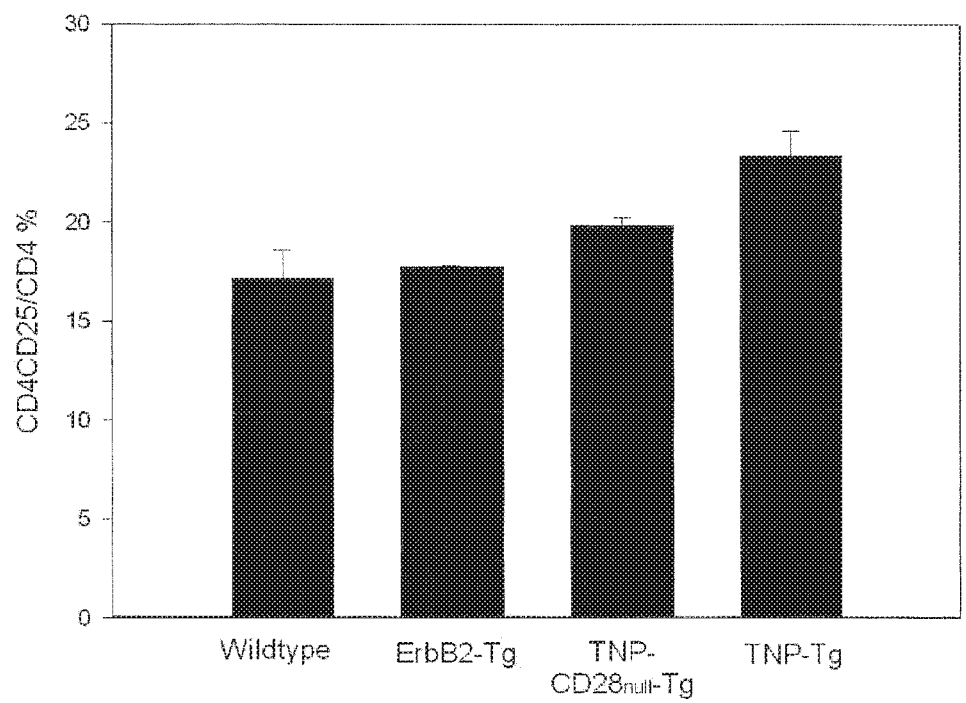
FIG. 3: Graph showing the ratio of CD4+CD25+ cells to CD4+ cells in splenocytes of wildtype and Tg mice. The groups are: wildtype mice, mice Tg for a chimeric receptor specific for an "irrelevant" antigen, ErbB2 (also referred to as ErbB2-Tg mice), TNP-Tg mice that have been transfected with a vector lacking the transgenic costimulatory CD28 domain (also referred to as TNPΔCD28-Tg mice), and TNP-Tg. TNP-Tg Tregs fully express the TNP-specific TpCR
Figure 4:
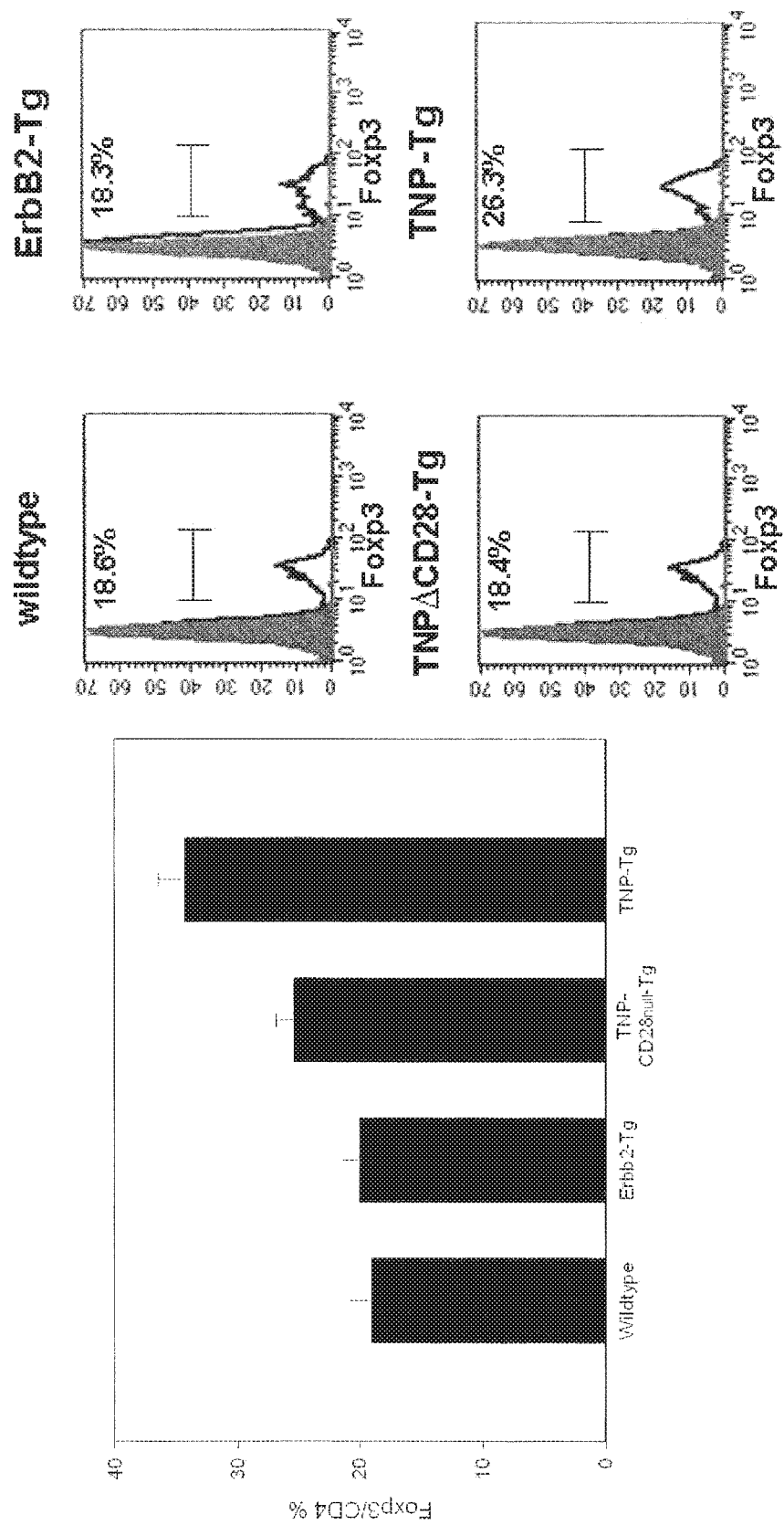
FIG. 4: Graph (left) showing Foxp3+/CD4 cell ratio in wildtype, ErbB2-Tg, TNPΔCD28-Tg, and TNP-Tg mice. Flow cytograms (right) showing splenic Foxp3 expression. Results compare wildtype, ErbB2-Tg, TNP-Tg and TNPΔCD28-Tg mice.

Peripheral lymphocytes from the spleen as well as gut-associated lymphocytes from the lamina propria of the colon were stained. As shown in FIG. 3, a CD4+CD25+ cell population (represented as the ratio of CD4+CD25+ cells among CD4+ T-cells) was elevated modestly in TNP-Tg mice in comparison to control mice (wildtype, ErbB2-Tg and TNP-CD28 null-Tg mice). In contrast, higher numbers of Foxp3+ cells were observed in TNP-Tg animals compared to the control animals in comparison to all other mouse types (FIG. 4).

Figure 5:
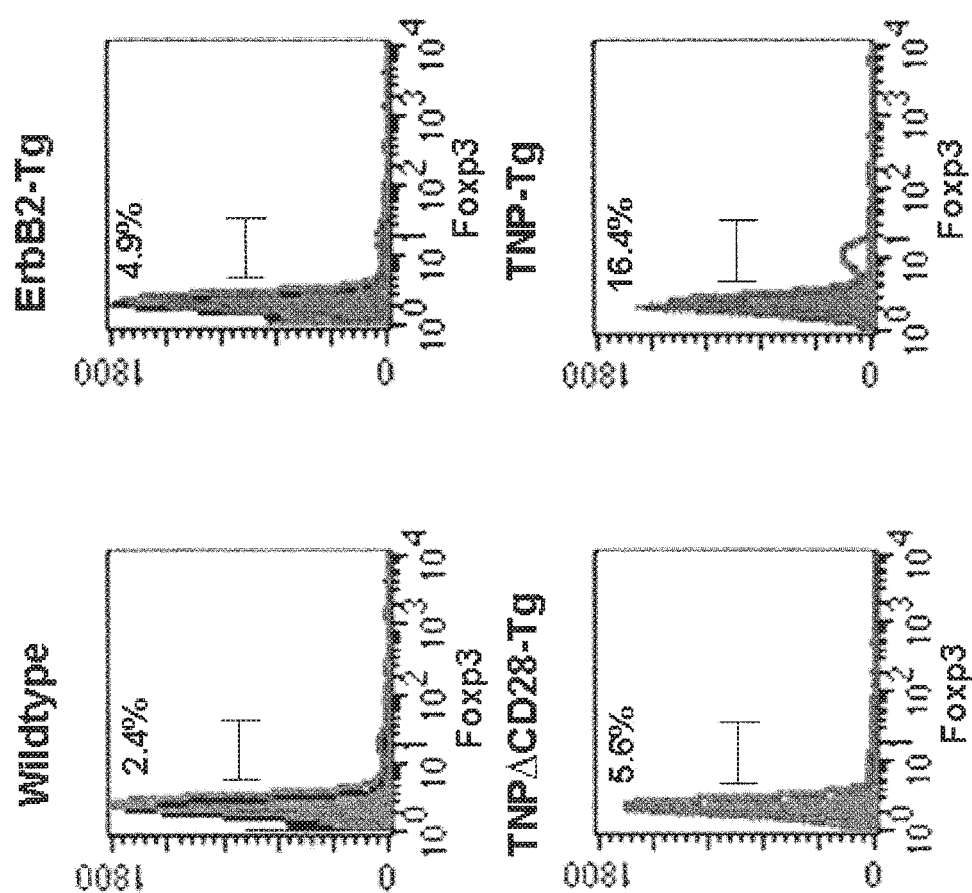
FIG. 5: Flow cytograms showing Foxp3 staining in sorted wildtype, ErbB2-Tg, TNP-Tg and TNP-ΔCD28-Tg CD4+ CD25+ effector T-cells.
Figure 6:
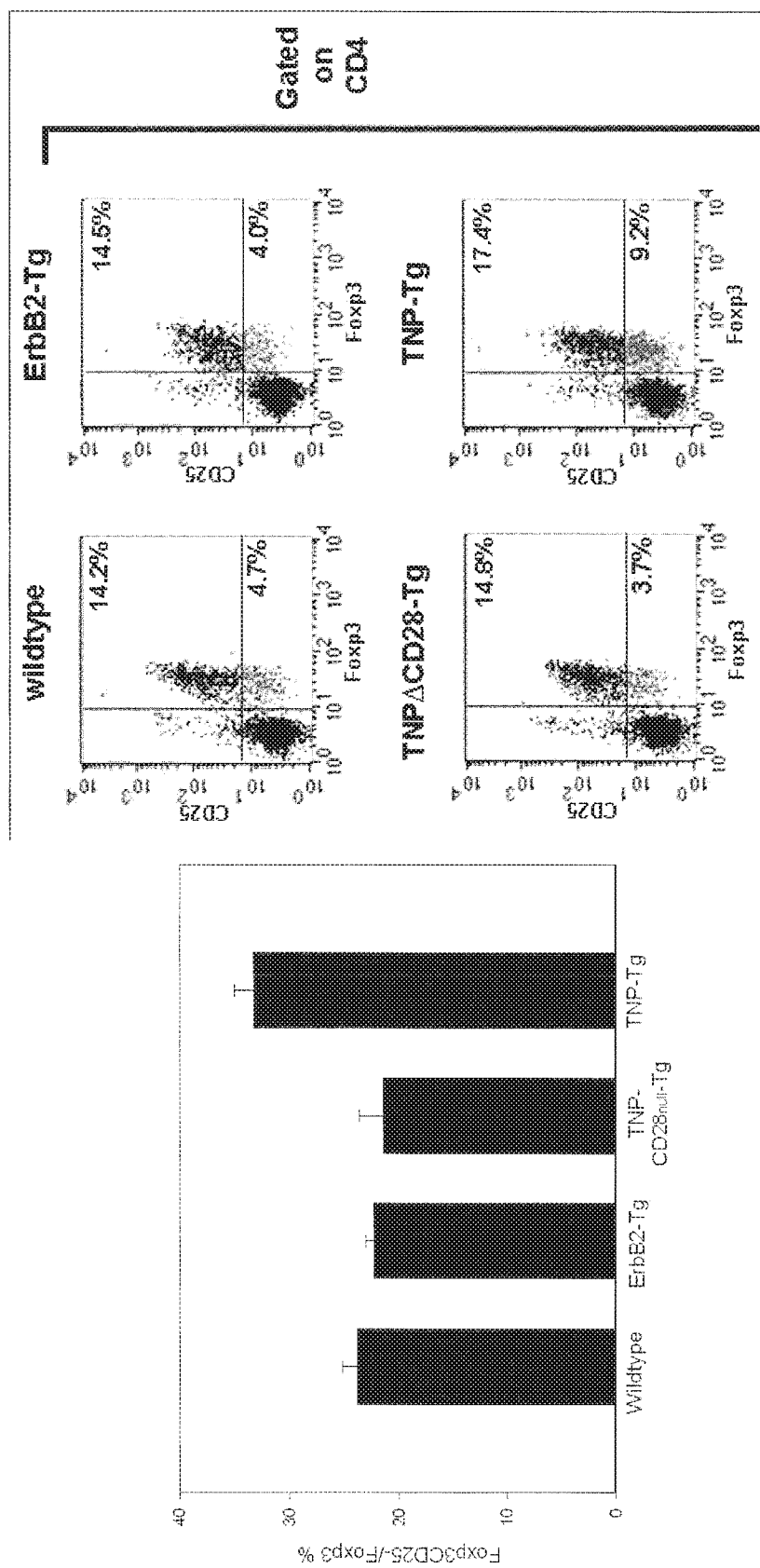
FIG. 6: Graph (left) showing ratio of Foxp3+ to CD25+/Foxp3+ cells. Flow cytogram (right) showing co-staining of Foxp3 and CD25. Results compare wildtype, ErbB2-Tg, TNP-Tg and TNP-ΔCD28-Tg splenocytes.

To resolve what may have appeared to be an inconsistency between the highly elevated Foxp3+ Treg population in TNP-Tg mice and the modestly elevated CD4+CD25+ Treg population in these mice, effector CD4+CD25− cells were isolated by cell sorting to a level of 99% purity. Isolated cells were stained for Foxp3 (FIG. 5). As expected, no positive Foxp3 staining was noted in T effector cells from wildtype, ErbB2-Tg and TNP-CD28null-Tg mice. In contrast, TNP-Tg T effector cells featured a significant population of Foxp3+ cells. This observation was further validated in whole spleen cell populations that were co-staining for Foxp3 and CD25 (FIG. 6). The presence of a significantly greater Foxp3+CD25− Treg population in TNP-Tg mice is supported by other recent results by the inventors' laboratory showing that the Sp6 mAb from which the scFv of the TNP-specific TpCR was derived recognizes cross-reactive endogenous thymic antigens. This results in either deletion or early release from the thymus to the periphery before several other immature T cell subsets, including immature CD25− Tregs.

Example IV

Figures 7, 8:
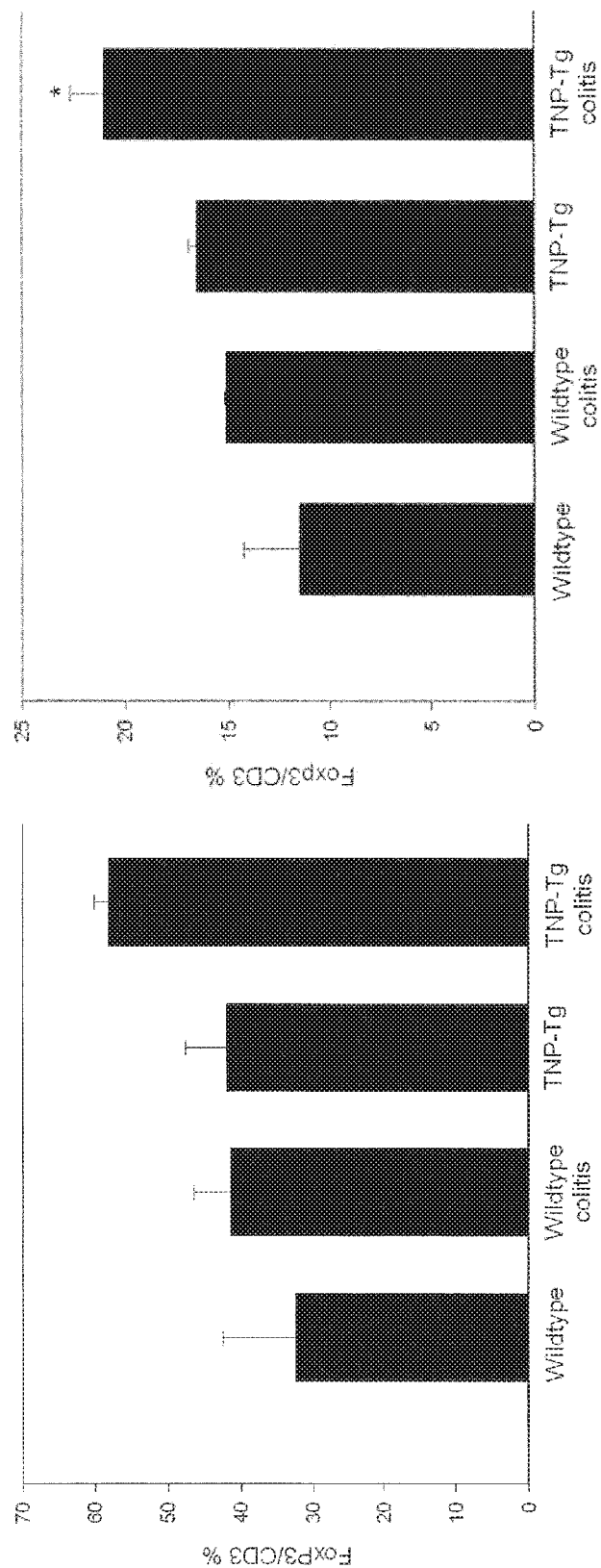
FIG. 7: Graph showing percentage of Foxp3+ splenocytes in the total CD3+ T-cell population following induction of TNBS colitis. Splenic lymphocytes were isolated from WT and TNP-Tg mice prior to or 48 hours following induction of TNP colitis, and double-stained with anti-Foxp3 and anti-CD3 antibodies.
FIG. 8: Graph showing percentage of Foxp3+ lymphocytes extracted from colonic lamina propria following induction of TNBS colitis. Lymphocytes were isolated from WT and TNP-Tg mice prior to and 48 hours following induction of TNP colitis, and double-stained as in FIG. 7. The percentage of Foxp3+ lymphocytes in the CD3+ population is presented as the average Foxp3/CD3 ratio+s.d. of each five-mouse group. Data shown are averages of two independent experiments performed. Differences in ratios between naïve and colitis-induced TNP-Tg mice were significant ($P<0.05$).

Induction of TNBS Colitis in TNP-Tg Mice Significant Elevated the Numbers of Foxp3+ Expressing Cells in Peripheral and Colon-Derived Lymphocyte Populations Induction of TNBS colitis results in further elevation in splenic (FIG. 7) and colon (FIG. 8) Foxp3+ Tregs in TNP-Tg (FIGS. 7 & 8, respectively). These results demonstrated that TNP-specific Treg expansion occurred following induction of colitis in Tg mice, reflecting Treg proliferation following antigen-specific activation by TNP.

Example V

In Vitro Functional Characterization of Redirected Tregs

A key prerequisite for the utility of Tregs expressing TNP-specific TpCR in the treatment of autoimmunity is verification of their regulatory activity, namely an ability to suppress T effector cell proliferation in a dose-dependent manner. Also examined was whether such Treg activation occurs as a result of TpCR signaling, and whether it was indeed independent of CD28-B7 interaction. A series of coculture experiments examined Tregs from the different Tg strains, as is outlined below.

Example VI

Figure 9:
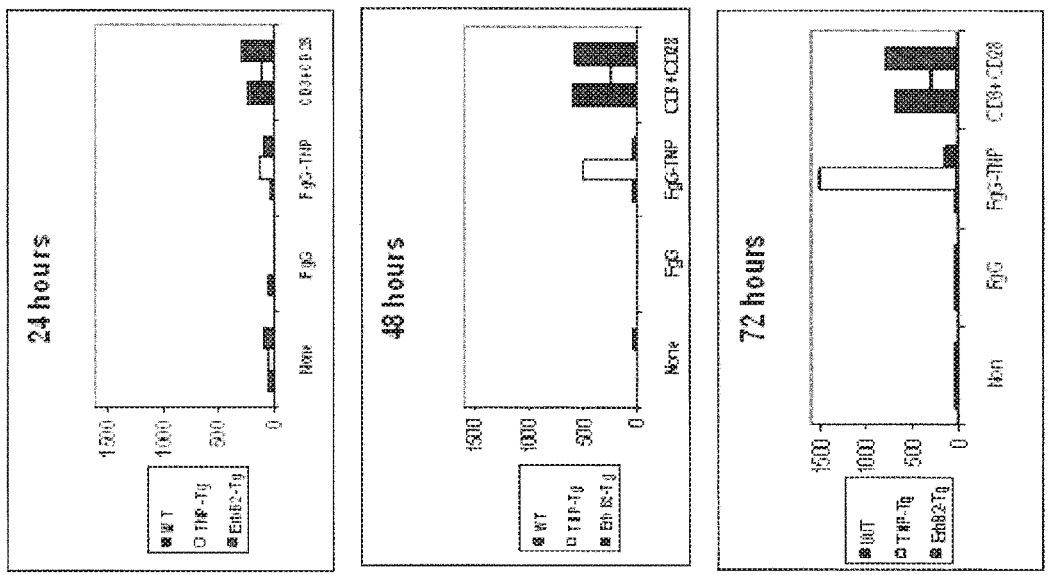
FIG. 9: Series of 6 graphs showing stimulation of proliferation of redirected Tregs (left) and T effector cells (right). by an antigen-nonspecific stimulus (anti CD3 and anti CD28 mAbs) and antigen-specific (TNP) stimulus.
Figure 9:
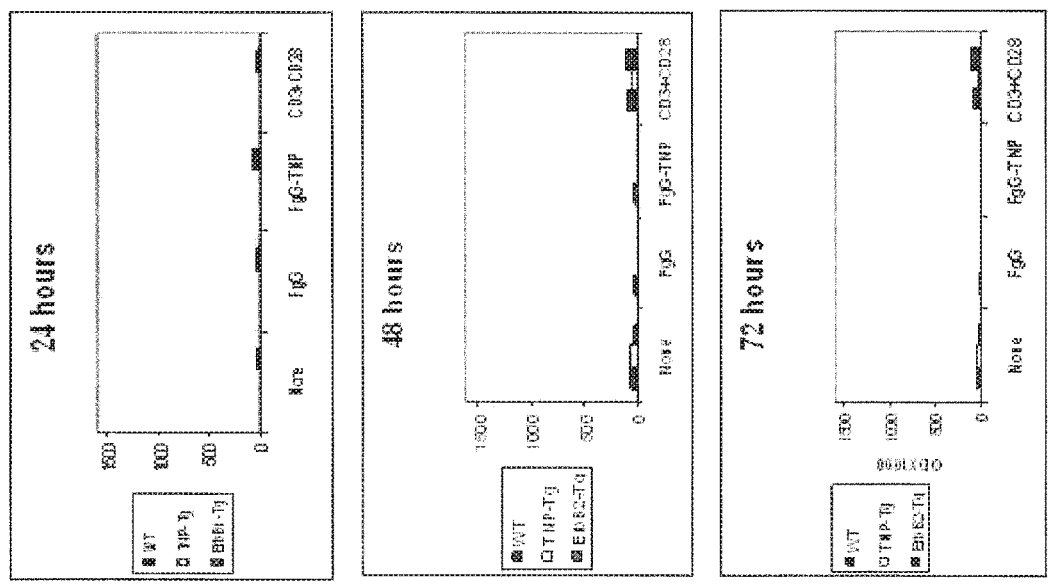

Tregs Bearing the TNP-Specific Chimeric Receptor Specifically Suppressed the Activity of T Effector Cells To characterize whether TNP-Tg Tregs retained their anergic properties, CD4+CD25+ Treg cells and CD4+ CD25– T effector cells from different Tg mouse founders (anti-TNP, anti-Erb-b2 control and wildtype (WT) mice) were purified from bulk splenocytes. $10^5$ cells were incubated in vitro for 24 h, 48 h or 72 hrs (FIG. 9) and activated non-specifically with anti CD3 and anti-CD28 Abs, or specifically with Fowl gamma globulin-modified TNP (FγG-TNP). T cell proliferation was measured using either the uptake of a dye (tetrazolium salt XTT) or radiolabeled Thymidine. IL2 secretion was measured using XTT staining of the IL-2-dependent CTLL-2 cell line.

All effector cell populations showed significantly increased proliferation and IL2 secretion following non-specific stimulation with anti-CD3+anti-CD28 Abs. Specific stimulation by FγG-TNP resulted in proliferation and IL2 secretion by T effector cells bearing TNP-chimeric receptor, but not by such T-cells from WT or anti-Erb-b2 Tg mice. In contrast, Tregs from wildtype mice, TNP-chimeric receptor Tg mice and Erb-b2 Tg mice retained their anergic properties: they did not undergo measurable proliferation or IL2 secretion when subjected to the non-specific stimulus or specific Ag.

To characterize whether polyclonal activation could trigger the suppressive action of TNP-Tg Tregs, these Tregs were cocultured in 96-well microplates (0.2 ml) with irradiated antigen presenting cells (APCs) and T effector cells (CD4+CD25-) at 1:1 ratios. Cells in these culture were activated either by (1) immobilized antigen "mimic" (anti-CD3+anti-CD28) or (2) soluble Concanavalin A (ConA). T cell proliferation was measured as Thymidine uptake and IL2 secretion was measured as growth of cells of the IL-2-dependent CTLL-2 cell line(XTT staining).

Figure 10:
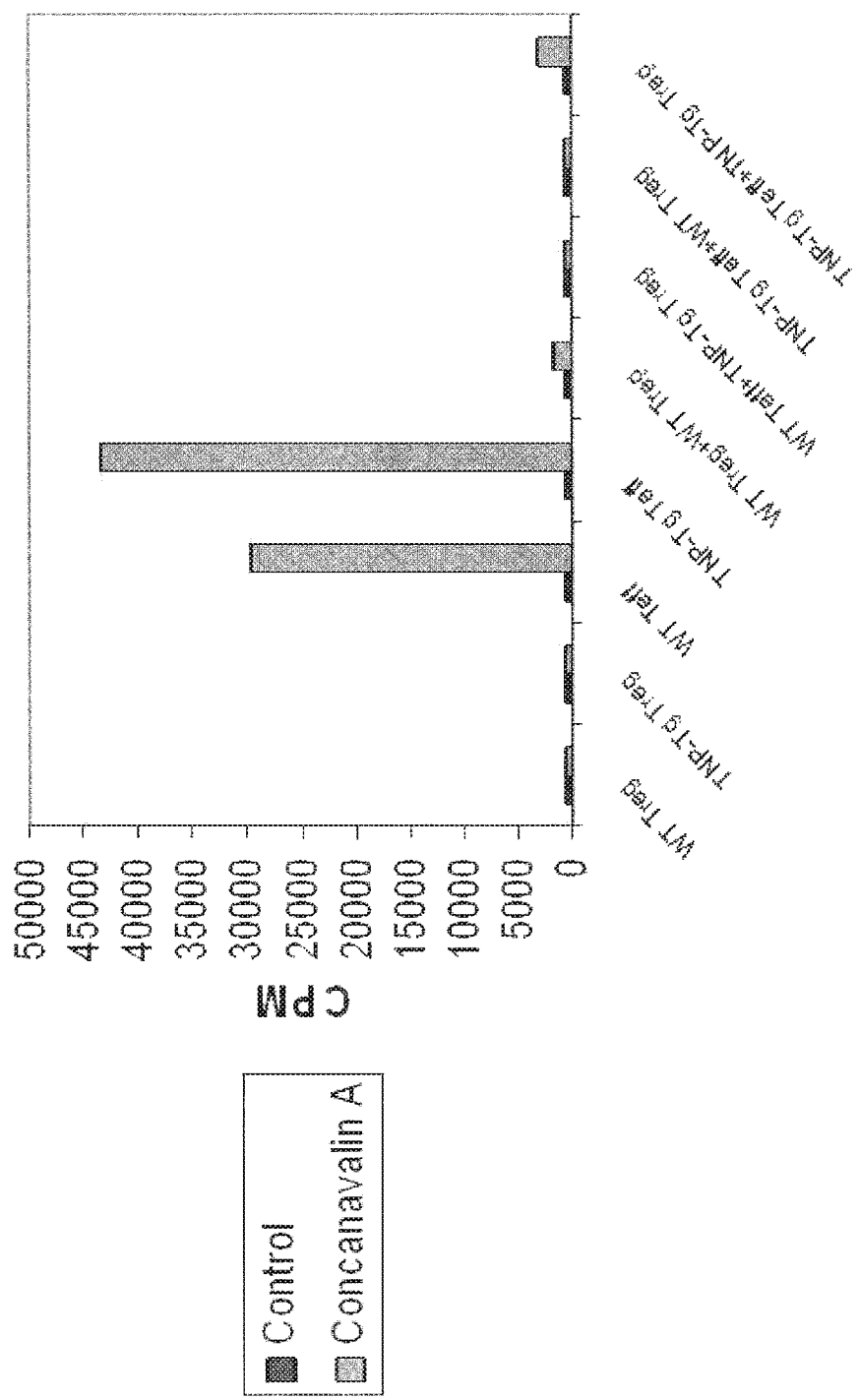
FIG. 10: Graph showing polyclonal activation with Concanavalin A (Con A) of cocultures of Tregs and T effectors cells (and control cultures of individual cell populations)

FIG. 10 shows a ConA experiment. Non-specific (polyclonal) stimulation of Tregs induced these cells to exhibit potent inhibition of T effector cell proliferation and IL2 secretion, irrespective of the origin of the Tregs or the presence of the chimeric receptor. Thus, genetic manipulation of Tregs of the type described here preserves their suppressive properties.

Example VII

Figure 11:
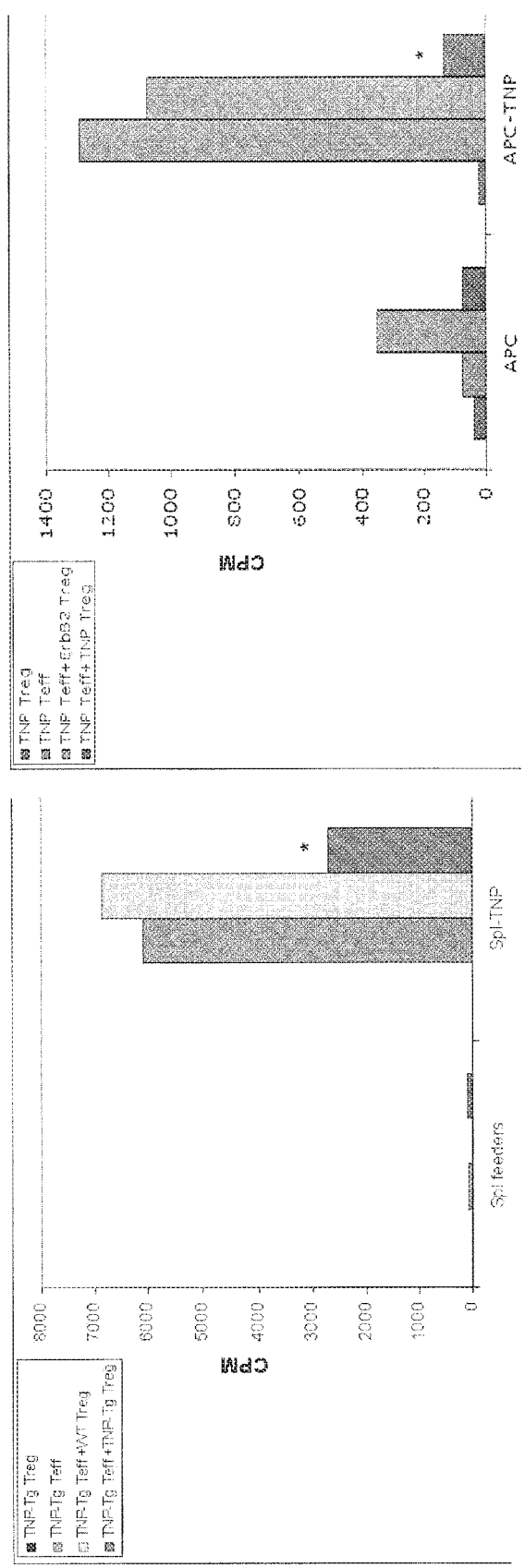
FIG. 11: Graphs showing Specific activation of TNP-Tg Tregs and their suppression of effector T-cells requires TNP and CD28-co-stimulation. In the left panel, specific (TNP) activation of Tregs is shown. WT or TNP-Tg Tregs ($5\times10^4$) were cocultured with WT or TNP-Tg Teff ($5\times10^4$) in the presence of irradiated, T-cell depleted, TNPylated splenic APC ($1.5\times10^5$). Teff proliferation was measured after 48 hours by $^3$H-Thymidine incorporation. Right panel: TNP-loaded APCs as stimulus.

Antigen-Specific Stimulation of Redirected Tregs Cells with TNP Results in Suppression of T Effector Cell Proliferation To study the antigen-specific Treg stimulation through the TpCR, coculture experiments were done in which TNP-loaded APCs provided the Ag presentation (FIG. 11). Comparisons of TNP-specific Treg stimulation was performed, comparing wildtype vs. TNP-Tg Tregs (FIG. 11, left panel) or ErbB2-Tg and TNP-Tg Tregs (FIG. 11, right panel). In the absence of TNP stimulation, T effector cell proliferation did not occur (left-most bars in both graphs). In contrast, incubation with TNP-modified APC's resulted in:
(1) marked proliferation of TNP-Tg but not of wildtype or ErbB2-Tg effector T-cells in the absence of Tregs; and
(2) activation of TNP-Tg, but not of WT or Erb-b2-Tg Tregs, manifest as suppression of effector cell proliferation by TNP-specific Tregs only.

These results proved the antigen-specific manner of activation and function of TNP specific TpCR Tregs cells in response to the antigen, TNP.

Figure 12:
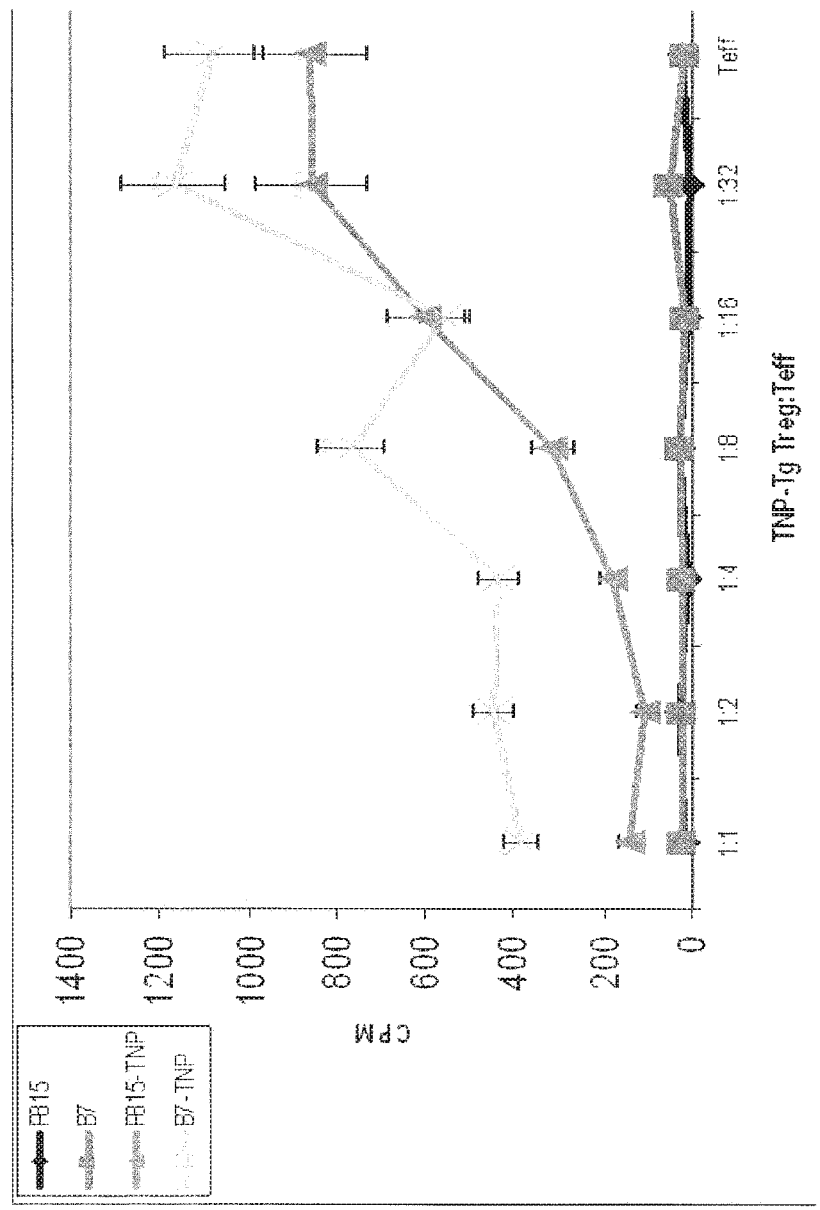
FIG. 12: Graph showing dose-response of TNP-specific stimulation of Treg cell+T effector cell cocultures. APCs were TNP-modified stimulator P815 mastocytoma cells, which do not express B7 (P815-TNP) or TNP-modified P815 cells into which the B7 gene was stably transfected (B7-TNP).

Co-culture of varying ratios of TNP-specific Tregs and TNP-specific effector T-cells (FIG. 12) demonstrated successful antigen-specific inhibition by Tregs at a ratio of 1 Treg to 8 T effector cells.

Studies supporting the existence of the bystander effects were carried out. Colitis was induced in mice as above using OXA as described in Example I. Adoptive transfer of TNP-specific Tregs alone did not protect these animals from colitis. However, in the presence of trace amounts of TNP applied to the colon, animals were protected from this OXA-induced colitis.

Example VIII

Figure 13:
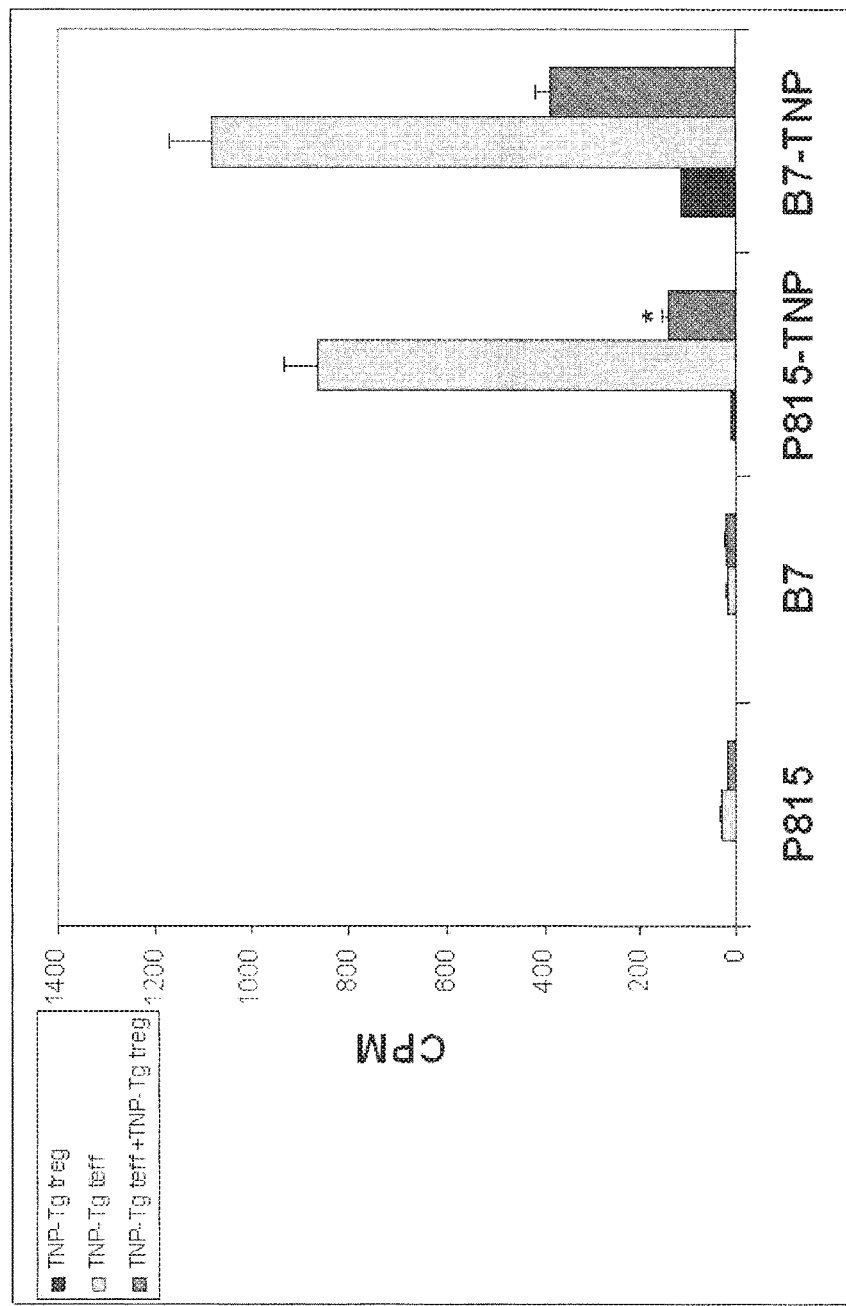
FIG. 13: Graph showing Specific activation of TNP-Tg Tregs and their suppression of effector T-cells requires TNP and CD28-co-stimulation. To establish whether costimulatory signaling is required for TNP-Tg Treg activation, coculture experiments were repeated using as APC irradiated P815 mastocytoma cells (1.5×105) that were either stably transfected (or not) with B7 cDNA. Teff cell proliferation was measured after 48 hours by $^3$H-Thymidine incorporation. Each group was cultured in triplicate and the experiment was repeated three times. The data shown represent mean (+s.d.) of triplicate cultures of a representative experiment. Differences in stimulation index between Teff+WT Tregs and Teff+TNP-Tg Tregs were significant (P<0.01).

Suppressive Activity of TpCR-Redirected Tregs is Independent of Costimulatory Receptors To assess the role of costimulatory signaling in the above TpCR-Tg model, coculture experiments as above were performed using as APC's (a) TNP-modified P815 cells, a cell line that does not express B7, or (b) TNP-loaded genetically modified P815 cells stably expressing the B7 gene (FIG. 13). Stimulation of TNP-Tg effector T-cells with TNP-P815 cells induced proliferation, which was markedly suppressed by TNP-Tg Tregs. Expression of B7 on these APC's did not promote any further Treg-mediated suppression. It was concluded that maximal Treg suppression occurred independently of B7. Some suppression was also noted with wildtype Tregs. This was explained by the pre-activation of these cells prior to their harvesting. Based on these results, it could be concluded that inclusion of the intra-cytoplasmic signaling domain of CD28 in the TpCR of redirected Treg cells results in full activation of their suppressive activity when stimulated by Ag irrespective of the presence of B7-CD28 costimulation.

Example IX

Functional Characterization of TNP-Specific Treg Activity In Vivo in Murine Colitis TNBS is a potent inducer of T-cell responses such as DTH/contact sensitization. This reactive hapten also induces autoimmune colitis when applied to the colon of pre-sensitized mice. To determine whether TpCR-bearing Tregs could suppress autoimmunity, the acute TNBS-mediated colitis model was employed. Intra-rectal administration of TNBS leads to its binding to colon proteins, rendering these modified proteins immunogenic so that they elicited a T cell mediated immune response. The suppressive effect of endogenous or exogenously transferred Tregs on autoimmune inflammatory disease was tested in this model. A different hapten, oxazolone (OXA) with similar sensitizing properties and which induces experimental colitis was used as a specificity control in vivo.

Example X

Figure 14:
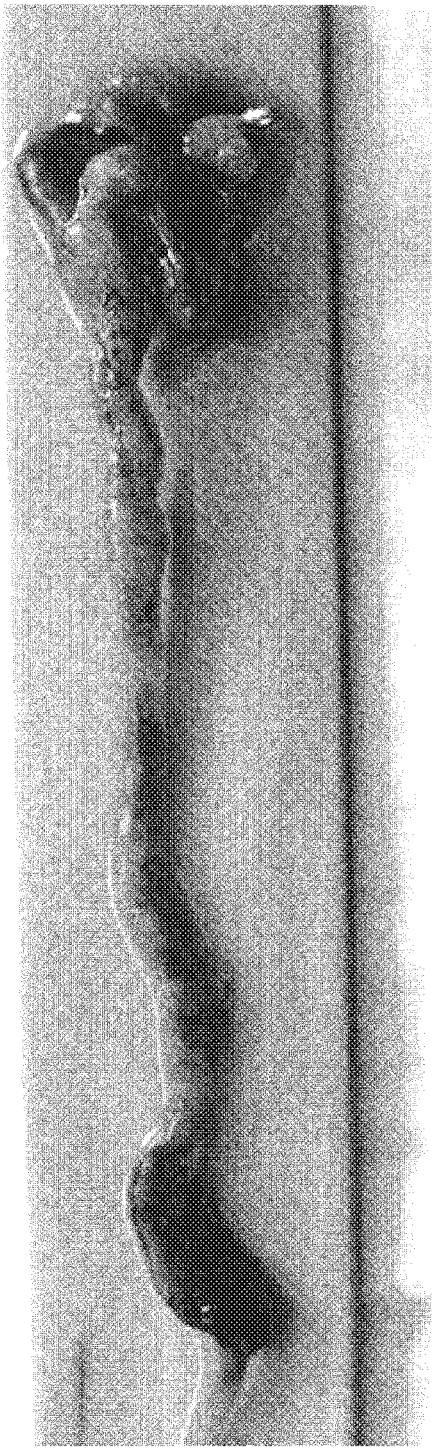
FIG. 14: Photograph of colon of wildtype mice (left) and TNP-Tg mice (right) four days after induction of high-dose TNBS colitis by intrarectal instillation of TNBS at day 0.
Figure 14:
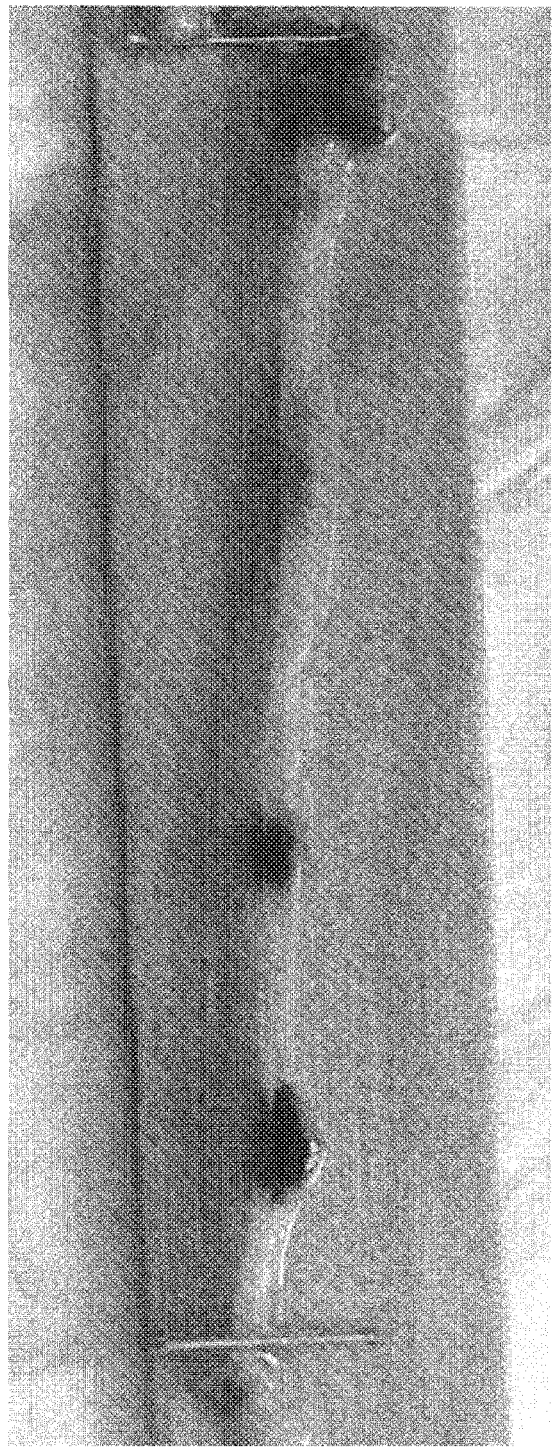

Transgenic Mice Whose Entire Treg Population Expresses the Chimeric Anti-TNP Receptor are Resistant to TNBS-Induced Colitis TNP hapten-mediated colitis was induced in Tg and WT mice by first sensitizing the animals with 150 µl of the 2,4,6-trinitrobenzenesulfonic acid (TNBS, Sigma-Aldrich) at a concentration of 2.5% in 50% ethanol painted on the skin on day 1. On day 8, the antigen was administered rectally (150 µl of 1% TNBS in 50% ethanol; high dose colitis). WT mice developed severe colitis within 2-5 days of rectal TNBS administration (FIG. 14, left panel). In contrast, 90% of the TNP-Tg mice had normal looking colons (FIG. 14, right). Colitis severity scores were as follows:

| Animals | Colitis score (Arbitrary Units) | Mortality |
|---|---|---|
| Wildtype | 12 ± 3.1 | 90 ± 20% |
| TNP-ΔCD28-Tg | 11.1 ± 4 | |
| ErbB2-Tg | 12.7 ± 3.2 | |
| TNP-Tg | 2 ± 2 (p < 0.05) | 20 ± 20% (p < 0.01) |

Figure 15:
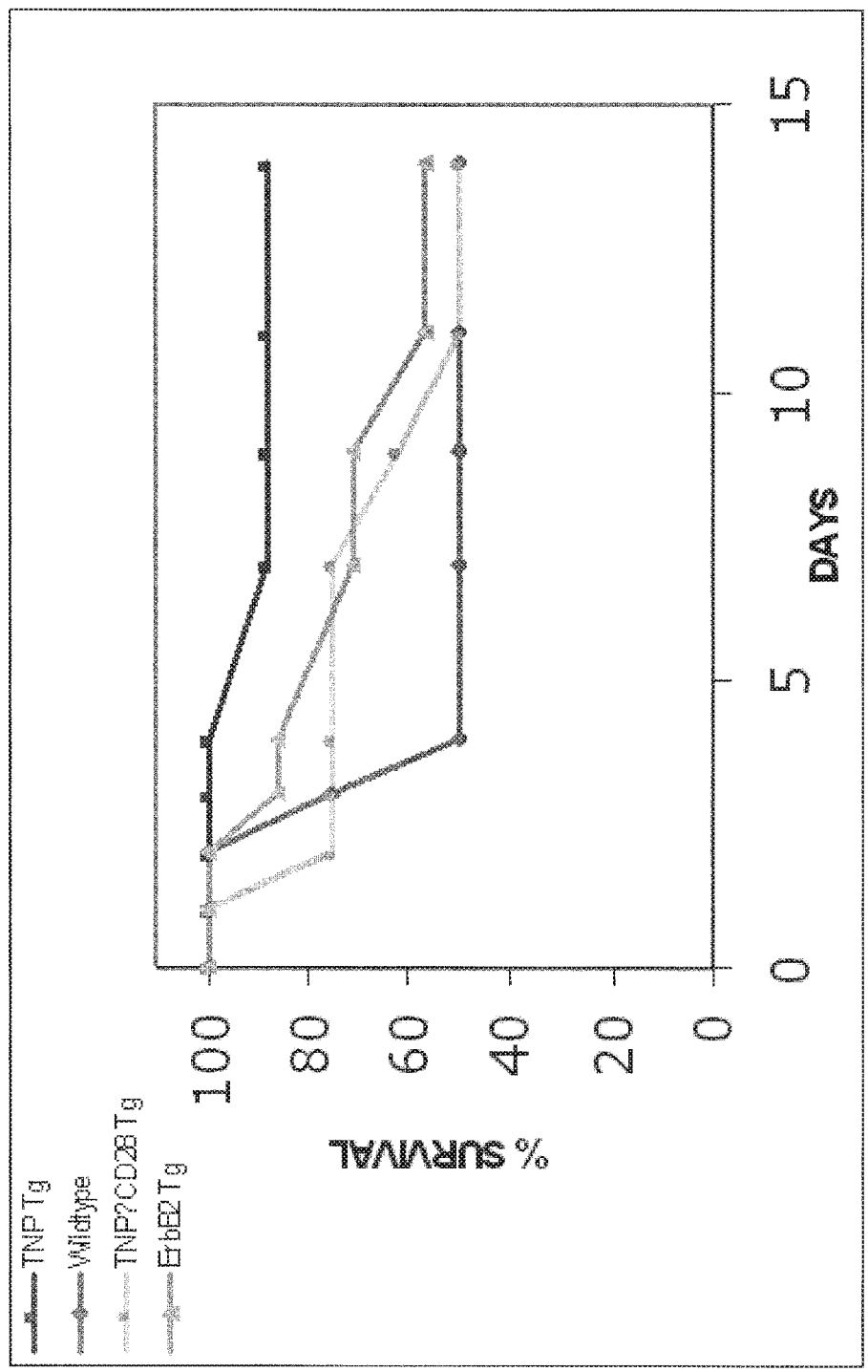
FIG. 15: Mortality curve of wild-type (WT), TNP-Tg, ErbB2-Tg and TNP-ΔCD28-Tg mice following induction of TNBS colitis by intrarectal instillation of TNBS at day 0.
Figure 16:
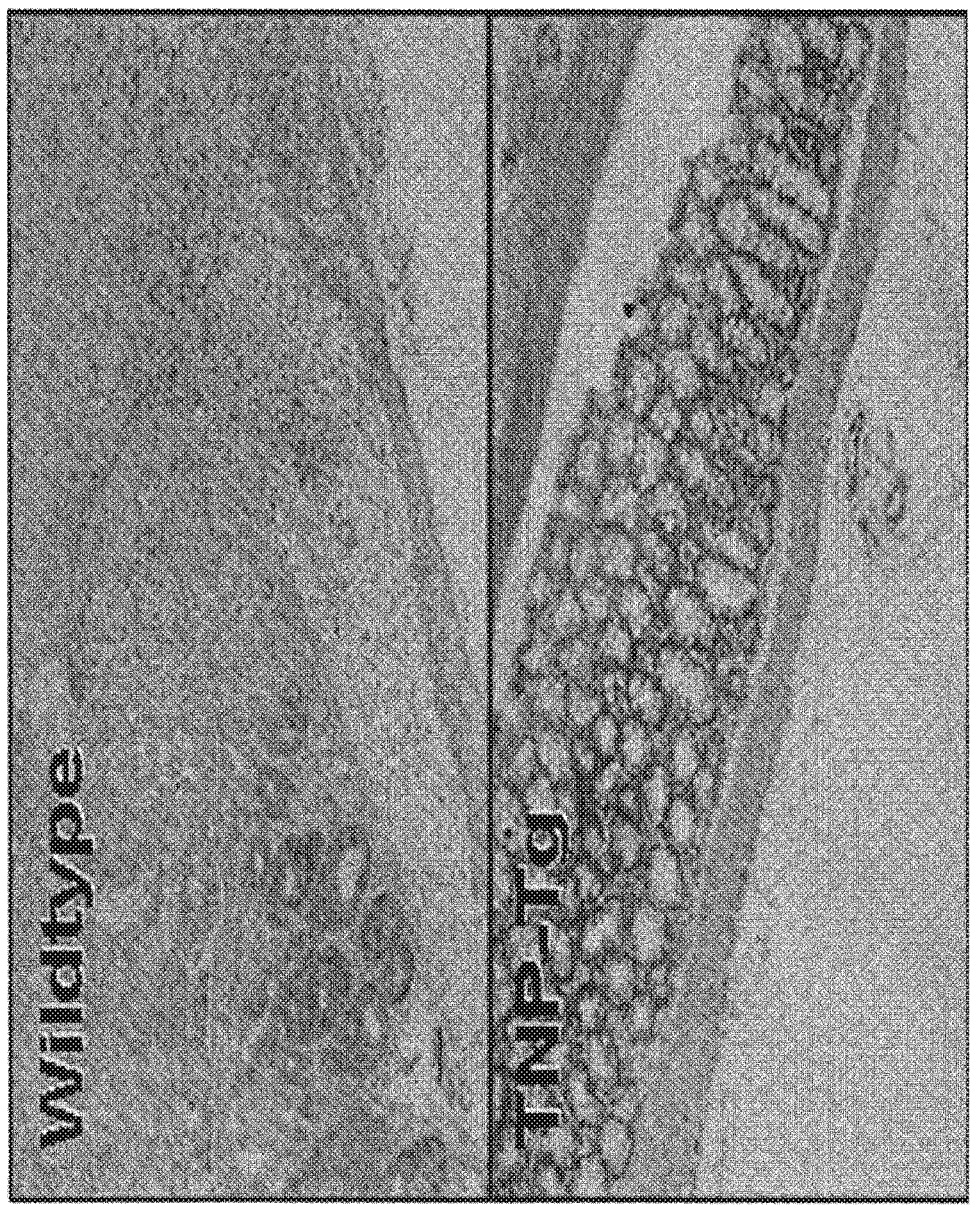
FIG. 16: Photomicrograph of stained tissue (H&E, 40×) of the colons from FIG. 14.

To produce mortality curves the above experiments were repeated with lower doses of TNBS (75 µl of 1% TNBS in 50% ethanol). Similar differences in colitis severity and in mortality were noted (FIG. 15). Microscopically, colons of wildtype, TNP-ΔCD28-Tg and ErbB2-Tg mice showed severe inflammation, necrosis, hemorrhage and in some cases perforation, while those of TNP-Tg mice appeared normal or near normal (FIG. 16).

Figure 17:
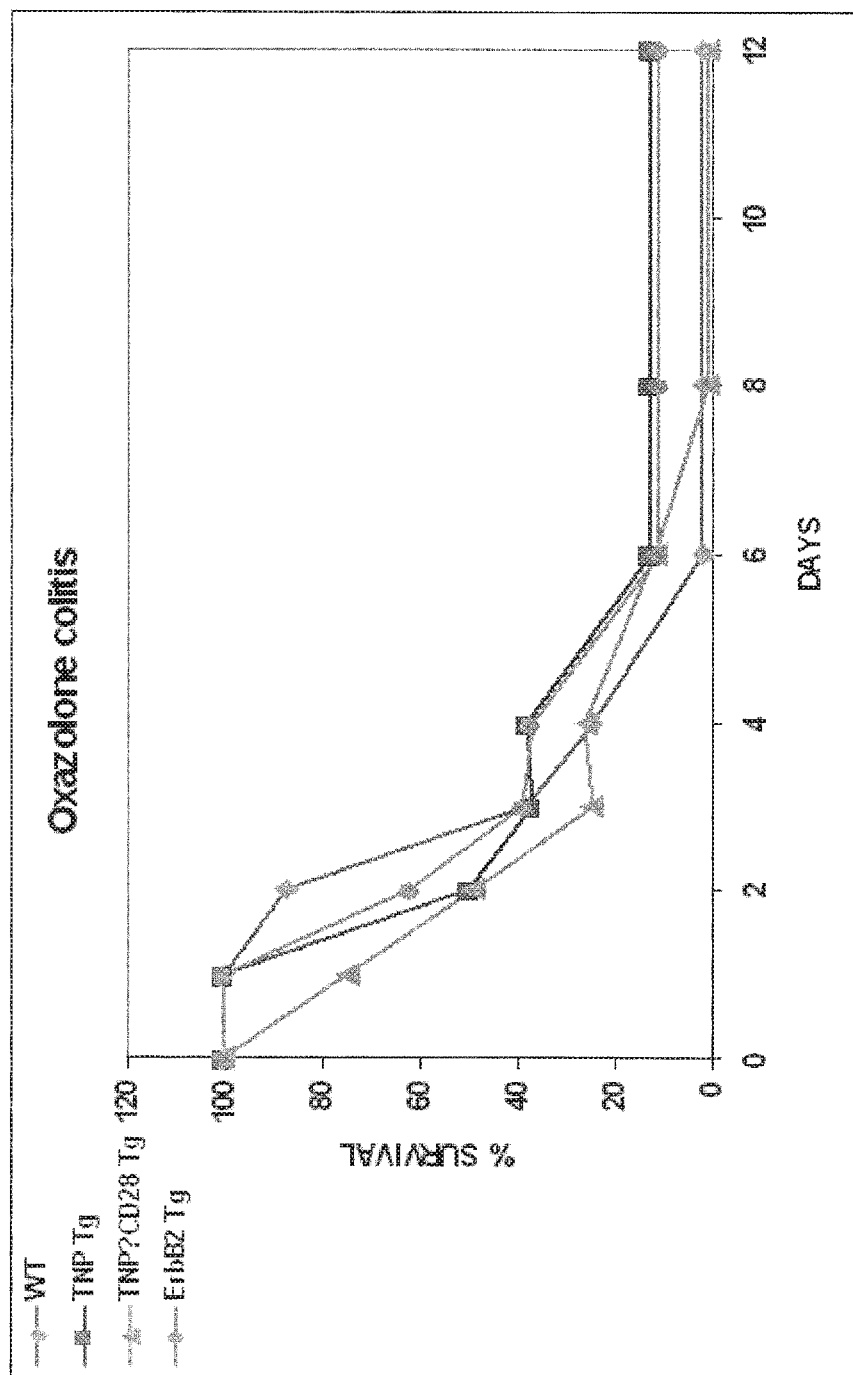
FIG. 17: Mortality curve of WT, TNP-Tg, ErbB2-Tg and TNP-ΔCD28-Tg mice following induction of colitis with oxazolone (OXA; a hapten/antigen that is distinct from TNP). These results serve as a control for Treg specificity in the experiment the results of which are shown in FIGS. 14-16. Colitis was induced using the unrelated hapten, oxazolone, which was intrarectally instilled in similar strains of mice (n=10).

Evidence of antigen specificity of the protection from hapten-mediated colitis came from studies of OXA-induced colitis. As shown in FIG. 17, no differences in mortality were noted between wildtype, TNP-Tg, TNP-ΔCD28-Tg and ErbB2-Tg mice. The same was true for macroscopic and microscopic colitis scores. From these in vivo experiments, it was concluded that the presence of a Treg cell population that uniformly expresses the anti-TNP chimeric receptor results in high grade protection against TNBS-induced inflammation, manifest as reduced colon inflammation and significantly improved survival. It is noteworthy that inclusion of CD28 costimulatory signaling in the CR significantly enhances TNP-Tg Treg suppressive function.

Example XI

Prolonged Stimulation with TNP Combined with TGF-β Promotes Conversion of Leads to TNP-Specific Effector T-Cells to TNP-Specific Tregs Naturally-occurring Tregs are thymus derived, express high levels of Foxp3 and suppress activation of effector lymphocytes. Antigen-specific activation of human effector T-cells may induce expression of Foxp3 in a subgroup of the activated effector cells, which in turn develop a regulatory phenotype. These induced regulatory T-cells were shown to be capable of cell-contact-dependent suppression of freshly isolated effector cells (Walker et al., 2003, supra). In mice, it has been demonstrated that prolonged exposure of effector cells to TGF-β induces Tregs both in vitro and in vivo (Fantini et al., 2004, 2006, supra). This small, peripherally generated population of inducible Tregs may be central in regulation and containment of ongoing immune response, while the inability to induce such Tregs may be responsible for a propensity to develop autoimmunity.

Figure 18:
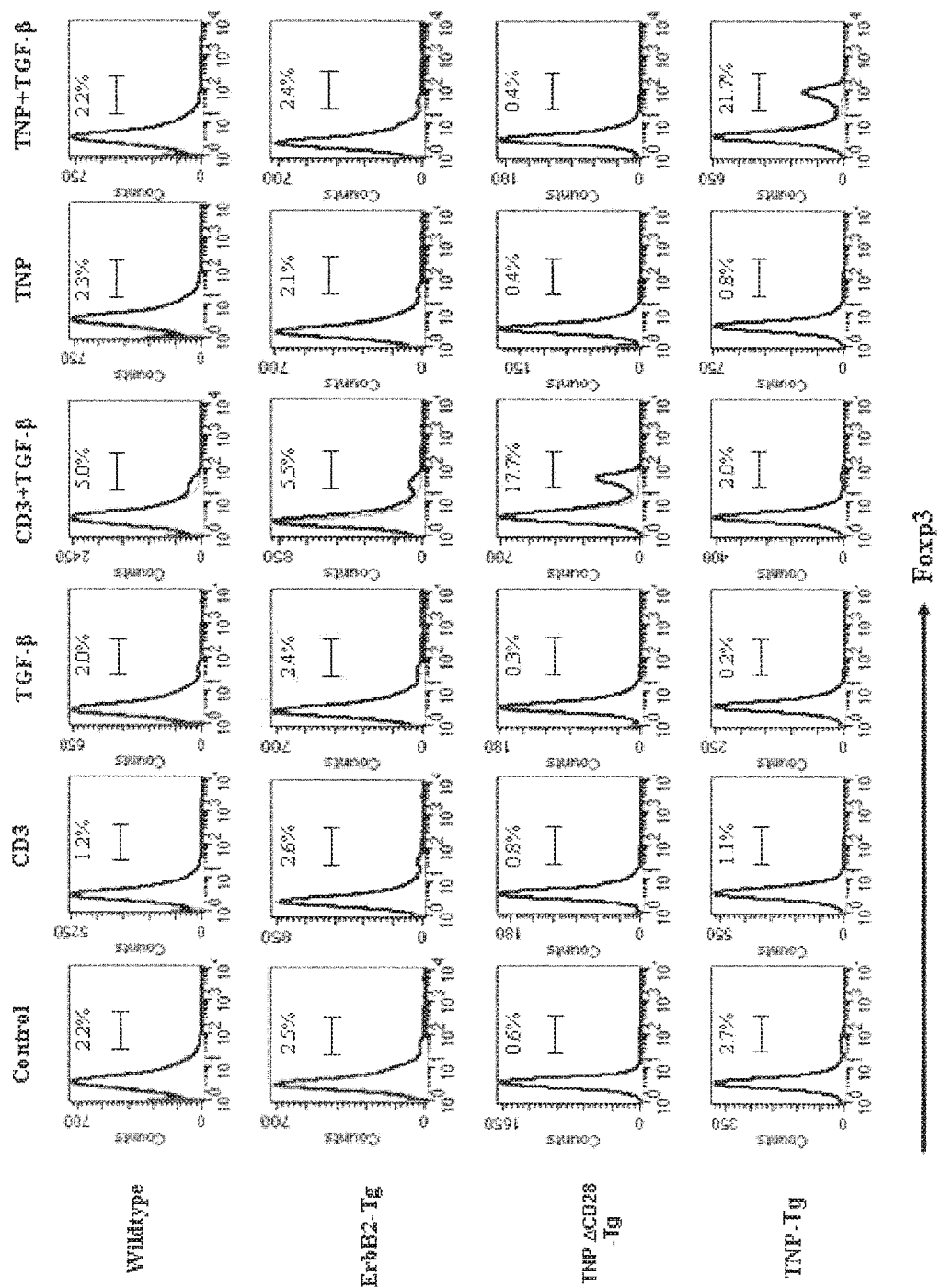
FIG. 18: Flow cytograms of Foxp3 staining of wildtype, ErbB2-Tg, TNP-ΔCD28-Tg and TNP-Tg T effector cells after a week of culture in the presence of the following "stimuli" (across top): anti-CD3, TGF-3, anti-CD3+TGF-β, TNP, or TNP+TGF-β.

To test whether such induction occurred after stimulation of T effector cells through the TpCR, wildtype, TNP-Tg, Erbb2-Tg and TNP-CD28null-Tg T effector cells were isolated by FACS sorting and cultured for 7 days in the presence of either (1) anti CD3 Ab, (2) murine TGFβ, (3_mAb to TNP, (4) anti-CD3 Ab+TGF-β, or (5) anti-TNP Ab+TGF-β. Induction of Foxp3 in cells "developing" from these effector T-cells was assessed after seven days of culture using intracellular Foxp3 staining (FIG. 18).

At time 0 to the time of T effector cell sorting, no Foxp3 staining was noted. A week of stimulation with anti-CD3+TGF-β, but not with TNP+TGF-β, resulted in a 2-fold increase in Foxp3+ cells in wildtype, ErbB2-tg and TNP-CD28null-Tg T effector cells. In contrast, a dramatic 30-fold increase in Foxp3+ cells was observed in TNP-Tg effector cells following exposure to TNP+TGF-0. Interestingly, no Foxp3 induction was noted in TNP-Tg T effector cells following incubation with anti CD3 Ab or with TGF-β, probably due to significant attenuation of CD3 expression in TNP-Tg T-cells (Morvinsky-Friedman et al, in press).

The foregoing results demonstrated that antigen-specific stimulation through the TpCR in the presence of TGF-β, led to induction of Ag-specific Tregs from T effector cells, further contributing to Treg expansion. This change was dependent both on the antigen-specificity of the Ab recognition unit of the TpCR and the intra-cytoplasmic CD28 signaling moiety.

According to the present invention, induction of Tregs in this manner permits the generation of large populations of TpCR-bearing Tregs that can be used in cell-based therapy of autoimmunity.

Example XII

Figure 19:
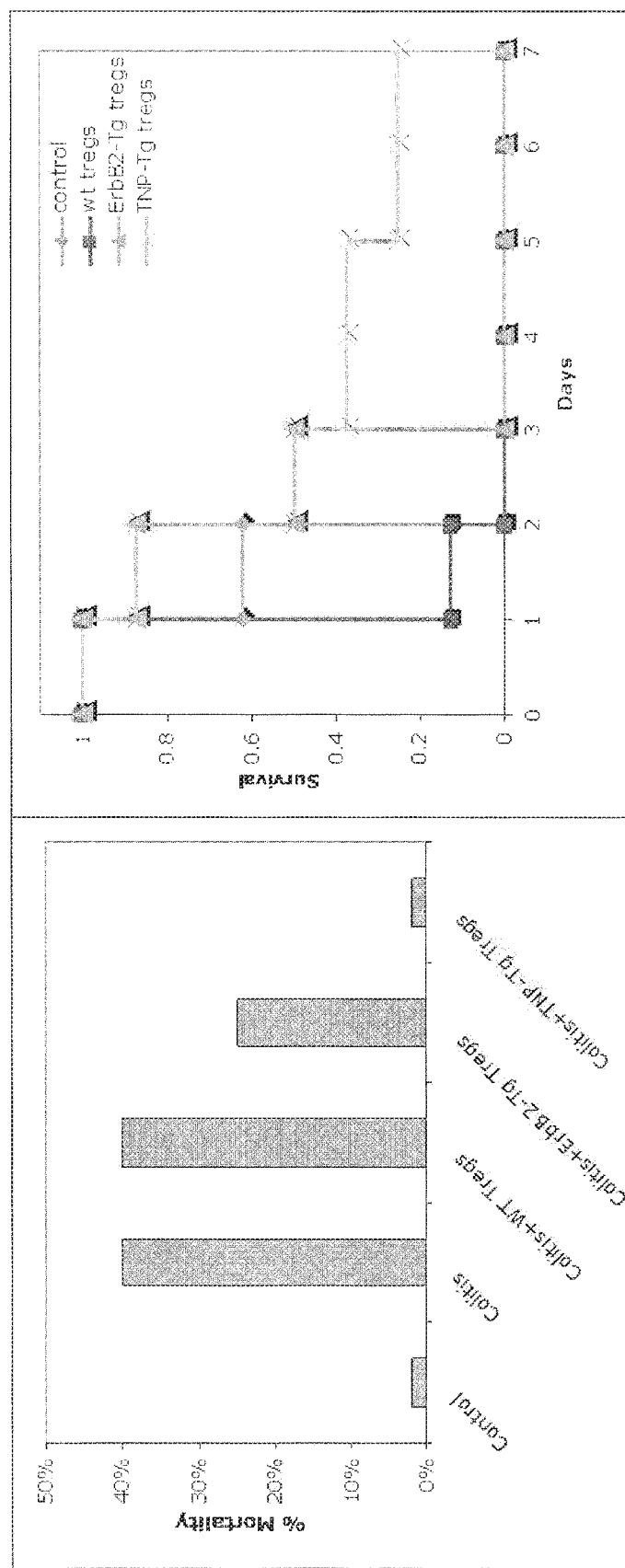
FIG. 19: Graphs showing mortality or survival rate of wildtype mice subjected to induction of moderate (left panel) and severe (right panel) TNBS colitis following adoptive transfer of the following Treg populations: WT, ErbB2-Tg, TNP-Tg and TNP-ΔCD28-Tg.
Figure 20:
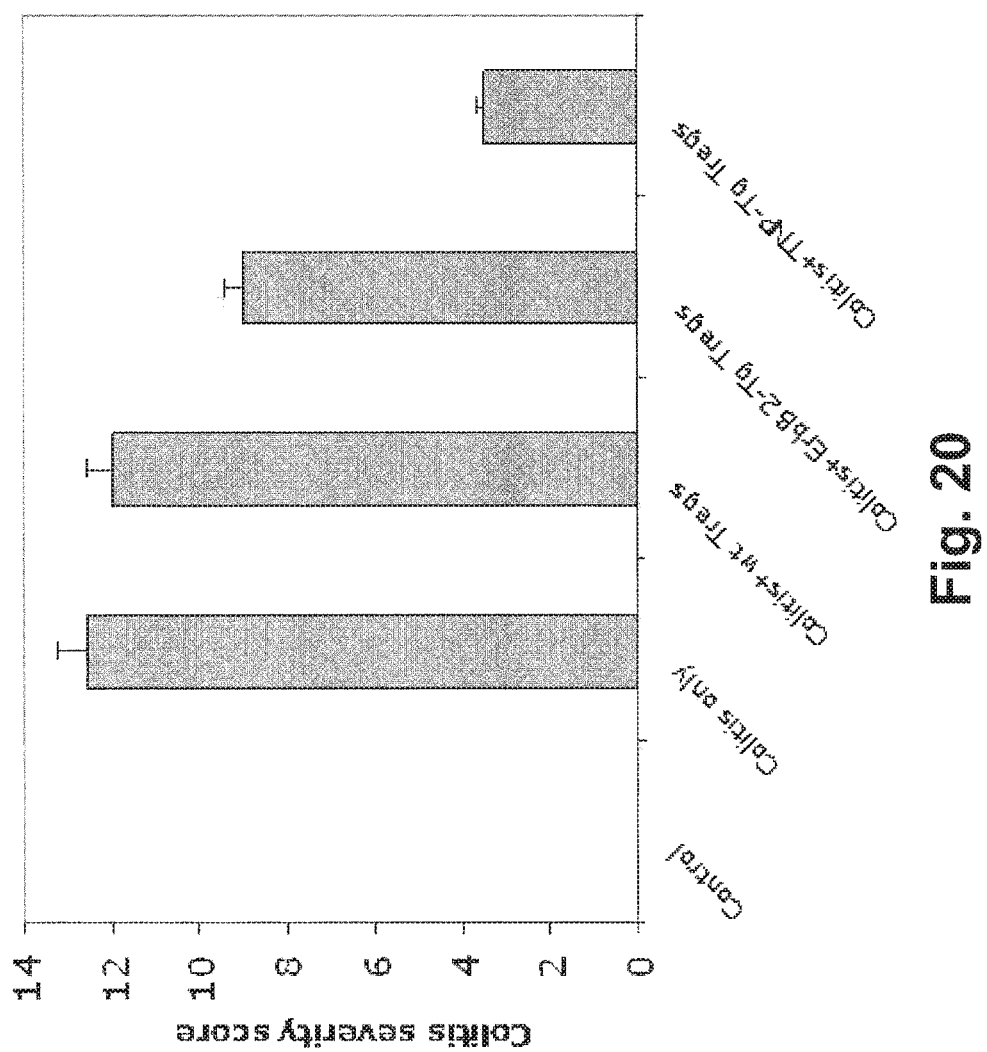
FIG. 20: Graph showing Wallach Colitis Severity Score of wildtype mice subjected to induction of TNBS colitis after adoptive transfer of cells from WT, ErbB2-Tg or TNP-Tg donors. TNBS colitis was induced in WT mice (n=8) on day 0. After 16 hours, Tregs (1×10$^5$) from TNP-Tg, ErbB2-Tg or WT mice were adoptively transferred to the recipient mice. Each experiment was repeated three times. The data shown represent the average of a representative experiment.
Figure 21:
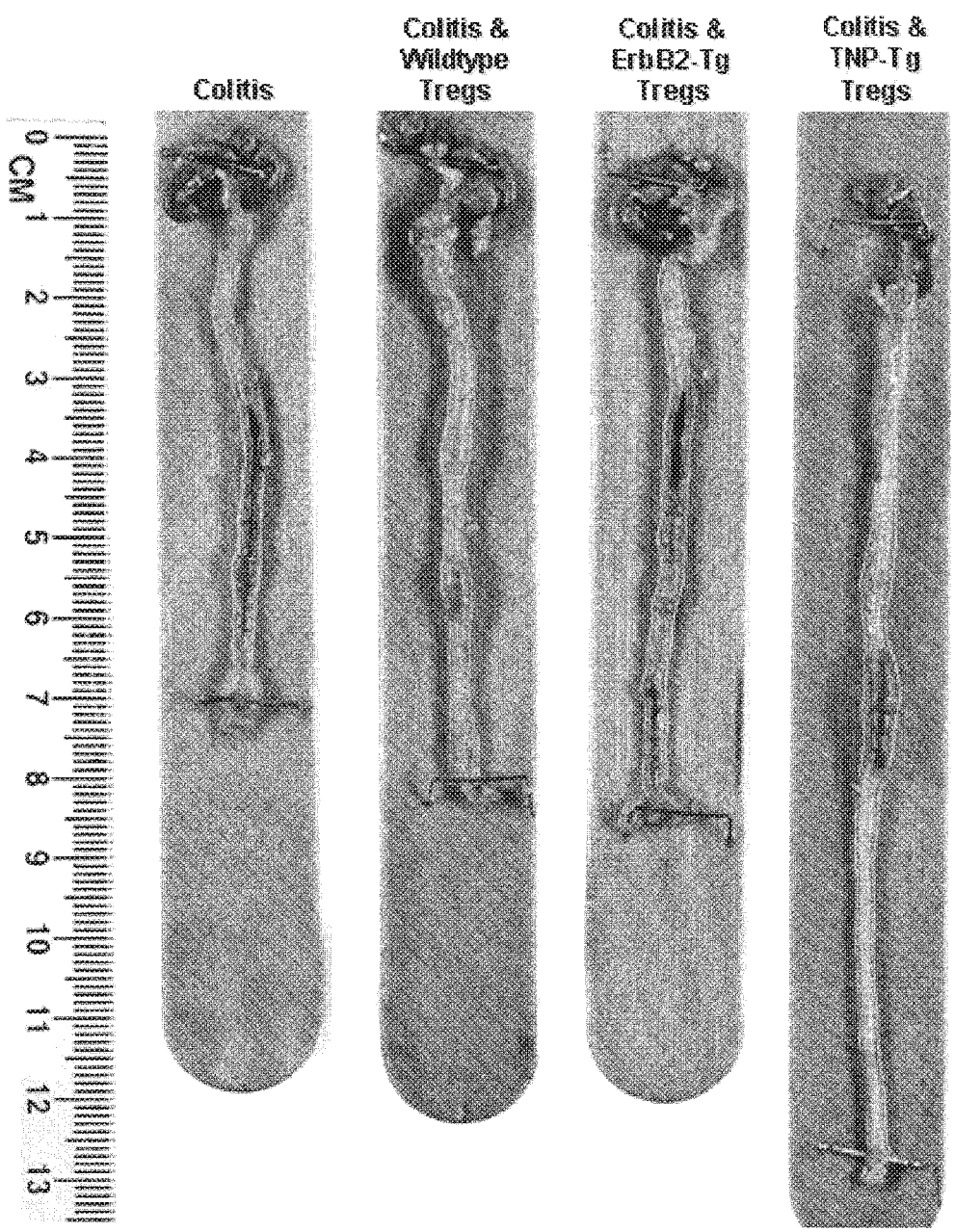
FIG. 21: Photograph of excised colons of wildtype mice in which TNBS colitis was induced, following adoptive transfer of wildtype, ErbB2-Tg and TNP-Tg mice in the experiment described in FIG. 20.
Figure 22:
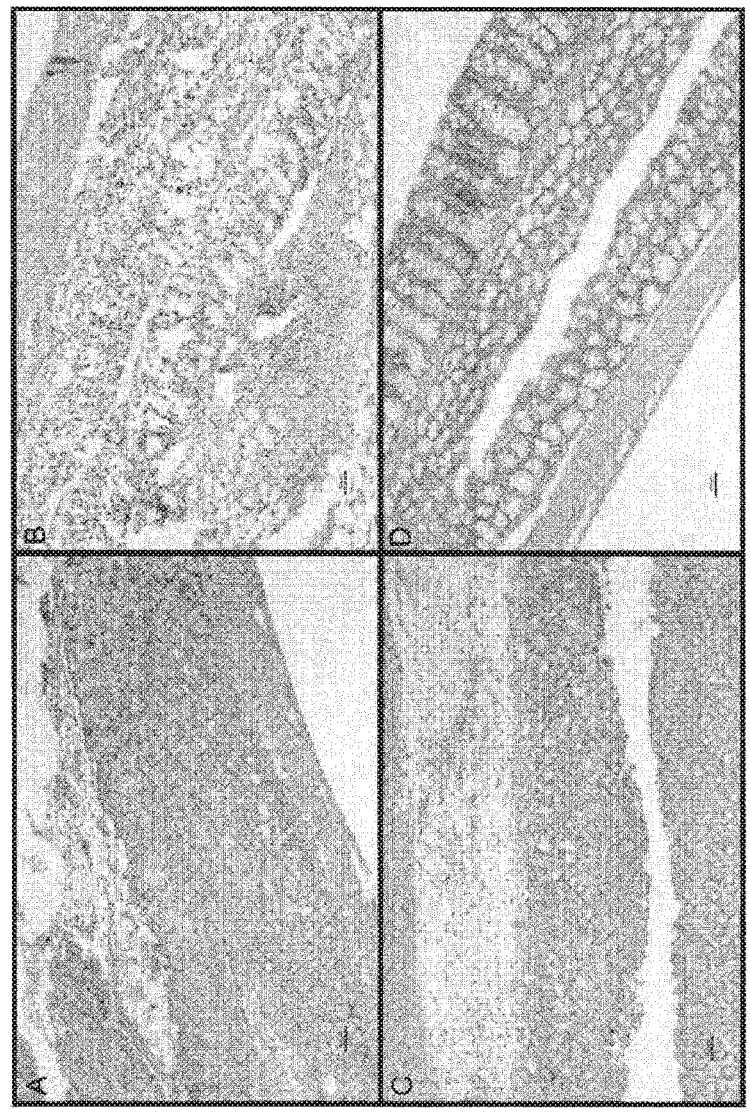
FIG. 22: Photomicrograph of stained colon tissue sections (H&E, 40×) from wildtype mice with TNBS colitis after adoptive transfer of Tregs from the following donors: (A) wildtype (B) ErbB2-Tg and (C) TNP-Tg. Panel D shows normal control colon.

Adoptive Transfer of TNP-Tg Tregs to WT Mice with TNBS Colitis Ameliorates Symptoms and Improved Survival Studies were conducted to establish that TNP-Tg Tregs are responsible for the resistance of TNP-Tg mice to TNBS colitis and to evaluate their therapeutic capacity in autoimmunity. Wildtype, TNP-Tg and Erb-b2-Tg Tregs were isolated and administered in varying numbers to wildtype mice a day after induction of TNBS colitis. As was previously described, adoptive transfer of large numbers of Tregs of any origin ($\geq 2 \times 10^5$) caused nonspecific attenuation of TNBS colitis. This is believed to result from the presence of a sufficiently large population of pre-activated Tregs that can exert their suppressive activity in the absence of antigen stimulation or specificity. In contrast, adoptive transfer of smaller numbers ($5 \times 10^4$) of TNP-Tg Tregs but not of wildtype or Erbb2-Tg Tregs, prolonged survival (FIG. 19), improved Wallach colitis severity scores (FIG. 20), and significantly improved macroscopic (FIG. 21) and microscopic (FIG. 22) appearance of colon tissue. FIG. 21 shows marked bowel shortening, a manifestation of colon inflammation (in WT and ErbB2-Tg, but not in TNP-Tg mice). FIG. 22 shows the severe transmural inflammation, necrosis, mucosal bleeding and loss of normal architecture in colons of WT mice with TNBS colitis that had received control (WT and ErbB2-Tg), but not in TNP-Tg colons.

Example XIII

Figure 23:
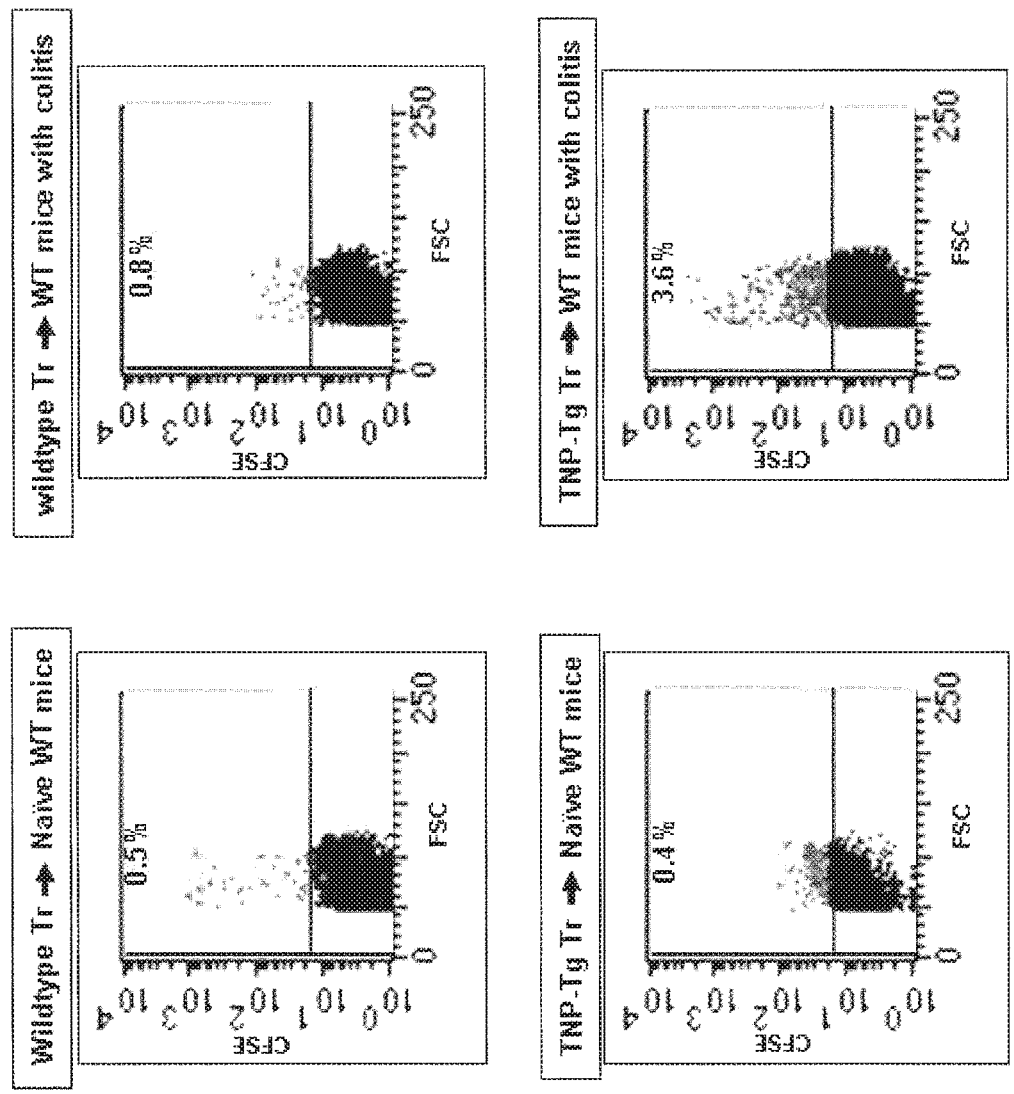
FIG. 23: Localization of Tregs in the colon. Flow cytograms of fluorescent staining Tregs labeled with the intracellular dye carboxyfluorescein diacetate succinimidyl ester (CFSE) in the colonic lamina propria of naïve mice or mice with TNBS-colitis. Labeled Tregs were intraperitoneally injected 24 hours following induction of TNBS colitis. Lymphocytes from lamina propria were obtained 16 hrs after adoptive transfer of 10$^6$ wildtype or TNP-Tg Tregs to indicated recipients. CFSE-labeled Tregs were 9-fold more abundant in diseased colons. Data shown represent the percentages of CFSE-positive cells in the corresponding gates of one representative mouse of each four-mouse group. Each experiment was repeated twice.

Migration/Trafficking of Redirected 'Tregs to Sites of Inflammation: Adoptively-Transferred TNP-Tg Tregs Localize to Colons in TNBS Induced Colitis Studies were done to garner additional support for the role of TNP-Tg Tregs in attenuating TNBS colitis by showing that these cells indeed localize to inflamed colon tissue. WT and TNP-Tg Tregs were isolated and stained with the fluorescent intracellular dye, carboxyfluorescein diacetate succinimidyl ester (CFSE). Following staining, $10^6$ Tregs were administered intraperitoneally(ip) to control WT mice or to WT mice in which TNBS colitis had been induced 12 hours earlier. Sixteen hours after this treatment, mice were sacrificed and lamina propria lymphocytes isolated from their colons. The protocol used was described above to isolate lamina propria lymphocytes. Thereafter, the cells were examined for the presence of CFSE-positive cells by FACS analysis. As shown in FIG. 23, very small numbers of adoptively-transferred WT or TNP-Tg Tregs reached the colons of normal mice. Induction of colitis led to a small increase (0.5% to 0.8%) in the number of WT CFSE-stained Tregs in colon tissue. In contrast, adoptive transfer of CFSE-labeled TNP-Tg Tregs to mice with colitis led to a significant increase in colon Treg population, ranging from 0.4% to 3.6%. This demonstrates that TNP-Tg Tregs localize in a TNBS-exposed target organ, where they exert their suppressive function.

Example XIV

Accumulation of Adoptively Transferred TNP-Tg Tregs within the Mucosal Layer of Colons of Mice with TNBS Colitis An important aspect of understanding the role of Tregs for adoptive therapy of autoimmune inflammation of the Treg in diseased organs, where they are expected to exert their suppressive effects. To demonstrate TNP-Tg-Treg localization, WT and TNP-Tg Tregs were labeled with CFSE and transferred to WT mice 24 hours following induction of TNBS colitis. While very small numbers of CFSE-labeled WT Tregs were observed in cell extracted from colonic lamina propria of naïve or TNBS colitis-induced mice, a nine-fold increase in TNP-Tg Tregs was noted (FIG. 23).

Figure 24:
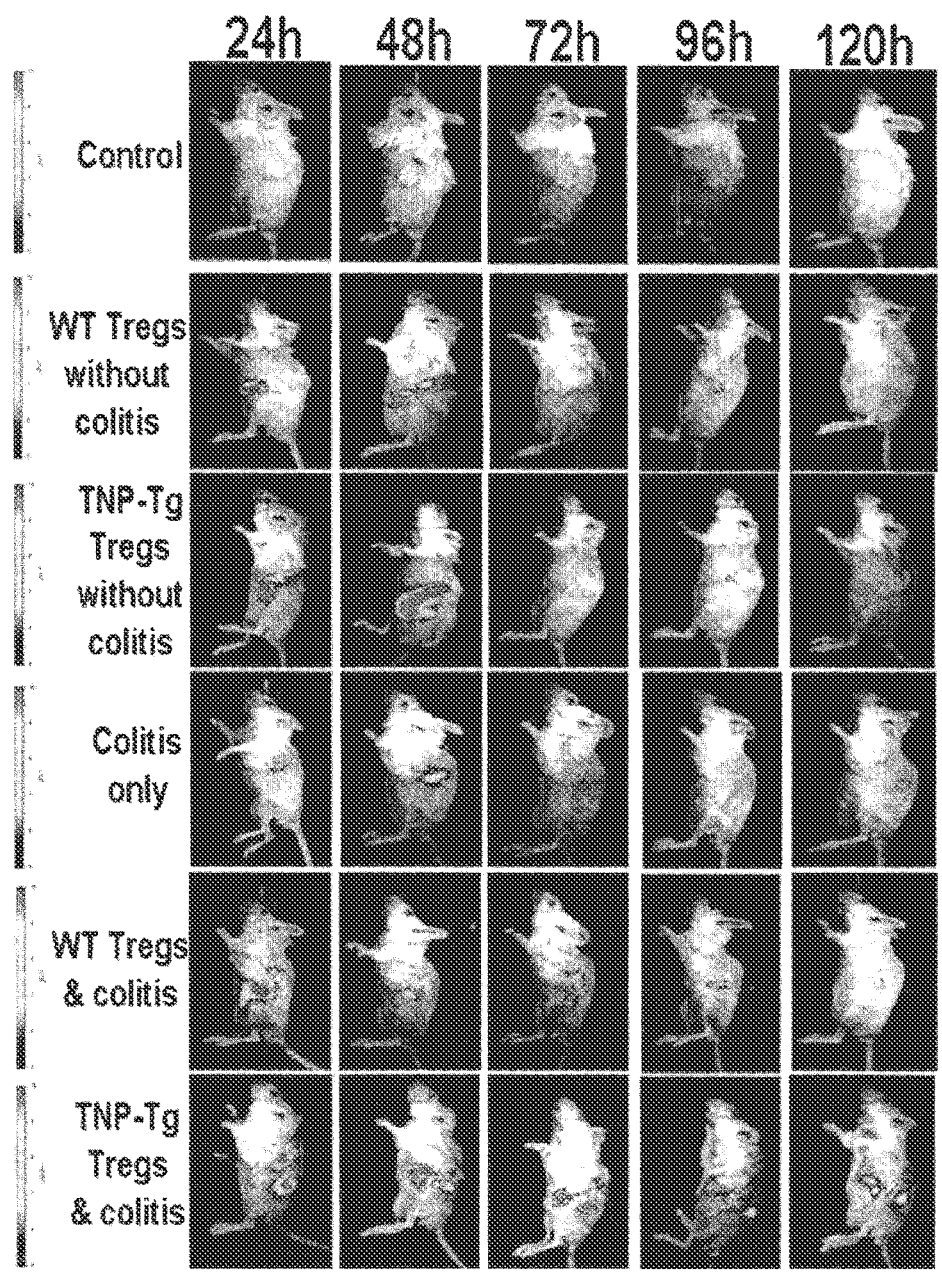
FIG. 24: Localization of Tregs in the colon. In-vivo imaging of WT mice receiving DiR-labeled wildtype and TNP-Tg Tregs (1×10$^6$) 16 hours following induction of TNP colitis (n=3). Mice were subjected to a whole body imaging (IVIS® 100 Series Imaging System) at 12 hour intervals. A single representative mouse out of three in each group is shown at all time points. Two independent experiments were performed, with similar results.

To study the kinetics of TNP-Tg Treg localization of in the living animal, the IVIS® 100 Series Imaging System was employed (Xenogen, Alameda Calif.). Wildtype and TNP-Tg Tregs, $1.5 \times 10^6$, labeled with the near-infrared lipophilic carbocyanine dye 1,1'-dioctadecyl-3,3,3',3'-tetramethylindotricarbocyanine iodide (DiR, Invitrogen USA), were administered ip to WT mice with or without TNBS colitis, who were monitored daily with the IVIS whole body CCCD camera (FIG. 24). A strong anterior-abdominal fluorescent signal, reflecting the bulk of injected Tregs, was noted in naïve mice 24-48 hours following ip injection of Tregs and disappeared thereafter due to Treg redistribution. In mice with TNBS colitis, a faint abdominal signal was noted for 72 hours, probably reflecting inflammation-related auto-fluorescence. In mice with TNBS colitis that received labeled WT Tregs, a week-moderate abdominal fluorescent signal could be recognized up to 96 hours following Treg transfer. In contrast, TNP-Tg Treg-administered to WT mice with TNBS colitis featured a distinct abdominal fluorescent signal for up to a week following cell transfer, substantially stronger than that of wildtype Tregs at all time points. These results reflect persistent TNP-Tg Treg localization within colons during the colitis.

Figure 25:
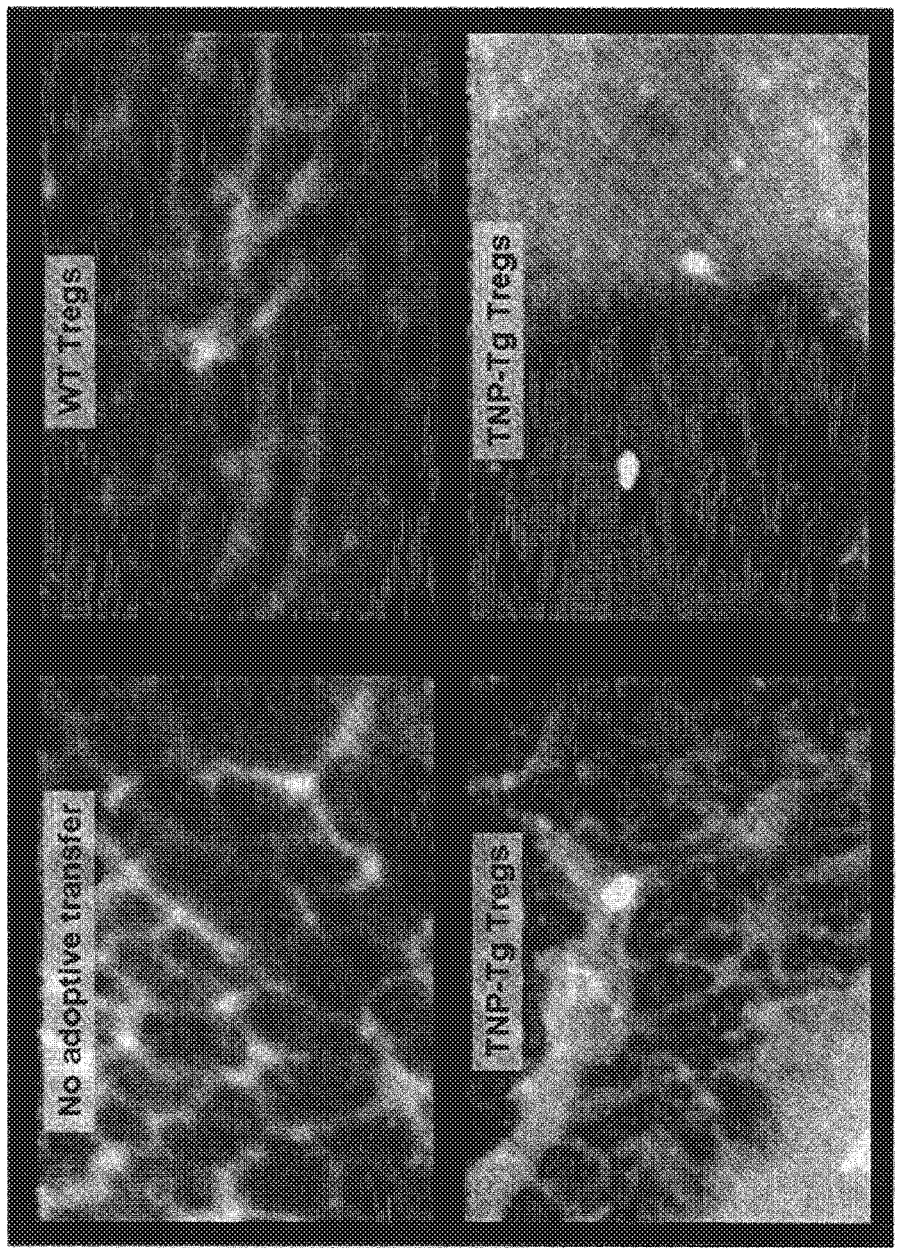
(FIG. 25: Localization of Tregs in the colon. In-situ fluorescent microendoscopic (Cell Vizio) evaluation of CFSE-labeled Tregs accumulating at the colonic pre-luminal mucosal layer. The experimental design is identical to the one described in FIG. 23. The figure shows representative frames taken 48 hours following adoptive transfer. Each group consisted of four mice, and each experiment was repeated twice.

To determine whether TNP-Tg Tregs reach the inner colonic mucosal layer, the location where most of TNBS-induced mucosal damage takes place, the Cell Vizio confocal microendo-scopy system was employed (Cell Vizio, MKT, Paris, France). An intrarectally-inserted 650 µm diameter confocal microendoscope enabled visualization of CFSE-labeled cells in up to a 150 µm bowel wall thickness (FIG. 25). Numerous adoptively transferred CFSE-labeled TNP-Tg, but no WT Tregs could be visualized in the inner mucosal layer of WT mice with TNBS colitis as early as 12 hours following systemic Treg transfer. This result indicates that TNP-Tg Tregs localize in response to colonic TNBS, within hours of their administration, and that they reach the deepest colonic mucosal layers, where they exert their suppressive functions.

Example XV

Figure 26:
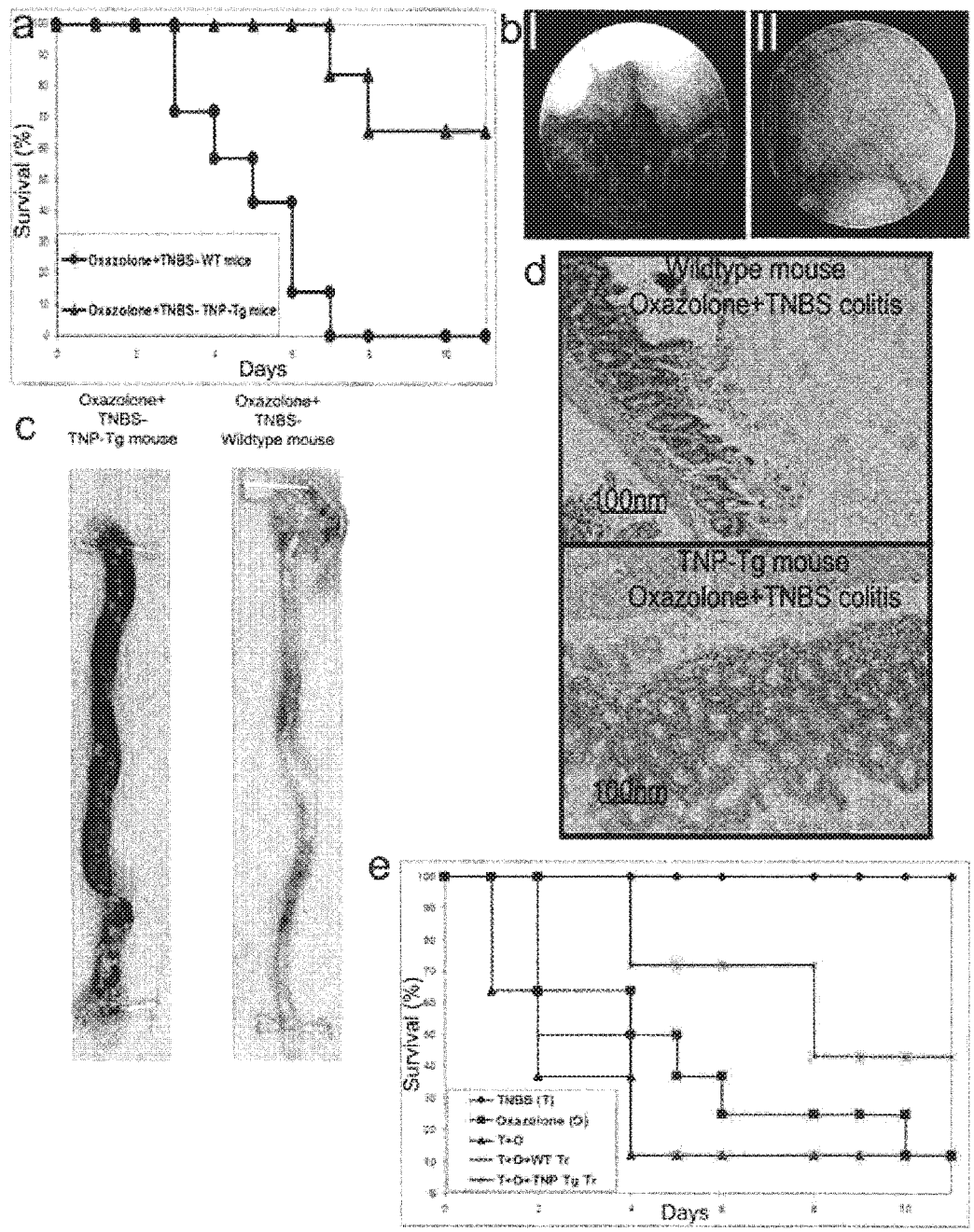
FIG. 26: Intrarectal administration of TNBS results in TNP-Tg Treg-mediated protective effect from oxazolone colitis. (a) Mortality rates of wildtype and TNP-Tg mice administered oxazolone±low doses of TNBS, 1 week following presensitization with oxazolone only. (b) Murine colonoscopy images of representative WT and TNP-Tg mice. (c) Macroscopic appearance of representative colons from various mouse groups. (d) Microscopic appearance of colons shown in c. (e) Adoptive transfer of Tregs (Tr) to oxazolone (O) pre-sensitized mice induced one week later with oxazolone (0) colitis in the presence of low dose of TNBS (T). WT or TNP-Tg Tregs were administered to mice (n=8) 16 hours after the induction of colitis.

Administration of TNP-Tg Tregs Specific to a Bystander Antigen (TNBS) Cures Colitis Mediated by a Pathogenic (Oxazolone) Antigen In contrast to hapten-mediated colitis, in which the eliciting antigen is predefined, the disease-causing antigen in inflammatory bowel disease (IBD) is unknown. To enable application of the 'T-body' approach in IBD, naïve TPCR-bearing Tregs were tested to determine whether they can be activated by a predetermined 'bystander' colon- or colitis-associated antigen, to perform their antigen-nonspecific suppressive action. To this end, WT and TNP-Tg mice were pre-sensitized to oxazolone only. A mixture of oxazolone and low doses of TNBS were introduced intrarectally. As is shown in FIG. 26a, concomitant challenge of WT mice with TNBS and oxazolone, was associated with a 100% one-week mortality rate, as compared to only a 15% one-week mortality of TNP-Tg mice (P<0.01). Similarly, significant mucosal inflammation was evident in both WT and TNP-Tg mice with oxazolone colitis (not shown), and was most severe in wild-type mice given TNBS+oxazolone (FIG. 26b, box I) resulting in severe bleeding, fibrin deposition and sloughing off of colonic mucosa.

In utter contrast, TNP-Tg mice administered TNBS+oxazolone featured normal-appearing colonic mucosa with scattered areas of mild colitis (FIG. 26b, box II). Macroscopically and microscopically, colons of concomitantly TNBS-treated and oxazolone-treated WT mice featured severe colitis, as opposed to the near-normal colons in TNP-Tg mice (FIGS. 26c and 26d, respectively.)

Notably, this "bystander" protective effect also occurred when TNP-Tg Tregs were adoptively transferred to oxazolone-presensitized wild-type mice which were intrarectally boosted with a mixture of oxazolone and low doses of TNBS (FIG. 26e, P<0.01)). In contrast, adoptively transferred WT Tregs did not have this curative effect, and the very low TNBS doses in the absence ofpre-sensitization were insufficient by themselves to induce TNBS colitis. These results demonstrate that Treg activation by a bystander antigen (TNBS) cause an improvement in colitis that has been induced by a different non-cross-reactive antigen (oxazolone).

Example XVI

Delivery of Foxp3 to Cell Nucleus by Vectors Comprising Chimeric Receptors

An experiment was conducted to verify that the Foxp3 can be expressed following transduction of A273 cells with retroviral vector constructs designed to transduce Treg cells. A fused gene was generated that included eGFP sequences encoding green fluorescent protein (referred to as eGFP or GFP). This was engineered as a bicistronic construct with the GFP sequence alone or linked with a Foxp3-encoding sequence (after an IRES) into vectors that comprised a chimeric receptor construct with the following extracellular recognition regions: See description of FIG. 27 for discussion of the chimeric receptor constructs used. 273 cells. transduced with vectors comprising the same chimeric receptors but with a bicistronic eGFP gene only (without Foxp3) served as controls for Foxp2 expression.

The results are shown in FIG. 27. The upper half of the Figure shows the GFP-only controls, whereas the lower half of the Figure shows GFP-Foxp3 constructs. The two-paneled rectangles in the Figure show light microscopic (left half) and fluorescence microscopic (right half) images of the same material (to visualize and localize the GFP).

All the control group expressed the eGFP in their cytoplasm only. In contrast, in cells that were transduced with the eGfP-Foxp3-fusion constructs, the nuclei were fluorescent (appearing as bright nuclear images) due to the transport to and expression of the Foxp3 transcription factor in the nuclei.

In another experiment not shown here, expression of chimeric receptor made of the full length MD2 protein (SEQ ID NO:5) or the CD14 protein (SEQ ID NO:4) was confirmed by the ability of transduced cells, which expressed the extracellular region of the CR on their surface, to bind the ligand of MD2 and CD14, bacterial LPS, which was provided in biotinylated form and revealed by secondary binding of fluorescent avidin.

Example XVII

Vectors Comprising Chimeric Receptors with LPS-Binding Extracellular Regions

Nucleic acid constructs and vectors that encode extracellular regions that comprise an anti-LPS antibody domain (e.g., SEQ ID NO:3 or the scFv-coding portion thereof) have been made and others can be made. Such vectors express extracellular polypeptide domains that are shown to bind LPS, for example in an assay using biotinylated LPS and detectably labeled (e.g., fluorescently labeled) avidin. See also Example XVI above.

Nucleic acid constructs and vectors that encode extracellular regions that comprise a LPS-binding nonantibody polypeptide have been made (e.g., SEQ ID NO:6-11, 13 and 14). Such constructs include bicistronic ones that also comprise Foxp3. Other such constructs can be made using the method described above along with methods well-known in the art. Such constructs (such as SEQ ID NO: 13 and 14) include those encoding full length CD14 (SEQ ID NO:4) or MD2 (SEQ ID NO:5) protein, and constructs encoding LPS-binding motifs therefrom (such as SEQ ID NO:6-9) and combinations (such as SEQ ID NO:10 and 11). The constructs that are made include those with CD28-FcRγ intracellular stimulatory/costimulatory regions and those that utilize others of the type disclosed herein.

Treg cells are redirected as described herein using the above constructs, including those that have been made and tested and those that can be made.

Such Treg cells are administered into subjects suffering from IBD, such as ulcerative colitis. Treg cells are administered in numbers in accordance with the above examples, or in numbers that are readily determined to be effective by those skilled in the art using only routine experimentation, and via routes of administration as exemplified above and disclosed throughout this document. These redirected Treg cells that express an LPS binding antibody region or another LPS-binding moiety on their surface (CD14, MD2, fragments thereof, or combinations of these) as part of their CR's are able to reduce the symptoms, intensity, severity and duration of the IBD in the subject to a significant degree compared to untreated control subjects or control subjects administered with control Tregs. (Such control Treg cells are ones not transduced to express the present CR's, or those redirected to be specific to antigens or ligands not present at the site of the IBD.) Introduction of LPS-related molecules or epitopes that bind to these same extracellular receptors on the redirected Treg cells to the sites of administration (and/or expected action) of the redirected Treg cells further facilitates their therapeutic activity.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of treating inflammatory bowel disease (IBD) in a mammalian subject in need thereof, comprising:
   administering to said mammalian subject an effective amount of redirected T lymphocytes endowed with Treg cell phenotype and specificity toward a target antigen that is present or expressed at a site of inflammation in the bowel, wherein said target antigen is a lipopolysaccharide (LPS) intestinal bacterial floral antigen, and wherein said redirected T lymphocytes comprise a chimeric nucleic acid molecule, comprising:
   (a) a first nucleic acid segment comprising a sequence encoding an extracellular recognition region specific for said target antigen, which region does not comprise an MHC protein extracellular domain, wherein said extracellular recognition region comprises an antibody-derived scFv domain that is specific for said selected target antigen;
   (b) a second nucleic acid segment comprising a sequence encoding a transmembrane region; and
   (c) a third nucleic acid segment comprising a sequence encoding an intracellular signaling region comprising a combination of T-cell signaling polypeptide moieties, said combination of moieties comprising at least one cytoplasmic domain of a T-cell costimulatory molecule and at least one cytoplasmic T-cell stimulatory domain, and which combination of moieties, when the chimeric nucleic acid molecule is transfected or transduced into a T cell and said extracellular recognition region binds to the target antigen, triggers activation of the transfected or transduced T cell;
   wherein said redirected T lymphocytes express, in one single, continuous chain, a chimeric receptor polypeptide comprising the extracellular recognition region, the transmembrane region, and the intracellular signaling region, such that the extracellular region thereof is displayed on the surface of the redirected T lymphocytes.

2. The method of claim 1, wherein said IBD is Crohn's disease or ulcerative colitis.

3. The method of claim 1, wherein said extracellular recognition region is linked to said transmembrane region through a flexible spacer.

4. The method of claim 1, wherein said extracellular recognition region is linked to said transmembrane region through a hinge from a molecule of the immunoglobulin superfamily.

5. The method of claim 4, wherein said intracellular signaling region comprises the CD3-ζ chain or the FcRγ chain.

6. The method of claim 1, wherein said intracellular signaling region comprises at least two different cytoplasmic domains of a T-cell costimulatory molecule.

7. The method of claim 1, wherein said T-cell costimulatory molecule is selected from the group consisting of CD28, OX40, CD40L, 4-1BB, and PD-1.

8. The method of claim 7, wherein said T-cell costimulatory molecule is CD28.

9. The method of claim 7, wherein said T-cell costimulatory molecule is 4-1BB.

10. The method of claim 1, wherein said redirected T lymphocytes further comprise a nucleotide sequence that encodes a polypeptide capable of causing the redirected T lymphocytes to express Foxp3.

11. The method of claim 1, wherein said redirected T lymphocytes are produced by obtaining a population of T-cells from the mammalian subject to be treated, transfecting said cells with said chimeric nucleic acid molecule and causing the cells to express Foxp3 by
   (i) stimulating the transfected cells to induce Foxp3 expression, or
   (ii) introducing an exogenous Foxp3-encoding construct into the transfected cells.

12. The method of claim 1, wherein said redirected T lymphocytes are produced by obtaining a mixed population of T-cells from the mammalian subject to be treated, enriching or purifying Treg cells from the mixed population of T-cells on the basis of the Treg cells' expression of CD4 and CD25 and/or Foxp3, and transfecting said enriched or purified Treg cells with said chimeric nucleic acid molecule.

13. The method of claim 1, wherein said redirected T lymphocytes are produced by:
   (a) obtaining
       (i) peripheral blood mononuclear cells,
       (ii) peripheral blood lymphocytes,
       (iii) T-cells enriched or purified from (i) or (ii), or
       (iv) a subset of T-cells enriched or purified from (iii);
   (b) exposing the cells obtained in (a), ex vivo, to an amount of TGF-β or other Treg-inducing cytokine or agent that is effective to induce expression of Foxp3 and convert T-cells to a Treg phenotype,
   (c) optionally, culturing and expanding said exposed cells of (a); and
   (d) before, after, or between said steps (a) and (b), transfecting said cells with said chimeric nucleic acid molecule.

14. The method of claim 1, wherein said redirected T lymphocytes are administered to said mammalian subject systemically, parenterally, regionally, or locally to a site of inflammation.

15. The method of claim 14, wherein said parenteral administration comprises intraluminal, intrathecal, intramuscular, intravenous, subcutaneous, intraperitoneal, or intra-articular administration.

16. The method of claim 1, wherein said mammalian subject is a human.

17. The method of claim 1, wherein said redirected T lymphocytes are administered at a dosage of about $10^6$ to about $10^{11}$ per administration.

* * * * *

SEQUENCE LISTING

```
<160> NUMBER OF SEQ ID NOS: 39

<210> SEQ ID NO 1
<211> LENGTH: 1176
<212> TYPE: DNA
<213> ORGANISM: Artificial Sequence
<220> FEATURE:
<223> OTHER INFORMATION: synthetic
<220> FEATURE:
<221> NAME/KEY: CDS
<222> LOCATION: (12)..(1163)

<400> SEQUENCE: 1
tctagactgc c atg gat ttt cag gtg cag att ttc agc ttc ctg cta atc        50
             Met Asp Phe Gln Val Gln Ile Phe Ser Phe Leu Leu Ile
              1               5                  10 agt gcc tca gtc ata atg tct aga gga gat att gtg atg acc cag tct        98
Ser Ala Ser Val Ile Met Ser Arg Gly Asp Ile Val Met Thr Gln Ser
    15                  20                  25 cca aaa ttc atg tcc aca tca gta gga ggc agg gtc agc atc acc tgc       146
Pro Lys Phe Met Ser Thr Ser Val Gly Gly Arg Val Ser Ile Thr Cys
30                  35                  40                  45
```

-continued

```
aag gcc agt cag aat gtg ggt act gct gta gcc tgg tat caa cag aaa    194
Lys Ala Ser Gln Asn Val Gly Thr Ala Val Ala Trp Tyr Gln Gln Lys
                 50                  55                  60 cca gga caa tct cct aaa cta ctg att tac tcg gca tcc aat cgg tac    242
Pro Gly Gln Ser Pro Lys Leu Leu Ile Tyr Ser Ala Ser Asn Arg Tyr
             65                  70                  75 act gga gtc cct gat cgc ttc aca ggc agt gga tct ggg aca gat ttc    290
Thr Gly Val Pro Asp Arg Phe Thr Gly Ser Gly Ser Gly Thr Asp Phe
         80                  85                  90 act ctc acc atc agc aat atg cag tct gaa gac ctg gca gat tat ttc    338
Thr Leu Thr Ile Ser Asn Met Gln Ser Glu Asp Leu Ala Asp Tyr Phe
     95                 100                 105 tgc cag caa tat agc agc tat cct ctc acg ttc ggt gct ggc acc aag    386
Cys Gln Gln Tyr Ser Ser Tyr Pro Leu Thr Phe Gly Ala Gly Thr Lys
110                 115                 120                 125 ctg gaa atw aaa ggg tcg act tcc ggt agc ggc aaa tcc tct gaa ggc    434
Leu Glu Xaa Lys Gly Ser Thr Ser Gly Ser Gly Lys Ser Ser Glu Gly
                130                 135                 140 aaa ggt cag gtc cag ctg cag cag tct gga cct gag ctg gtg aag cct    482
Lys Gly Gln Val Gln Leu Gln Gln Ser Gly Pro Glu Leu Val Lys Pro
            145                 150                 155 ggg gct tca gtg agg ata tcc tgc aag gct tct ggc tac acc ttc aca    530
Gly Ala Ser Val Arg Ile Ser Cys Lys Ala Ser Gly Tyr Thr Phe Thr
        160                 165                 170 agc tac tat ata cac tgg gtg aag cag agg cct gga cag gga ctt gag    578
Ser Tyr Tyr Ile His Trp Val Lys Gln Arg Pro Gly Gln Gly Leu Glu
    175                 180                 185 tgg att gga tgg att tat cct gga aat gtt aat act aag tac aat gag    626
Trp Ile Gly Trp Ile Tyr Pro Gly Asn Val Asn Thr Lys Tyr Asn Glu
190                 195                 200                 205 aag ttc aag ggc aag gcc aca ctg act gca gac aaa tcc tcc agc aca    674
Lys Phe Lys Gly Lys Ala Thr Leu Thr Ala Asp Lys Ser Ser Ser Thr
                210                 215                 220 gcc tac atg cag ctc agc agc ctg acc tct gag gac tct gcg gtc tat    722
Ala Tyr Met Gln Leu Ser Ser Leu Thr Ser Glu Asp Ser Ala Val Tyr
            225                 230                 235 ttc tgt gca aga aac tac ggt agt agc tac ggg ctt gct tac tgg ggc    770
Phe Cys Ala Arg Asn Tyr Gly Ser Ser Tyr Gly Leu Ala Tyr Trp Gly
        240                 245                 250 caa gga act acg gtc acc gtg aaa ggg aaa cac ctt tgt cca agt ccc    818
Gln Gly Thr Thr Val Thr Val Lys Gly Lys His Leu Cys Pro Ser Pro
    255                 260                 265 cta ttt ccc gga cct tct aag ccc ttt tgg gtg ctg gtg gtg gtt ggt    866
Leu Phe Pro Gly Pro Ser Lys Pro Phe Trp Val Leu Val Val Val Gly
270                 275                 280                 285 gga gtc ctg gct tgc tat agc ttg cta gta aca gtg gcc ttt att att    914
Gly Val Leu Ala Cys Tyr Ser Leu Leu Val Thr Val Ala Phe Ile Ile
                290                 295                 300 ttc tgg gtg agg agt aag agg agc agg ctc ctg cac agt gac tac atg    962
Phe Trp Val Arg Ser Lys Arg Ser Arg Leu Leu His Ser Asp Tyr Met
            305                 310                 315 aac atg act ccc cgc cgc ccc ggg ccc acc cgc aag cat tac cag ccc   1010
Asn Met Thr Pro Arg Arg Pro Gly Pro Thr Arg Lys His Tyr Gln Pro
        320                 325                 330 tat gcc cca cca cgc gac ttc gca gcc tat aga tct caa gtg cga aag   1058
Tyr Ala Pro Pro Arg Asp Phe Ala Ala Tyr Arg Ser Gln Val Arg Lys
    335                 340                 345 gca gct ata acc agc tat gag aaa tca gat ggt gtt tac acg ggc ctg   1106
Ala Ala Ile Thr Ser Tyr Glu Lys Ser Asp Gly Val Tyr Thr Gly Leu
```

```
                 350                 355                 360                 365
agc acc agg aac cag gag act tac gag act ctg aag cat gag aaa cca           1154
Ser Thr Arg Asn Gln Glu Thr Tyr Glu Thr Leu Lys His Glu Lys Pro
                 370                 375                 380 cca cag tag ctttagactc gag                                                1176
Pro Gln <210> SEQ ID NO 2
<211> LENGTH: 383
<212> TYPE: PRT
<213> ORGANISM: Artificial Sequence
<220> FEATURE:
<221> NAME/KEY: misc_feature
<222> LOCATION: (128)..(128)
<223> OTHER INFORMATION: The 'Xaa' at location 128 stands for Ile.
<220> FEATURE:
<223> OTHER INFORMATION: Synthetic Construct

<400> SEQUENCE: 2

Met Asp Phe Gln Val Gln Ile Phe Ser Phe Leu Leu Ile Ser Ala Ser
1               5                   10                  15

Val Ile Met Ser Arg Gly Asp Ile Val Met Thr Gln Ser Pro Lys Phe
            20                  25                  30

Met Ser Thr Ser Val Gly Gly Arg Val Ser Ile Thr Cys Lys Ala Ser
        35                  40                  45

Gln Asn Val Gly Thr Ala Val Ala Trp Tyr Gln Gln Lys Pro Gly Gln
    50                  55                  60

Ser Pro Lys Leu Leu Ile Tyr Ser Ala Ser Asn Arg Tyr Thr Gly Val
65                  70                  75                  80

Pro Asp Arg Phe Thr Gly Ser Gly Ser Gly Thr Asp Phe Thr Leu Thr
                85                  90                  95

Ile Ser Asn Met Gln Ser Glu Asp Leu Ala Asp Tyr Phe Cys Gln Gln
            100                 105                 110

Tyr Ser Ser Tyr Pro Leu Thr Phe Gly Ala Gly Thr Lys Leu Glu Xaa
        115                 120                 125

Lys Gly Ser Thr Ser Gly Ser Gly Lys Ser Ser Glu Gly Lys Gly Gln
    130                 135                 140

Val Gln Leu Gln Gln Ser Gly Pro Glu Leu Val Lys Pro Gly Ala Ser
145                 150                 155                 160

Val Arg Ile Ser Cys Lys Ala Ser Gly Tyr Thr Phe Thr Ser Tyr Tyr
                165                 170                 175

Ile His Trp Val Lys Gln Arg Pro Gly Gln Gly Leu Glu Trp Ile Gly
            180                 185                 190

Trp Ile Tyr Pro Gly Asn Val Asn Thr Lys Tyr Asn Glu Lys Phe Lys
        195                 200                 205

Gly Lys Ala Thr Leu Thr Ala Asp Lys Ser Ser Ser Thr Ala Tyr Met
    210                 215                 220

Gln Leu Ser Ser Leu Thr Ser Glu Asp Ser Ala Val Tyr Phe Cys Ala
225                 230                 235                 240

Arg Asn Tyr Gly Ser Ser Tyr Gly Leu Ala Tyr Trp Gly Gln Gly Thr
                245                 250                 255

Thr Val Thr Val Lys Gly Lys His Leu Cys Pro Ser Pro Leu Phe Pro
            260                 265                 270

Gly Pro Ser Lys Pro Phe Trp Val Leu Val Val Val Gly Gly Val Leu
        275                 280                 285

Ala Cys Tyr Ser Leu Leu Val Thr Val Ala Phe Ile Ile Phe Trp Val
    290                 295                 300
```

```
Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
            325                 330                 335

Pro Arg Asp Phe Ala Ala Tyr Arg Ser Gln Val Arg Lys Ala Ala Ile
            340                 345                 350

Thr Ser Tyr Glu Lys Ser Asp Gly Val Tyr Thr Gly Leu Ser Thr Arg
            355                 360                 365

Asn Gln Glu Thr Tyr Glu Thr Leu Lys His Glu Lys Pro Pro Gln
370                 375                 380
```

<210> SEQ ID NO 3
<211> LENGTH: 383
<212> TYPE: PRT
<213> ORGANISM: Artificial Sequence
<220> FEATURE:
<223> OTHER INFORMATION: Synthetic Construct

<400> SEQUENCE: 3

```
Met Asp Phe Gln Val Gln Ile Phe Ser Phe Leu Leu Ile Ser Ala Ser
1               5                   10                  15

Val Ile Met Ser Arg Gly Asp Ile Val Met Thr Gln Ser Pro Lys Phe
                20                  25                  30

Met Ser Thr Ser Val Gly Gly Arg Val Ser Ile Thr Cys Lys Ala Ser
            35                  40                  45

Gln Asn Val Gly Thr Ala Val Ala Trp Tyr Gln Gln Lys Pro Gly Gln
        50                  55                  60

Ser Pro Lys Leu Leu Ile Tyr Ser Ala Ser Asn Arg Tyr Thr Gly Val
65                  70                  75                  80

Pro Asp Arg Phe Thr Gly Ser Gly Ser Gly Thr Asp Phe Thr Leu Thr
                85                  90                  95

Ile Ser Asn Met Gln Ser Glu Asp Leu Ala Asp Tyr Phe Cys Gln Gln
            100                 105                 110

Tyr Ser Ser Tyr Pro Leu Thr Phe Gly Ala Gly Thr Lys Leu Glu Ile
        115                 120                 125

Lys Gly Ser Thr Ser Gly Ser Gly Lys Ser Ser Glu Gly Lys Gly Gln
130                 135                 140

Val Gln Leu Gln Gln Ser Gly Pro Glu Leu Val Lys Pro Gly Ala Ser
145                 150                 155                 160

Val Arg Ile Ser Cys Lys Ala Ser Gly Tyr Thr Phe Thr Ser Tyr Tyr
                165                 170                 175

Ile His Trp Val Lys Gln Arg Pro Gly Gln Gly Leu Glu Trp Ile Gly
            180                 185                 190

Trp Ile Tyr Pro Gly Asn Val Asn Thr Lys Tyr Asn Glu Lys Phe Lys
        195                 200                 205

Gly Lys Ala Thr Leu Thr Ala Asp Lys Ser Ser Ser Thr Ala Tyr Met
210                 215                 220

Gln Leu Ser Ser Leu Thr Ser Glu Asp Ser Ala Val Tyr Phe Cys Ala
225                 230                 235                 240

Arg Asn Tyr Gly Ser Ser Tyr Gly Leu Ala Tyr Trp Gly Gln Gly Thr
                245                 250                 255

Thr Val Thr Val Lys Gly Lys His Leu Cys Pro Ser Pro Leu Phe Pro
            260                 265                 270

Gly Pro Ser Lys Pro Phe Trp Val Leu Val Val Val Gly Gly Val Leu
        275                 280                 285
```

```
Ala Cys Tyr Ser Leu Leu Val Thr Val Ala Phe Ile Ile Phe Trp Val
    290                 295                 300

Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Gln Val Arg Lys Ala Ala Ile
                340                 345                 350

Thr Ser Tyr Glu Lys Ser Asp Gly Val Tyr Thr Gly Leu Ser Thr Arg
            355                 360                 365

Asn Gln Glu Thr Tyr Glu Thr Leu Lys His Glu Lys Pro Pro Gln
        370                 375                 380

<210> SEQ ID NO 4
<211> LENGTH: 7881
<212> TYPE: DNA
<213> ORGANISM: Artificial Sequence
<220> FEATURE:
<223> OTHER INFORMATION: synthetic
<220> FEATURE:
<221> NAME/KEY: CDS
<222> LOCATION: (1420)..(2586)

<400> SEQUENCE: 4
gattgactga gtcgcccggg tacccgtgta tccaataaac cctcttgcag ttgcatccga      60
cttgtggtct cgctgttcct tgggagggtc tcctctgagt gattgactac ccgtcagcgg     120
gggtctttca tttgggggct cgtccgggat cgggagaccc ctgcccaggg accaccgacc     180
caccaccggg aggtaagctg ccagcaact tatctgtgtc tgtccgattg tctagtgtct     240
atgactgatt ttatgcgcct cgtcggtac tagttagcta actagctctg tatctggcgg     300
acccgtggtg gaactgacga gttcggaaca cccggccgca accctgggag acgtcccagg     360
gacttcgggg ccgttttttg tggccccgacc tgagtcctaa aatcccgatc gtttaggact     420
ctttggtgca ccccccttag aggagggata tgtggttctg gtaggagacg agaacctaaa     480
acagttcccg cctccgtctg aattttttgct ttcggtttgg gaccgaagcc gcgccgcgcg     540
tcttgtctgc tgcagcatcg ttctgtgttg tctctgtctg actgtgtttc tgtatttgtc     600
tgaaaatatg ggcccgggct agcctgttac cactccctta agtttgacct taggtcactg     660
gaaagatgtc gagcggatcg ctcacaacca gtcggtagat gtcaagaaga gacgttgggt     720
taccttctgc tctgcagaat ggccaacctt taacgtcgga tggccgcgag acggcacctt     780
taaccgagac ctcatcaccc aggttaagat caaggtcttt tcacctggcc cgcatggaca     840
cccagaccag gtccctaca tcgtgacctg ggaagcttg gcttttgacc ccctccctg       900 ggtcaagccc tttgtacacc ctaagcctcc gcctcctctt cctccatccg cccgtctct      960 ccccttgaa cctcctcgtt cgaccccgcc tcgatcctcc ctttatccag ccctcactcc     1020
ttctctaggc gccccatat ggccatatga gatcttatat ggggcacccc cgccccttgt     1080
aaacttccct gaccctgaca tgacaagagt tactaacagc ccctctctcc aagctcactt     1140
acaggctctc tacttagtcc agcacgaagt ctggagacct ctggcggcag cctaccaaga     1200
acaactggac cgaccggtgg tacctcaccc ttaccgagtc ggcgacacag tgtgggtccg     1260
ccgacaccag actaagaacc tagaacctcg ctggaaagga ccttacacag tcctgctgac     1320
cacccccacc gccctcaaag tagacggcat cgcagcttgg atacacgccg cccacgtgaa     1380
ggctgccgac cccggggggtg gaccatcctc tagactgcc atg gat ttt cag gtg     1434
```

|                                                                                                   |      |
|---------------------------------------------------------------------------------------------------|------|
|                                         Met Asp Phe Gln Val<br>                                         1               5 |      |
| cag att ttc agc ttc ctg cta atc agt gcc tca gtc ata atg tct aga<br>Gln Ile Phe Ser Phe Leu Leu Ile Ser Ala Ser Val Ile Met Ser Arg<br>            10              15              20 | 1482 |
| gga gat att gtg ctc aca cag tct cca tcc tcc ctg gct gtg tca gca<br>Gly Asp Ile Val Leu Thr Gln Ser Pro Ser Ser Leu Ala Val Ser Ala<br>        25              30              35 | 1530 |
| gga gag aag gtc act atg agc tgc aaa tcc agt cag agt ctg ctc aac<br>Gly Glu Lys Val Thr Met Ser Cys Lys Ser Ser Gln Ser Leu Leu Asn<br>    40              45              50 | 1578 |
| agt aga acc cga aag aac tac ttg gct tgg tac cag cag aaa cca ggg<br>Ser Arg Thr Arg Lys Asn Tyr Leu Ala Trp Tyr Gln Gln Lys Pro Gly<br>55              60              65 | 1626 |
| cag tct cct aaa ctg ctg atc tac tgg gca tcc act agg gaa tct ggg<br>Gln Ser Pro Lys Leu Leu Ile Tyr Trp Ala Ser Thr Arg Glu Ser Gly<br>70              75              80              85 | 1674 |
| gtc cct gat cgc ttc aca ggc agt gga tct ggg aca gat ttc act ctc<br>Val Pro Asp Arg Phe Thr Gly Ser Gly Ser Gly Thr Asp Phe Thr Leu<br>            90              95              100 | 1722 |
| acc atc agc agt gtg cag gct gaa gac ctg gca gtt tat tac tgc aag<br>Thr Ile Ser Ser Val Gln Ala Glu Asp Leu Ala Val Tyr Tyr Cys Lys<br>        105             110             115 | 1770 |
| caa tct tat aat ctg tac acg ttc gga ggg ggg acc aag ctg gaa ata<br>Gln Ser Tyr Asn Leu Tyr Thr Phe Gly Gly Gly Thr Lys Leu Glu Ile<br>    120             125             130 | 1818 |
| aaa ggg tcg act tcc ggt agc ggc aaa tcc tct gaa ggc aaa ggt gag<br>Lys Gly Ser Thr Ser Gly Ser Gly Lys Ser Ser Glu Gly Lys Gly Glu<br>135             140             145 | 1866 |
| gtc cag ctg cag cag tct gga ggt ggc ctg gtg cag cct gga gga tcc<br>Val Gln Leu Gln Gln Ser Gly Gly Gly Leu Val Gln Pro Gly Gly Ser<br>150             155             160             165 | 1914 |
| ctg aaa ctc tcc tgt gca gcc tca gga ttc gat ttt agt aga tac tgg<br>Leu Lys Leu Ser Cys Ala Ala Ser Gly Phe Asp Phe Ser Arg Tyr Trp<br>            170             175             180 | 1962 |
| atg agt tgg gtc cgg cag gct cca ggg aaa ggg cta gaa tgg att gga<br>Met Ser Trp Val Arg Gln Ala Pro Gly Lys Gly Leu Glu Trp Ile Gly<br>        185             190             195 | 2010 |
| gaa att aat cca gat agc agt acg ata aac tat acg cca tct cta aag<br>Glu Ile Asn Pro Asp Ser Ser Thr Ile Asn Tyr Thr Pro Ser Leu Lys<br>    200             205             210 | 2058 |
| gat aaa ttc atc atc tcc aga gac aac gcc aaa aat acg ctg tac ctg<br>Asp Lys Phe Ile Ile Ser Arg Asp Asn Ala Lys Asn Thr Leu Tyr Leu<br>215             220             225 | 2106 |
| caa atg agc aaa gtg aga tct gag gac aca gcc ctt tat tac tgt gca<br>Gln Met Ser Lys Val Arg Ser Glu Asp Thr Ala Leu Tyr Tyr Cys Ala<br>230             235             240             245 | 2154 |
| aga cgt tat ggt aac tac tgg tac ttc gat gtc tgg ggc gca ggg acc<br>Arg Arg Tyr Gly Asn Tyr Trp Tyr Phe Asp Val Trp Gly Ala Gly Thr<br>            250             255             260 | 2202 |
| acg gtc acc gtg aaa ggg aaa cac ctt tgt cca agt ccc cta ttt ccc<br>Thr Val Thr Val Lys Gly Lys His Leu Cys Pro Ser Pro Leu Phe Pro<br>        265             270             275 | 2250 |
| gga cct tct aag ccc ttt tgg gtg ctg gtg gtg gtt ggt gga gtc ctg<br>Gly Pro Ser Lys Pro Phe Trp Val Leu Val Val Val Gly Gly Val Leu<br>    280             285             290 | 2298 |
| gct tgc tat agc ttg cta gta aca gtg gcc ttt att att ttc tgg gtg<br>Ala Cys Tyr Ser Leu Leu Val Thr Val Ala Phe Ile Ile Phe Trp Val<br>295             300             305 | 2346 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agg | agt | aag | agg | agc | agg | ctc | ctg | cac | agt | gac | tac | atg | aac | atg | act |      |
| Arg | Ser | Lys | Arg | Ser | Arg | Leu | Leu | His | Ser | Asp | Tyr | Met | Asn | Met | Thr | 2394 |
| 310 |     |     |     |     | 315 |     |     |     |     | 320 |     |     |     |     | 325 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ccc | cgc | cgc | ccc | ggg | ccc | acc | cgc | aag | cat | tac | cag | ccc | tat | gcc | cca |      |
| Pro | Arg | Arg | Pro | Gly | Pro | Thr | Arg | Lys | His | Tyr | Gln | Pro | Tyr | Ala | Pro | 2442 |
|     |     |     |     | 330 |     |     |     |     | 335 |     |     |     |     | 340 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | cgc | gac | ttc | gca | gcc | tat | aga | tct | caa | gtg | cga | aag | gca | gct | ata |      |
| Pro | Arg | Asp | Phe | Ala | Ala | Tyr | Arg | Ser | Gln | Val | Arg | Lys | Ala | Ala | Ile | 2490 |
|     |     |     |     | 345 |     |     |     |     | 350 |     |     |     |     | 355 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | agc | tat | gag | aaa | tca | gat | ggt | gtt | tac | acg | ggc | ctg | agc | acc | agg |      |
| Thr | Ser | Tyr | Glu | Lys | Ser | Asp | Gly | Val | Tyr | Thr | Gly | Leu | Ser | Thr | Arg | 2538 |
|     |     |     | 360 |     |     |     |     | 365 |     |     |     |     | 370 |     |     |      |

|     |     |     |     |     |     |     |     |     |     |     |     |     |      |
| --- | --- | --- | --- | --- | --- | --- | --- | --- | --- | --- | --- | --- | ---- |
| aac | cag | gag | act | tac | gag | act | ctg | aag | cat | gag | aaa | cca | cca cag tag |
| Asn | Gln | Glu | Thr | Tyr | Glu | Thr | Leu | Lys | His | Glu | Lys | Pro | Pro Gln | 2586
|     |     | 375 |     |     |     |     | 380 |     |     |     |     | 385 |      |

```
ctttagactc gagcgggatc aattccgccc ccccctaac gttactggcc gaagccgctt      2646
ggaataaggc cggtgtgcgt ttgtctatat gttattttcc accatattgc cgtcttttgg      2706
caatgtgagg gcccggaaac ctggcccgt cttcttgacg agcattccta ggggtctttc       2766
ccctctcgcc aaaggaatgc aaggtctgtt gaatgtcgtg aaggaagcag ttcctctgga      2826
agcttcttga agacaaacaa cgtctgtagc gacccttttgc aggcagcgga accccccacc    2886
tggcgacagg tgcctctgcg gccaaaagcc acgtgtataa gatacacctg caaaggcggc     2946
acaaccccag tgccacgttg tgagttggat agttgtggaa agagtcaaat ggctctcctc     3006
aagcgtattc aacaggggc tgaaggatgc ccagaaggta ccccattgta tgggatctga       3066 tctgggggcct cggtgcacat gctttacatg tgtttagtcg aggttaaaaa aacgtctagg   3126 cccccccgaac cacggggacg tggttttcct ttgaaaaaca cgataatagc atgctgagca    3186
agggcgagga gctgttcacc ggggtggtgc ccatcctggt cgagctggac ggcgacgtaa    3246
acggccacaa gttcagcgtg tccggcgagg gcgagggcga tgccacctac ggcaagctga   3306 cctgaagtt catctgcacc accggcaagc tgcccgtgcc ctggcccacc ctcgtgacca     3366
ccttcgccta cggcctgcag tgcttcgccc gctaccccga ccacatgaag cagcacgact    3426
tcttcaagtc cgccatgccc gaaggctacg tccaggagcg caccatcttc ttcaaggacg    3486
acggcaacta caagaccccgc gccgaggtga agttcgaggg cgacaccctg gtgaaccgca   3546
tcgagctgaa gggcatcgac ttcaaggagg acggcaacat cctggggcac aagctggagt   3606
acaactacaa cagccacaac gtctatatca tggccgacaa gcagaagaac ggcatcaagg    3666
tgaacttcaa gatccgccac aacatcgagg acggcagcgt gcagctcgcc gaccactacc   3726
agcagaacac ccccatcggc gacggccccg tgctgctgcc cgacaaccac tacctgagca    3786
cccagtccgc cctgagcaaa gaccccaacg agaagcgcga tcacatggtc ctgctggagt   3846
tcgtgaccgc cgccgggatc actctcggca tggacgagct gtacaagtga gtgtaaactc   3906
gaggatccgc gccgctcgcg actcgagaga tccggattag tccaatttgt taaagacagg   3966
atatcagtgg tccaggctct agttttgact caacaatatc accagctgaa gcctatagag   4026
tacgagccat agataaaata aaagatttta tttagtctcc agaaaaaggg gggaatgaaa     4086
gaccccacct gtaggtttgg caagctagct taagtaacgc cattttgcag gcatggaaaa  4146
atacataact gagaatagag aagttcagat caaggtcagg aacagatgga acagctgaat    4206
atgggccaaa caggatatct gtggtaagca gttcctgccc cggctcaggg ccaagaacag   4266
atggaacagc tgaatatggg ccaaacagga tatctgtggt aagcagttcc tgccccggct   4326
cagggccaag aacagatggt ccccagatgc ggtccagccc tcagcagttt ctagagaacc    4386
```

```
atcagatgtt tccagggtgc cccaaggacc tgaaatgacc ctgtgcctta tttgaactaa    4446
ccaatcagtt cgcttctcgc ttctgttcgc gcgcttctgc tccccgagct caataaaaga    4506
gcccacaacc cctcactcgg ggcgccagtc ctccgattga ctgagtcgcc cgggtacccg    4566
tgtatccaat aaaccctctt gcagttgcat ccgacttgtg gtctcgctgt tccttgggag    4626
ggtctcctct gagtgattga ctacccgtca gcggggtct ttcacatgca gcatgtatca     4686
aaattaattt ggttttttt cttaagtatt tacattaaat ggccatagtc tgctcgatcg      4746
aggagctttt tgcaaaagcc taggcctcca aaaagcctc ttcactactt ctggaatagc     4806
tcagaggccg aggcggcctc ggcctctgca taaataaaaa aaattagtca gccatgcatg    4866
gtaatagcga tgactaatac gtagatgtac tgccaagtag gaaagtccca taaggtcatg   4926
tactgggcat aatgccaggc gggccattta ccgtcattga cgtcaatagg gggcgtactt    4986
ggcatatgat acacttgatg tactgccaag tgggcagttt accgtaaata ctccacccat    5046
tgacgtcaat ggaaagtccc tattggcgtt actatgggaa catacgtcat tattgacgtc   5106
aatgggcggg ggtcgttggg cggtcagcca ggcgggccat ttaccgtaag ttatgtaacg   5166
gactctagcc catcgatggg aattccggtc tccctatagt gagtcgtatt aatttcgata   5226
agccagacca ttccttgcgg cggcggtgct caacggcctc aacctactac tgggctgctt   5286
cctaatgcag gagtcgcata agggagagcg tcgaatggtg cactctcagt acaatctgct   5346
ctgatgccgc atagttaagc cagccccgac acccgccaac acccgctgac gcgccctgac   5406
gggcttgtct gctcccggca tccgcttaca gacaagctgt gaccgtctcc gggagctgca   5466
tgtgtcagag gttttcaccg tcatcaccga acgcgcgag acgaaagggc ctcgtgatac    5526 gcctatttt ataggttaat gtcatgataa taatggtttc ttagacgtca ggtggcactt    5586
ttcggggaaa tgtgcgcgga acccctattt gtttattttt ctaaatacat tcaaatatgt   5646
atccgctcat gagacaataa ccctgataaa tgcttcaata atattgaaaa aggaagagta   5706
tgagtattca acatttccgt gtcgccctta ttccctttt tgcggcattt tgccttcctg    5766
tttttgctca cccagaaacg ctggtgaaag taaaagatgc tgaagatcag ttgggtgcac   5826
gagtgggtta catcgaactg gatctcaaca gcggtaagat ccttgagagt tttcgccccg   5886
aagaacgttt tccaatgatg agcactttta aagttctgct atgtggcgcg gtattatccc   5946
gtattgacgc cgggcaagag caactcggtc gccgcataca ctattctcag aatgacttgg   6006
ttgagtactc accagtcaca gaaaagcatc ttacggatgg catgacagta agagaattat   6066
gcagtgctgc cataaccatg agtgataaca ctgcggccaa cttacttctg acaacgatcg   6126
gaggaccgaa ggagctaacc gcttttttgc acaacatggg ggatcatgta actcgccttg   6186
atcgttggga accggagctg aatgaagcca taccaaacga cgagcgtgac accacgatgc   6246
ctgtagcaat ggcaacaacg ttgcgcaaac tattaactgg cgaactactt actctagctt   6306
cccggcaaca attaatagac tggatggagg cggataaagt tgcaggacca cttctgcgct   6366
cggcccttcc ggctggctgg tttattgctg ataaatctgg agccggtgag cgtgggtctc   6426
gcggtatcat tgcagcactg gggccagatg gtaagccctc ccgtatcgta gttatctaca   6486
cgacggggag tcaggcaact atggatgaac gaaatagaca gatcgctgag ataggtgcct   6546
cactgattaa gcattggtaa ctgtcagacc aagtttactc atatatactt tagattgatt   6606
taaaacttca tttttaattt aaaaggatct aggtgaagat cctttttgat aatctcatga   6666
ccaaaatccc ttaacgtgag ttttcgttcc actgagcgtc agaccccgga gaaagatca    6726
```

| | | |
|---|---|---|
| aaggatcttc ttgagatcct ttttttctgc gcgtaatctg ctgcttgcaa acaaaaaaac | 6786 | |
| caccgctacc agcggtggtt tgtttgccgg atcaagagct accaactctt tttccgaagg | 6846 | |
| taactggctt cagcagagcg cagataccaa atactgttct tctagtgtag ccgtagttag | 6906 | |
| gccaccactt caagaactct gtagcaccgc ctacatacct cgctctgcta atcctgttac | 6966 | |
| cagtggctgc tgccagtggc gataagtcgt gtcttaccgg gttggactca agacgatagt | 7026 | |
| taccggataa ggcgcagcgg tcgggctgaa cggggggttc gtgcacacag cccagcttgg | 7086 | |
| agcgaacgac ctacaccgaa ctgagatacc tacagcgtga gctatgagaa agcgccacgc | 7146 | |
| ttcccgaagg gagaaaggcg gacaggtatc cggtaagcgg cagggtcgga acaggagagc | 7206 | |
| gcacgaggga gcttccaggg ggaaacgcct ggtatcttta tagtcctgtc gggtttcgcc | 7266 | |
| acctctgact tgagcgtcga ttttgtgat gctcgtcagg ggggcggagc ctatggaaaa | 7326 | |
| acgccagcaa cgcggccttt ttacggttcc tggccttttg ctggcctttt gctcacatgt | 7386 | |
| tctttcctgc gttatcccct gattctgtgg ataaccgtat taccgccttt gagtgagctg | 7446 | |
| ataccgctcg ccgcagccga acgaccgagc gcagcgagtc agtgagcgag gaagcggaag | 7506 | |
| agcgcccaat acgcaaaccg cctctccccg cgcgttggcc gattcattaa tgcagcaatt | 7566 | |
| agtcagcaac catagtcccg cccctaactc cgcccatccc gcccctaact ccgcccagtt | 7626 | |
| ccgcccattc tccgccccat gcatggtgat gcggttttgg cagtacatca atgggcgtgg | 7686 | |
| atagcggttt gactcacggg gatttccaag tctccacccc attgacgtca atgggagttt | 7746 | |
| gttttggcac caaaatcaac gggactttcc aaaatgtcgt aacaactccg ccccattgac | 7806 | |
| gcaaatgggc ggtaggcgtg tacggtggga ggtctatata agcagagctc gtttagtgaa | 7866 | |
| ccgcgccagt cctcc | 7881 | |

<210> SEQ ID NO 5
<211> LENGTH: 388
<212> TYPE: PRT
<213> ORGANISM: Artificial Sequence
<220> FEATURE:
<223> OTHER INFORMATION: Synthetic Construct

<400> SEQUENCE: 5

Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Ser Pro Ser Ser
            20                  25                  30

Leu Ala Val Ser Ala Gly Glu Lys Val Thr Met Ser Cys Lys Ser Ser
        35                  40                  45

Gln Ser Leu Leu Asn Ser Arg Thr Arg Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
                85                  90                  95

Thr Asp Phe Thr Leu Thr Ile Ser Ser Val Gln Ala Glu Asp Leu Ala
            100                 105                 110

Val Tyr Tyr Cys Lys Gln Ser Tyr Asn Leu Tyr Thr Phe Gly Gly Gly
        115                 120                 125

Thr Lys Leu Glu Ile Lys Gly Ser Thr Ser Gly Ser Gly Lys Ser Ser
    130                 135                 140

Glu Gly Lys Gly Glu Val Gln Leu Gln Gln Ser Gly Gly Gly Leu Val
145                 150                 155                 160

Gln Pro Gly Gly Ser Leu Lys Leu Ser Cys Ala Ala Ser Gly Phe Asp
                165                 170                 175

Phe Ser Arg Tyr Trp Met Ser Trp Val Arg Gln Ala Pro Gly Lys Gly
            180                 185                 190

Leu Glu Trp Ile Gly Glu Ile Asn Pro Asp Ser Ser Thr Ile Asn Tyr
        195                 200                 205

Thr Pro Ser Leu Lys Asp Lys Phe Ile Ile Ser Arg Asp Asn Ala Lys
210                 215                 220

Asn Thr Leu Tyr Leu Gln Met Ser Lys Val Arg Ser Glu Asp Thr Ala
225                 230                 235                 240

Leu Tyr Tyr Cys Ala Arg Arg Tyr Gly Asn Tyr Trp Tyr Phe Asp Val
            245                 250                 255

Trp Gly Ala Gly Thr Thr Val Thr Val Lys Gly Lys His Leu Cys Pro
        260                 265                 270

Ser Pro Leu Phe Pro Gly Pro Ser Lys Pro Phe Trp Val Leu Val Val
    275                 280                 285

Val Gly Gly Val Leu Ala Cys Tyr Ser Leu Leu Val Thr Val Ala Phe
290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
            325                 330                 335

Gln Pro Tyr Ala Pro Pro Arg Asp Phe Ala Ala Tyr Arg Ser Gln Val
        340                 345                 350

Arg Lys Ala Ala Ile Thr Ser Tyr Glu Lys Ser Asp Gly Val Tyr Thr
    355                 360                 365

Gly Leu Ser Thr Arg Asn Gln Glu Thr Tyr Glu Thr Leu Lys His Glu
370                 375                 380

Lys Pro Pro Gln
385

<210> SEQ ID NO 6
<211> LENGTH: 375
<212> TYPE: PRT
<213> ORGANISM: Homo sapiens
<220> FEATURE:
<221> NAME/KEY: misc_feature
<223> OTHER INFORMATION: CD14 protein

<400> SEQUENCE: 6

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
        35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
            85                  90                  95

Gly Ala Ala Gln Val Pro Ala Gln Leu Leu Val Gly Ala Leu Arg Val
        100                 105                 110

Leu Ala Tyr Ser Arg Leu Lys Glu Leu Thr Leu Glu Asp Leu Lys Ile

```
            115                 120                 125
Thr Gly Thr Met Pro Pro Leu Pro Leu Glu Ala Thr Gly Leu Ala Leu
    130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

Cys Ala Ala Leu Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
    370                 375

<210> SEQ ID NO 7
<211> LENGTH: 159
<212> TYPE: PRT
<213> ORGANISM: Homo sapiens
<220> FEATURE:
<221> NAME/KEY: misc_feature
<223> OTHER INFORMATION: MD-2 protein

<400> SEQUENCE: 7

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95
```

```
Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Val Val Glu Ala Ile Ser Gly Ser Pro Glu Glu Met
    130                 135                 140

Leu Phe Cys Leu Glu Phe Val Ile Leu His Gln Pro Asn Ser Asn
145                 150                 155
```

<210> SEQ ID NO 8
<211> LENGTH: 504
<212> TYPE: DNA
<213> ORGANISM: Artificial Sequence
<220> FEATURE:
<223> OTHER INFORMATION: synthetic
<220> FEATURE:
<221> NAME/KEY: CDS
<222> LOCATION: (1)..(504)

<400> SEQUENCE: 8

```
atg gat ttt cag gtg cag att ttc agc ttc ctg cta atc agt gcc tca       48
Met Asp Phe Gln Val Gln Ile Phe Ser Phe Leu Leu Ile Ser Ala Ser
1               5                   10                  15 gtc ata atg tct aga cag gtt cct gct cag cta ctg gta ggc gcc ctg       96
Val Ile Met Ser Arg Gln Val Pro Ala Gln Leu Leu Val Gly Ala Leu
            20                  25                  30 cgt gtg cta gcg tac tcc cgc ctc aag gtc acc gtg aaa ggg aaa cac      144
Arg Val Leu Ala Tyr Ser Arg Leu Lys Val Thr Val Lys Gly Lys His
        35                  40                  45 ctt tgt cca agt ccc cta ttt ccc gga cct tct aag ccc ttt tgg gtg      192
Leu Cys Pro Ser Pro Leu Phe Pro Gly Pro Ser Lys Pro Phe Trp Val
    50                  55                  60 ctg gtg gtg gtt ggt gga gtc ctg gct tgc tat agc ttg cta gta aca      240
Leu Val Val Val Gly Gly Val Leu Ala Cys Tyr Ser Leu Leu Val Thr
65                  70                  75                  80 gtg gcc ttt att att ttc tgg gtg agg agt aag agg agc agg ctc ctg      288
Val Ala Phe Ile Ile Phe Trp Val Arg Ser Lys Arg Ser Arg Leu Leu
                85                  90                  95 cac agt gac tac atg aac atg act ccc cgc cgc ccc ggg ccc acc cgc      336
His Ser Asp Tyr Met Asn Met Thr Pro Arg Arg Pro Gly Pro Thr Arg
            100                 105                 110 aag cat tac cag ccc tat gcc cca cca cgc gac ttc gca gcc tat aga      384
Lys His Tyr Gln Pro Tyr Ala Pro Pro Arg Asp Phe Ala Ala Tyr Arg
        115                 120                 125 tct caa gtg cga aag gca gct ata acc agc tat gag aaa tca gat ggt      432
Ser Gln Val Arg Lys Ala Ala Ile Thr Ser Tyr Glu Lys Ser Asp Gly
    130                 135                 140 gtt tac acg ggc ctg agc acc agg aac cag gag act tac gag act ctg      480
Val Tyr Thr Gly Leu Ser Thr Arg Asn Gln Glu Thr Tyr Glu Thr Leu
145                 150                 155                 160 aag cat gag aaa cca cca cag tag                                      504
Lys His Glu Lys Pro Pro Gln
                165
```

<210> SEQ ID NO 9
<211> LENGTH: 167
<212> TYPE: PRT
<213> ORGANISM: Artificial Sequence
<220> FEATURE:
<223> OTHER INFORMATION: Synthetic Construct

<400> SEQUENCE: 9

```
Met Asp Phe Gln Val Gln Ile Phe Ser Phe Leu Leu Ile Ser Ala Ser
1               5                   10                  15

Val Ile Met Ser Arg Gln Val Pro Ala Gln Leu Leu Val Gly Ala Leu
            20                  25                  30

Arg Val Leu Ala Tyr Ser Arg Leu Lys Val Thr Val Lys Gly Lys His
        35                  40                  45

Leu Cys Pro Ser Pro Leu Phe Pro Gly Pro Ser Lys Pro Phe Trp Val
    50                  55                  60

Leu Val Val Val Gly Gly Val Leu Ala Cys Tyr Ser Leu Leu Val Thr
65                  70                  75                  80

Val Ala Phe Ile Ile Phe Trp Val Arg Ser Lys Arg Ser Arg Leu Leu
                85                  90                  95

His Ser Asp Tyr Met Asn Met Thr Pro Arg Arg Pro Gly Pro Thr Arg
            100                 105                 110

Lys His Tyr Gln Pro Tyr Ala Pro Pro Arg Asp Phe Ala Ala Tyr Arg
        115                 120                 125

Ser Gln Val Arg Lys Ala Ala Ile Thr Ser Tyr Glu Lys Ser Asp Gly
    130                 135                 140

Val Tyr Thr Gly Leu Ser Thr Arg Asn Gln Glu Thr Tyr Glu Thr Leu
145                 150                 155                 160

Lys His Glu Lys Pro Pro Gln
                165

<210> SEQ ID NO 10
<211> LENGTH: 3984
<212> TYPE: DNA
<213> ORGANISM: Artificial Sequence
<220> FEATURE:
<223> OTHER INFORMATION: synthetic

<400> SEQUENCE: 10
atggattttc aggtgcagat tttcagcttc ctgctaatca gtgcctcagt cataatgtct      60
agacaggttc ctgctcagct actggtaggc gccctgcgtg tgctagcgta ctcccgcctc     120
aaggtcaccg tgaaagggaa acacctttgt ccaagtcccc tatttccgg accttctaag      180 cccttttggg tgctggtggt ggttggtgga gtcctggctt gctatagctt gctagtaaca     240
gtggccttta ttattttctg ggtgaggagt aagaggagca ggctcctgca cagtgactac     300
atgaacatga ctccccgccg ccccgggccc accgcaagc attaccagcc ctatgcccca      360
ccacgcgact cgcagcccta tagatctcaa gtgcgaaagg cagctataac cagctatgag     420
aaatcagatg gtgtttacac gggcctgagc accaggaacc aggagactta cgagactctg     480
aagcatgaga aaccaccaca gtagctttag actcgagcgg gatcaattcc gcccccccc      540 taacgttact ggccgaagcc gcttggaata aggccggtgt gcgtttgtct atatgttatt     600
ttccaccata ttgccgtctt ttggcaatgt gagggcccgg aaacctggcc ctgtcttctt     660
gacgagcatt cctaggggtc tttcccctct cgccaaagga atgcaaggtc tgttgaatgt     720
cgtgaaggaa gcagttcctc tggaagcttc ttgaagacaa caacgtctg tagcgaccct      780 ttgcaggcag cggaaccccc cacctggcga caggtgcctc tgcggccaaa agccacgtgt     840
ataagataca cctgcaaagg cggcacaacc ccagtgccac gttgtgagtt ggatagttgt     900
ggaaagagtc aaatggctct cctcaagcgt attcaacaag gggctgaagg atgcccagaa     960
ggtaccccat gtatgggat ctgatctggg gcctcggtgc acatgcttta catgtgttta     1020
gtcgaggtta aaaaaacgtc taggcccccc gaaccacggg gacgtggttt tcctttgaaa    1080
```

```
aacacgataa tagcatgcag cgctaccggt cgccaccatg gtgagcaagg gcgaggagct    1140
gttcaccggg gtggtgccca tcctggtcga gctggacggc gacgtaaacg gccacaagtt    1200
cagcgtgtcc ggcgagggcg agggcgatgc cacctacggc aagctgaccc tgaagttcat    1260
ctgcaccacc ggcaagctgc ccgtgccctg gcccaccctc gtgaccaccc tgacctacgg    1320
cgtgcagtgc ttcagccgct accccgacca catgaagcag cacgacttct tcaagtccgc    1380
catgcccgaa ggctacgtcc aggagcgcac catcttcttc aaggacgacg gcaactacaa    1440
gacccgcgcc gaggtgaagt tcgagggcga caccctggtg aaccgcatcg agctgaaggg    1500
catcgacttc aaggaggacg gcaacatcct ggggcacaag ctggagtaca actacaacag    1560
ccacaacgtc tatatcatgg ccgacaagca gaagaacggc atcaaggtga acttcaagat    1620
ccgccacaac atcgaggacg gcagcgtgca gctcgccgac cactaccagc agaacacccc    1680
catcggcgac ggccccgtgc tgctgcccga caaccactac ctgagcaccc agtccgccct    1740
gagcaaagac cccaacgaga gcgcgatca catggtcctg ctggagttcg tgaccgccgc    1800
cgggatcact ctcggcatgg acgagctgta caagtccggc cggactcaga tctcgagctc    1860
aagcttcgaa ttcatgccca accccaggcc tggcaagccc tcggcccctt ccttggccct    1920
tggcccatcc ccaggagcct cgcccagctg gagggctgca cccaaagcct cagacctgct    1980
gggggcccgg ggcccagggg gaaccttcca gggccgagat cttcgaggcg gggcccatgc    2040
ctcctcttct tccttgaacc ccatgccacc atcgcagctg cagctgccca cactgccct    2100 agtcatggtg caccctccg gggcacggct gggccccttg ccccacttac aggcactcct    2160
ccaggacagg ccacatttca tgcaccagct ctcaacggtg gatgcccacg cccggacccc    2220
tgtgctgcag gtgcaccccc tggagagccc agccatgatc agcctcacac cacccaccac    2280
cgccactggg gtcttctccc tcaaggcccg gcctggcctc ccacctggga tcaacgtggc    2340
cagcctggaa tgggtgtcca gggagccggc actgctctgc accttcccaa atcccagtgc    2400
acccaggaag gacagcaccc tttcggctgt gccccagagc tcctaccac tgctggcaaa    2460 tggtgtctgc aagtggcccg gatgtgagaa ggtcttcgaa gagccagagg acttcctcaa    2520
gcactgccag gcggaccatc ttctggatga agggcagg gcacaatgtc tcctccagag    2580
agagatggta cagtctctgg agcagcagct ggtgctggag aaggagaagc tgagtgccat    2640
gcaggcccac ctggctggga aaatggcact gaccaaggct tcatctgtgg catcatccga    2700
caagggctcc tgctgcatcg tagctgctgg cagccaaggc cctgtcgtcc cagcctggtc    2760
tggcccccgg gaggcccctg acagcctgtt tgctgtccgg aggcacctgt ggggtagcca    2820
tggaaacagc acattcccag agttcctcca caacatggac tacttcaagt tccacaacat    2880
gcgaccccct ttcacctacg ccacgctcat ccgctgggcc atcctggagg ctccagagaa    2940
gcagcggaca ctcaatgaga tctaccactg gttcacacgc atgtttgcct tcttcagaaa    3000
ccatcctgcc acctggaaga cgccatccg ccacaacctg agtctgcaca agtgctttgt    3060
gcgggtggag agcgagaagg gggctgtgtg gaccgtggat gagctggagt ccgcaagaa    3120 acggagccag aggcccagca ggtgttccaa ccctacacct ggcccctgag gatccgcgcc    3180
gctcgcgctc gagagatccg gattagtcca atttgttaaa gacaggatat cagtggtcca    3240
ggctctagtt ttgactcaac aatatcacca gctgaagcct atagagtacg agccatagat    3300
aaaataaaag attttattta gtctccagaa aagggggga atgaaagacc ccacctgtag    3360
gtttggcaag ctagcttaag taacgccatt ttgcaggcat ggaaaatac ataactgaga    3420 atagagaagt tcagatcaag gtcaggaaca gatggaacag ctgaatatgg gccaaacagg    3480
```

```
atatctgtgg taagcagttc ctgccccggc tcagggccaa gaacagatgg aacagctgaa    3540
tatgggccaa acaggatatc tgtggtaagc agttcctgcc ccggctcagg gccaagaaca    3600
gatggtcccc agatgcggtc cagccctcag cagtttctag agaaccatca gatgtttcca    3660
gggtgcccca aggacctgaa atgacccgt gccttatttg aactaaccaa tcagttcgct    3720
tctcgcttct gttcgcgcgc ttctgctccc cgagctcaat aaaagagccc acaacccctc    3780
actcggggcg ccagtcctcc gattgactga gtcgcccggg tacccgtgta tccaataaac    3840
cctcttgcag ttgcatccga cttgtggtct cgctgttcct tgggagggtc tcctctgagt    3900
gattgactac ccgtcagcgg gggtctttca catgcagcat gtatcaaaat taatttggtt    3960
ttttttctta agtatttaca ttaa                                           3984
```

<210> SEQ ID NO 11
<211> LENGTH: 489
<212> TYPE: DNA
<213> ORGANISM: Artificial Sequence
<220> FEATURE:
<223> OTHER INFORMATION: synthetic
<220> FEATURE:
<221> NAME/KEY: CDS
<222> LOCATION: (1)..(489)

<400> SEQUENCE: 11

```
atg gat ttt cag gtg cag att ttc agc ttc ctg cta atc agt gcc tca    48
Met Asp Phe Gln Val Gln Ile Phe Ser Phe Leu Leu Ile Ser Ala Ser
1               5                   10                  15 gtc ata atg tct aga ttc tcc ttc aag gga ata aaa ttt tct aag gga    96
Val Ile Met Ser Arg Phe Ser Phe Lys Gly Ile Lys Phe Ser Lys Gly
            20                  25                  30 aaa tac aaa ggt cac ctc gtg aaa ggg aaa cac ctt tgt cca agt ccc    144
Lys Tyr Lys Gly His Leu Val Lys Gly Lys His Leu Cys Pro Ser Pro
        35                  40                  45 cta ttt ccc gga cct tct aag ccc ttt tgg gtg ctg gtg gtg gtt ggt    192
Leu Phe Pro Gly Pro Ser Lys Pro Phe Trp Val Leu Val Val Val Gly
    50                  55                  60 gga gtc ctg gct tgc tat agc ttg cta gta aca gtg gcc ttt att att    240
Gly Val Leu Ala Cys Tyr Ser Leu Leu Val Thr Val Ala Phe Ile Ile
65                  70                  75                  80 ttc tgg gtg agg agt aag agg agc agg ctc ctg cac agt gac tac atg    288
Phe Trp Val Arg Ser Lys Arg Ser Arg Leu Leu His Ser Asp Tyr Met
                85                  90                  95 aac atg act ccc cgc cgc ccc ggg ccc acc cgc aag cat tac cag ccc    336
Asn Met Thr Pro Arg Arg Pro Gly Pro Thr Arg Lys His Tyr Gln Pro
            100                 105                 110 tat gcc cca cca cgc gac ttc gca gcc tat aga tct caa gtg cga aag    384
Tyr Ala Pro Pro Arg Asp Phe Ala Ala Tyr Arg Ser Gln Val Arg Lys
        115                 120                 125 gca gct ata acc agc tat gag aaa tca gat ggt gtt tac acg ggc ctg    432
Ala Ala Ile Thr Ser Tyr Glu Lys Ser Asp Gly Val Tyr Thr Gly Leu
    130                 135                 140 agc acc agg aac cag gag act tac gag act ctg aag cat gag aaa cca    480
Ser Thr Arg Asn Gln Glu Thr Tyr Glu Thr Leu Lys His Glu Lys Pro
145                 150                 155                 160 cca cag tag                                                         489
Pro Gln
```

<210> SEQ ID NO 12
<211> LENGTH: 162
<212> TYPE: PRT

<213> ORGANISM: Artificial Sequence
<220> FEATURE:
<223> OTHER INFORMATION: Synthetic Construct

<400> SEQUENCE: 12

```
Met Asp Phe Gln Val Gln Ile Phe Ser Phe Leu Leu Ile Ser Ala Ser
1               5                   10                  15

Val Ile Met Ser Arg Phe Ser Phe Lys Gly Ile Lys Phe Ser Lys Gly
                20                  25                  30

Lys Tyr Lys Gly His Leu Val Lys Gly Lys His Leu Cys Pro Ser Pro
            35                  40                  45

Leu Phe Pro Gly Pro Ser Lys Pro Phe Trp Val Leu Val Val Val Gly
        50                  55                  60

Gly Val Leu Ala Cys Tyr Ser Leu Leu Val Thr Val Ala Phe Ile Ile
65                  70                  75                  80

Phe Trp Val Arg Ser Lys Arg Ser Arg Leu Leu His Ser Asp Tyr Met
                85                  90                  95

Asn Met Thr Pro Arg Arg Pro Gly Pro Thr Arg Lys His Tyr Gln Pro
            100                 105                 110

Tyr Ala Pro Pro Arg Asp Phe Ala Ala Tyr Arg Ser Gln Val Arg Lys
        115                 120                 125

Ala Ala Ile Thr Ser Tyr Glu Lys Ser Asp Gly Val Tyr Thr Gly Leu
130                 135                 140

Ser Thr Arg Asn Gln Glu Thr Tyr Glu Thr Leu Lys His Glu Lys Pro
145                 150                 155                 160

Pro Gln
```

<210> SEQ ID NO 13
<211> LENGTH: 3160
<212> TYPE: DNA
<213> ORGANISM: Artificial Sequence
<220> FEATURE:
<223> OTHER INFORMATION: synthetic

<400> SEQUENCE: 13

```
atggattttc aggtgcagat ttcagcttc  ctgctaatca gtgcctcagt cataatgtct       60
agattctcct tcaagggaat aaaattttct aagggaaaat acaaaggtca cctcgtgaaa      120
gggaaacacc tttgtccaag tcccctattt cccggacctt ctaagccctt tgggtgctg       180
gtggtggttg gtggagtcct ggcttgctat agcttgctag taacagtggc ctttattatt      240
ttctgggtga ggagtaagag gagcaggctc ctgcacagtg actacatgaa catgactccc      300
cgccgccccg ggcccacccg caagcattac cagccctatg cccaccacg  cgacttcgca      360
gcctatagat ctcaagtgcg aaaggcagct ataaccagct atgagaaatc agatggtgtt      420
tacacgggcc tgagcaccag gaaccaggag acttacgaga ctctgaagca tgagaaacca      480
ccacagtagc tttagactcg agcgggatca attccgcccc ccccctaacg ttactggccg      540
aagccgcttg gaataaggcc ggtgtgcgtt tgtctatatg ttattttcca ccatattgcc      600
gtcttttggc aatgtgaggg cccggaaacc tggccctgtc ttcttgacga gcattcctag      660
gggtctttcc cctctcgcca aggaatgcaa ggtctgttg  aatgtcgtga aggaagcagt      720
tcctctggaa gcttcttgaa gacaaacaac gtctgtagcg acccttttgca ggcagcggaa      780
ccccccacct ggcgacaggt gcctctgcgg ccaaaagcca cgtgtataag atacacctgc      840
aaaggcggca caaccccagt gccacgttgt gagttggata gttgtggaaa gagtcaaatg      900
gctctcctca gcgtattca  acaagggggct gaaggatgcc cagaaggtac cccattgtat      960
```

```
gggatctgat ctggggcctc ggtgcacatg ctttacatgt gtttagtcga ggttaaaaaa   1020
acgtctaggc cccccgaacc acggggacgt ggttttcctt tgaaaaacac gataatagca   1080
tgcagcgcta ccggtcgcca ccatggtgag caagggcgag gagctgttca ccggggtggt   1140
gcccatcctg gtcgagctgg acggcgacgt aaacggccac aagttcagcg tgtccggcga   1200
gggcgagggc gatgccacct acggcaagct gaccctgaag ttcatctgca ccaccggcaa   1260
gctgcccgtg ccctggccca ccctcgtgac caccctgacc tacggcgtgc agtgcttcag   1320
ccgctacccc gaccacatga agcagcacga cttcttcaag tccgccatgc ccgaaggcta   1380
cgtccaggag cgcaccatct tcttcaagga cgacggcaac tacaagaccc gcgccgaggt   1440
gaagttcgag ggcgacaccc tggtgaaccg catcgagctg aagggcatcg acttcaagga   1500
ggacggcaac atcctggggc acaagctgga gtacaactac aacagccaca cgtctatat    1560 catggccgac aagcagaaga acggcatcaa ggtgaacttc aagatccgcc acaacatcga   1620
ggacggcagc gtgcagctcg ccgaccacta ccagcagaac ccccatcg cgacggccc       1680 cgtgctgctg cccgacaacc actacctgag cacccagtcc gccctgagca agacccccaa   1740
cgagaagcgc gatcacatgg tcctgctgga gttcgtgacc gccgccggga tcactctcgg   1800
catggacgag ctgtacaagt ccggccggac tcagatctcg agctcaagct tcgaattcat   1860
gcccaacccc aggcctggca gccctcggc cccttccttg gccttggcc catcccagg      1920 agcctcgccc agctggaggg ctgcacccaa agcctcagac ctgctggggg ccggggccc    1980 aggggaacc ttccagggcc gagatcttcg aggcggggcc catgcctcct cttcttcctt    2040
gaaccccatg ccaccatcgc agctgcagct gcccacactg cccctagtca tggtggcacc   2100
ctccggggca cggctgggcc ccttgcccca cttacaggca ctcctccagg acaggccaca   2160
tttcatgcac cagctctcaa cggtggatgc ccacgcccgg acccctgtgc tgcaggtgca   2220
ccccctggag agcccagcca tgatcagcct cacaccaccc accaccgcca ctggggtctt   2280
ctccctcaag gcccggcctg gcctcccacc tgggatcaac gtggccagcc tggaatgggt   2340
gtccagggag ccggcactgc tctgcacctt cccaaatccc agtgcaccca ggaaggacag   2400
caccctttcg gctgtgcccc agagctccta cccactgctg gcaaatggtg tctgcaagtg   2460
gcccggatgt gagaaggtct tcgaagagcc agaggacttc ctcaagcact gccaggcgga   2520
ccatcttctg gatgagaagg gcagggcaca atgtctcctc agagagaga tggtacagtc    2580 tctggagcag cagctggtgc tggagaagga gaagctgagt gccatgcagg cccacctggc   2640
tgggaaaatg gcactgacca aggcttcatc tgtggcatca tccgacaagg gctcctgctg   2700
catcgtagct gctggcagcc aaggccctgt cgtcccagcc tggtctggcc ccggggaggc   2760
ccctgacagc ctgtttgctg tccggaggca cctgtggggt agccatggaa acagcacatt   2820
cccagagttc ctccacaaca tggactactt caagttccac aacatgcgac cccctttcac   2880
ctacgccacg ctcatccgct gggccatcct ggaggctcca gagaagcagc ggacactcaa   2940
tgagatctac cactggttca cacgcatgtt tgccttcttc agaaaccatc ctgccacctg   3000
gaagaacgcc atccgccaca acctgagtct gcacaagtgc tttgtgcggg tggagagcga   3060 gaaggggct gtgtggaccg tggatgagct ggagttccgc aagaaacgga gccagaggcc    3120
cagcaggtgt tccaaccca cacctggccc ctgaggatcc                          3160
```

<210> SEQ ID NO 14
<211> LENGTH: 588
<212> TYPE: DNA

<213> ORGANISM: Artificial Sequence
<220> FEATURE:
<223> OTHER INFORMATION: synthetic
<220> FEATURE:
<221> NAME/KEY: CDS
<222> LOCATION: (1)..(588)

<400> SEQUENCE: 14

```
atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tct aga ttc tcc ttc aag gga ata aaa ttt tct aag gga      96
Val Ile Met Ser Arg Phe Ser Phe Lys Gly Ile Lys Phe Ser Lys Gly
            20                  25                  30 aaa tac aaa ggg tcg act tcc ggt agc ggc aaa tcc tct gaa ggc aaa     144
Lys Tyr Lys Gly Ser Thr Ser Gly Ser Gly Lys Ser Ser Glu Gly Lys
        35                  40                  45 ggt cag gtt cct gct cag cta ctg gta ggc gcc ctg cgt gtg cta gcg     192
Gly Gln Val Pro Ala Gln Leu Leu Val Gly Ala Leu Arg Val Leu Ala
    50                  55                  60 tac tcc cgc ctc aag gtc acc gtg aaa ggg aaa cac ctt tgt cca agt     240
Tyr Ser Arg Leu Lys Val Thr Val Lys Gly Lys His Leu Cys Pro Ser
65                  70                  75                  80 ccc cta ttt ccc gga cct tct aag ccc ttt tgg gtg ctg gtg gtg gtt     288
Pro Leu Phe Pro Gly Pro Ser Lys Pro Phe Trp Val Leu Val Val Val
                85                  90                  95 ggt gga gtc ctg gct tgc tat agc ttg cta gta aca gtg gcc ttt att     336
Gly Gly Val Leu Ala Cys Tyr Ser Leu Leu Val Thr Val Ala Phe Ile
            100                 105                 110 att ttc tgg gtg agg agt aag agg agc agg ctc ctg cac agt gac tac     384
Ile Phe Trp Val Arg Ser Lys Arg Ser Arg Leu Leu His Ser Asp Tyr
        115                 120                 125 atg aac atg act ccc cgc cgc ccc ggg ccc acc cgc aag cat tac cag     432
Met Asn Met Thr Pro Arg Arg Pro Gly Pro Thr Arg Lys His Tyr Gln
    130                 135                 140 ccc tat gcc cca cca cgc gac ttc gca gcc tat aga tct caa gtg cga     480
Pro Tyr Ala Pro Pro Arg Asp Phe Ala Ala Tyr Arg Ser Gln Val Arg
145                 150                 155                 160 aag gca gct ata acc agc tat gag aaa tca gat ggt gtt tac acg ggc     528
Lys Ala Ala Ile Thr Ser Tyr Glu Lys Ser Asp Gly Val Tyr Thr Gly
                165                 170                 175 ctg agc acc agg aac cag gag act tac gag act ctg aag cat gag aaa     576
Leu Ser Thr Arg Asn Gln Glu Thr Tyr Glu Thr Leu Lys His Glu Lys
            180                 185                 190 cca cca cag tag                                                     588
Pro Pro Gln
        195
```

<210> SEQ ID NO 15
<211> LENGTH: 195
<212> TYPE: PRT
<213> ORGANISM: Artificial Sequence
<220> FEATURE:
<223> OTHER INFORMATION: Synthetic Construct

<400> SEQUENCE: 15

```
Met Asp Phe Gln Val Gln Ile Phe Ser Phe Leu Leu Ile Ser Ala Ser
1               5                   10                  15

Val Ile Met Ser Arg Phe Ser Phe Lys Gly Ile Lys Phe Ser Lys Gly
            20                  25                  30

Lys Tyr Lys Gly Ser Thr Ser Gly Ser Gly Lys Ser Ser Glu Gly Lys
        35                  40                  45
```

```
Gly Gln Val Pro Ala Gln Leu Leu Val Gly Ala Leu Arg Val Leu Ala
        50                  55                  60
Tyr Ser Arg Leu Lys Val Thr Val Lys Gly Lys His Leu Cys Pro Ser
 65                  70                  75                  80
Pro Leu Phe Pro Gly Pro Ser Lys Pro Phe Trp Val Leu Val Val Val
                85                  90                  95
Gly Gly Val Leu Ala Cys Tyr Ser Leu Leu Val Thr Val Ala Phe Ile
            100                 105                 110
Ile Phe Trp Val Arg Ser Lys Arg Ser Arg Leu Leu His Ser Asp Tyr
        115                 120                 125
Met Asn Met Thr Pro Arg Arg Pro Gly Pro Thr Arg Lys His Tyr Gln
    130                 135                 140
Pro Tyr Ala Pro Pro Arg Asp Phe Ala Ala Tyr Arg Ser Gln Val Arg
145                 150                 155                 160
Lys Ala Ala Ile Thr Ser Tyr Glu Lys Ser Asp Gly Val Tyr Thr Gly
                165                 170                 175
Leu Ser Thr Arg Asn Gln Glu Thr Tyr Glu Thr Leu Lys His Glu Lys
            180                 185                 190
Pro Pro Gln
    195

<210> SEQ ID NO 16
<211> LENGTH: 3259
<212> TYPE: DNA
<213> ORGANISM: Artificial Sequence
<220> FEATURE:
<223> OTHER INFORMATION: synthetic

<400> SEQUENCE: 16
atggattttc aggtgcagat tttcagcttc ctgctaatca gtgcctcagt cataatgtct      60
agattctcct tcaagggaat aaaattttct aagggaaaat acaaagggtc gacttccggt     120
agcggcaaat cctctgaagg caaaggtcag gttcctgctc agctactggt aggcgccctg     180
cgtgtgctag cgtactcccg cctcaaggtc accgtgaaag ggaaacacct ttgtccaagt     240
cccctatttc ccggaccttc taagccctt tgggtgctgg tggtggttgg tggagtcctg     300
gcttgctata gcttgctagt aacagtggcc tttattattt tctgggtgag gagtaagagg     360
agcaggctcc tgcacagtga ctacatgaac atgactcccc gccgcccgg gcccacccgc     420 aagcattacc agccctatgc cccaccacgc gacttcgcag cctatagatc tcaagtgcga     480
aaggcagcta taaccagcta tgagaaatca gatggtgttt acacgggcct gagcaccagg     540
aaccaggaga cttacgagac tctgaagcat gagaaaccac acagtagct ttagactcga     600 gcgggatcaa ttccgccccc ccctaacgt tactggccga agccgcttgg aataaggccg     660
gtgtgcgttt gtctatatgt tattttccac catattgccg tcttttggca atgtgagggc     720
ccggaaacct ggccctgtct tcttgacgag cattcctagg ggtctttccc ctctcgccaa     780
aggaatgcaa ggtctgttga atgtcgtgaa ggaagcagtt cctctggaag cttcttgaag     840
acaaacaacg tctgtagcga ccctttgcag gcagcggaac cccccacctg gcgacaggtg     900
cctctgcggc caaagccac gtgtataaga tacacctgca aaggcggcac aaccccagtg     960
ccacgttgtg agttggatag ttgtggaaag agtcaaatgg ctctcctcaa gcgtattcaa    1020
caaggggctg aaggatgccc agaaggtacc ccattgtatg ggatctgatc tggggcctcg    1080
gtgcacatgc tttacatgtg tttagtcgag gttaaaaaaa cgtctaggcc cccgaacca     1140
```

```
cggggacgtg gttttcctttt gaaaaacacg ataatagcat gcagcgctac cggtcgccac    1200
catggtgagc aagggcgagg agctgttcac cggggtggtg cccatcctgg tcgagctgga    1260
cggcgacgta aacggccaca gttcagcgt gtccggcgag ggcgagggcg atgccaccta     1320
cggcaagctg accctgaagt tcatctgcac caccggcaag ctgcccgtgc cctggcccac    1380
cctcgtgacc accctgacct acggcgtgca gtgcttcagc cgctaccccg accacatgaa    1440
gcagcacgac ttcttcaagt ccgccatgcc cgaaggctac gtccaggagc gcaccatctt    1500
cttcaaggac gacggcaact acaagacccg cgccgaggtg aagttcgagg gcgacaccct    1560
ggtgaaccgc atcgagctga agggcatcga cttcaaggag gacggcaaca tcctggggca    1620
caagctggag tacaactaca acagccacaa cgtctatatc atggccgaca agcagaagaa    1680
cggcatcaag gtgaacttca gatccgcca caacatcgag gacggcagcg tgcagctcgc    1740
cgaccactac cagcagaaca cccccatcgg cgacggcccc gtgctgctgc ccgacaacca    1800
ctacctgagc acccagtccg ccctgagcaa agaccccaac gagaagcgcg atcacatggt    1860
cctgctggag ttcgtgaccg ccgccgggat cactctcggc atggacgagc tgtacaagtc    1920
cggccggact cagatctcga gctcaagctt cgaattcatg cccaacccca ggcctggcaa    1980
gccctcggcc ccttccttgg cccttggccc atccccagga gctcgcccca gctggagggc    2040
tgcacccaaa gcctcagacc tgctgggggc ccggggccca ggggaacct tccagggccg     2100 agatcttcga ggcggggccc atgcctcctc ttcttccttg aacccccatgc caccatcgca    2160 gctgcagctg cccacactgc cctagtcat ggtggcaccc tccggggcac ggctgggccc     2220
cttgccccac ttacaggcac tcctccagga caggccacat ttcatgcacc agctctcaac    2280
ggtggatgcc cacgcccgga cccctgtgct gcaggtgcac cccctggaga gcccagccat    2340
gatcagcctc acaccaccca ccaccgccac tgggtcttc tccctcaagg cccggcctgg     2400
cctcccacct gggatcaacg tggccagcct ggaatgggtg tccagggagc cggcactgct    2460
ctgcaccttc ccaaatccca gtgcacccag gaaggacagc accctttcgg ctgtgccccca   2520 gagctcctac ccactgctgg caaatggtgt ctgcaagtgg cccggatgtg agaaggtctt    2580
cgaagagcca gaggacttcc tcaagcactg ccaggcggac catcttctgg atgagaaggg    2640
cagggcacaa tgtctcctcc agagagagat ggtacagtct ctggagcagc agctggtgct    2700
ggagaaggag aagctgagtg ccatgcaggc ccacctggct gggaaaatgg cactgaccaa    2760
ggcttcatct gtggcatcat ccgacaaggg ctcctgctgc atcgtagctg ctggcagcca    2820
aggccctgtc gtcccagcct ggtctggccc cggggaggcc cctgacagcc tgtttgctgt    2880
ccggaggcac ctgtggggta gccatggaaa cagcacattc ccagagttcc tccacaacat    2940
ggactacttc aagttccaca acatgcgacc cccttttcacc tacgccacgc tcatccgctg    3000
ggccatcctg gaggctccag agaagcagcg gacactcaat gagatctacc actggttcac    3060
acgcatgttt gccttcttca gaaaccatcc tgccacctgg aagaacgcca tccgccacaa    3120
cctgagtctg cacaagtgct ttgtgcgggt ggagagcgag aaggggctg tgtggaccgt     3180 ggatgagctg gagttccgca gaaacggag ccagaggccc agcaggtgtt ccaaccctac     3240
acctggcccc tgaggatcc                                                  3259
```

<210> SEQ ID NO 17
<211> LENGTH: 14
<212> TYPE: PRT
<213> ORGANISM: Artificial Sequence
<220> FEATURE:
<223> OTHER INFORMATION: synthetic

<400> SEQUENCE: 17

Gly Ser Thr Ser Gly Ser Gly Lys Ser Ser Glu Gly Lys Gly
1               5                   10

<210> SEQ ID NO 18
<211> LENGTH: 927
<212> TYPE: DNA
<213> ORGANISM: Artificial Sequence
<220> FEATURE:
<223> OTHER INFORMATION: synthetic
<220> FEATURE:
<221> NAME/KEY: CDS
<222> LOCATION: (1)..(927)

<400> SEQUENCE: 18

```
atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tct aga atg tta cca ttt ctg ttt ttt tcc acc ctg ttt      96
Val Ile Met Ser Arg Met Leu Pro Phe Leu Phe Phe Ser Thr Leu Phe
            20                  25                  30 tct tcc ata ttt act gaa gct cag aag cag tat tgg gtc tgc aac tca     144
Ser Ser Ile Phe Thr Glu Ala Gln Lys Gln Tyr Trp Val Cys Asn Ser
        35                  40                  45 tcc gat gca agt att tca tac acc tac tgt gat aaa atg caa tac cca     192
Ser Asp Ala Ser Ile Ser Tyr Thr Tyr Cys Asp Lys Met Gln Tyr Pro
    50                  55                  60 att tca att aat gtt aac ccc tgt ata gaa ttg aaa gga tcc aaa gga     240
Ile Ser Ile Asn Val Asn Pro Cys Ile Glu Leu Lys Gly Ser Lys Gly
65                  70                  75                  80 tta ttg cac att ttc tac att cca agg aga gat tta aag caa tta tat     288
Leu Leu His Ile Phe Tyr Ile Pro Arg Arg Asp Leu Lys Gln Leu Tyr
                85                  90                  95 ttc aat ctc tat ata act gtc aac acc atg aat ctt cca aag cgc aaa     336
Phe Asn Leu Tyr Ile Thr Val Asn Thr Met Asn Leu Pro Lys Arg Lys
            100                 105                 110 gaa gtt att tgc cga gga tct gat gac gat tac tct ttt tgc aga gct     384
Glu Val Ile Cys Arg Gly Ser Asp Asp Asp Tyr Ser Phe Cys Arg Ala
        115                 120                 125 ctg aag gga gag act gtg aat aca aca ata tca ttc tcc ttc aag gga     432
Leu Lys Gly Glu Thr Val Asn Thr Thr Ile Ser Phe Ser Phe Lys Gly
    130                 135                 140 ata aaa ttt tct aag gga aaa tac aaa tgt gtt gtt gaa gct att tct     480
Ile Lys Phe Ser Lys Gly Lys Tyr Lys Cys Val Val Glu Ala Ile Ser
145                 150                 155                 160 ggg agc cca gaa gaa atg ctc ttt tgc ttg gag ttt gtc atc cta cac     528
Gly Ser Pro Glu Glu Met Leu Phe Cys Leu Glu Phe Val Ile Leu His
                165                 170                 175 caa cct aat tca aat ggt cac ctc gtg aaa ggg aaa cac ctt tgt cca     576
Gln Pro Asn Ser Asn Gly His Leu Val Lys Gly Lys His Leu Cys Pro
            180                 185                 190 agt ccc cta ttt ccc gga cct tct aag ccc ttt tgg gtg ctg gtg gtg     624
Ser Pro Leu Phe Pro Gly Pro Ser Lys Pro Phe Trp Val Leu Val Val
        195                 200                 205 gtt ggt gga gtc ctg gct tgc tat agc ttg cta gta aca gtg gcc ttt     672
Val Gly Gly Val Leu Ala Cys Tyr Ser Leu Leu Val Thr Val Ala Phe
    210                 215                 220 att att ttc tgg gtg agg agt aag agg agc agg ctc ctg cac agt gac     720
Ile Ile Phe Trp Val Arg Ser Lys Arg Ser Arg Leu Leu His Ser Asp
225                 230                 235                 240
```

```
tac atg aac atg act ccc cgc cgc ccc ggg ccc acc cgc aag cat tac      768
Tyr Met Asn Met Thr Pro Arg Arg Pro Gly Pro Thr Arg Lys His Tyr
                245                 250                 255 cag ccc tat gcc cca cca cgc gac ttc gca gcc tat aga tct caa gtg      816
Gln Pro Tyr Ala Pro Pro Arg Asp Phe Ala Ala Tyr Arg Ser Gln Val
            260                 265                 270 cga aag gca gct ata acc agc tat gag aaa tca gat ggt gtt tac acg      864
Arg Lys Ala Ala Ile Thr Ser Tyr Glu Lys Ser Asp Gly Val Tyr Thr
        275                 280                 285 ggc ctg agc acc agg aac cag gag act tac gag act ctg aag cat gag      912
Gly Leu Ser Thr Arg Asn Gln Glu Thr Tyr Glu Thr Leu Lys His Glu
    290                 295                 300 aaa cca cca cag tag                                                   927
Lys Pro Pro Gln
305

<210> SEQ ID NO 19
<211> LENGTH: 308
<212> TYPE: PRT
<213> ORGANISM: Artificial Sequence
<220> FEATURE:
<223> OTHER INFORMATION: Synthetic Construct

<400> SEQUENCE: 19

Met Asp Phe Gln Val Gln Ile Phe Ser Phe Leu Leu Ile Ser Ala Ser
1               5                   10                  15

Val Ile Met Ser Arg Met Leu Pro Phe Leu Phe Ser Thr Leu Phe
            20                  25                  30

Ser Ser Ile Phe Thr Glu Ala Gln Lys Gln Tyr Trp Val Cys Asn Ser
        35                  40                  45

Ser Asp Ala Ser Ile Ser Tyr Thr Tyr Cys Asp Lys Met Gln Tyr Pro
    50                  55                  60

Ile Ser Ile Asn Val Asn Pro Cys Ile Glu Leu Lys Gly Ser Lys Gly
65                  70                  75                  80

Leu Leu His Ile Phe Tyr Ile Pro Arg Arg Asp Leu Lys Gln Leu Tyr
                85                  90                  95

Phe Asn Leu Tyr Ile Thr Val Asn Thr Met Asn Leu Pro Lys Arg Lys
            100                 105                 110

Glu Val Ile Cys Arg Gly Ser Asp Asp Tyr Ser Phe Cys Arg Ala
        115                 120                 125

Leu Lys Gly Glu Thr Val Asn Thr Thr Ile Ser Phe Ser Phe Lys Gly
    130                 135                 140

Ile Lys Phe Ser Lys Gly Lys Tyr Lys Cys Val Val Glu Ala Ile Ser
145                 150                 155                 160

Gly Ser Pro Glu Glu Met Leu Phe Cys Leu Glu Phe Val Ile Leu His
                165                 170                 175

Gln Pro Asn Ser Asn Gly His Leu Val Lys Gly Lys His Leu Cys Pro
            180                 185                 190

Ser Pro Leu Phe Pro Gly Pro Ser Lys Pro Phe Trp Val Leu Val Val
        195                 200                 205

Val Gly Gly Val Leu Ala Cys Tyr Ser Leu Leu Val Thr Val Ala Phe
    210                 215                 220

Ile Ile Phe Trp Val Arg Ser Lys Arg Ser Arg Leu Leu His Ser Asp
225                 230                 235                 240

Tyr Met Asn Met Thr Pro Arg Arg Pro Gly Pro Thr Arg Lys His Tyr
                245                 250                 255

Gln Pro Tyr Ala Pro Pro Arg Asp Phe Ala Ala Tyr Arg Ser Gln Val
```

```
                260             265             270
Arg Lys Ala Ala Ile Thr Ser Tyr Glu Lys Ser Asp Gly Val Tyr Thr
            275                 280                 285

Gly Leu Ser Thr Arg Asn Gln Glu Thr Tyr Glu Thr Leu Lys His Glu
        290                 295                 300

Lys Pro Pro Gln
305

<210> SEQ ID NO 20
<211> LENGTH: 4408
<212> TYPE: DNA
<213> ORGANISM: Artificial Sequence
<220> FEATURE:
<223> OTHER INFORMATION: synthetic

<400> SEQUENCE: 20
```

| | | | | | |
|---|---|---|---|---|---|
| atggattttc | aggtgcagat | tttcagcttc | ctgctaatca | gtgcctcagt | cataatgtct | 60 |
| agaatgttac | catttctgtt | ttttccacc | ctgttttctt | ccatatttac | tgaagctcag | 120 |
| aagcagtatt | gggtctgcaa | ctcatccgat | gcaagtattt | catacaccta | ctgtgataaa | 180 |
| atgcaatacc | caatttcaat | taatgttaac | ccctgtatag | aattgaaagg | atccaaagga | 240 |
| ttattgcaca | ttttctacat | tccaaggaga | gatttaaagc | aattatattt | caatctctat | 300 |
| ataactgtca | acaccatgaa | tcttccaaag | cgcaaagaag | ttatttgccg | aggatctgat | 360 |
| gacgattact | cttttttgcag | agctctgaag | ggagagactg | tgaatacaac | aatatcattc | 420 |
| tccttcaagg | gaataaaatt | ttctaaggga | aaatacaaat | gtgttgttga | agctatttct | 480 |
| gggagcccag | aagaaatgct | cttttgcttg | gagtttgtca | tcctacacca | acctaattca | 540 |
| aatggtcacc | tcgtgaaagg | gaaacacctt | tgtccaagtc | ccctatttcc | cggaccttct | 600 |
| aagccctttt | gggtgctggt | ggtggttggt | ggagtcctgg | cttgctatag | cttgctagta | 660 |
| acagtggcct | ttattatttt | ctgggtgagg | agtaagagga | gcaggctcct | gcacagtgac | 720 |
| tacatgaaca | tgactccccg | ccgccccggg | cccacccgca | agcattacca | gccctatgcc | 780 |
| ccaccacgcg | acttcgcagc | ctatagatct | caagtgcgaa | aggcagctat | aaccagctat | 840 |
| gagaaatcag | atggtgttta | cacgggcctg | agcaccagga | accaggagac | ttacgagact | 900 |
| ctgaagcatg | agaaaccacc | acagtagctt | tagactcgag | cgggatcaat | tccgcccccc | 960 |
| ccctaacgtt | actggccgaa | gccgcttgga | ataaggccgg | tgtgcgtttg | tctatatgtt | 1020 |
| attttccacc | atattgccgt | cttttggcaa | tgtgagggcc | cggaaacctg | gccctgtctt | 1080 |
| cttgacgagc | attcctaggg | gtctttcccc | tctcgccaaa | ggaatgcaag | gtctgttgaa | 1140 |
| tgtcgtgaag | gaagcagttc | ctctggaagc | ttcttgaaga | caaacaacgt | ctgtagcgac | 1200 |
| cctttgcagg | cagcggaacc | ccccacctgg | cgacaggtgc | ctctgcggcc | aaaagccacg | 1260 |
| tgtataagat | acacctgcaa | aggcggcaca | accccagtgc | cacgttgtga | gttggatagt | 1320 |
| tgtggaaaga | gtcaaatggc | tctcctcaag | cgtattcaac | aaggggctga | aggatgccca | 1380 |
| gaaggtaccc | cattgtatgg | gatctgatct | ggggcctcgg | tgcacatgct | ttacatgtgt | 1440 |
| ttagtcgagg | ttaaaaaaac | gtctaggccc | cccgaaccac | ggggacgtgg | ttttcctttg | 1500 |
| aaaaacacga | taatagcatg | cagcgctacc | ggtcgccacc | atggtgagca | agggcgagga | 1560 |
| gctgttcacc | ggggtggtgc | ccatcctggt | cgagctggac | ggcgacgtaa | acggccacaa | 1620 |
| gttcagcgtg | tccggcgagg | gcgagggcga | tgccacctac | ggcaagctga | ccctgaagtt | 1680 |
| catctgcacc | accggcaagc | tgcccgtgcc | ctggcccacc | ctcgtgacca | ccctgaccta | 1740 |

```
cggcgtgcag tgcttcagcc gctaccccga ccacatgaag cagcacgact tcttcaagtc      1800
cgccatgccc gaaggctacg tccaggagcg caccatcttc ttcaaggacg acggcaacta      1860
caagacccgc gccgaggtga agttcgaggg cgacaccctg gtgaaccgca tcgagctgaa      1920
gggcatcgac ttcaaggagg acggcaacat cctggggcac aagctggagt acaactacaa      1980
cagccacaac gtctatatca tggccgacaa gcagaagaac ggcatcaagg tgaacttcaa      2040
gatccgccac aacatcgagg acggcagcgt gcagctcgcc gaccactacc agcagaacac      2100
ccccatcggc gacggccccg tgctgctgcc cgacaaccac tacctgagca cccagtccgc      2160
cctgagcaaa gaccccaacg agaagcgcga tcacatggtc ctgctggagt tcgtgaccgc      2220
cgccgggatc actctcggca tggacgagct gtacaagtcc ggccggactc agatctcgag      2280
ctcaagcttc gaattcatgc caaccccag gcctggcaag ccctcggccc cttccttggc      2340
ccttggccca tccccaggag cctcgcccag ctggagggct gcacccaaag cctcagacct      2400 gctggggggcc cggggcccag ggggaacctt ccagggccga gatcttcgag gcggggccca      2460
tgcctcctct tcttccttga accccatgcc accatcgcag ctgcagctgc ccacactgcc      2520
cctagtcatg gtggcaccct ccggggcacg gctgggcccc ttgccccact acaggcact      2580 cctccaggac aggccacatt tcatgcacca gctctcaacg gtggatgccc acgcccggac      2640
ccctgtgctg caggtgcacc ccctggagag cccagccatg atcagcctca caccacccac      2700
caccgccact ggggtcttct ccctcaaggc ccggcctggc ctcccacctg ggatcaacgt      2760
ggccagcctg gaatgggtgt ccagggagcc ggcactgctc tgcaccttcc caaatcccag      2820
tgcacccagg aaggacagca ccctttcggc tgtgccccag agctcctacc cactgctggc      2880
aaatggtgtc tgcaagtggc ccggatgtga aaggtcttc gaagagccag aggacttcct      2940
caagcactgc caggcggacc atcttctgga tgagaagggc agggcacaat gtctcctcca      3000
gagagagatg gtacagtctc tggagcagca gctggtgctg gagaaggaga agctgagtgc      3060
catgcaggcc cacctggctg gaaaaatggc actgaccaag gcttcatctg tggcatcatc      3120
cgacaagggc tcctgctgca tcgtagctgc tggcagccaa ggccctgtcg tcccagcctg      3180
gtctggcccc cggggaggcc ctgacagcct gtttgctgtc cggaggcacc tgtggggtag      3240
ccatggaaac agcacattcc cagagttcct ccacaacatg gactacttca gttccacaa      3300 catgcgaccc cctttcacct acgccacgct catccgctgg gccatcctgg aggctccaga      3360
gaagcagcgg acactcaatg agatctacca ctggttcaca cgcatgtttg ccttcttcag      3420
aaaccatcct gccacctgga gaacgccat ccgccacaac ctgagtctgc acaagtgctt      3480
tgtgcgggtg gagagcgaga agggggctgt gtggaccgtg gatgagctgg agttccgcaa      3540
gaaacggagc cagaggccca gcaggtgttc aaccctaca cctggcccct gaggatccgc      3600
gccgctcgcg actcgagaga tccggattag tccaatttgt taaagacagg atatcagtgg      3660
tccaggctct agttttgact caacaatatc accagctgaa gcctatagag tacgagccat      3720
agataaaata aaagatttta tttagtctcc agaaaaaggg gggaatgaaa gaccccacct      3780
gtaggtttgg caagctagct taagtaacgc cattttgcag gcatggaaaa atacataact      3840
gagaatagag aagttcagat caaggtcagg aacagatgga acagctgaat atgggccaaa      3900
caggatatct gtggtaagca gttcctgccc cggctcaggg ccaagaacag atggaacagc      3960
tgaatatggg ccaaacagga tatctgtggt aagcagttcc tgccccggct cagggccaag      4020
aacagatggt cccagatgc ggtccagccc tcagcagttt ctagagaacc atcagatgtt      4080
tccagggtgc cccaaggacc tgaaatgacc ctgtgcctta tttgaactaa ccaatcagtt      4140
```

```
cgcttctcgc ttctgttcgc gcgcttctgc tccccgagct caataaaaga gcccacaacc    4200
cctcactcgg ggcgccagtc ctccgattga ctgagtcgcc cgggtacccg tgtatccaat    4260
aaaccctctt gcagttgcat ccgacttgtg gtctcgctgt tccttgggag gtctcctct    4320 gagtgattga ctaccgtca gcgggggtct ttcacatgca gcatgtatca aaattaattt    4380 ggttttttt cttaagtatt tacattaa                                        4408
```

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
agtccgggca ggtctacttt                                                  20

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
gaggcaacct gaccactctc                                                  20

<210> SEQ ID NO 23
<211> LENGTH: 19
<212> TYPE: DNA
<213> ORGANISM: Artificial Sequence
<220> FEATURE:
<223> OTHER INFORMATION: synthetic

<400> SEQUENCE: 23
tctggaggaa ctggcaaaa                                                   19

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
tgagctcatt gaatgcttgg                                                  20

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
tacagggctt tcgattcagc                                                  20

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
cgcacacagc agttcttctc					20

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
tccttgggaa gcaattgaag					20

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
aactggccac agttttcagg					20

<210> SEQ ID NO 29
<211> LENGTH: 21
<212> TYPE: DNA
<213> ORGANISM: Artificial Sequence
<220> FEATURE:
<223> OTHER INFORMATION: synthetic

<400> SEQUENCE: 29
ctaagcaagg acggcgaatg t					21

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
ggctgggaac aggatactgg					20

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
gcctgcggac tctaccataa					20

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
cagggatgac atgtgtctgg					20

<210> SEQ ID NO 33
<211> LENGTH: 20

<212> TYPE: DNA
<213> ORGANISM: Artificial Sequence
<220> FEATURE:
<223> OTHER INFORMATION: synthetic

<400> SEQUENCE: 33
gtgttcctac ccccaatgtg					20

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
cttgctcagt gtccttgctg					20

<210> SEQ ID NO 35
<211> LENGTH: 388
<212> TYPE: PRT
<213> ORGANISM: Artificial Sequence
<220> FEATURE:
<223> OTHER INFORMATION: synthetic

<400> SEQUENCE: 35

```
Met Asp Phe Gln Val Gln Ile Phe Ser Phe Leu Leu Ile Ser Ala Ser
1               5                   10                  15

Val Ile Met Ser Arg Gly Asp Ile Val Leu Thr Gln Ser Pro Ser Ser
            20                  25                  30

Leu Ala Val Ser Ala Gly Glu Lys Val Thr Met Ser Cys Lys Ser Ser
        35                  40                  45

Gln Ser Leu Leu Asn Ser Arg Thr Arg Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
                85                  90                  95

Thr Asp Phe Thr Leu Thr Ile Ser Ser Val Gln Ala Glu Asp Leu Ala
            100                 105                 110

Val Tyr Tyr Cys Lys Gln Ser Tyr Asn Leu Tyr Thr Phe Gly Gly Gly
        115                 120                 125

Thr Lys Leu Glu Ile Lys Gly Ser Thr Ser Gly Ser Gly Lys Ser Ser
    130                 135                 140

Glu Gly Lys Gly Glu Val Gln Leu Gln Gln Ser Gly Gly Gly Leu Val
145                 150                 155                 160

Gln Pro Gly Gly Ser Leu Lys Leu Ser Cys Ala Ala Ser Gly Phe Asp
                165                 170                 175

Phe Ser Arg Tyr Trp Met Ser Trp Val Arg Gln Ala Pro Gly Lys Gly
            180                 185                 190

Leu Glu Trp Ile Gly Glu Ile Asn Pro Asp Ser Ser Thr Ile Asn Tyr
        195                 200                 205

Thr Pro Ser Leu Lys Asp Lys Phe Ile Ile Ser Arg Asp Asn Ala Lys
    210                 215                 220

Asn Thr Leu Tyr Leu Gln Met Ser Lys Val Arg Ser Glu Asp Thr Ala
225                 230                 235                 240

Leu Tyr Tyr Cys Ala Arg Arg Tyr Gly Asn Tyr Trp Tyr Phe Asp Val
                245                 250                 255
```

```
Trp Gly Ala Gly Thr Thr Val Thr Val Lys Gly Lys His Leu Cys Pro
            260                 265                 270

Ser Pro Leu Phe Pro Gly Pro Ser Lys Pro Phe Trp Val Leu Val Val
            275                 280                 285

Val Gly Gly Val Leu Ala Cys Tyr Ser Leu Leu Val Thr Val Ala Phe
            290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Gln Val
            340                 345                 350

Arg Lys Ala Ala Ile Thr Ser Tyr Glu Lys Ser Asp Gly Val Tyr Thr
            355                 360                 365

Gly Leu Ser Thr Arg Asn Gln Glu Thr Tyr Glu Thr Leu Lys His Glu
            370                 375                 380

Lys Pro Pro Gln
385

<210> SEQ ID NO 36
<211> LENGTH: 167
<212> TYPE: PRT
<213> ORGANISM: Artificial Sequence
<220> FEATURE:
<223> OTHER INFORMATION: synthetic

<400> SEQUENCE: 36

Met Asp Phe Gln Val Gln Ile Phe Ser Phe Leu Leu Ile Ser Ala Ser
1               5                   10                  15

Val Ile Met Ser Arg Gln Val Pro Ala Gln Leu Leu Val Gly Ala Leu
            20                  25                  30

Arg Val Leu Ala Tyr Ser Arg Leu Lys Val Thr Val Lys Gly Lys His
            35                  40                  45

Leu Cys Pro Ser Pro Leu Phe Pro Gly Pro Ser Lys Pro Phe Trp Val
50                  55                  60

Leu Val Val Val Gly Gly Val Leu Ala Cys Tyr Ser Leu Leu Val Thr
65                  70                  75                  80

Val Ala Phe Ile Ile Phe Trp Val Arg Ser Lys Arg Ser Arg Leu Leu
            85                  90                  95

His Ser Asp Tyr Met Asn Met Thr Pro Arg Arg Pro Gly Pro Thr Arg
            100                 105                 110

Lys His Tyr Gln Pro Tyr Ala Pro Pro Arg Asp Phe Ala Ala Tyr Arg
            115                 120                 125

Ser Gln Val Arg Lys Ala Ala Ile Thr Ser Tyr Glu Lys Ser Asp Gly
            130                 135                 140

Val Tyr Thr Gly Leu Ser Thr Arg Asn Gln Glu Thr Tyr Glu Thr Leu
145                 150                 155                 160

Lys His Glu Lys Pro Pro Gln
                165

<210> SEQ ID NO 37
<211> LENGTH: 162
<212> TYPE: PRT
<213> ORGANISM: Artificial Sequence
<220> FEATURE:
<223> OTHER INFORMATION: synthetic

<400> SEQUENCE: 37
```

```
Met Asp Phe Gln Val Gln Ile Phe Ser Phe Leu Leu Ile Ser Ala Ser
1               5                   10                  15

Val Ile Met Ser Arg Phe Ser Phe Lys Gly Ile Lys Phe Ser Lys Gly
            20                  25                  30

Lys Tyr Lys Gly His Leu Val Lys Gly Lys His Leu Cys Pro Ser Pro
        35                  40                  45

Leu Phe Pro Gly Pro Ser Lys Pro Phe Trp Val Leu Val Val Gly
    50                  55                  60

Gly Val Leu Ala Cys Tyr Ser Leu Leu Val Thr Val Ala Phe Ile Ile
65                  70                  75                  80

Phe Trp Val Arg Ser Lys Arg Ser Arg Leu Leu His Ser Asp Tyr Met
                85                  90                  95

Asn Met Thr Pro Arg Arg Pro Gly Pro Thr Arg Lys His Tyr Gln Pro
            100                 105                 110

Tyr Ala Pro Pro Arg Asp Phe Ala Ala Tyr Arg Ser Gln Val Arg Lys
        115                 120                 125

Ala Ala Ile Thr Ser Tyr Glu Lys Ser Asp Gly Val Tyr Thr Gly Leu
    130                 135                 140

Ser Thr Arg Asn Gln Glu Thr Tyr Glu Thr Leu Lys His Glu Lys Pro
145                 150                 155                 160

Pro Gln
```

<210> SEQ ID NO 38
<211> LENGTH: 195
<212> TYPE: PRT
<213> ORGANISM: Artificial Sequence
<220> FEATURE:
<223> OTHER INFORMATION: synthetic

<400> SEQUENCE: 38

```
Met Asp Phe Gln Val Gln Ile Phe Ser Phe Leu Leu Ile Ser Ala Ser
1               5                   10                  15

Val Ile Met Ser Arg Phe Ser Phe Lys Gly Ile Lys Phe Ser Lys Gly
            20                  25                  30

Lys Tyr Lys Gly Ser Thr Ser Gly Ser Gly Lys Ser Ser Glu Gly Lys
        35                  40                  45

Gly Gln Val Pro Ala Gln Leu Leu Val Gly Ala Leu Arg Val Leu Ala
    50                  55                  60

Tyr Ser Arg Leu Lys Val Thr Val Lys Gly Lys His Leu Cys Pro Ser
65                  70                  75                  80

Pro Leu Phe Pro Gly Pro Ser Lys Pro Phe Trp Val Leu Val Val Val
                85                  90                  95

Gly Gly Val Leu Ala Cys Tyr Ser Leu Leu Val Thr Val Ala Phe Ile
            100                 105                 110

Ile Phe Trp Val Arg Ser Lys Arg Ser Arg Leu Leu His Ser Asp Tyr
        115                 120                 125

Met Asn Met Thr Pro Arg Arg Pro Gly Pro Thr Arg Lys His Tyr Gln
    130                 135                 140

Pro Tyr Ala Pro Pro Arg Asp Phe Ala Ala Tyr Arg Ser Gln Val Arg
145                 150                 155                 160

Lys Ala Ala Ile Thr Ser Tyr Glu Lys Ser Asp Gly Val Tyr Thr Gly
                165                 170                 175

Leu Ser Thr Arg Asn Gln Glu Thr Tyr Glu Thr Leu Lys His Glu Lys
            180                 185                 190
```

```
Pro Pro Gln
    195
```

<210> SEQ ID NO 39
<211> LENGTH: 308
<212> TYPE: PRT
<213> ORGANISM: Artificial Sequence
<220> FEATURE:
<223> OTHER INFORMATION: synthetic

<400> SEQUENCE: 39

```
Met Asp Phe Gln Val Gln Ile Phe Ser Phe Leu Leu Ile Ser Ala Ser
1               5                   10                  15

Val Ile Met Ser Arg Met Leu Pro Phe Leu Phe Ser Thr Leu Phe
            20                  25                  30

Ser Ser Ile Phe Thr Glu Ala Gln Lys Gln Tyr Trp Val Cys Asn Ser
        35                  40                  45

Ser Asp Ala Ser Ile Ser Tyr Thr Tyr Cys Asp Lys Met Gln Tyr Pro
    50                  55                  60

Ile Ser Ile Asn Val Asn Pro Cys Ile Glu Leu Lys Gly Ser Lys Gly
65                  70                  75                  80

Leu Leu His Ile Phe Tyr Ile Pro Arg Arg Asp Leu Lys Gln Leu Tyr
                85                  90                  95

Phe Asn Leu Tyr Ile Thr Val Asn Thr Met Asn Leu Pro Lys Arg Lys
            100                 105                 110

Glu Val Ile Cys Arg Gly Ser Asp Asp Tyr Ser Phe Cys Arg Ala
        115                 120                 125

Leu Lys Gly Glu Thr Val Asn Thr Thr Ile Ser Phe Ser Phe Lys Gly
    130                 135                 140

Ile Lys Phe Ser Lys Gly Lys Tyr Lys Cys Val Val Glu Ala Ile Ser
145                 150                 155                 160

Gly Ser Pro Glu Glu Met Leu Phe Cys Leu Glu Phe Val Ile Leu His
                165                 170                 175

Gln Pro Asn Ser Asn Gly His Leu Val Lys Gly Lys His Leu Cys Pro
            180                 185                 190

Ser Pro Leu Phe Pro Gly Pro Ser Lys Pro Phe Trp Val Leu Val Val
        195                 200                 205

Val Gly Gly Val Leu Ala Cys Tyr Ser Leu Leu Val Thr Val Ala Phe
    210                 215                 220

Ile Ile Phe Trp Val Arg Ser Lys Arg Ser Arg Leu Leu His Ser Asp
225                 230                 235                 240

Tyr Met Asn Met Thr Pro Arg Arg Pro Gly Pro Thr Arg Lys His Tyr
                245                 250                 255

Gln Pro Tyr Ala Pro Pro Arg Asp Phe Ala Ala Tyr Arg Ser Gln Val
            260                 265                 270

Arg Lys Ala Ala Ile Thr Ser Tyr Glu Lys Ser Asp Gly Val Tyr Thr
        275                 280                 285

Gly Leu Ser Thr Arg Asn Gln Glu Thr Tyr Glu Thr Leu Lys His Glu
    290                 295                 300

Lys Pro Pro Gln
305
```